United States Patent
Lieberman et al.

(10) Patent No.: US 11,242,553 B2
(45) Date of Patent: Feb. 8, 2022

(54) MIRNA TARGETS

(71) Applicant: Children's Medical Center Corporation, Boston, MA (US)

(72) Inventors: Judy Lieberman, Brookline, MA (US); Shen Mynn Tan, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/761,791

(22) PCT Filed: Jan. 17, 2014

(86) PCT No.: PCT/US2014/012046
§ 371 (c)(1),
(2) Date: Jul. 17, 2015

(87) PCT Pub. No.: WO2014/113668
PCT Pub. Date: Jul. 24, 2014

(65) Prior Publication Data
US 2015/0353991 A1 Dec. 10, 2015

Related U.S. Application Data

(60) Provisional application No. 61/754,392, filed on Jan. 18, 2013.

(51) Int. Cl.
*C12Q 1/6816* (2018.01)
*C12N 15/10* (2006.01)
*C12N 15/113* (2010.01)
*C12Q 1/6886* (2018.01)

(52) U.S. Cl.
CPC ....... *C12Q 1/6816* (2013.01); *C12N 15/1006* (2013.01); *C12N 15/113* (2013.01); *C12Q 1/6886* (2013.01); *C12N 2310/141* (2013.01); *C12Q 2600/178* (2013.01)

(58) Field of Classification Search
CPC .............. C12N 15/1096; C12N 2310/141
See application file for complete search history.

(56) References Cited

U.S. PATENT DOCUMENTS

| | | | | |
|---|---|---|---|---|
| 8,841,073 B2 * | 9/2014 | Landthaler | ........... | C12Q 1/6869 435/6.11 |
| 2004/0175732 A1 | 9/2004 | Rana | | |
| 2010/0029501 A1 | 2/2010 | Samal et al. | | |
| 2010/0279283 A1 * | 11/2010 | Raghunath | ........... | C12Q 1/6806 435/6.12 |
| 2011/0060135 A1 * | 3/2011 | Tzertzinis | ........... | C12N 15/1013 536/23.1 |
| 2011/0287412 A1 * | 11/2011 | Landthaler | ........... | C12Q 1/6869 435/6.1 |
| 2012/0015351 A1 | 1/2012 | Lee et al. | | |
| 2012/0040851 A1 | 2/2012 | Lieberman et al. | | |

FOREIGN PATENT DOCUMENTS

WO   WO 2010033818 A2 *  3/2010  ........... C12N 15/111

OTHER PUBLICATIONS

Hafner et al. Transcriptome-wide identification of RNA-binding protein and microRNA target sites by PAR-CLIP. Cell, vol. 141, pp. 129-141, Apr. 2010, and pp. S1-S18 of Supplemental Information.*
Nonne et al. Tandem affinity purification of miRNA target mRNAs (TAP-Tar). Nucleic Acids Research, vol. 38, No. 4, p. e20, Dec. 2009, printed as pp. 1/5-5/5.*
Richardson et al. The PLIN4 variant rs8887 modulates obesity related phenotypes in humans trhough creation of a novel miR-522 seed site. PLoS ONE, vol. 6, No. 4, e17944, Apr. 2011, printed as pp. 1/11-11/11.*
Wingender, E. The TRANSFAC project as an example of framework technology that supports the analysis of genomic regulation. Briefings in Informatics, vol. 9, No. 4, pp. 326-332, Apr. 2008. (Year: 2008).*
Ingenuity Pathway Analysis—QIAGEN Bioinformatics, https://www.qiagenbioinformatics.com/products/igenuity-pathway-analysis/, printed as pp. 1/5-5/5 on Oct. 13, 2017 (Year: 2017).*
Tech Tip #64: Immunoprecipitation (IP) technical guide and protocols. TR0064.0. Thermo Scientific Inc., 2009, pp. 1-12. (Year: 2009).*
Pokric et al. Effects of polyethylene glycol and dextrans on immunoprecipitations: A two-cross immunodiffusion study. Analytical Biochemistry, vol. 146, pp. 374-388, 1985. (Year: 1985).*
Jung et al. MicroRNA in Aging: From Discovery to Biology, vol. 13, pp. 548-557, Nov. 2012. (Year: 2012).*
Lal et al. Capture of MicroRNA-bound mRNAs identifies the tumor suppressor miR-34a as a regulator of growth factor signaling. PLoS Genetics, vol. 7, No. 11, e1002363, Nov. 10, 2011, printed as pp. 1-17. (Year: 2011).*
The International Search Report and Written Opinion issued in corresponding international application Ser. No. PCT/US2014/012046, dated May 1, 2014, 13 pages.

* cited by examiner

*Primary Examiner* — Jennifer Dunston
(74) *Attorney, Agent, or Firm* — Mintz Levin Cohn Ferris Glovsky and Popeo, P.C.; Peter F. Corless

(57) ABSTRACT

The present invention provides systems and methods for identifying, isolating, and/or characterizing microRNAs, their targets, and microRNA response elements, and for predicting their biological function.

8 Claims, 86 Drawing Sheets
Specification includes a Sequence Listing.

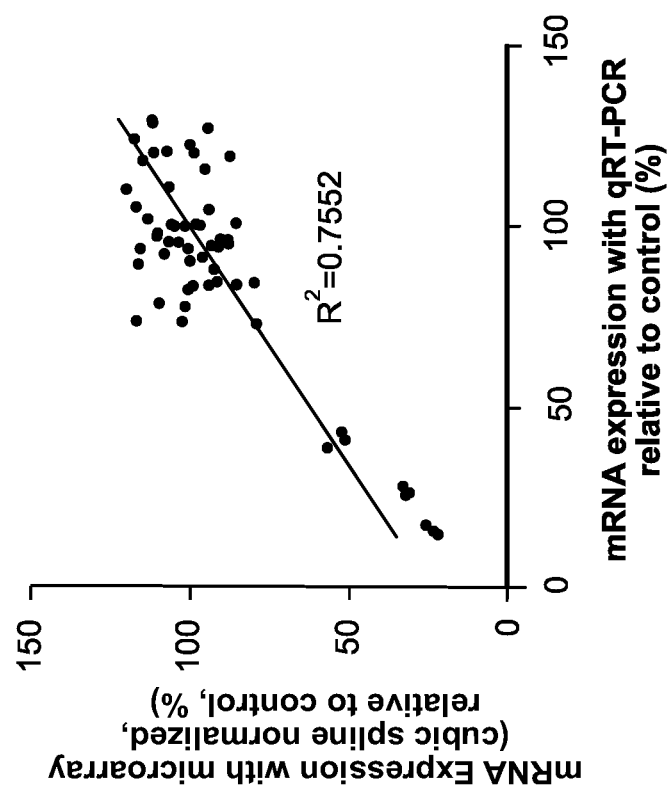
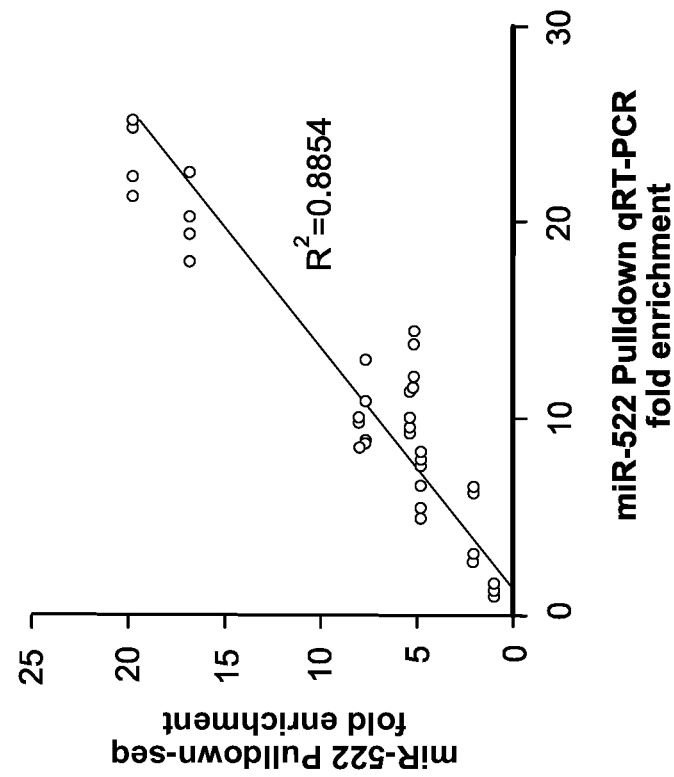
FIG. 3B
FIG. 3A (SEQ ID NO: 5) miR-522: 3' TGTGAGATTTCCCTTGGTAAAA 5'

FIG. 6A

| Transcription factor | p-value | Motif | Number of genes | Function |
|---|---|---|---|---|
| ELK1 | $1.77 \times 10^{-5}$ | CCGGAART | 113 | Regulates cytoskeleton and migration. Identified here as a target of miR-522 |
| E2F | $9.83 \times 10^{-5}$ | GGCGSG | 281 | Targets down-regulated upon EMT Regulator of G1/S cell cycle progression E2F3 identified here as a target of miR-522 |
| TEAD2 | $8.40 \times 10^{-4}$ | GVGGMGG | 184 | Hippo signaling transcriptional regulator Positive regulator of PAX3 |
| PAX3 | $3.76 \times 10^{-3}$ | CGTCACGSTY | 101 | Developmental regulator Positive regulator of MET |

FIG. 6B

| Top associated network functions | IPA score |
|---|---|
| Cellular movement, embryonic development, cell morphology | 71 |
| Gene expression, cell cycle, connective tissue development and function | 44 |
| Cell signaling, connective tissue disorders, developmental disorder | 35 |
| Cellular movement, hematological system development and function, immune cell trafficking | 32 |
| Cardiovascular system development and function, embryonic development, organ development | 17 |

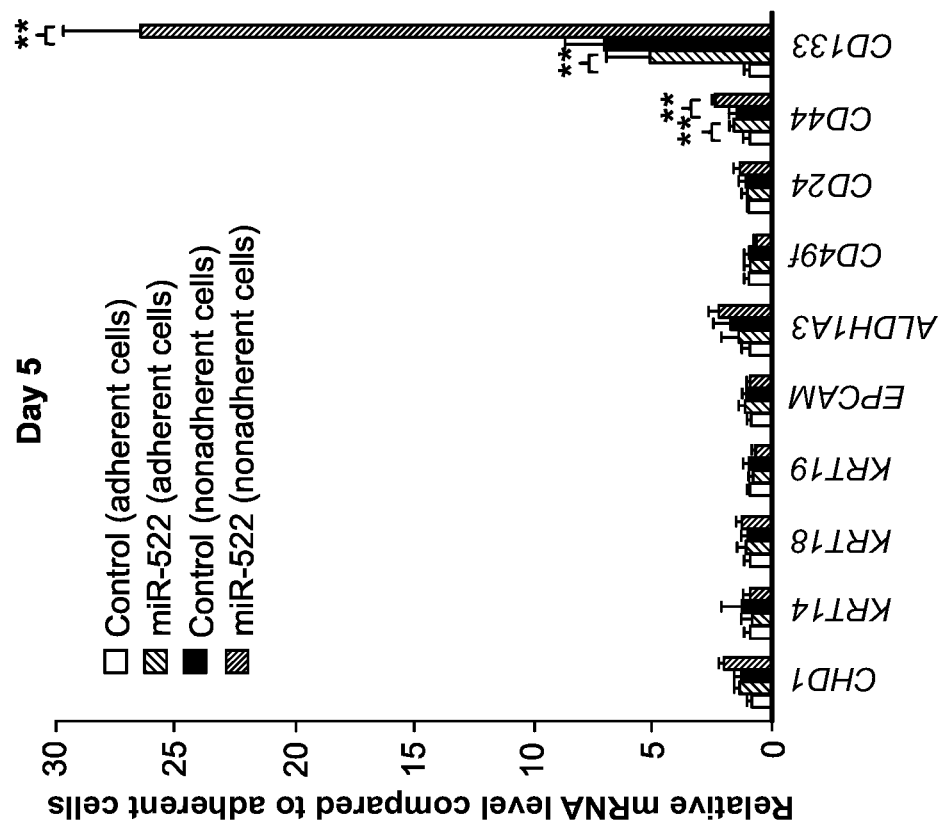
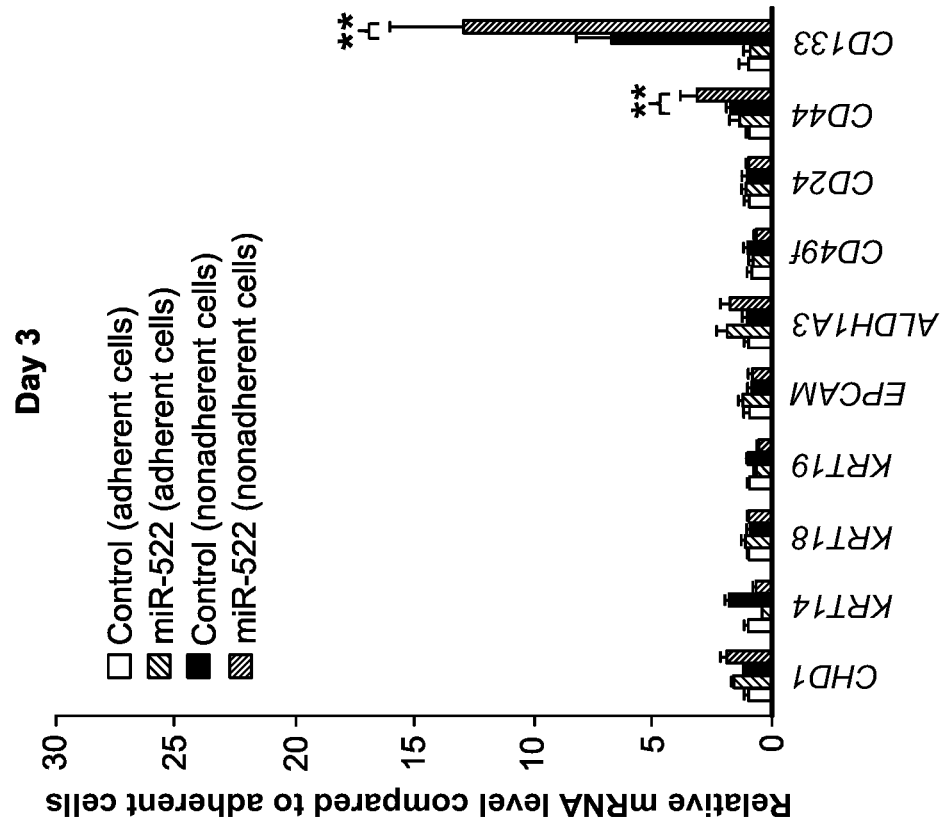
FIG. 9A

FIG. 9B
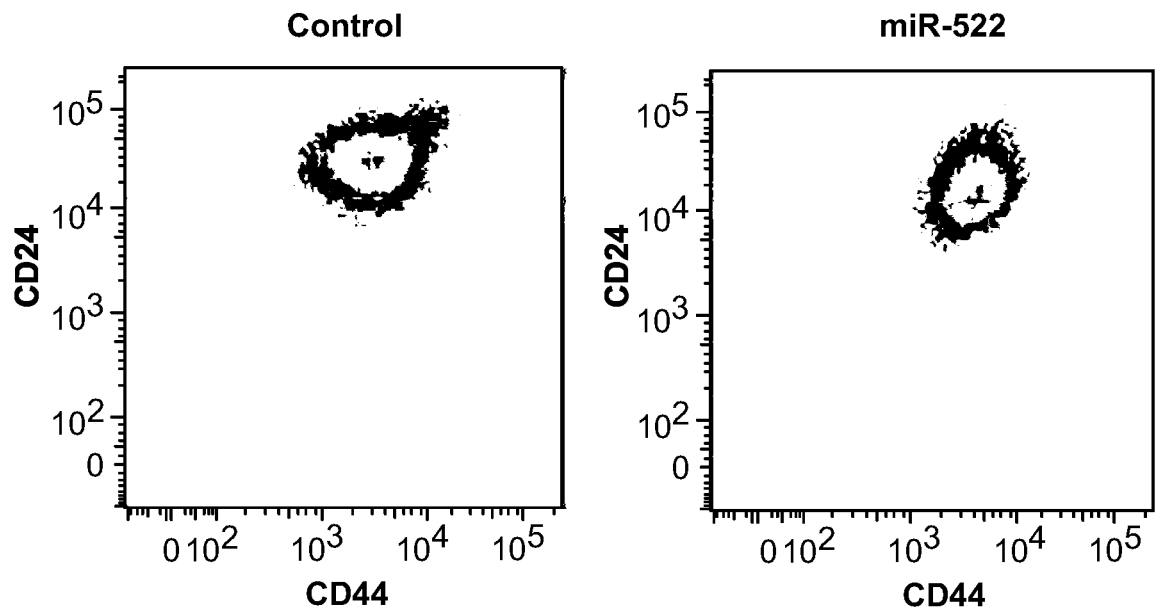
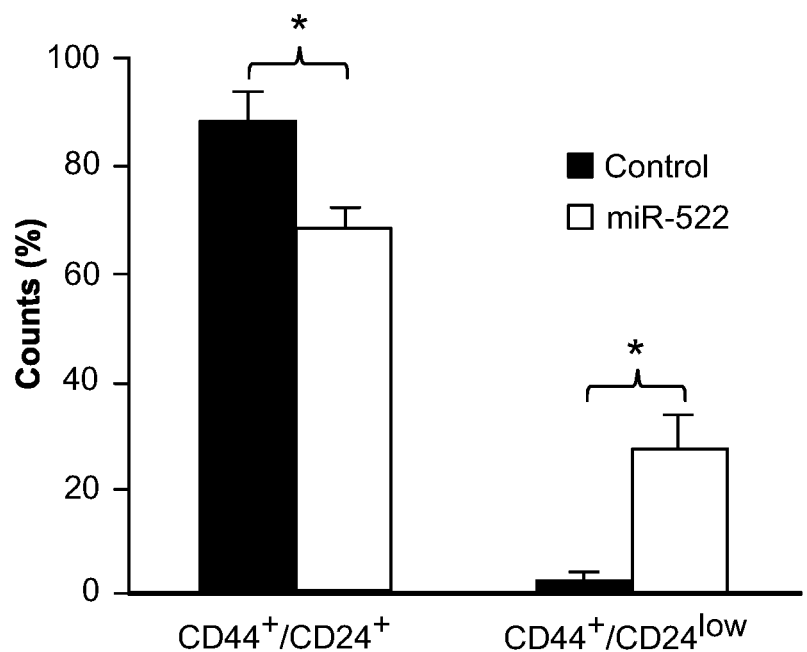
FIG. 9C

FIG. 12

| Test experiment | Tested | Positive | Positive rate |
|---|---|---|---|
| let-7a Transcript down-regulations | 543 | 295 | 54.3% |
| miR-34a Transcript down-regulation | 657 | 343 | 52.2% |
| miR-522 Transcript down-regulation | 428 | 255 | 59.6% |
| miR-522 protein down-regulation | 30 | 22 | 73.3% |
| miR-522 3'UTR MRE luciferase assay | 30 | 25 | 83.3% |

TRANSFAC Analysis

A

| Transcription Factor | P-value | Motif | Number of Genes | Function |
|---|---|---|---|---|
| SP1 | 3.15x10⁻¹⁰ | GGGGCGGGGC | 319 | Involved in many cellular processes |
| E2F | 8.66x10⁻⁷ | GGCGSG | 374 | Regulator of G1/S cell cycle progression |
| LRF | 1.63x10⁻⁴ | VNNRMCCCC | 513 | Regulates neuronal & cell development |
| ELK1 | 2.77x10⁻⁴ | CCGGAART | 136 | Regulates cytoskeleton and migration |
| AP2 | 1.86x10⁻³ | GSCCSCRGGCNRNR | 360 | |

IPA Analysis

B

| Top 5 Associated Network Functions | IPA Score |
|---|---|
| Amino Acid Metabolism, Small Molecule Biochemistry, Infectious Disease | 57 |
| Cell Cycle, Connective Tissue Disorders, Inflammatory Disease | 53 |
| RNA Post Transcriptional Modification, Amino Acid Metabolism, Molecular Transport | 51 |
| Cellular Compromise, Cellular Function and Maintenance, Protein Degradation | 45 |
| | 44 |

| Gene name | Pulldown-seq Fold enrichment | Pulldown-seq p-value | Overexpression (miR-522/Control) | Overexpression FDR | EntrezGene | Ensembl Gene ID |
|---|---|---|---|---|---|---|
| RPS13 | 78.96 | 0.00 | 0.96 | 0.7362 | 6207 | ENSG00000110700 |
| ADA | 78.50 | 0.00 | 1.07 | 0.6921 | 100 | ENSG00000196839 |
| RP11-159C21.4 | 63.86 | 0.00 | - | NA | | ENSG00000228929 |
| CTC-534A2.2 | 56.63 | 0.01 | - | NA | | ENSG00000253251 |
| CTD-2184D3.1 | 45.84 | 0.00 | - | NA | | ENSG00000242327 |
| HMGA1P2 | 36.52 | 0.02 | - | NA | | ENSG00000248641 |
| LYRM5 | 32.70 | 0.01 | 0.86 | 0.1422 | 144363 | ENSG00000205707 |
| RP5-1132H15.2 | 32.47 | 0.00 | - | NA | | ENSG00000205596 |
| UPF3AP2 | 28.47 | 0.00 | - | NA | | ENSG00000214832 |
| BANF1P3 | 27.31 | 0.00 | - | NA | | ENSG00000237758 |
| GOLGA7 | 25.90 | 0.00 | 0.34 | 0 | 51125 | ENSG00000147533 |
| RP11-471L13.3 | 23.51 | 0.00 | - | NA | | ENSG00000263648 |
| C1D | 22.40 | 0.00 | 0.92 | 0.4648 | 10438 | ENSG00000197223 |
| AC092664.1 | 21.53 | 0.00 | - | NA | | ENSG00000233370 |
| BANF1 | 20.65 | 0.03 | 0.22 | 0 | 8815 | ENSG00000175334 |
| PFN1P9 | 20.53 | 0.00 | - | NA | | ENSG00000227205 |
| GYG1 | 20.00 | 0.00 | 1.04 | 0.8092 | 2992 | ENSG00000163754 |
| FKBP1A | 19.81 | 0.00 | 0.48 | 0 | 2280 | ENSG00000088832 |
| DNAJC25 | 19.71 | 0.00 | 0.49 | 0 | 548645 | ENSG00000059769 |
| PFN1 | 19.13 | 0.00 | 0.52 | 0 | 5216 | ENSG00000108518 |
| DET1 | 18.44 | 0.01 | 0.79 | 0.0022 | 55070 | ENSG00000140543 |
| FBXL12 | 18.31 | 0.00 | 0.57 | 0 | 54850 | ENSG00000127452 |
| ELK1 | 17.08 | 0.00 | 0.38 | 0 | 2002 | ENSG00000126767 |
| TXNDC9 | 16.88 | 0.00 | 0.56 | 0 | 10190 | ENSG00000115514 |
| ERGIC1 | 16.79 | 0.00 | 0.53 | 0 | 57222 | ENSG00000113719 |
| PFN1P1 | 16.76 | 0.00 | - | NA | | ENSG00000233328 |
| AC073346.2 | 16.41 | 0.00 | - | NA | | ENSG00000214194 |
| DEDD2 | 15.40 | 0.00 | 0.61 | 0 | 162989 | ENSG00000160570 |
| SNAPIN | 15.32 | 0.00 | 0.83 | 0.073 | 23557 | ENSG00000143553 |
| DYNLT1 | 15.29 | 0.00 | 0.85 | 0.0134 | 6993 | ENSG00000146425 |
| SERPINB8 | 15.04 | 0.00 | 1.08 | 0.5965 | 5271 | ENSG00000166401 |
| RP11-533F5.2 | 14.87 | 0.00 | - | NA | | ENSG00000227040 |
| FAM161A | 14.58 | 0.01 | 0.85 | 0.0859 | 84140 | ENSG00000170264 |

FIG. 17B

| Gene | | | | ENSG |
|---|---|---|---|---|
| RPS2P5 | 14.41 | 0.00 | - | ENSG00000240342 |
| TMEM55A | 14.30 | 0.02 | 0.94 | 55529 | ENSG00000155099 |
| COMMD6 | 13.90 | 0.00 | 0.77 | 170622 | ENSG00000188243 |
| MRPL48P1 | 13.73 | 0.05 | - | ENSG00000238076 |
| ZNF280C | 13.05 | 0.00 | 0.79 | 55609 | ENSG00000056277 |
| ARV1 | 12.92 | 0.00 | 0.54 | 64801 | ENSG00000173409 |
| MRPS14 | 12.75 | 0.00 | 0.96 | 63931 | ENSG00000120333 |
| BCDIN3D | 12.25 | 0.00 | 0.88 | 144233 | ENSG00000186666 |
| THAP9-AS1 | 11.67 | 0.00 | - | 100499177 | ENSG00000251022 |
| SPSB1 | 11.59 | 0.00 | 0.65 | 80176 | ENSG00000171621 |
| UBE2Q2 | 11.53 | 0.00 | 0.24 | 92912 | ENSG00000140367 |
| FKBP1C | 11.34 | 0.00 | - | ENSG00000198225 |
| MRPL48 | 11.16 | 0.00 | 0.81 | 51642 | ENSG00000175581 |
| HOXA1 | 10.89 | 0.00 | 0.93 | 3198 | ENSG00000105991 |
| ZFVE21 | 10.70 | 0.00 | 0.42 | 79038 | ENSG00000100711 |
| RP11-136I13.1 | 10.28 | 0.00 | - | ENSG00000250613 |
| C8orf76 | 10.20 | 0.00 | 0.79 | 84933 | ENSG00000189376 |
| FAM120AOS | 10.15 | 0.00 | 0.78 | 158293 | ENSG00000188938 |
| SSBP4 | 10.10 | 0.01 | 0.41 | 170463 | ENSG00000130511 |
| FAM96AP2 | 9.97 | 0.01 | - | ENSG00000224566 |
| RPS2 | 9.95 | 0.00 | 0.88 | 6187 | ENSG00000140988 |
| NHLRC1 | 9.87 | 0.00 | 1.04 | 378884 | ENSG00000187566 |
| RP11-637I8.2 | 9.76 | 0.00 | - | ENSG00000259918 |
| ARL8A | 9.66 | 0.00 | 0.94 | 127829 | ENSG00000143862 |
| HDHD1 | 9.58 | 0.00 | - | 8226 | ENSG00000130021 |
| PDE6D | 9.57 | 0.00 | 0.49 | 5147 | ENSG00000156973 |
| GTF3A | 9.54 | 0.00 | 0.91 | 2971 | ENSG00000122034 |
| RSU1 | 9.40 | 0.00 | 0.31 | 6251 | ENSG00000148484 |
| GTF2H5 | 9.23 | 0.00 | 0.83 | 404672 | ENSG00000185068 |
| RPS2P46 | 8.91 | 0.00 | - | ENSG00000189343 |
| FAM57A | 8.84 | 0.03 | 0.50 | 79850 | ENSG00000167695 |
| AC005255.3 | 8.83 | 0.00 | - | ENSG00000256210 |
| CHCHD7 | 8.77 | 0.00 | 0.83 | 79145 | ENSG00000170791 |
| ANAPC13 | 8.72 | 0.00 | 1.05 | 25847 | ENSG00000129055 |

FIG. 17C

| Gene | | | | ENSG |
|---|---|---|---|---|
| COX7C | 8.66 | 0.00 | 0.92 | | ENSG00000127184 |
| CAMK2N1 | 8.56 | 0.02 | 0.70 | | ENSG00000162545 |
| SRD5A1P1 | 8.55 | 0.00 | | NA | ENSG00000232549 |
| CAPZA2 | 8.21 | 0.00 | 0.39 | 1350 | ENSG00000198898 |
| MAL2 | 8.02 | 0.01 | | 0 | ENSG00000147676 |
| PSMA6P2 | 7.90 | 0.00 | | NA | ENSG00000229083 |
| C8orf40 | 7.83 | 0.00 | 0.64 | NA | ENSG00000176209 |
| C12orf5 | 7.83 | 0.01 | 0.61 | 0 | ENSG00000078237 |
| USP25 | 7.83 | 0.00 | 1.08 | 0 | ENSG00000155313 |
| GOLGA1 | 7.82 | 0.01 | 0.63 | 0.589 | ENSG00000136935 |
| PIGH | 7.82 | 0.00 | 0.95 | 0 | ENSG00000100564 |
| RNF2 | 7.79 | 0.00 | 1.04 | 0.6964 | ENSG00000121481 |
| NDUFA8 | 7.78 | 0.00 | 0.59 | 0.8371 | ENSG00000119421 |
| ECI2 | 7.70 | 0.00 | | 0 | ENSG00000198721 |
| SDE2 | 7.70 | 0.00 | | NA | ENSG00000143751 |
| M6PR | 7.69 | 0.00 | 0.61 | NA | ENSG00000003056 |
| RP11-480I12.2 | 7.69 | 0.00 | | 0 | ENSG00000235449 |
| MEX3D | 7.59 | 0.00 | 0.49 | NA | ENSG00000181588 |
| ANXA5 | 7.54 | 0.00 | 0.35 | 0 | ENSG00000164111 |
| TPM3P8 | 7.50 | 0.00 | | 0 | ENSG00000183022 |
| NME6 | 7.26 | 0.00 | 0.75 | NA | ENSG00000172113 |
| MSANTD2 | 7.25 | 0.02 | | 0.0003 | ENSG00000120458 |
| AP1M1 | 7.24 | 0.01 | 0.57 | NA | ENSG00000072958 |
| RP11-175B9.3 | 7.23 | 0.00 | | NA | ENSG00000236439 |
| DTWD1 | 7.10 | 0.00 | 0.81 | 0.0081 | ENSG00000104047 |
| RAB23 | 7.07 | 0.00 | 0.29 | 0 | ENSG00000112210 |
| GCFC2 | 7.05 | 0.00 | | NA | ENSG00000005436 |
| MAX | 7.00 | 0.00 | 0.80 | 0.0083 | ENSG00000125952 |
| TMEM106C | 6.97 | 0.00 | 0.83 | 0.0148 | ENSG00000134291 |
| SRSF4 | 6.95 | 0.00 | | NA | ENSG00000116350 |
| SRD5A1 | 6.95 | 0.00 | 0.37 | 0 | ENSG00000145545 |
| MRPL22 | 6.91 | 0.00 | 0.46 | 0 | ENSG00000082515 |
| MON1A | 6.90 | 0.00 | 0.87 | 0.1504 | ENSG00000164077 |
| RP11-320A16.1 | 6.82 | 0.00 | | NA | ENSG00000261549 |

FIG. 17D

| Gene | | | | |
|---|---|---|---|---|
| ARMC10 | 6.82 | 0.00 | 0.71 | 0 | 83787 | ENSG00000170632 |
| IER2 | 6.79 | 0.00 | 0.96 | 0.8235 | 9592 | ENSG00000160888 |
| PSMA6P1 | 6.79 | 0.00 | - | NA | | ENSG00000215414 |
| ASNA1 | 6.78 | 0.00 | 0.77 | 0.006 | 439 | ENSG00000198356 |
| CCNB1IP1 | 6.75 | 0.00 | 1.32 | 0.0004 | 57820 | ENSG00000100814 |
| PPIL1 | 6.75 | 0.00 | 0.85 | 0.0326 | 51645 | ENSG00000137168 |
| TMEM167A | 6.74 | 0.00 | 0.33 | 0 | 153339 | ENSG00000174695 |
| LSM5 | 6.73 | 0.01 | 1.03 | 0.8854 | 23658 | ENSG00000106355 |
| FBXO25 | 6.72 | 0.00 | 0.89 | 0.2921 | 26260 | ENSG00000147364 |
| POPDC3 | 6.68 | 0.01 | 0.65 | 0 | 64208 | ENSG00000132429 |
| ZNF7 | 6.66 | 0.01 | 0.93 | 0.5131 | 7553 | ENSG00000147789 |
| HMGA2 | 6.65 | 0.00 | 0.94 | 0.6799 | 8091 | ENSG00000149948 |
| FAM96A | 6.64 | 0.00 | 0.86 | 0.0286 | 84191 | ENSG00000166797 |
| TXNL4B | 6.60 | 0.00 | 1.01 | 0.9508 | 54957 | ENSG00000140830 |
| RAB8B | 6.58 | 0.00 | 0.67 | 0 | 51762 | ENSG00000166128 |
| ATPBD4 | 6.54 | 0.01 | 0.58 | 0 | 89978 | ENSG00000134146 |
| CCNC | 6.48 | 0.00 | 0.70 | 0 | 892 | ENSG00000112237 |
| KLF8 | 6.44 | 0.00 | 1.07 | 0.6104 | 11279 | ENSG00000102349 |
| NUP54 | 6.41 | 0.00 | 0.51 | 0 | 53371 | ENSG00000138750 |
| GBP4 | 6.37 | 0.01 | 1.57 | 0 | 115361 | ENSG00000162654 |
| HIAT1 | 6.35 | 0.00 | 0.68 | 0 | 64645 | ENSG00000156875 |
| SAT2 | 6.23 | 0.01 | 0.87 | 0.1589 | 112483 | ENSG00000141504 |
| PPIL1P1 | 6.17 | 0.04 | - | NA | | ENSG00000237951 |
| THEM4 | 6.16 | 0.00 | 0.81 | 0.0064 | 117145 | ENSG00000159445 |
| XRCC6BP1 | 6.12 | 0.00 | 0.62 | 0 | 91419 | ENSG00000166896 |
| RBPMS | 6.10 | 0.00 | 0.69 | 0 | 11030 | ENSG00000157110 |
| CCDC91 | 6.02 | 0.02 | 0.55 | 0 | 55297 | ENSG00000123106 |
| DHFR | 6.01 | 0.00 | 0.58 | 0 | 1719 | ENSG00000228716 |
| ATPAF1 | 5.99 | 0.01 | 0.63 | 0 | 64756 | ENSG00000123472 |
| EPB41L2 | 5.88 | 0.00 | 0.50 | 0 | 2037 | ENSG00000079819 |
| SLC44A3 | 5.85 | 0.01 | 0.71 | 0 | 126969 | ENSG00000143036 |
| TGDS | 5.79 | 0.00 | 0.67 | 0 | 23483 | ENSG00000088451 |
| ACPL2 | 5.78 | 0.02 | 0.53 | 0 | 92370 | ENSG00000155893 |
| C1orf52 | 5.78 | 0.00 | 0.54 | 0 | 148423 | ENSG00000162642 |

FIG. 17E

| Gene | Col1 | Col2 | Col3 | ID | ENSG |
|---|---|---|---|---|---|
| CCNH | 5.76 | 0.00 | 0.60 | 0 | 902 | ENSG00000134480 |
| FAHD1 | 5.76 | 0.00 | 0.53 | 0 | 81889 | ENSG00000180185 |
| YARS2 | 5.72 | 0.00 | 0.74 | 0 | 51067 | ENSG00000139131 |
| MNAT1 | 5.72 | 0.02 | 1.92 | 0 | 4331 | ENSG00000020426 |
| DHFRP1 | 5.71 | 0.00 | - | NA | | ENSG00000188985 |
| CEP85 | 5.70 | 0.00 | - | NA | 64793 | ENSG00000130695 |
| ADCYAP1 | 5.70 | 0.04 | 0.46 | 0 | 116 | ENSG00000141433 |
| NDUFA5 | 5.69 | 0.01 | 1.06 | 0.6593 | 4698 | ENSG00000128609 |
| BRD7P4 | 5.62 | 0.01 | - | NA | | ENSG00000218676 |
| MPZL1 | 5.61 | 0.00 | 1.27 | 0.0012 | 9019 | ENSG00000197965 |
| C21orf91 | 5.61 | 0.00 | 0.81 | 0.016 | 54149 | ENSG00000154642 |
| AC004014.4 | 5.60 | 0.00 | - | NA | | ENSG00000227968 |
| MUL1 | 5.59 | 0.00 | 0.65 | 0 | 79594 | ENSG00000090432 |
| PWP1 | 5.55 | 0.01 | 0.97 | 0.8736 | 11137 | ENSG00000136045 |
| NKIRAS1 | 5.55 | 0.00 | 0.50 | 0 | 28512 | ENSG00000197885 |
| YAF2 | 5.52 | 0.00 | 0.66 | 0 | 10138 | ENSG00000015153 |
| LMO7 | 5.51 | 0.00 | 0.71 | 0 | 4008 | ENSG00000136153 |
| FECH | 5.49 | 0.00 | 0.51 | 0 | 2235 | ENSG00000066926 |
| SRI | 5.49 | 0.00 | 0.25 | 0 | 6717 | ENSG00000075142 |
| STAC | 5.48 | 0.00 | 0.64 | 0 | 6769 | ENSG00000144681 |
| MAPKAPK3 | 5.47 | 0.00 | 0.66 | 0 | 7867 | ENSG00000114738 |
| CLDND1 | 5.47 | 0.00 | 0.48 | 0 | 56650 | ENSG00000080822 |
| PYCR2 | 5.46 | 0.00 | 0.69 | 0 | 29920 | ENSG00000143811 |
| RP11-416N13.1 | 5.46 | 0.01 | - | NA | | ENSG00000224172 |
| SFT2D1 | 5.40 | 0.02 | 1.00 | 0.9975 | 113402 | ENSG00000198818 |
| CHMP3 | 5.39 | 0.00 | - | NA | 51652 | ENSG00000115561 |
| DCLRE1B | 5.39 | 0.00 | 0.71 | 0 | 64858 | ENSG00000118655 |
| ZNF461 | 5.38 | 0.00 | 0.93 | 0.6291 | 92283 | ENSG00000197808 |
| MARCH1 | 5.38 | 0.00 | - | NA | 64757 | ENSG00000186205 |
| UPF3AP1 | 5.35 | 0.00 | - | NA | | ENSG00000226478 |
| FAM188A | 5.31 | 0.00 | 0.80 | 0.0016 | 80013 | ENSG00000148481 |
| ATG12 | 5.30 | 0.00 | 0.88 | 0.1533 | 9140 | ENSG00000145782 |
| HMGA1 | 5.29 | 0.01 | 0.69 | 0 | 3159 | ENSG00000137309 |
| RP11-90E9.1 | 5.18 | 0.04 | - | NA | | ENSG00000258204 |

FIG. 17F

| Gene | Val1 | Val2 | Val3 | Val4 | ENSG |
|---|---|---|---|---|---|
| CASD1 | 5.16 | 0.01 | 0.86 | 0.116 | 64921 | ENSG00000127995 |
| SMAP1 | 5.16 | 0.04 | 0.88 | 0.2602 | 60682 | ENSG00000112305 |
| DTWD2 | 5.15 | 0.04 | 1.09 | 0.5603 | 285605 | ENSG00000169570 |
| AKD1 | 5.13 | 0.02 | - | NA | 221264 | ENSG00000155085 |
| YWHAZ | 5.12 | 0.00 | 0.52 | 0 | 7534 | ENSG00000164924 |
| MANEAL | 5.12 | 0.00 | 0.96 | 0.8302 | 149175 | ENSG00000185090 |
| ZC3H8 | 5.09 | 0.01 | 1.15 | 0.1994 | 84524 | ENSG00000144161 |
| AEN | 5.09 | 0.00 | 0.94 | 0.6999 | 64782 | ENSG00000181026 |
| MKL1 | 5.09 | 0.02 | 0.81 | 0.0264 | 57591 | ENSG00000196588 |
| ZBTB6 | 5.06 | 0.01 | 0.90 | 0.371 | 10773 | ENSG00000186130 |
| AC092296.1 | 5.06 | 0.04 | - | NA | | ENSG00000222730 |
| PHAX | 5.03 | 0.00 | 0.52 | 0 | 51808 | ENSG00000164902 |
| DNM3 | 4.97 | 0.03 | 1.28 | 0.003 | 26052 | ENSG00000197959 |
| TRIB1 | 4.96 | 0.00 | 1.18 | 0.0675 | 10221 | ENSG00000173334 |
| CDKN1B | 4.95 | 0.00 | 0.68 | 0 | 1027 | ENSG00000111276 |
| AC068538.2 | 4.95 | 0.05 | - | NA | | ENSG00000204637 |
| CPSF7 | 4.95 | 0.00 | - | NA | 79869 | ENSG00000149532 |
| HDDC2 | 4.95 | 0.00 | 0.73 | 0 | 51020 | ENSG00000111906 |
| TULP3 | 4.91 | 0.02 | 0.71 | 0 | 7289 | ENSG00000078246 |
| PLBD2 | 4.91 | 0.03 | - | NA | 196463 | ENSG00000151176 |
| DCAF4 | 4.90 | 0.00 | 0.92 | 0.509 | 26094 | ENSG00000119599 |
| RPP30 | 4.89 | 0.01 | 0.74 | 0 | 10556 | ENSG00000148688 |
| ZNF155 | 4.88 | 0.01 | 0.79 | 0.0073 | 7711 | ENSG00000204920 |
| LAMTOR2 | 4.88 | 0.01 | - | NA | 28956 | ENSG00000116586 |
| CASP14 | 4.88 | 0.01 | 0.84 | 0.1142 | 23581 | ENSG00000105141 |
| RP11-67F24.1 | 4.84 | 0.01 | - | NA | | ENSG00000184100 |
| POLDIP2 | 4.83 | 0.01 | - | NA | 342897 | ENSG00000004142 |
| NCCRP1 | 4.81 | 0.01 | 1.33 | 0.0005 | 51094 | ENSG00000188505 |
| ADIPOR1 | 4.80 | 0.00 | 0.52 | 0 | 7163 | ENSG00000159346 |
| TPD52 | 4.79 | 0.01 | 0.48 | 0 | 100506930 | ENSG00000076554 |
| LINC00665 | 4.78 | 0.01 | - | NA | | ENSG00000232677 |
| YWHAZP2 | 4.73 | 0.00 | - | NA | 152559 | ENSG00000213236 |
| PAQR3 | 4.72 | 0.00 | 0.84 | 0.0378 | 51567 | ENSG00000163291 |
| TDP2 | 4.69 | 0.00 | - | NA | | ENSG00000111802 |

FIG. 17H

| Gene | | | | | |
|---|---|---|---|---|---|
| TRAPPC3 | 4.25 | 0.04 | 0.48 | 0 | 27095 | ENSG00000054116 |
| PIM1 | 4.24 | 0.01 | 1.02 | 0.9332 | 5292 | ENSG00000137193 |
| FAM136A | 4.24 | 0.00 | 0.53 | 0 | 84908 | ENSG00000035141 |
| SCAMP5 | 4.24 | 0.04 | 1.10 | 0.3946 | 192683 | ENSG00000198794 |
| RP11-305B6.1 | 4.23 | 0.00 | - | NA | | ENSG00000259137 |
| APIP | 4.22 | 0.00 | 0.80 | 0.0026 | 51074 | ENSG00000149089 |
| EI24 | 4.19 | 0.00 | 0.58 | 0 | 9538 | ENSG00000149547 |
| EMP2 | 4.18 | 0.00 | 0.95 | 0.7615 | 2013 | ENSG00000213853 |
| RP11-543P15.1 | 4.18 | 0.00 | - | NA | | ENSG00000227081 |
| BX842568.2 | 4.18 | 0.00 | - | NA | | ENSG00000223723 |
| BUB3 | 4.16 | 0.00 | 0.76 | 0 | 9184 | ENSG00000154473 |
| MAPKAPK2 | 4.15 | 0.02 | 0.61 | 0.0024 | 9261 | ENSG00000162889 |
| IL1RAP | 4.15 | 0.02 | 1.30 | NA | 3556 | ENSG00000196083 |
| CNOT7P1 | 4.14 | 0.00 | - | NA | | ENSG00000233229 |
| STX10 | 4.14 | 0.02 | 0.48 | 0 | 8677 | ENSG00000104915 |
| ARPP19 | 4.13 | 0.01 | 0.57 | 0 | 10776 | ENSG00000128989 |
| YWHAZP3 | 4.11 | 0.01 | - | NA | | ENSG00000229932 |
| ZNF234 | 4.07 | 0.02 | 0.97 | 0.8847 | 10780 | ENSG00000263002 |
| ARMC10P1 | 4.06 | 0.01 | - | NA | | ENSG00000178660 |
| PDIA5 | 4.02 | 0.02 | 0.52 | 0 | 10954 | ENSG00000065485 |
| PIGN | 3.99 | 0.01 | 1.18 | 0.1047 | 23556 | ENSG00000197563 |
| RNF187 | 3.99 | 0.02 | 0.71 | 0 | 149603 | ENSG00000168159 |
| GNL3L | 3.98 | 0.02 | 0.81 | 0.0153 | 54552 | ENSG00000130119 |
| MINK1 | 3.94 | 0.05 | 0.90 | 0.4023 | 50488 | ENSG00000141503 |
| RCC2P7 | 3.93 | 0.04 | - | NA | | ENSG00000220666 |
| RCC2 | 3.89 | 0.03 | 0.47 | 0 | 55920 | ENSG00000179051 |
| SPG21 | 3.88 | 0.00 | 0.70 | 0 | 51324 | ENSG00000090487 |
| NET1 | 3.88 | 0.00 | 0.66 | 0 | 10276 | ENSG00000173848 |
| ZNF211 | 3.88 | 0.00 | 0.97 | 0.8856 | 10520 | ENSG00000121417 |
| FOXP1 | 3.86 | 0.01 | 0.77 | 0.0004 | 27086 | ENSG00000114861 |
| ADO | 3.86 | 0.00 | 0.64 | 0 | 84890 | ENSG00000181915 |
| EI24P2 | 3.85 | 0.00 | - | NA | | ENSG00000236257 |
| RBM22 | 3.83 | 0.01 | 0.71 | 0 | 55696 | ENSG00000086589 |
| C16orf72 | 3.83 | 0.00 | 0.70 | 0 | 29035 | ENSG00000182831 |

FIG. 17I

| Gene | Val1 | Val2 | Val3 | Val4 | ENSG ID |
|---|---|---|---|---|---|
| MRPL47 | 3.82 | 0.01 | 0.63 | | ENSG00000136522 |
| SUMF2 | 3.81 | 0.00 | 1.40 | | ENSG00000129103 |
| DMTF1 | 3.80 | 0.03 | 0.94 | | ENSG00000135164 |
| CX3CL1 | 3.79 | 0.00 | 0.84 | | ENSG00000006210 |
| PNRC2 | 3.79 | 0.04 | 0.77 | | ENSG00000189266 |
| REP3 | 3.78 | 0.01 | 1.10 | | ENSG00000165476 |
| SLC29A2 | 3.78 | 0.01 | 1.08 | | ENSG00000174669 |
| BBS12 | 3.77 | 0.03 | 0.95 | | ENSG00000181004 |
| SLC25A5P2 | 3.74 | 0.02 | - | | ENSG00000235064 |
| CYB5R4 | 3.74 | 0.02 | 0.40 | 0.6474 | ENSG00000065615 |
| PGAM1 | 3.73 | 0.01 | 0.55 | 0.0252 | ENSG00000171314 |
| RSL24D1 | 3.73 | 0.04 | 0.76 | 0 | ENSG00000137876 |
| MZT1 | 3.72 | 0.03 | - | 0.455 | ENSG00000204899 |
| TMEM248 | 3.69 | 0.03 | 0.51 | 0.6015 | ENSG00000106609 |
| EIF2A | 3.69 | 0.01 | 0.80 | 0.7621 | ENSG00000144895 |
| ASH2L | 3.67 | 0.01 | - | NA | ENSG00000129691 |
| MSMO1 | 3.66 | 0.05 | 0.92 | 0 | ENSG00000052802 |
| LYAR | 3.65 | 0.00 | - | 0 | ENSG00000145220 |
| MIS18BP1 | 3.65 | 0.02 | 0.52 | 0 | ENSG00000129534 |
| C1orf198 | 3.64 | 0.01 | 0.88 | NA | ENSG00000119280 |
| ATP6V0B | 3.64 | 0.00 | 1.44 | 0.0007 | ENSG00000117410 |
| JUN | 3.64 | 0.00 | 0.64 | NA | ENSG00000177606 |
| RAD51AP1 | 3.63 | 0.01 | 1.11 | 0.4408 | ENSG00000111247 |
| XPNPEP3 | 3.62 | 0.04 | 0.72 | NA | ENSG00000196236 |
| SEPT15 | 3.62 | 0.01 | 1.30 | 0 | ENSG00000183291 |
| TGIF1 | 3.62 | 0.00 | 0.59 | 0.224 | ENSG00000177426 |
| CDKN2A | 3.61 | 0.00 | 1.08 | 0 | ENSG00000147889 |
| ZNF92 | 3.60 | 0.01 | 0.87 | 0.3926 | ENSG00000146757 |
| TMSB4X | 3.60 | 0.01 | 0.60 | 0 | ENSG00000205542 |
| SLC38A9 | 3.60 | 0.02 | 1.05 | 0.0027 | ENSG00000177058 |
| ZNF281 | 3.59 | 0.03 | - | 0 | ENSG00000162702 |
| RBM48 | 3.58 | 0.03 | - | 0.5605 | ENSG00000127993 |
| RP11-621H8.2 | 3.58 | 0.00 | - | 0.5126 | ENSG00000259493 |
| FAM175B | 3.57 | 0.02 | 0.52 | 0 | ENSG00000165660 |

FIG. 17J

| Gene | | | | |
|---|---|---|---|---|
| TMEM170A | 3.56 | 0.01 | 1.04 | 0.8479 | 124491 | ENSG00000166822 |
| RP3-486I3.4 | 3.56 | 0.02 | - | NA | | ENSG00000233558 |
| RP11-453E17.1 | 3.56 | 0.03 | - | NA | | ENSG00000248049 |
| ATP5G2 | 3.55 | 0.02 | 0.86 | 0.0353 | 550112 | ENSG00000135390 |
| ELOVL7 | 3.55 | 0.01 | 1.05 | 0.8091 | 517 | ENSG00000164181 |
| LAMTOR3 | 3.52 | 0.00 | - | NA | 79993 | ENSG00000109270 |
| GJA5 | 3.52 | 0.04 | 0.81 | 0.0144 | 8649 | ENSG00000143140 |
| ATP6AP2 | 3.52 | 0.03 | 0.70 | 0 | 2702 | ENSG00000182220 |
| REXO2 | 3.52 | 0.01 | 0.51 | 0 | 10159 | ENSG00000076043 |
| LIN54 | 3.51 | 0.00 | 0.76 | 0.0008 | 25996 | ENSG00000189308 |
| HSF2 | 3.50 | 0.00 | 0.70 | 0 | 132660 | ENSG00000025156 |
| PCBP1 | 3.50 | 0.05 | 0.90 | 0.1669 | 3298 | ENSG00000169564 |
| LINC00849 | 3.49 | 0.03 | - | NA | 5093 | ENSG00000234635 |
| KDELR1 | 3.48 | 0.01 | 1.00 | 0.9925 | 100996629 | ENSG00000105438 |
| MED28 | 3.48 | 0.01 | 1.23 | 0.0042 | 10945 | ENSG00000118579 |
| TXNDC12 | 3.48 | 0.00 | 0.35 | 0 | 80306 | ENSG00000117862 |
| GM2A | 3.48 | 0.00 | 0.76 | 0.003 | 51060 | ENSG00000196743 |
| SCML1 | 3.48 | 0.03 | 0.75 | 0.0003 | 2760 | ENSG00000047634 |
| SHOC2 | 3.46 | 0.00 | 0.64 | 0 | 6322 | ENSG00000108061 |
| DIMT1 | 3.45 | 0.00 | - | NA | 8036 | ENSG00000086189 |
| ZDHHC6 | 3.45 | 0.04 | 0.50 | 0 | 27292 | ENSG00000023041 |
| ARRDC3 | 3.44 | 0.01 | 1.29 | 0.0015 | 64429 | ENSG00000113369 |
| CSRNP1 | 3.43 | 0.00 | - | NA | 57561 | ENSG00000144655 |
| MYB | 3.43 | 0.02 | 0.68 | 0 | 64651 | ENSG00000118513 |
| MID2 | 3.43 | 0.04 | 1.26 | 0.0143 | 4602 | ENSG00000080561 |
| RP11-490H24.5 | 3.42 | 0.03 | - | NA | 11043 | ENSG00000216285 |
| ERHP1 | 3.42 | 0.00 | - | NA | | ENSG00000254270 |
| MANSC1 | 3.42 | 0.01 | 0.96 | 0.8493 | 54682 | ENSG00000111261 |
| ZNF225 | 3.41 | 0.00 | 0.95 | 0.7581 | 7768 | ENSG00000256294 |
| RAC1P2 | 3.39 | 0.04 | - | NA | | ENSG00000249936 |
| ACYP2 | 3.36 | 0.03 | 0.74 | 0 | 98 | ENSG00000170634 |
| YWHAZP4 | 3.36 | 0.03 | - | NA | | ENSG00000213131 |
| RTN3P1 | 3.36 | 0.01 | - | NA | | ENSG00000251333 |
| PCTP | 3.35 | 0.03 | 0.82 | 0.0707 | 58488 | ENSG00000141179 |

FIG. 17K

| Gene | Val1 | Val2 | Val3 | Val4 | Ensembl ID |
|---|---|---|---|---|---|
| TGIF2 | 3.34 | 0.01 | 0.94 | 60436 | ENSG00000118707 |
| TAF9B | 3.34 | 0.05 | 1.03 | 51616 | ENSG00000187325 |
| SLC25A32 | 3.30 | 0.03 | 0.84 | 81034 | ENSG00000164933 |
| ANKRD13C | 3.30 | 0.00 | 0.70 | 81573 | ENSG00000118454 |
| GPR180 | 3.29 | 0.01 | 0.91 | 160897 | ENSG00000152749 |
| PTGES3P1 | 3.29 | 0.02 | - | - | ENSG00000234518 |
| ZNF534 | 3.28 | 0.02 | 0.98 | 147658 | ENSG00000198633 |
| BRD7 | 3.28 | 0.00 | 0.83 | 29117 | ENSG00000166164 |
| CCAR1 | 3.28 | 0.01 | 0.96 | 55749 | ENSG00000060339 |
| AC007395.4 | 3.27 | 0.03 | - | - | ENSG00000231386 |
| TCTN3 | 3.26 | 0.01 | 0.74 | 26123 | ENSG00000119977 |
| PIP4K2A | 3.23 | 0.01 | 0.60 | 5305 | ENSG00000150867 |
| RP11-307I14.2 | 3.20 | 0.03 | - | - | ENSG00000220105 |
| MAST4 | 3.19 | 0.03 | 1.03 | 375449 | ENSG00000069020 |
| EDN1 | 3.17 | 0.02 | 1.35 | 1906 | ENSG00000078401 |
| HIST1H2AL | 3.17 | 0.03 | - | 8329 | ENSG00000198374 |
| RPS5 | 3.17 | 0.02 | 0.95 | 6193 | ENSG00000083845 |
| HEBP2 | 3.16 | 0.01 | 1.12 | 23593 | ENSG00000051620 |
| TAF1C | 3.15 | 0.05 | 0.59 | 9013 | ENSG00000103168 |
| ADAM17 | 3.15 | 0.02 | 0.81 | 6868 | ENSG00000151694 |
| GOLPH3 | 3.15 | 0.00 | 0.81 | 64083 | ENSG00000113384 |
| ELAVL1 | 3.15 | 0.04 | 0.67 | 1994 | ENSG00000066044 |
| RNF4 | 3.14 | 0.02 | 0.84 | 6047 | ENSG00000063978 |
| CWF19L1 | 3.11 | 0.05 | 0.84 | 55280 | ENSG00000095485 |
| HIGD2A | 3.11 | 0.00 | 1.07 | 192286 | ENSG00000146066 |
| TBC1D22B | 3.07 | 0.02 | 0.92 | 55633 | ENSG00000065491 |
| SRPR | 3.06 | 0.01 | 1.01 | 6734 | ENSG00000182934 |
| COL15A1 | 3.06 | 0.02 | 0.62 | 1306 | ENSG00000204291 |
| RAB14 | 3.05 | 0.02 | 0.84 | 51552 | ENSG00000119396 |
| RFK | 3.05 | 0.02 | 0.90 | 55312 | ENSG00000135002 |
| HNRNPL | 3.05 | 0.04 | 0.73 | 3191 | ENSG00000104824 |
| NARS | 3.04 | 0.02 | 1.03 | 4677 | ENSG00000134440 |
| RASSF5 | 3.02 | 0.01 | 0.86 | 83593 | ENSG00000136653 |
| DPH3 | 3.01 | 0.02 | 0.47 | 285381 | ENSG00000154813 |

FIG. 17L

| Gene | | | | | Ensembl ID |
|---|---|---|---|---|---|
| USP36 | 3.00 | 0.03 | 0.94 | 57602 | ENSG00000055483 |
| CDK5R1 | 2.99 | 0.04 | 0.82 | 8851 | ENSG00000176749 |
| FN3KRP | 2.98 | 0.02 | 0.71 | 79672 | ENSG00000141560 |
| ZNF532 | 2.97 | 0.01 | 0.76 | 55205 | ENSG00000074657 |
| CDC42SE1 | 2.95 | 0.00 | 1.02 | 56882 | ENSG00000197622 |
| MORF4L1P1 | 2.94 | 0.00 | - | | ENSG00000218283 |
| CUL1 | 2.93 | 0.01 | 0.45 | 8454 | ENSG00000055130 |
| PPIL2 | 2.93 | 0.03 | 0.93 | 23759 | ENSG00000100023 |
| PDE12 | 2.93 | 0.00 | 0.71 | 201626 | ENSG00000174840 |
| THAP5 | 2.92 | 0.02 | 0.95 | 168451 | ENSG00000177683 |
| DTX4 | 2.91 | 0.00 | 0.81 | 23220 | ENSG00000110042 |
| TOP1 | 2.91 | 0.01 | 0.96 | 7150 | ENSG00000198900 |
| TBC1D25 | 2.91 | 0.04 | 1.09 | 4943 | ENSG00000068354 |
| DAPK1 | 2.90 | 0.02 | 0.68 | 1612 | ENSG00000196730 |
| RP11-459A10.1 | 2.90 | 0.02 | - | | ENSG00000237730 |
| HCCS | 2.89 | 0.04 | 0.80 | 3052 | ENSG00000004961 |
| YWHAQ | 2.89 | 0.01 | 0.87 | 10971 | ENSG00000134308 |
| ZBTB33 | 2.85 | 0.00 | 1.08 | 10009 | ENSG00000177485 |
| AZIN1 | 2.84 | 0.04 | 0.56 | 51582 | ENSG00000155096 |
| RP11-1H8.2 | 2.84 | 0.05 | - | | ENSG00000259917 |
| TRAF6 | 2.83 | 0.01 | 1.26 | 7189 | ENSG00000175104 |
| BNIP2 | 2.82 | 0.00 | 1.27 | 663 | ENSG00000140299 |
| ZNF473 | 2.81 | 0.01 | 0.70 | 25888 | ENSG00000142528 |
| RMDN1 | 2.81 | 0.01 | 0.93 | 51115 | ENSG00000176623 |
| SNX6 | 2.81 | 0.01 | 1.22 | 58533 | ENSG00000129515 |
| C6orf211 | 2.81 | 0.00 | 0.81 | 79624 | ENSG00000146476 |
| CHRAC1 | 2.80 | 0.01 | 0.46 | 54108 | ENSG00000104472 |
| NR6A1 | 2.80 | 0.02 | 1.23 | 2649 | ENSG00000148200 |
| E2F3 | 2.79 | 0.01 | 0.82 | 1871 | ENSG00000112242 |
| RTKN2 | 2.79 | 0.02 | 0.70 | 219790 | ENSG00000182010 |
| ASCC1 | 2.78 | 0.04 | 0.66 | 51008 | ENSG00000138303 |
| S100PBP | 2.78 | 0.00 | 0.77 | 64766 | ENSG00000116497 |
| TMSB4XP8 | 2.77 | 0.01 | - | | ENSG00000187653 |
| DNTTIP2 | 2.76 | 0.00 | 1.07 | 30836 | ENSG00000067334 |

FIG. 17M

| Gene | | | | Ensembl ID |
|---|---|---|---|---|
| SIAH1 | 2.75 | 0.04 | 0.86 | 0.0787 | 6477 | ENSG00000196470 |
| HKR1 | 2.74 | 0.00 | 1.01 | 0.9739 | 284459 | ENSG00000181666 |
| PARP12 | 2.73 | 0.04 | 2.40 | 0 | 64761 | ENSG00000059378 |
| LSM11 | 2.72 | 0.02 | 0.81 | 0.0132 | 134353 | ENSG00000155858 |
| DUSP4 | 2.72 | 0.04 | 1.40 | 0 | 1846 | ENSG00000120875 |
| MAP3K13 | 2.71 | 0.03 | 1.35 | 0.0001 | 9175 | ENSG00000073803 |
| RP11-288G3.2 | 2.71 | 0.04 | - | NA | | ENSG00000233503 |
| SLC25A5 | 2.71 | 0.00 | 0.82 | 0.0623 | 292 | ENSG00000005022 |
| IRF6 | 2.70 | 0.03 | 0.79 | 0.0067 | 3664 | ENSG00000117595 |
| RBMX | 2.70 | 0.00 | - | NA | 27687 | ENSG00000147274 |
| NHLRC3 | 2.70 | 0.03 | 0.54 | 0 | 26787 | ENSG00000188811 |
| ZNF776 | 2.70 | 0.01 | 1.01 | 0.9792 | 387921 | ENSG00000152443 |
| C10orf118 | 2.70 | 0.00 | 0.92 | 0.5887 | 284309 | ENSG00000165813 |
| RTN3 | 2.70 | 0.01 | 0.53 | 0 | 55088 | ENSG00000133318 |
| GINS1 | 2.68 | 0.00 | 0.93 | 0.5254 | 10313 | ENSG00000101003 |
| LARP1B | 2.68 | 0.03 | 0.58 | 0 | 9837 | ENSG00000138709 |
| WARS | 2.68 | 0.00 | 1.05 | 0.8043 | 55132 | ENSG00000140105 |
| CCDC25 | 2.68 | 0.02 | 0.48 | 0 | 7453 | ENSG00000147419 |
| LZIC | 2.68 | 0.03 | 0.63 | 0 | 55246 | ENSG00000162441 |
| ACTR1A | 2.67 | 0.01 | 0.65 | 0 | 84328 | ENSG00000138107 |
| RCAN3 | 2.67 | 0.01 | 0.55 | 0 | 10121 | ENSG00000117602 |
| ZNF561 | 2.67 | 0.02 | 1.14 | 0.2465 | 11123 | ENSG00000171469 |
| CIAO1 | 2.66 | 0.00 | 0.89 | 0.227 | 93134 | ENSG00000144021 |
| TSNAX | 2.66 | 0.01 | 0.69 | 0 | 9391 | ENSG00000116918 |
| C17orf80 | 2.65 | 0.03 | 1.02 | 0.9247 | 7257 | ENSG00000141219 |
| BRIX1 | 2.64 | 0.00 | 0.83 | 0.0423 | 55028 | ENSG00000113460 |
| AP3M1 | 2.64 | 0.01 | 0.94 | 0.6683 | 55299 | ENSG00000185009 |
| MOB4 | 2.64 | 0.02 | - | NA | 26985 | ENSG00000115540 |
| RP11-469E19.1 | 2.63 | 0.05 | - | NA | 25843 | ENSG00000237931 |
| KIAA0247 | 2.63 | 0.04 | 0.64 | 0 | 9766 | ENSG00000100647 |
| STOM | 2.62 | 0.02 | 1.27 | 0.0004 | 2040 | ENSG00000148175 |
| AGGF1 | 2.60 | 0.01 | 0.80 | 0.0093 | 55109 | ENSG00000164252 |
| RALA | 2.59 | 0.01 | 0.59 | 0 | 5898 | ENSG00000006451 |
| DUT | 2.58 | 0.01 | 0.44 | 0 | 1854 | ENSG00000128951 |

FIG. 17N

| Gene | | | | ENSG |
|---|---|---|---|---|
| FASTKD5 | 2.56 | 0.02 | 0.96 | 0.7989 | 60493 | ENSG00000215251 |
| BMPR1A | 2.56 | 0.01 | 0.52 | 0 | 657 | ENSG00000107779 |
| ZNF12 | 2.55 | 0.01 | 1.07 | 0.689 | 7559 | ENSG00000164631 |
| CCDC82 | 2.55 | 0.03 | 0.96 | 0.8046 | 79780 | ENSG00000149231 |
| GATAD2B | 2.55 | 0.03 | 0.68 | 0 | 57459 | ENSG00000143614 |
| VEGFA | 2.55 | 0.04 | 0.78 | 0.0064 | 7422 | ENSG00000112715 |
| FAM114A1 | 2.53 | 0.04 | 0.50 | 0 | 92689 | ENSG00000197712 |
| ERH | 2.53 | 0.03 | 0.72 | 0 | 2079 | ENSG00000100632 |
| RBPJ | 2.52 | 0.03 | 1.20 | 0.0346 | 3516 | ENSG00000168214 |
| JOSD1 | 2.52 | 0.03 | 0.52 | 0 | 9929 | ENSG00000100221 |
| SLC17A5 | 2.52 | 0.03 | 1.13 | 0.2018 | 26503 | ENSG00000119899 |
| RFC3 | 2.51 | 0.00 | 0.44 | 0 | 5983 | ENSG00000133119 |
| RPGRIP1L | 2.50 | 0.01 | 1.02 | 0.9348 | 23322 | ENSG00000103494 |
| NPAT | 2.50 | 0.05 | 0.98 | 0.9289 | 4863 | ENSG00000149308 |
| PTGES3 | 2.49 | 0.02 | 0.91 | 0.5908 | 10728 | ENSG00000110958 |
| PPIG | 2.49 | 0.04 | 1.10 | 0.5834 | 9360 | ENSG00000138398 |
| FUCA2 | 2.48 | 0.03 | 0.59 | 0 | 2519 | ENSG00000001036 |
| STAM2 | 2.48 | 0.04 | 0.68 | 0 | 10254 | ENSG00000115145 |
| KIAA1429 | 2.48 | 0.00 | 0.82 | 0.0153 | 25962 | ENSG00000164944 |
| MBNL2 | 2.48 | 0.01 | 0.72 | 0 | 10150 | ENSG00000139793 |
| RP11-297L17.6 | 2.47 | 0.02 | - | NA | | ENSG00000234337 |
| GPCPD1 | 2.45 | 0.01 | - | NA | 56261 | ENSG00000125772 |
| CLK4 | 2.44 | 0.04 | 1.05 | 0.7894 | 57396 | ENSG00000113240 |
| MSL1 | 2.44 | 0.05 | 0.79 | 0.0062 | 339287 | ENSG00000188895 |
| STK4 | 2.43 | 0.02 | 1.07 | 0.5384 | 6789 | ENSG00000101109 |
| ARL5B | 2.43 | 0.00 | 0.97 | 0.8678 | 221079 | ENSG00000165997 |
| SNX9 | 2.42 | 0.01 | 1.04 | 0.804 | 51429 | ENSG00000130340 |
| HCG11 | 2.42 | 0.02 | - | NA | 493812 | ENSG00000228223 |
| ZXDA | 2.41 | 0.03 | 0.87 | 0.1005 | 7789 | ENSG00000198205 |
| MX1 | 2.40 | 0.00 | 3.81 | 0 | 4599 | ENSG00000157601 |
| ZNF800 | 2.40 | 0.00 | 0.90 | 0.4868 | 168850 | ENSG00000048405 |
| CDC42P6 | 2.40 | 0.03 | - | NA | | ENSG00000237350 |
| TUSC2 | 2.39 | 0.04 | 1.06 | 0.7645 | 11334 | ENSG00000114383 |
| C2orf44 | 2.39 | 0.02 | 0.76 | 0.0005 | 80304 | ENSG00000163026 |

FIG. 17O

| Gene | | | | ENSG ID |
|---|---|---|---|---|
| EPB41L4B | 2.39 | 0.05 | 0.90 | 0.4062 | 54566 | ENSG00000095203 |
| POP4 | 2.39 | 0.01 | 0.66 | 0 | 10775 | ENSG00000105171 |
| ARID4B | 2.39 | 0.01 | 0.89 | 0.3171 | 51742 | ENSG00000054267 |
| ZNF529 | 2.39 | 0.02 | 1.15 | 0.1805 | 57711 | ENSG00000018020 |
| THOC5 | 2.37 | 0.01 | 0.81 | 0.0122 | 8563 | ENSG00000100296 |
| SLC1A3 | 2.37 | 0.01 | 0.37 | 0 | 6507 | ENSG00000079215 |
| CENPI | 2.37 | 0.04 | 0.61 | 0 | 2491 | ENSG00000102384 |
| ORC5 | 2.36 | 0.03 | - | NA | 5001 | ENSG00000164815 |
| CLIC4 | 2.36 | 0.01 | 0.88 | 0.2037 | 25932 | ENSG00000169504 |
| FEM1C | 2.35 | 0.03 | 0.55 | 0 | 56929 | ENSG00000145780 |
| MORF4L1 | 2.35 | 0.04 | 1.29 | 0.0025 | 10933 | ENSG00000185787 |
| FAM53C | 2.34 | 0.05 | 0.65 | 0 | 51307 | ENSG00000120709 |
| FUT8 | 2.34 | 0.03 | 0.77 | 0.0017 | 2530 | ENSG00000033170 |
| CDC42 | 2.33 | 0.04 | 0.90 | 0.311 | 998 | ENSG00000070831 |
| ZNF805 | 2.33 | 0.01 | 0.83 | 0.0689 | 390980 | ENSG00000204524 |
| C11orf57 | 2.31 | 0.01 | 1.08 | 0.5617 | 55216 | ENSG00000150776 |
| PDGFC | 2.30 | 0.01 | 0.70 | 0 | 56034 | ENSG00000145431 |
| WAC | 2.30 | 0.01 | 0.72 | 0.0001 | 51322 | ENSG00000095787 |
| ZNF562 | 2.29 | 0.01 | 0.81 | 0.012 | 54811 | ENSG00000171466 |
| DHX40 | 2.29 | 0.02 | 0.51 | 0 | 79665 | ENSG00000108406 |
| OTUD4 | 2.28 | 0.02 | 0.91 | 0.4297 | 54726 | ENSG00000164164 |
| NUDT5 | 2.28 | 0.01 | 0.81 | 0.0022 | 11164 | ENSG00000165609 |
| YOD1 | 2.28 | 0.01 | 0.84 | 0.0384 | 55432 | ENSG00000180667 |
| PA2G4P4 | 2.27 | 0.01 | 1.05 | 0.7583 | 647033 | ENSG00000230457 |
| EIF1AD | 2.26 | 0.02 | 1.00 | 0.9952 | 84285 | ENSG00000175376 |
| BCL2L1 | 2.25 | 0.04 | 0.82 | 0.0264 | 598 | ENSG00000171552 |
| TNRC6A | 2.25 | 0.04 | 0.91 | 0.4871 | 27327 | ENSG00000090905 |
| ZC3H7B | 2.24 | 0.01 | 1.00 | 0.9903 | 23264 | ENSG00000100403 |
| DCUN1D4 | 2.24 | 0.01 | 0.60 | 0 | 23142 | ENSG00000109184 |
| CYR61 | 2.24 | 0.04 | 0.69 | 0 | 3491 | ENSG00000142871 |
| CTD-2015B23.2 | 2.24 | 0.02 | - | NA | | ENSG00000226432 |
| PCNP | 2.23 | 0.02 | 0.65 | 0 | 57092 | ENSG00000081154 |
| ATP1B1 | 2.23 | 0.02 | 0.67 | 0 | 481 | ENSG00000143153 |
| PSMG2 | 2.23 | 0.03 | 0.99 | 0.9346 | 56984 | ENSG00000128789 |

FIG. 17P

| Gene | Col1 | Col2 | Col3 | Col4 | ENSG |
|---|---|---|---|---|---|
| TM9SF3 | 2.22 | 0.01 | 0.83 | 0.0272 | 56889 | ENSG00000077147 |
| TUBBP1 | 2.21 | 0.01 | | NA | 128637 | ENSG00000127589 |
| TBC1D20 | 2.20 | 0.04 | 0.99 | 0.969 | 388969 | ENSG00000125875 |
| C2orf68 | 2.20 | 0.03 | 1.15 | 0.1413 | 28976 | ENSG00000168887 |
| ACAD9 | 2.20 | 0.03 | 0.54 | 0 | | ENSG00000177646 |
| GDI2P1 | 2.19 | 0.03 | | NA | | ENSG00000229165 |
| OLR1 | 2.19 | 0.04 | 0.51 | 0 | 4973 | ENSG00000173391 |
| BMI1 | 2.18 | 0.05 | 0.66 | 0 | 648 | ENSG00000168283 |
| TOR1AIP1 | 2.18 | 0.02 | 0.41 | 0 | 26092 | ENSG00000143337 |
| USP8 | 2.17 | 0.03 | 0.70 | 0 | 9101 | ENSG00000138592 |
| DBR1 | 2.17 | 0.02 | 0.92 | 0.6091 | 51163 | ENSG00000138231 |
| EXOC2 | 2.17 | 0.01 | 0.65 | 0 | 55770 | ENSG00000112685 |
| VAPA | 2.17 | 0.02 | 1.17 | 0.0711 | 9218 | ENSG00000101558 |
| ATG9A | 2.16 | 0.03 | 1.12 | 0.2656 | 79065 | ENSG00000198925 |
| SIK1 | 2.15 | 0.02 | 1.35 | 0.0001 | 150094 | ENSG00000142178 |
| SEC31A | 2.12 | 0.03 | 0.94 | 0.7056 | 22872 | ENSG00000138674 |
| SLC25A24 | 2.11 | 0.03 | 0.80 | 0.0032 | 29957 | ENSG00000085491 |
| HADHB | 2.11 | 0.00 | 0.96 | 0.835 | 3032 | ENSG00000138029 |
| UBE2H | 2.10 | 0.05 | 1.39 | 0 | 7328 | ENSG00000186591 |
| CDC117 | 2.09 | 0.02 | 0.65 | 0 | 150275 | ENSG00000159873 |
| CCDC71L | 2.09 | 0.05 | | NA | 168455 | ENSG00000253276 |
| RBMXL1 | 2.08 | 0.03 | | NA | 494115 | ENSG00000213516 |
| SEPT2P1 | 2.08 | 0.01 | | NA | | ENSG00000227850 |
| GNA13 | 2.08 | 0.04 | 0.68 | 0 | 10672 | ENSG00000120063 |
| NCEH1 | 2.07 | 0.00 | | NA | 57552 | ENSG00000144959 |
| PITHD1 | 2.07 | 0.04 | | NA | 57095 | ENSG00000057757 |
| RP11-384B12.2 | 2.07 | 0.04 | | NA | | ENSG00000235251 |
| FTSJD1 | 2.07 | 0.02 | 1.03 | 0.91 | 55783 | ENSG00000180917 |
| SNHG16 | 2.07 | 0.03 | | NA | 677848 | ENSG00000163597 |
| PTP4A2 | 2.06 | 0.01 | 0.56 | 0 | 8073 | ENSG00000184007 |
| RNF217 | 2.06 | 0.04 | 1.36 | 0.0002 | 154214 | ENSG00000146373 |
| C1GALT1 | 2.05 | 0.02 | 1.02 | 0.9476 | 56913 | ENSG00000106392 |
| PPATP1 | 2.04 | 0.05 | | NA | | ENSG00000241293 |
| EIF4EBP2 | 2.04 | 0.01 | 0.96 | 0.8175 | 1979 | ENSG00000148730 |

FIG. 17Q

| | | | | | |
|---|---|---|---|---|---|
| TMEM50A | 2.04 | 0.04 | 0.66 | 0 | 23585 | ENSG00000183726 |
| GDI2 | 2.03 | 0.01 | 1.18 | 0.0471 | 2665 | ENSG00000057608 |
| NPTN | 2.02 | 0.04 | 0.82 | 0.0027 | 27020 | ENSG00000156642 |
| MAT2B | 2.01 | 0.05 | 1.15 | 0.1005 | 27430 | ENSG00000038274 |

FIG. 18A

| Common molecular function | miR-522 downregulated (p-value) | miR-522 Pulldown-seq targets (p-value) | # Molecules (miR-522 Pulldown-seq targets) |
|---|---|---|---|
| proliferation of cells | 2.07E-15 | 1.07E-09 | 52 |
| expression of RNA | 1.86E-07 | 1.79E-13 | 44 |
| cell death | 3.91E-12 | 2.90E-06 | 44 |
| transcription of RNA | 3.38E-08 | 4.39E-14 | 42 |
| necrosis | 6.76E-15 | 8.61E-08 | 40 |
| apoptosis | 1.87E-13 | 1.29E-06 | 39 |
| organismal death | 2.00E-10 | 1.67E-06 | 36 |
| differentiation of cells | 9.10E-07 | 2.29E-06 | 31 |
| cell cycle progression | 3.62E-12 | 4.84E-12 | 30 |
| cell survival | 1.85E-09 | 1.26E-09 | 30 |
| proliferation of tumor cell lines | 6.18E-11 | 7.09E-09 | 30 |
| cell viability | 4.47E-08 | 8.67E-10 | 29 |
| cell movement | 3.01E-10 | 8.33E-05 | 28 |
| cell death of tumor cell lines | 3.43E-14 | 4.87E-07 | 27 |
| quantity of cells | 8.78E-08 | 1.42E-05 | 27 |
| migration of cells | 6.62E-09 | 3.08E-05 | 27 |
| hematological neoplasia | 3.08E-15 | 7.43E-10 | 24 |
| lymphohematopoietic cancer | 1.04E-14 | 1.46E-09 | 24 |
| activation of DNA endogenous promoter | 6.40E-04 | 1.52E-08 | 24 |
| digestive organ tumor | 8.69E-11 | 6.28E-04 | 23 |
| transactivation | 9.93E-08 | 3.11E-11 | 22 |
| apoptosis of tumor cell lines | 5.39E-13 | 7.49E-06 | 22 |
| interphase | 1.29E-09 | 1.91E-09 | 21 |
| morphology of cells | 1.49E-10 | 3.80E-04 | 21 |
| mammary tumor | 2.40E-16 | 8.26E-05 | 19 |
| organization of cytoplasm | 2.82E-09 | 8.86E-04 | 19 |
| development of cardiovascular system | 1.09E-05 | 2.76E-05 | 19 |
| cell transformation | 5.62E-08 | 1.08E-09 | 18 |
| cell viability of tumor cell lines | 5.02E-06 | 4.74E-07 | 18 |
| breast cancer | 1.70E-13 | 1.17E-04 | 18 |
| organization of cytoskeleton | 2.21E-09 | 8.80E-04 | 18 |

FIG. 18B

| | | | |
|---:|---:|---:|---:|
| quantity of blood cells | 3.34E-04 | 1.52E-04 | 18 |
| morphology of cardiovascular system | 8.00E-04 | 1.36E-07 | 18 |
| cell death of connective tissue cells | 4.83E-13 | 6.47E-07 | 17 |
| microtubule dynamics | 2.03E-06 | 3.61E-04 | 17 |
| genital tumor | 5.38E-05 | 2.10E-03 | 17 |
| neuronal cell death | 5.12E-06 | 1.02E-05 | 16 |
| abnormal morphology of cells | 1.82E-05 | 6.80E-04 | 16 |
| size of body | 1.84E-04 | 1.40E-04 | 16 |
| quantity of leukocytes | 5.20E-04 | 3.07E-04 | 16 |
| development of blood cells | 8.24E-04 | 3.55E-06 | 16 |
| lymphomagenesis | 1.27E-10 | 4.94E-08 | 15 |
| hematologic cancer | 6.94E-10 | 5.23E-06 | 15 |
| proliferation of blood cells | 1.08E-05 | 4.93E-04 | 15 |
| cell death of immune cells | 3.61E-05 | 3.47E-05 | 15 |
| endocrine gland tumor | 1.32E-04 | 9.17E-07 | 15 |
| development of blood vessel | 2.99E-04 | 1.72E-04 | 15 |
| G1 phase | 5.40E-04 | 2.35E-08 | 15 |
| metabolism of DNA | 3.83E-06 | 6.63E-07 | 14 |
| proliferation of muscle cells | 4.37E-05 | 3.91E-08 | 14 |
| formation of cellular protrusions | 8.16E-05 | 2.36E-04 | 14 |
| arrest in interphase | 3.11E-07 | 1.78E-06 | 13 |
| psoriasis | 3.89E-08 | 8.75E-05 | 13 |
| benign neoplasia | 5.23E-06 | 5.77E-04 | 13 |
| cell movement of tumor cell lines | 9.04E-10 | 6.71E-04 | 13 |
| phosphorylation of protein | 3.12E-06 | 8.04E-04 | 13 |
| proliferation of lymphocytes | 5.27E-06 | 1.05E-03 | 13 |
| proliferation of breast cancer cell lines | 1.23E-05 | 1.11E-06 | 13 |
| colon cancer | 2.98E-05 | 4.53E-05 | 13 |
| G1/S phase | 3.41E-05 | 2.09E-10 | 13 |
| apoptosis of connective tissue cells | 8.80E-10 | 2.65E-07 | 12 |
| lymphatic node tumor | 2.32E-07 | 3.20E-07 | 12 |
| proliferation of fibroblast cell lines | 1.30E-06 | 1.01E-05 | 12 |
| cell death of fibroblast cell lines | 7.29E-08 | 2.58E-05 | 12 |
| survival of organism | 4.98E-07 | 1.10E-03 | 12 |

FIG. 18C

| | | | |
|---|---|---|---|
| cell death of epithelial cells | 1.27E-05 | 1.91E-05 | 12 |
| synthesis of DNA | 2.97E-05 | 3.57E-05 | 12 |
| colony formation of cells | 3.05E-05 | 3.63E-05 | 12 |
| proliferation of smooth muscle cells | 1.43E-04 | 9.49E-08 | 12 |
| S phase | 2.15E-09 | 1.16E-06 | 11 |
| non-Hodgkin's disease | 7.18E-07 | 1.65E-06 | 11 |
| interphase of tumor cell lines | 5.70E-06 | 7.67E-06 | 11 |
| migration of tumor cell lines | 3.07E-09 | 8.25E-04 | 11 |
| proliferation of T lymphocytes | 1.74E-06 | 2.07E-03 | 11 |
| morphology of embryonic tissue | 6.53E-04 | 1.34E-03 | 11 |
| arrest in cell cycle progression | 1.80E-07 | 3.69E-05 | 10 |
| differentiation of tumor cell lines | 7.35E-06 | 1.36E-04 | 10 |
| development of cytoplasm | 4.30E-07 | 3.09E-04 | 10 |
| morphology of head | 2.73E-06 | 7.85E-04 | 10 |
| proliferation of tumor cells | 5.11E-08 | 8.86E-04 | 10 |
| renal cancer | 4.29E-06 | 9.86E-04 | 10 |
| invasion of tumor cell lines | 5.20E-12 | 1.75E-03 | 10 |
| DNA replication | 6.45E-05 | 2.89E-06 | 10 |
| arrest in G1 phase | 2.77E-04 | 2.89E-06 | 10 |
| cell death of cervical cancer cell lines | 5.29E-04 | 2.12E-05 | 10 |
| quantity of hematopoietic progenitor cells | 6.26E-04 | 5.12E-04 | 10 |
| senescence of cells | 1.15E-06 | 3.46E-06 | 9 |
| arrest in growth of cells | 7.12E-06 | 3.59E-06 | 9 |
| apoptosis of fibroblasts | 3.87E-09 | 3.72E-06 | 9 |
| differentiation of hematopoietic progenitor cells | 1.38E-04 | 1.14E-05 | 9 |
| apoptosis of cervical cancer cell lines | 1.91E-04 | 1.53E-05 | 9 |
| cell death of epithelial cell lines | 2.15E-04 | 5.85E-05 | 9 |
| bone marrow cancer | 3.13E-04 | 1.29E-03 | 9 |
| leukemia | 4.55E-04 | 7.48E-04 | 9 |
| pancreatic tumor | 4.91E-04 | 1.18E-04 | 9 |
| sprouting | 6.58E-04 | 1.51E-04 | 9 |
| neoplasia of tumor cell lines | 2.58E-07 | 3.60E-05 | 8 |
| apoptosis of colon cancer cell lines | 1.46E-09 | 5.13E-05 | 8 |
| development of tumor | 8.06E-08 | 7.08E-04 | 8 |

FIG. 18D

| | | | |
|---:|---:|---:|---:|
| formation of cytoskeleton | 6.69E-06 | 1.28E-03 | 8 |
| apoptosis of fibroblast cell lines | 2.47E-05 | 1.20E-03 | 8 |
| development of muscle | 4.62E-05 | 1.70E-03 | 8 |
| entry into S phase | 5.81E-05 | 2.14E-06 | 8 |
| apoptosis of epithelial cells | 6.13E-05 | 4.31E-05 | 8 |
| G1 phase of tumor cell lines | 1.47E-04 | 2.40E-05 | 8 |
| cell death of tumor cells | 1.94E-04 | 1.83E-03 | 8 |
| repression of RNA | 5.39E-04 | 1.90E-05 | 8 |
| interphase of fibroblast cell lines | 8.82E-07 | 4.24E-06 | 7 |
| T-cell non-Hodgkin's disease | 4.98E-07 | 1.25E-05 | 7 |
| cell movement of connective tissue cells | 6.51E-06 | 2.08E-04 | 7 |
| plasma cell dyscrasia | 2.48E-09 | 9.05E-04 | 7 |
| cytostasis | 1.29E-08 | 1.66E-03 | 7 |
| abnormal morphology of vasculature | 1.06E-05 | 2.57E-05 | 7 |
| cell death of prostate cancer cell lines | 1.89E-05 | 1.36E-04 | 7 |
| differentiation of stem cells | 2.78E-05 | 1.76E-04 | 7 |
| non-small cell lung cancer | 3.68E-05 | 1.44E-03 | 7 |
| cell movement of fibroblast cell lines | 5.26E-05 | 2.10E-05 | 7 |
| formation of actin filaments | 1.56E-04 | 1.44E-03 | 7 |
| tumorigenesis of tumor cell lines | 2.26E-04 | 1.56E-05 | 7 |
| cell death of cancer cells | 2.92E-04 | 2.11E-03 | 7 |
| proliferation of leukemia cell lines | 7.71E-04 | 2.02E-04 | 7 |
| acute myeloid leukemia | 8.51E-04 | 5.59E-05 | 7 |
| quantity of tumor cell lines | 4.04E-07 | 1.13E-04 | 6 |
| cell movement of fibroblasts | 5.17E-06 | 4.57E-04 | 6 |
| apoptosis of prostate cancer cell lines | 2.64E-05 | 4.07E-04 | 6 |
| apoptosis of hematopoietic cells | 4.17E-05 | 1.46E-03 | 6 |
| formation of actin stress fibers | 6.61E-05 | 1.89E-03 | 6 |
| migration of connective tissue cells | 1.11E-04 | 3.29E-04 | 6 |
| cell death of leukocyte cell lines | 1.65E-04 | 1.27E-03 | 6 |
| development of extraembryonic tissue | 1.83E-04 | 3.45E-06 | 6 |
| M phase | 2.34E-04 | 1.59E-03 | 6 |
| G1/S phase transition of tumor cell lines | 2.59E-04 | 4.98E-06 | 6 |
| contact growth inhibition | 2.71E-04 | 1.76E-04 | 6 |

FIG. 18E

| | | | |
|---:|---:|---:|---:|
| delay in initiation of interphase | 3.12E-04 | 4.63E-07 | 6 |
| interphase of bone cancer cell lines | 3.12E-04 | 4.63E-07 | 6 |
| apoptosis of epithelial cell lines | 3.60E-04 | 2.09E-03 | 6 |
| arrest in growth of tumor cell lines | 3.97E-04 | 5.31E-05 | 6 |
| large-cell lymphoma | 5.11E-04 | 1.03E-05 | 6 |
| S phase of fibroblast cell lines | 1.25E-07 | 1.10E-05 | 5 |
| cell cycle progression of fibroblast cell lines | 9.91E-08 | 4.69E-05 | 5 |
| apoptosis of thymocytes | 3.31E-05 | 1.18E-03 | 5 |
| G1 phase of fibroblast cell lines | 8.43E-05 | 2.90E-05 | 5 |
| cell viability of breast cancer cell lines | 1.79E-04 | 1.08E-03 | 5 |
| arrest in G1 phase of tumor cell lines | 3.50E-04 | 1.67E-03 | 5 |
| diffuse B-cell lymphoma | 8.34E-04 | 3.12E-05 | 5 |
| re-entry into S phase | 2.57E-06 | 4.40E-05 | 4 |
| re-entry into cell cycle progression | 3.48E-08 | 1.14E-04 | 4 |
| osteosarcoma | 7.68E-06 | 4.52E-04 | 4 |
| quantity of epithelial cells | 8.65E-06 | 1.67E-03 | 4 |
| initiation of S phase | 2.21E-05 | 2.44E-05 | 4 |
| self-renewal of stem cells | 6.72E-05 | 6.01E-05 | 4 |
| arrest in interphase of fibroblast cell lines | 8.43E-05 | 4.52E-04 | 4 |
| lactation | 1.58E-04 | 6.93E-04 | 4 |
| cell viability of hippocampal neurons | 7.28E-04 | 4.89E-05 | 4 |
| cell cycle progression of lung cell lines | 4.48E-05 | 1.34E-04 | 3 |
| size of tumor cell lines | 6.72E-05 | 1.26E-03 | 3 |
| senescence of lung cell lines | 7.59E-05 | 1.36E-03 | 3 |
| cell cycle progression of fibroblasts | 1.33E-04 | 1.89E-03 | 3 |
| self-renewal of neural stem cells | 5.11E-04 | 6.40E-05 | 3 |
| arrest in G1 phase of bone cancer cell lines | 5.90E-04 | 9.26E-04 | 3 |
| phagocytosis by macrophage cancer cell lines | 7.52E-04 | 9.49E-05 | 3 |
| re-entry into S phase of bone cancer cell lines | 1.59E-06 | 9.91E-04 | 2 |
| re-entry into cell cycle progression of fibroblasts | 6.65E-05 | 7.73E-04 | 2 |
| immortalization of epithelial cells | 1.40E-04 | 1.23E-03 | 2 |
| re-entry into S phase of fibroblast cell lines | 1.40E-04 | 1.23E-03 | 2 |
| premature senescence of tumor cell lines | 1.91E-04 | 1.50E-03 | 2 |
| initiation of senescence stage of fibroblast cell lines | 3.45E-04 | 8.43E-05 | 2 |

FIG. 18F

| miR-522 down-regulated genes (IPA directly connected) | miR-522 Pulldown-seq target genes (IPA directly connected) |
|---|---|
| ACTR1A | ACTR1A |
| ADAM17 | ACTR3B |
| ADIPOR1 | ADCYAP1 |
| APIP | AGR2 |
| ARID4B | AHNAK |
| ARPP19 | AK5 |
| ASCC1 | AKR1C1/AKR1C2 |
| ASH2L | ALDH3A2 |
| ATG12 | ARHGAP22 |
| ATP1B1 | ARL3 |
| ATP5G2 | ARPC5 |
| AZIN1 | ATG5 |
| BANF1 | ATXN1 |
| BCDIN3D | BAG3 |
| BCL2L1 | BANF1 |
| BMI1 | BCL11B |
| BMPR1A | BCL2 |
| BNIP2 | BLMH |
| BRIX1 | BMI1 |
| BUB3 | BMP4 |
| C11orf57 | BMPR1A |
| C16orf72 | C10orf54 |
| C1orf198 | CAPZA2 |
| C2orf68 | CASP3 |
| CAMK2N1 | CAV1 |
| CAPZA2 | CCNE1 |
| CASD1 | CCNH |
| CCAR1 | CD44 |
| CCDC117 | CDC40 |
| CCDC25 | CDC45 |
| CCNC | CDCA8 |

FIG. 18G

| | |
|---|---|
| CCNH | CDK19 |
| CDC42 | CDKN2A |
| CDC42SE1 | CERK |
| CDK5R1 | CHRAC1 |
| CDKN1B | CHUK |
| CDKN2A | COL12A1 |
| CHRAC1 | COL18A1 |
| CLIC4 | COL5A2 |
| CNEP1R1 | COMMD3 |
| CNOT7 | COPS8 |
| COL15A1 | CORO1C |
| CSRNP1 | CRTAP |
| CUL1 | CTBP1 |
| CX3CL1 | CTGF |
| CYR61 | CUL1 |
| DAPK1 | DGCR14 |
| DCUN1D4 | DHFR |
| DEK | DIMT1 |
| DHFR | DNAJB6 |
| DMTF1 | DOCK7 |
| DPH3 | DPP4 |
| DYNLT1 | DUT |
| E2F3 | EIF2S1 |
| EDN1 | EIF4A1 |
| EIF1AD | ELK1 |
| EIF4EBP2 | ENAH |
| ELAVL1 | EPB41L2 |
| ELK1 | EXOC2 |
| EPB41L2 | EXOC4 |
| EPB41L4B | EXT2 |
| ERGIC1 | FAHD1 |
| ERH | FAM53C |
| EXOC2 | FBXL12 |
| FAM120AOS | FBXL17 |

FIG. 18H

| | |
|---|---|
| FAM175B | FBXO8 |
| FAM53C | FECH |
| FAM98A | FERMT2 |
| FBXL12 | FKBP1A |
| FBXO25 | FSCN1 |
| FECH | FST |
| FEM1C | FUS |
| FKBP1A | FXYD3 |
| FOXA1 | GAB2 |
| FOXP1 | GJB2 |
| GATAD2B | GSTM3 |
| GDI2 | HDAC4 |
| GM2A | HNRNPUL2 |
| GNA13 | HNRPDL |
| GNL3L | HSPH1 |
| GOLPH3 | HTRA1 |
| GPR180 | ID1 |
| GTF3A | ID2 |
| HCCS | INHBB |
| HIAT1 | ITGA2 |
| HIST1H2AG (includes others) | ITGB1 |
| HMGA1 | KDM2B |
| HMGA2 | KIAA0101 |
| HNRNPL | KIAA0368 |
| HSF2 | KRT13 |
| IER2 | KRT14 |
| JOSD1 | KRT16 |
| JUN | KRT5 |
| KDELR1 | KRT6B |
| KIAA0247 | LBR |
| KIAA1429 | LIMS1 |
| LAMTOR2 | LLPH |
| LAMTOR3 | LTB |
| LARP1B | MAL2 |

FIG. 18I

| | |
|---|---|
| LIN54 | MAPKAPK2 |
| LITAF | MAPKAPK3 |
| LMO7 | MARCH5 |
| LSM11 | MECP2 |
| LYAR | MELK |
| M6PR | MEX3D |
| MAL2 | MME |
| MAP3K13 | MMP7 |
| MAPKAPK2 | MPZL1 |
| MAPKAPK3 | MT1E |
| MAT2B | MT1G |
| MAX | MTDH |
| MBNL2 | MXD1 |
| MED28 | MXD4 |
| MEX3D | MYBL1 |
| MIS18BP1 | NAP1L1 |
| MKL1 | NEXN |
| MNAT1 | NFIC |
| MOB4 | NKIRAS1 |
| MORF4L1 | NOTCH1 |
| MPZL1 | NPHP3 |
| MSMO1 | PAK2 |
| MX1 | PALLD |
| MYB | PCBP2 |
| NCCRP1 | PDE6D |
| NET1 | PDIA5 |
| NPAT | PDXK |
| NUDT5 | PFKFB2 |
| OLR1 | PFN1 |
| ORC5 | PGAM1 |
| OTUD4 | PHAX |
| PARP12 | PKP2 |
| PCBP1 | PMEPA1 |
| PCNP | PPME1 |

FIG. 18J

| | |
|---|---|
| PDE6D | PPP1R12A |
| PFN1 | PRKAA1 |
| PGAM1 | PRKCI |
| PIGN | PTPN1 |
| PIM1 | PTPN11 |
| PITHD1 | PTRF |
| PLEKHA1 | RABEP1 |
| PPME1 | RAD51AP1 |
| PSMA6 | RALA |
| PTGES3 | RB1CC1 |
| PWP1 | RBBP4 |
| RAB8A | RBBP9 |
| RAD51AP1 | RBL2 |
| RALA | RBM17 |
| RASSF5 | RCC2 |
| RBM48 | RDX |
| RBMX | REXO2 |
| RBPJ | RFC3 |
| RCC2 | RFC5 |
| REXO2 | RFX5 |
| RFC3 | RPL28 |
| RNF187 | RPRD1A |
| RNF2 | RRP15 |
| RNF4 | RSU1 |
| RPS13 | RUFY3 |
| RPS2 | SCARB2 |
| RPS5 | SDC1 |
| RSL24D1 | SDE2 |
| RSU1 | SEPT2 |
| S100PBP | SERBP1 |
| SAP130 | SERPINB2 |
| SCML1 | SF3A1 |
| SDE2 | SFRP1 |
| SEC31A | SH3BP4 |

FIG. 18K

| | |
|---|---|
| SHOC2 | SHOC2 |
| SIAH1 | SKP2 |
| SIK1 | SNRNP200 |
| SLC25A32 | SPDEF |
| SLC25A5 | SRI |
| SLC39A11 | SRPK1 |
| SNX6 | SRSF4 |
| SNX9 | SSBP4 |
| SOX4 | SSX2IP |
| SPSB1 | STK39 |
| SRD5A1 | STMN1 |
| SRSF4 | SUCLG2 |
| STAM2 | SYNCRIP |
| STK4 | TAGLN |
| SUMF2 | TCF3 |
| TBC1D20 | TDP2 |
| TBC1D22B | TFDP1 |
| TBPL1 | THBS1 |
| TDP2 | TIMP3 |
| TFDP1 | TPD52 |
| TGIF1 | TPM1 |
| TGIF2 | TPM2 |
| THAP5 | TPM4 |
| TIMP3 | TRAF5 |
| TM9SF3 | TRAPPC3 |
| TMSB10/TMSB4X | TTC19 |
| TOP1 | TUBB |
| TOR1AIP1 | U2AF1 |
| TPD52 | UBA2 |
| TPM3 | UBE2L3 |
| TRAF6 | UNC119 |
| TRIB1 | VPS41 |
| TXNL4B | WIPI2 |
| UBE2H | WT1 |

FIG. 18L

| | |
|---|---|
| UBE2Q2 | YAF2 |
| UNC119 | YWHAZ |
| USP8 | ZDHHC6 |
| VAPA | ZFP91 |
| VEGFA | |
| WASL | |
| YAF2 | |
| YOD1 | |
| YWHAQ | |
| YWHAZ | |
| ZBTB33 | |
| ZNF12 | |
| ZNF234 | |
| ZNF281 | |
| ZNF473 | |
| ZNF529 | |
| ZNF532 | |
| ZNF561 | |
| ZNF562 | |
| ZNF800 | |

FIG. 19A

| Gene Name | Pulldown-seq Fold enrichment | Pulldown-seq p-value | EntrezGene ID | Ensembl Gene ID |
|---|---|---|---|---|
| PCGF2 | Inf | 0.00 | 7703 | ENSG00000056661 |
| RRAS | Inf | 0.00 | 6237 | ENSG00000126458 |
| SLMO1 | Inf | 0.00 | 10650 | ENSG00000141391 |
| MT1E | Inf | 0.01 | 4493 | ENSG00000169715 |
| TAX1BP3 | Inf | 0.02 | 30851 | ENSG00000213977 |
|  | Inf | 0.04 |  | ENSG00000259079 |
|  | 72.16 | 0.00 |  | ENSG00000253251 |
| PPP1R11P1 | 60.66 | 0.00 |  | ENSG00000236216 |
| SLC35G2 | 46.82 | 0.01 | 80723 | ENSG00000168917 |
| CDK20 | 38.31 | 0.03 | 23552 | ENSG00000156345 |
| LINC00707 | 31.40 | 0.00 | 100507127 | ENSG00000238266 |
| STX1A | 27.46 | 0.00 | 6804 | ENSG00000106089 |
| FOSL1 | 26.06 | 0.00 | 8061 | ENSG00000175592 |
|  | 23.77 | 0.01 |  | ENSG00000260860 |
| SLC29A1 | 23.29 | 0.00 | 2030 | ENSG00000112759 |
| SLC29A3 | 20.45 | 0.00 | 55315 | ENSG00000198246 |
| DYRK1B | 19.88 | 0.00 | 9149 | ENSG00000105204 |
|  | 19.83 | 0.01 |  | ENSG00000250983 |
| MARCH3 | 18.96 | 0.00 | 115123 | ENSG00000173926 |
| NINJ1 | 18.76 | 0.00 | 4814 | ENSG00000131669 |
| MPV17L2 | 18.71 | 0.00 | 84769 | ENSG00000254858 |
| TSEN15P1 | 17.21 | 0.01 |  | ENSG00000230865 |
| DGAT1 | 16.70 | 0.00 | 8694 | ENSG00000185000 |
|  | 16.24 | 0.04 |  | ENSG00000261183 |
| IGBP1P4 | 14.92 | 0.00 |  | ENSG00000250325 |
| CRIP2 | 14.86 | 0.00 | 1397 | ENSG00000182809 |
| TP53INP2 | 14.26 | 0.00 | 58476 | ENSG00000078804 |
| DUSP7 | 14.22 | 0.00 | 1849 | ENSG00000164086 |
| TRAPPC1 | 14.19 | 0.03 | 58485 | ENSG00000170043 |
| RGCC | 13.82 | 0.01 | 28984 | ENSG00000102760 |
|  | 13.45 | 0.02 |  | ENSG00000236496 |
| ZFP36 | 12.76 | 0.00 | 7538 | ENSG00000128016 |
| C2orf15 | 12.16 | 0.00 | 51263 | ENSG00000241962 |
| TMEM55A | 12.10 | 0.02 | 55529 | ENSG00000155099 |
| RPLP1 | 12.01 | 0.00 | 6176 | ENSG00000137818 |
| HSD11B2 | 11.80 | 0.01 | 3291 | ENSG00000176387 |
| NIPSNAP1 | 11.64 | 0.00 | 8508 | ENSG00000184117 |
| TMA7 | 11.31 | 0.00 | 51372 | ENSG00000232112 |
| CCNK | 10.96 | 0.00 | 8812 | ENSG00000090061 |
| SMIM20 | 10.73 | 0.00 | 389203 | ENSG00000250317 |
| LCN2 | 10.50 | 0.00 | 3934 | ENSG00000148346 |
| LY6E | 10.33 | 0.00 | 4061 | ENSG00000160932 |
| FOSL1P1 | 10.22 | 0.00 |  | ENSG00000248394 |
| DLL1 | 10.00 | 0.04 | 28514 | ENSG00000198719 |
| GORASP2 | 9.93 | 0.00 | 26003 | ENSG00000115806 |
| C16orf58 | 9.87 | 0.00 | 64755 | ENSG00000140688 |

FIG. 19B

| | | | | |
|---|---|---|---|---|
| | 9.72 | 0.01 | | ENSG00000218976 |
| REEP6 | 9.70 | 0.02 | 92840 | ENSG00000115255 |
| TMEM109 | 9.21 | 0.00 | 79073 | ENSG00000110108 |
| ZCCHC17 | 9.18 | 0.00 | 51538 | ENSG00000121766 |
| BTG2 | 8.60 | 0.01 | 7832 | ENSG00000159388 |
| | 8.57 | 0.00 | | ENSG00000260174 |
| FAM127C | 8.55 | 0.01 | 441518 | ENSG00000212747 |
| | 8.52 | 0.01 | | ENSG00000251211 |
| GAPDHP63 | 8.51 | 0.01 | | ENSG00000218582 |
| CAMKMT | 8.45 | 0.04 | 79823 | ENSG00000143919 |
| | 8.44 | 0.00 | | ENSG00000218175 |
| ACD | 8.41 | 0.00 | 65057 | ENSG00000102977 |
| FAM86A | 8.37 | 0.00 | 196483 | ENSG00000118894 |
| FAM120AOS | 8.27 | 0.00 | 158293 | ENSG00000188938 |
| RAC2 | 8.21 | 0.00 | 5880 | ENSG00000128340 |
| HMMR | 8.18 | 0.00 | 3161 | ENSG00000072571 |
| EIF3H | 8.15 | 0.00 | 8667 | ENSG00000147677 |
| ARPC4 | 8.05 | 0.00 | 10093 | ENSG00000241553 |
| PSME1 | 7.94 | 0.00 | 5720 | ENSG00000092010 |
| RCN1P2 | 7.89 | 0.00 | | ENSG00000214455 |
| CCDC167 | 7.89 | 0.00 | 154467 | ENSG00000198937 |
| TMEM256 | 7.84 | 0.01 | 254863 | ENSG00000205544 |
| EIF3G | 7.84 | 0.00 | 8666 | ENSG00000130811 |
| SH3GL1 | 7.83 | 0.00 | 6455 | ENSG00000141985 |
| GOT2P2 | 7.81 | 0.04 | | ENSG00000230849 |
| GRHPR | 7.81 | 0.00 | 9380 | ENSG00000137106 |
| RBBP4P5 | 7.62 | 0.01 | | ENSG00000256737 |
| NUDT22 | 7.61 | 0.00 | 84304 | ENSG00000149761 |
| ZDHHC12 | 7.56 | 0.00 | 84885 | ENSG00000160446 |
| C8orf58 | 7.37 | 0.00 | 541565 | ENSG00000241852 |
| EFNA1 | 7.36 | 0.00 | 1942 | ENSG00000169242 |
| DCAKD | 7.33 | 0.00 | 79877 | ENSG00000172992 |
| FAM76A | 7.29 | 0.00 | 199870 | ENSG00000009780 |
| SERPINF2 | 7.20 | 0.00 | 5345 | ENSG00000167711 |
| GABRA3 | 7.10 | 0.00 | 2556 | ENSG00000011677 |
| ZNF581 | 7.04 | 0.03 | 51545 | ENSG00000171425 |
| SLC35B1 | 7.01 | 0.00 | 10237 | ENSG00000121073 |
| NCAPH | 6.96 | 0.00 | 23397 | ENSG00000121152 |
| ARV1 | 6.93 | 0.00 | 64801 | ENSG00000173409 |
| SHMT2 | 6.92 | 0.00 | 6472 | ENSG00000182199 |
| UBALD2 | 6.77 | 0.04 | 283991 | ENSG00000185262 |
| ARRDC3 | 6.68 | 0.00 | 57561 | ENSG00000113369 |
| FAM127B | 6.68 | 0.00 | 26071 | ENSG00000203950 |
| SMAD7 | 6.66 | 0.00 | 4092 | ENSG00000101665 |
| UCP2 | 6.63 | 0.00 | 7351 | ENSG00000175567 |
| RARA | 6.61 | 0.00 | 5914 | ENSG00000131759 |
| PRDM13 | 6.60 | 0.01 | 59336 | ENSG00000112238 |

FIG. 19C

| | | | | |
|---|---|---|---|---|
| TSKU | 6.57 | 0.00 | 25987 | ENSG00000182704 |
| ASNA1 | 6.56 | 0.00 | 439 | ENSG00000198356 |
| SYNGR2 | 6.55 | 0.00 | 9144 | ENSG00000108639 |
| IGBP1P1 | 6.55 | 0.01 | 280655 | ENSG00000226677 |
| GNAI2 | 6.53 | 0.00 | 2771 | ENSG00000114353 |
| RCN1 | 6.52 | 0.00 | 5954 | ENSG00000049449 |
| SYVN1 | 6.50 | 0.00 | 84447 | ENSG00000162298 |
| IKBKE | 6.49 | 0.00 | 9641 | ENSG00000143466 |
| JOSD2 | 6.49 | 0.00 | 126119 | ENSG00000161677 |
| C10orf10 | 6.47 | 0.00 | 11067 | ENSG00000165507 |
| MDH2 | 6.44 | 0.00 | 4191 | ENSG00000146701 |
| VAMP2 | 6.39 | 0.00 | 6844 | ENSG00000220205 |
| ZDHHC4 | 6.39 | 0.01 | 55146 | ENSG00000136247 |
| LZTS2 | 6.38 | 0.00 | 84445 | ENSG00000107816 |
| RFX2 | 6.38 | 0.03 | 5990 | ENSG00000087903 |
| CHRAC1 | 6.35 | 0.00 | 54108 | ENSG00000104472 |
| SIRT6 | 6.32 | 0.01 | 51548 | ENSG00000077463 |
| ATPBD4 | 6.32 | 0.00 | 89978 | ENSG00000134146 |
| BCL7B | 6.30 | 0.00 | 9275 | ENSG00000106635 |
| HN1 | 6.29 | 0.00 | 51155 | ENSG00000189159 |
| BABAM1 | 6.25 | 0.00 | 29086 | ENSG00000105393 |
| FSTL3 | 6.22 | 0.03 | 10272 | ENSG00000070404 |
| CYSTM1 | 6.22 | 0.00 | 84418 | ENSG00000120306 |
| TSEN15 | 6.19 | 0.00 | 116461 | ENSG00000198860 |
| ARHGDIB | 6.18 | 0.00 | 397 | ENSG00000111348 |
| MYLK-AS1 | 6.13 | 0.05 | 100506826 | ENSG00000239523 |
| MVD | 6.06 | 0.00 | 4597 | ENSG00000167508 |
| PDZD11 | 6.05 | 0.04 | 51248 | ENSG00000120509 |
| SERPINB8 | 6.02 | 0.00 | 5271 | ENSG00000166401 |
| SCARNA21 | 6.02 | 0.01 | 677763 | ENSG00000252835 |
| CIZ1 | 6.02 | 0.00 | 25792 | ENSG00000148337 |
| NFIX | 5.99 | 0.00 | 4784 | ENSG00000008441 |
| COMMD6 | 5.99 | 0.00 | 170622 | ENSG00000188243 |
| NDUFA7 | 5.93 | 0.00 | 4701 | ENSG00000167774 |
| NUMBL | 5.88 | 0.00 | 9253 | ENSG00000105245 |
| TRMT61A | 5.84 | 0.00 | 115708 | ENSG00000166166 |
| | 5.83 | 0.04 | | ENSG00000265242 |
| CCNG2 | 5.81 | 0.00 | 901 | ENSG00000138764 |
| GRN | 5.78 | 0.00 | 2896 | ENSG00000030582 |
| GYLTL1B | 5.78 | 0.00 | 120071 | ENSG00000165905 |
| RALGDS | 5.78 | 0.00 | 5900 | ENSG00000160271 |
| TNFRSF12A | 5.78 | 0.00 | 51330 | ENSG00000006327 |
| | 5.76 | 0.02 | | ENSG00000257316 |
| MRPS2 | 5.76 | 0.00 | 51116 | ENSG00000122140 |
| TIRAP | 5.72 | 0.01 | 114609 | ENSG00000150455 |
| | 5.71 | 0.00 | 100507458 | ENSG00000263072 |
| DEDD2 | 5.68 | 0.00 | 162989 | ENSG00000160570 |

FIG. 19D

| | | | | |
|---|---|---|---|---|
| SHKBP1 | 5.66 | 0.00 | 92799 | ENSG00000160410 |
| APOA1BP | 5.62 | 0.00 | 128240 | ENSG00000163382 |
| PRSS16 | 5.61 | 0.01 | 10279 | ENSG00000112812 |
| PLAUR | 5.53 | 0.00 | 5329 | ENSG00000011422 |
| CNN2 | 5.52 | 0.00 | 1265 | ENSG00000064666 |
| FUT1 | 5.50 | 0.00 | 2523 | ENSG00000174951 |
| COX10 | 5.48 | 0.00 | 1352 | ENSG00000006695 |
| TMEM184B | 5.48 | 0.00 | 25829 | ENSG00000198792 |
| RASSF7 | 5.48 | 0.00 | 8045 | ENSG00000099849 |
| SAP30BP | 5.45 | 0.00 | 29115 | ENSG00000161526 |
| E2F5 | 5.45 | 0.00 | 1875 | ENSG00000133740 |
| ZNF222 | 5.42 | 0.00 | 7673 | ENSG00000159885 |
| | 5.41 | 0.03 | | ENSG00000237493 |
| TBC1D2 | 5.37 | 0.00 | 55357 | ENSG00000095383 |
| PAQR7 | 5.35 | 0.00 | 164091 | ENSG00000182749 |
| CALCOCO2 | 5.34 | 0.00 | 10241 | ENSG00000136436 |
| DMKN | 5.33 | 0.00 | 93099 | ENSG00000161249 |
| | 5.31 | 0.01 | | ENSG00000235912 |
| PFDN1 | 5.31 | 0.00 | 5201 | ENSG00000113068 |
| SLC25A39 | 5.29 | 0.00 | 51629 | ENSG00000013306 |
| C10orf54 | 5.27 | 0.00 | 64115 | ENSG00000107738 |
| C9orf69 | 5.25 | 0.00 | 90120 | ENSG00000238227 |
| MOGS | 5.25 | 0.00 | 7841 | ENSG00000115275 |
| CD320 | 5.19 | 0.00 | 51293 | ENSG00000167775 |
| TUFT1 | 5.18 | 0.00 | 7286 | ENSG00000143367 |
| CRTC2 | 5.17 | 0.00 | 200186 | ENSG00000160741 |
| CNN2P9 | 5.14 | 0.00 | | ENSG00000213149 |
| RPS18P12 | 5.12 | 0.00 | | ENSG00000230897 |
| COMTD1 | 5.11 | 0.00 | 118881 | ENSG00000165644 |
| FBXO46 | 5.09 | 0.00 | 23403 | ENSG00000177051 |
| WDR34 | 5.09 | 0.00 | 89891 | ENSG00000119333 |
| | 5.04 | 0.00 | | ENSG00000223784 |
| DNAL4 | 5.03 | 0.01 | 10126 | ENSG00000100246 |
| SNHG7 | 5.01 | 0.00 | 84973 | ENSG00000233016 |
| GINS1 | 4.99 | 0.00 | 9837 | ENSG00000101003 |
| AXIN2 | 4.99 | 0.00 | 8313 | ENSG00000168646 |
| KDELR1 | 4.99 | 0.00 | 10945 | ENSG00000105438 |
| TGIF2 | 4.98 | 0.00 | 60436 | ENSG00000118707 |
| MMGT1 | 4.97 | 0.00 | 93380 | ENSG00000169446 |
| SLC25A44 | 4.97 | 0.00 | 9673 | ENSG00000160785 |
| EPHB6 | 4.95 | 0.00 | 2051 | ENSG00000106123 |
| ABCD1 | 4.95 | 0.00 | 215 | ENSG00000101986 |
| STOM | 4.93 | 0.00 | 2040 | ENSG00000148175 |
| ULBP2 | 4.91 | 0.00 | 80328 | ENSG00000131015 |
| FLOT2 | 4.90 | 0.00 | 2319 | ENSG00000132589 |
| CRAT | 4.90 | 0.00 | 1384 | ENSG00000095321 |
| LFNG | 4.89 | 0.01 | 3955 | ENSG00000106003 |

FIG. 19E

| Gene | Val1 | Val2 | ID1 | Ensembl ID |
|---|---|---|---|---|
| PDLIM7 | 4.87 | 0.00 | 9260 | ENSG00000196923 |
| AAGAB | 4.86 | 0.00 | 79719 | ENSG00000103591 |
| XBP1 | 4.86 | 0.00 | 7494 | ENSG00000100219 |
| LTBR | 4.84 | 0.00 | 4055 | ENSG00000111321 |
| C6orf1 | 4.83 | 0.03 | 221491 | ENSG00000186577 |
| LIMD2 | 4.81 | 0.00 | 80774 | ENSG00000136490 |
| TP73 | 4.76 | 0.02 | 7161 | ENSG00000078900 |
| RPL31P63 | 4.74 | 0.05 | | ENSG00000236735 |
| | 4.74 | 0.00 | | ENSG00000253683 |
| CDPF1 | 4.74 | 0.00 | 150383 | ENSG00000205643 |
| GRINA | 4.73 | 0.00 | 2907 | ENSG00000178719 |
| FAM127A | 4.73 | 0.00 | 8933 | ENSG00000134590 |
| SHMT1P1 | 4.70 | 0.01 | | ENSG00000224751 |
| LMBR1L | 4.69 | 0.00 | 55716 | ENSG00000139636 |
| HMGN4 | 4.69 | 0.00 | 10473 | ENSG00000182952 |
| SEPT3 | 4.69 | 0.00 | 55964 | ENSG00000100167 |
| CRTC1 | 4.66 | 0.01 | 23373 | ENSG00000105662 |
| CTD-2369P2.2 | 4.65 | 0.00 | | ENSG00000175898 |
| CNN2P6 | 4.64 | 0.05 | | ENSG00000213854 |
| IGBP1 | 4.63 | 0.00 | 3476 | ENSG00000089289 |
| PEA15 | 4.62 | 0.00 | 8682 | ENSG00000162734 |
| INPP5K | 4.62 | 0.01 | 51763 | ENSG00000132376 |
| TMED1 | 4.60 | 0.00 | 11018 | ENSG00000099203 |
| GAS1 | 4.60 | 0.00 | 2619 | ENSG00000180447 |
| DERL1 | 4.60 | 0.00 | 79139 | ENSG00000136986 |
| MUC1 | 4.58 | 0.00 | 4582 | ENSG00000185499 |
| GALT | 4.57 | 0.00 | 2592 | ENSG00000213930 |
| MPP2 | 4.57 | 0.05 | 4355 | ENSG00000108852 |
| SEMA4C | 4.57 | 0.00 | 54910 | ENSG00000168758 |
| CBLC | 4.55 | 0.00 | 23624 | ENSG00000142273 |
| ALG3 | 4.55 | 0.01 | 10195 | ENSG00000214160 |
| LSM3 | 4.51 | 0.00 | 27258 | ENSG00000170860 |
| HSD17B10 | 4.50 | 0.00 | 3028 | ENSG00000072506 |
| PPARG | 4.49 | 0.00 | 5468 | ENSG00000132170 |
| HIST2H2BF | 4.46 | 0.00 | 440689 | ENSG00000203814 |
| | 4.46 | 0.00 | | ENSG00000242299 |
| COMMD9 | 4.43 | 0.00 | 29099 | ENSG00000110442 |
| POC1B | 4.42 | 0.00 | 282809 | ENSG00000139323 |
| GINS3 | 4.40 | 0.00 | 64785 | ENSG00000181938 |
| CDYL | 4.36 | 0.00 | 9425 | ENSG00000153046 |
| LINC00116 | 4.35 | 0.00 | 205251 | ENSG00000175701 |
| | 4.35 | 0.01 | | ENSG00000232019 |
| MFSD5 | 4.35 | 0.00 | 84975 | ENSG00000182544 |
| ENO2 | 4.35 | 0.03 | 2026 | ENSG00000111674 |
| PIGT | 4.33 | 0.00 | 51604 | ENSG00000124155 |
| PLD2 | 4.32 | 0.00 | 5338 | ENSG00000129219 |
| ZSWIM1 | 4.31 | 0.00 | 90204 | ENSG00000168612 |

FIG. 19F

| | | | | |
|---|---|---|---|---|
| CCND3 | 4.27 | 0.00 | 896 | ENSG00000112576 |
| DNAJB12 | 4.27 | 0.00 | 54788 | ENSG00000148719 |
| DMWD | 4.26 | 0.00 | 1762 | ENSG00000185800 |
| TEAD3 | 4.25 | 0.00 | 7005 | ENSG00000007866 |
| CNPPD1 | 4.24 | 0.00 | 27013 | ENSG00000115649 |
| PEF1 | 4.24 | 0.00 | 553115 | ENSG00000162517 |
| | 4.24 | 0.00 | | ENSG00000223886 |
| MRPL10 | 4.23 | 0.00 | 124995 | ENSG00000159111 |
| C9orf152 | 4.22 | 0.02 | 401546 | ENSG00000188959 |
| CYB561A3 | 4.21 | 0.00 | 220002 | ENSG00000162144 |
| MPHOSPH6 | 4.21 | 0.00 | 10200 | ENSG00000135698 |
| PLEKHF1 | 4.20 | 0.00 | 79156 | ENSG00000166289 |
| TK1 | 4.20 | 0.00 | 7083 | ENSG00000167900 |
| CTSA | 4.18 | 0.00 | 5476 | ENSG00000064601 |
| EIF4EBP1 | 4.17 | 0.00 | 1978 | ENSG00000187840 |
| VAT1 | 4.15 | 0.00 | 10493 | ENSG00000108828 |
| MKL1 | 4.14 | 0.00 | 57591 | ENSG00000196588 |
| LMAN2L | 4.13 | 0.00 | 81562 | ENSG00000114988 |
| MAPK13 | 4.11 | 0.00 | 5603 | ENSG00000156711 |
| LINC00667 | 4.10 | 0.00 | 339290 | ENSG00000263753 |
| SYDE1 | 4.10 | 0.00 | 85360 | ENSG00000105137 |
| RHBDD2 | 4.10 | 0.02 | 57414 | ENSG00000005486 |
| POLR2H | 4.09 | 0.00 | 5437 | ENSG00000163882 |
| SGPP1 | 4.07 | 0.00 | 81537 | ENSG00000126821 |
| R3HDM1 | 4.06 | 0.00 | 23518 | ENSG00000048991 |
| STX5 | 4.06 | 0.00 | 6811 | ENSG00000162236 |
| C8orf37 | 4.06 | 0.00 | 157657 | ENSG00000156172 |
| FAM161B | 4.06 | 0.01 | 145483 | ENSG00000156050 |
| GGA3 | 4.05 | 0.00 | 23163 | ENSG00000125447 |
| ATP5SL | 4.04 | 0.01 | 55101 | ENSG00000105341 |
| RBM38 | 4.04 | 0.00 | 55544 | ENSG00000132819 |
| FTSJ1 | 4.03 | 0.00 | 24140 | ENSG00000068438 |
| GLTP | 3.97 | 0.00 | 51228 | ENSG00000139433 |
| SCAMP2 | 3.96 | 0.00 | 10066 | ENSG00000140497 |
| ZNF16 | 3.95 | 0.00 | 7564 | ENSG00000170631 |
| LRRC8A | 3.95 | 0.00 | 56262 | ENSG00000136802 |
| USP30 | 3.95 | 0.00 | 84749 | ENSG00000135093 |
| CDK18 | 3.95 | 0.03 | 5129 | ENSG00000117266 |
| | 3.94 | 0.03 | 494127 | ENSG00000224887 |
| | 3.88 | 0.00 | | ENSG00000213315 |
| TFG | 3.87 | 0.00 | 10342 | ENSG00000114354 |
| SOSTDC1 | 3.87 | 0.00 | 25928 | ENSG00000171243 |
| LAMTOR1 | 3.87 | 0.00 | 55004 | ENSG00000149357 |
| ARPP19 | 3.86 | 0.00 | 10776 | ENSG00000128989 |
| ALAD | 3.85 | 0.03 | 210 | ENSG00000148218 |
| PSMB6 | 3.84 | 0.00 | 5694 | ENSG00000142507 |
| MAF1 | 3.84 | 0.00 | 84232 | ENSG00000179632 |

FIG. 19G

| | | | | |
|---|---|---|---|---|
| FAM195B | 3.83 | 0.05 | 348262 | ENSG00000225663 |
| CPA4 | 3.83 | 0.00 | 51200 | ENSG00000128510 |
| MED8 | 3.82 | 0.00 | 112950 | ENSG00000159479 |
| GPR157 | 3.82 | 0.00 | 80045 | ENSG00000180758 |
| CXCL16 | 3.81 | 0.00 | 58191 | ENSG00000161921 |
| UBA52P6 | 3.81 | 0.00 | | ENSG00000215221 |
| ANKRD1 | 3.81 | 0.02 | 27063 | ENSG00000148677 |
| DBNDD1 | 3.80 | 0.00 | 79007 | ENSG00000003249 |
| TOLLIP | 3.79 | 0.00 | 54472 | ENSG00000078902 |
| PPIL4 | 3.79 | 0.00 | 85313 | ENSG00000131013 |
| AQP3 | 3.78 | 0.00 | 360 | ENSG00000165272 |
| TMEM79 | 3.78 | 0.00 | 84283 | ENSG00000163472 |
| ZDHHC16 | 3.77 | 0.00 | 84287 | ENSG00000171307 |
| B4GALT3 | 3.75 | 0.00 | 8703 | ENSG00000158850 |
| NISCH | 3.74 | 0.00 | 11188 | ENSG00000010322 |
| SCD5 | 3.71 | 0.00 | 79966 | ENSG00000145284 |
| | 3.69 | 0.00 | | ENSG00000217227 |
| TPD52 | 3.69 | 0.00 | 7163 | ENSG00000076554 |
| | 3.69 | 0.01 | | ENSG00000244157 |
| SLC35C1 | 3.69 | 0.00 | 55343 | ENSG00000181830 |
| MPC1 | 3.68 | 0.01 | 51660 | ENSG00000060762 |
| GLRX5 | 3.68 | 0.00 | 51218 | ENSG00000182512 |
| TMLHE | 3.67 | 0.00 | 55217 | ENSG00000185973 |
| LZTFL1 | 3.67 | 0.02 | 54585 | ENSG00000163818 |
| ATPAF1 | 3.67 | 0.00 | 64756 | ENSG00000123472 |
| | 3.66 | 0.02 | | ENSG00000233947 |
| | 3.66 | 0.03 | | ENSG00000225026 |
| SLC13A3 | 3.66 | 0.00 | 64849 | ENSG00000158296 |
| SMPD1 | 3.66 | 0.03 | 6609 | ENSG00000166311 |
| PLA2G15 | 3.65 | 0.05 | 23659 | ENSG00000103066 |
| TMUB1 | 3.64 | 0.01 | 83590 | ENSG00000164897 |
| PCBD1 | 3.62 | 0.02 | 5092 | ENSG00000166228 |
| | 3.61 | 0.05 | | ENSG00000239622 |
| DCAF4 | 3.60 | 0.00 | 26094 | ENSG00000119599 |
| BMP4 | 3.60 | 0.00 | 652 | ENSG00000125378 |
| C7orf49 | 3.59 | 0.00 | 78996 | ENSG00000122783 |
| AP2S1 | 3.58 | 0.00 | 1175 | ENSG00000042753 |
| PPARD | 3.57 | 0.00 | 5467 | ENSG00000112033 |
| LPCAT3 | 3.56 | 0.00 | 10162 | ENSG00000111684 |
| ARHGAP1 | 3.56 | 0.00 | 392 | ENSG00000175220 |
| GEMIN6 | 3.55 | 0.02 | 79833 | ENSG00000152147 |
| PSMB10 | 3.54 | 0.00 | 5699 | ENSG00000205220 |
| TEAD2 | 3.50 | 0.00 | 8463 | ENSG00000074219 |
| SLC48A1 | 3.50 | 0.00 | 55652 | ENSG00000211584 |
| SLC2A4RG | 3.49 | 0.01 | 56731 | ENSG00000125520 |
| INTS9 | 3.49 | 0.00 | 55756 | ENSG00000104299 |
| CRISPLD2 | 3.49 | 0.00 | 83716 | ENSG00000103196 |

FIG. 19H

| | | | | |
|---|---|---|---|---|
| PRSS8 | 3.48 | 0.00 | 5652 | ENSG00000052344 |
| | 3.48 | 0.03 | | ENSG00000248930 |
| CCNE2 | 3.47 | 0.00 | 9134 | ENSG00000175305 |
| HERPUD1 | 3.47 | 0.00 | 9709 | ENSG00000051108 |
| EIF1AD | 3.47 | 0.00 | 84285 | ENSG00000175376 |
| VPS72 | 3.46 | 0.00 | 6944 | ENSG00000163159 |
| RHBDF1 | 3.45 | 0.02 | 64285 | ENSG00000007384 |
| PARP16 | 3.44 | 0.01 | 54956 | ENSG00000138617 |
| MVK | 3.44 | 0.02 | 4598 | ENSG00000110921 |
| TESK1 | 3.42 | 0.00 | 7016 | ENSG00000107140 |
| | 3.42 | 0.03 | | ENSG00000229399 |
| CTDSP1 | 3.41 | 0.00 | 58190 | ENSG00000144579 |
| C5orf22 | 3.41 | 0.00 | 55322 | ENSG00000082213 |
| ATP5D | 3.41 | 0.01 | 513 | ENSG00000099624 |
| LYSMD2 | 3.41 | 0.01 | 256586 | ENSG00000140280 |
| | 3.40 | 0.01 | | ENSG00000204637 |
| AP1M1 | 3.39 | 0.00 | 8907 | ENSG00000072958 |
| SNX15 | 3.38 | 0.00 | 29907 | ENSG00000110025 |
| LSR | 3.38 | 0.00 | 51599 | ENSG00000105699 |
| SGTA | 3.37 | 0.00 | 6449 | ENSG00000104969 |
| PCBP4 | 3.37 | 0.00 | 57060 | ENSG00000090097 |
| ASS1P11 | 3.37 | 0.00 | | ENSG00000225308 |
| NCCRP1 | 3.34 | 0.02 | 342897 | ENSG00000188505 |
| PYGO2 | 3.34 | 0.00 | 90780 | ENSG00000163348 |
| TAF5 | 3.33 | 0.00 | 6877 | ENSG00000148835 |
| PCGF1 | 3.33 | 0.01 | 84759 | ENSG00000115289 |
| ASS1P1 | 3.32 | 0.03 | | ENSG00000220517 |
| ALDH3B2 | 3.32 | 0.00 | 222 | ENSG00000132746 |
| TRIB3 | 3.31 | 0.00 | 57761 | ENSG00000101255 |
| HCN3 | 3.31 | 0.02 | 57657 | ENSG00000143630 |
| TUBA1A | 3.29 | 0.01 | 7846 | ENSG00000167552 |
| RPL37AP8 | 3.27 | 0.02 | | ENSG00000176343 |
| SCARNA5 | 3.25 | 0.00 | 677775 | ENSG00000252010 |
| ZNF253 | 3.24 | 0.01 | 56242 | ENSG00000256771 |
| ECE2 | 3.24 | 0.01 | 9718 | ENSG00000145194 |
| PLK1 | 3.24 | 0.00 | 5347 | ENSG00000166851 |
| PEX19 | 3.23 | 0.00 | 5824 | ENSG00000162735 |
| CDKN3 | 3.23 | 0.00 | 1033 | ENSG00000100526 |
| SFT2D1 | 3.21 | 0.00 | 113402 | ENSG00000198818 |
| ESYT3 | 3.21 | 0.01 | 83850 | ENSG00000158220 |
| UROS | 3.20 | 0.00 | 7390 | ENSG00000188690 |
| CCAR1 | 3.20 | 0.00 | 55749 | ENSG00000060339 |
| SNAPC1 | 3.20 | 0.00 | 6617 | ENSG00000023608 |
| FAM219A | 3.20 | 0.00 | 203259 | ENSG00000164970 |
| TMUB2 | 3.20 | 0.00 | 79089 | ENSG00000168591 |
| RNF38 | 3.18 | 0.00 | 152006 | ENSG00000137075 |
| TP53I11 | 3.18 | 0.00 | 9537 | ENSG00000175274 |

FIG. 19I

| | | | | |
|---|---|---|---|---|
| FUT3 | 3.17 | 0.00 | 2525 | ENSG00000171124 |
| METTL23 | 3.17 | 0.01 | 124512 | ENSG00000181038 |
| | 3.17 | 0.01 | | ENSG00000255353 |
| GAPDHP40 | 3.16 | 0.00 | | ENSG00000248626 |
| EME1 | 3.16 | 0.01 | 146956 | ENSG00000154920 |
| APH1A | 3.16 | 0.00 | 51107 | ENSG00000117362 |
| TMEM199 | 3.15 | 0.04 | 147007 | ENSG00000244045 |
| C9orf89 | 3.14 | 0.03 | 84270 | ENSG00000165233 |
| WIPI1 | 3.14 | 0.00 | 55062 | ENSG00000070540 |
| BRPF3 | 3.14 | 0.00 | 27154 | ENSG00000096070 |
| ADAM15 | 3.13 | 0.00 | 8751 | ENSG00000143537 |
| PTGIS | 3.13 | 0.03 | 5740 | ENSG00000124212 |
| FADS3 | 3.12 | 0.01 | 3995 | ENSG00000221968 |
| TMEM173 | 3.11 | 0.02 | 340061 | ENSG00000184584 |
| SEMA4B | 3.11 | 0.00 | 10509 | ENSG00000185033 |
| C21orf33 | 3.10 | 0.00 | 8209 | ENSG00000160221 |
| SCMH1 | 3.10 | 0.00 | 22955 | ENSG00000010803 |
| COPS7B | 3.10 | 0.00 | 64708 | ENSG00000144524 |
| BCL2L13 | 3.09 | 0.00 | 23786 | ENSG00000099968 |
| CCND1 | 3.08 | 0.00 | 595 | ENSG00000110092 |
| PTTG3P | 3.08 | 0.00 | 26255 | ENSG00000213005 |
| IFI35 | 3.08 | 0.00 | 3430 | ENSG00000068079 |
| TMCC1 | 3.06 | 0.00 | 23023 | ENSG00000172765 |
| ADCK4 | 3.05 | 0.00 | 79934 | ENSG00000123815 |
| ATF7 | 3.05 | 0.01 | 11016 | ENSG00000170653 |
| TNFRSF1A | 3.03 | 0.00 | 7132 | ENSG00000067182 |
| TM9SF4 | 3.03 | 0.00 | 9777 | ENSG00000101337 |
| DDA1 | 3.02 | 0.01 | 79016 | ENSG00000130311 |
| TMEM206 | 3.02 | 0.00 | 55248 | ENSG00000065600 |
| PDGFB | 3.02 | 0.00 | 5155 | ENSG00000100311 |
| MRPL16 | 3.00 | 0.00 | 54948 | ENSG00000166902 |
| CHST12 | 3.00 | 0.01 | 55501 | ENSG00000136213 |
| SFXN2 | 2.99 | 0.00 | 118980 | ENSG00000156398 |
| GAPDHP1 | 2.99 | 0.00 | | ENSG00000228232 |
| SNX12 | 2.99 | 0.00 | 29934 | ENSG00000147164 |
| TARBP2 | 2.99 | 0.01 | 6895 | ENSG00000139546 |
| PLXNA3 | 2.99 | 0.01 | 55558 | ENSG00000130827 |
| C1orf159 | 2.98 | 0.01 | 54991 | ENSG00000131591 |
| GAPDH | 2.98 | 0.00 | 2597 | ENSG00000111640 |
| NFKBIA | 2.96 | 0.00 | 4792 | ENSG00000100906 |
| VEGFB | 2.96 | 0.00 | 7423 | ENSG00000173511 |
| ETHE1 | 2.95 | 0.02 | 23474 | ENSG00000105755 |
| DBN1 | 2.95 | 0.00 | 1627 | ENSG00000113758 |
| NDUFB11 | 2.95 | 0.00 | 54539 | ENSG00000147123 |
| ATXN7L2 | 2.95 | 0.00 | 127002 | ENSG00000162650 |
| PDE4B | 2.94 | 0.03 | 5142 | ENSG00000184588 |
| SPRYD4 | 2.94 | 0.00 | 283377 | ENSG00000176422 |

FIG. 19J

| | | | | |
|---|---|---|---|---|
| FAM73B | 2.94 | 0.01 | 84895 | ENSG00000148343 |
| C1orf63 | 2.93 | 0.00 | 57035 | ENSG00000117616 |
| NENF | 2.92 | 0.01 | 29937 | ENSG00000117691 |
| | 2.91 | 0.00 | | ENSG00000234925 |
| IDH3G | 2.91 | 0.00 | 3421 | ENSG00000067829 |
| C1orf74 | 2.91 | 0.00 | 148304 | ENSG00000162757 |
| SLC10A3 | 2.91 | 0.00 | 8273 | ENSG00000126903 |
| TOB2 | 2.90 | 0.00 | 10766 | ENSG00000183864 |
| RPIA | 2.89 | 0.04 | 22934 | ENSG00000153574 |
| ZC3H3 | 2.89 | 0.03 | 23144 | ENSG00000014164 |
| SLC35A4 | 2.88 | 0.00 | 113829 | ENSG00000176087 |
| MOAP1 | 2.86 | 0.00 | 64112 | ENSG00000165943 |
| C19orf48 | 2.86 | 0.00 | 84798 | ENSG00000167747 |
| APCDD1 | 2.85 | 0.03 | 147495 | ENSG00000154856 |
| ERGIC1 | 2.85 | 0.00 | 57222 | ENSG00000113719 |
| CAV1 | 2.84 | 0.00 | 857 | ENSG00000105974 |
| NDFIP1 | 2.83 | 0.00 | 80762 | ENSG00000131507 |
| | 2.83 | 0.00 | | ENSG00000228360 |
| PXDC1 | 2.83 | 0.00 | 221749 | ENSG00000168994 |
| TMEM234 | 2.83 | 0.04 | 56063 | ENSG00000160055 |
| NUCB1 | 2.83 | 0.00 | 4924 | ENSG00000104805 |
| FRMD4A | 2.83 | 0.03 | 55691 | ENSG00000151474 |
| FBXL12 | 2.82 | 0.00 | 54850 | ENSG00000127452 |
| ZDHHC18 | 2.82 | 0.03 | 84243 | ENSG00000204160 |
| MYC | 2.82 | 0.00 | 4609 | ENSG00000136997 |
| RPAP2 | 2.81 | 0.01 | 79871 | ENSG00000122484 |
| NRSN2 | 2.81 | 0.01 | 80023 | ENSG00000125841 |
| MAX | 2.80 | 0.00 | 4149 | ENSG00000125952 |
| C19orf66 | 2.79 | 0.02 | 55337 | ENSG00000130813 |
| LAMTOR3 | 2.78 | 0.00 | 8649 | ENSG00000109270 |
| TANGO2 | 2.78 | 0.03 | 128989 | ENSG00000183597 |
| MINK1 | 2.78 | 0.00 | 50488 | ENSG00000141503 |
| POM121 | 2.78 | 0.00 | 9883 | ENSG00000196313 |
| RHPN1 | 2.78 | 0.03 | 114822 | ENSG00000158106 |
| PDZK1IP1 | 2.77 | 0.02 | 10158 | ENSG00000162366 |
| TSEN34 | 2.77 | 0.00 | 79042 | ENSG00000170892 |
| PDRG1 | 2.76 | 0.00 | 81572 | ENSG00000088356 |
| E2F3 | 2.75 | 0.00 | 1871 | ENSG00000112242 |
| ZDHHC24 | 2.75 | 0.04 | 254359 | ENSG00000174165 |
| SLC25A11 | 2.75 | 0.01 | 8402 | ENSG00000108528 |
| TMSB10P1 | 2.75 | 0.00 | | ENSG00000228499 |
| CTSH | 2.75 | 0.01 | 1512 | ENSG00000103811 |
| TIGD6 | 2.75 | 0.01 | 81789 | ENSG00000164296 |
| RPL37A | 2.74 | 0.00 | 6168 | ENSG00000197756 |
| ATP6V0D1 | 2.73 | 0.01 | 9114 | ENSG00000159720 |
| FERMT2 | 2.73 | 0.00 | 10979 | ENSG00000073712 |
| BCL9 | 2.73 | 0.00 | 607 | ENSG00000116128 |

FIG. 19K

| | | | | |
|---|---|---|---|---|
| EVI5L | 2.73 | 0.00 | 115704 | ENSG00000142459 |
| SNORA53 | 2.72 | 0.00 | 677832 | ENSG00000212443 |
| CETN2 | 2.72 | 0.00 | 1069 | ENSG00000147400 |
| SLC37A3 | 2.72 | 0.00 | 84255 | ENSG00000157800 |
| NAPG | 2.71 | 0.00 | 8774 | ENSG00000134265 |
| APEH | 2.71 | 0.00 | 327 | ENSG00000164062 |
| TMEM216 | 2.71 | 0.03 | 51259 | ENSG00000187049 |
| SEZ6L2 | 2.69 | 0.00 | 26470 | ENSG00000174938 |
| NR6A1 | 2.69 | 0.00 | 2649 | ENSG00000148200 |
| LITAF | 2.69 | 0.00 | 9516 | ENSG00000189067 |
| INTS3 | 2.68 | 0.00 | 65123 | ENSG00000143624 |
| | 2.68 | 0.05 | | ENSG00000231386 |
| COPS7A | 2.67 | 0.00 | 50813 | ENSG00000111652 |
| KXD1 | 2.67 | 0.00 | 79036 | ENSG00000105700 |
| ATP6V0E1 | 2.66 | 0.00 | 8992 | ENSG00000113732 |
| KBTBD4 | 2.66 | 0.00 | 55709 | ENSG00000123444 |
| WSB2 | 2.66 | 0.00 | 55884 | ENSG00000176871 |
| CDKN2A | 2.65 | 0.00 | 1029 | ENSG00000147889 |
| CERS4 | 2.65 | 0.00 | 79603 | ENSG00000090661 |
| RNF181 | 2.64 | 0.00 | 51255 | ENSG00000168894 |
| ASS1 | 2.64 | 0.00 | 445 | ENSG00000130707 |
| ARAF | 2.64 | 0.04 | 369 | ENSG00000078061 |
| FOXN2 | 2.64 | 0.00 | 3344 | ENSG00000170802 |
| | 2.64 | 0.00 | | ENSG00000240311 |
| RRP36 | 2.64 | 0.00 | 88745 | ENSG00000124541 |
| CITED2 | 2.64 | 0.00 | 10370 | ENSG00000164442 |
| PHBP11 | 2.63 | 0.03 | | ENSG00000227621 |
| UBR7 | 2.63 | 0.00 | 55148 | ENSG00000012963 |
| YOD1 | 2.63 | 0.00 | 55432 | ENSG00000180667 |
| ARTN | 2.63 | 0.00 | 9048 | ENSG00000117407 |
| IVL | 2.62 | 0.00 | 3713 | ENSG00000163207 |
| HIST1H2BI | 2.62 | 0.00 | 8339 | ENSG00000168242 |
| ANKRD13D | 2.61 | 0.01 | 338692 | ENSG00000172932 |
| SLC4A11 | 2.60 | 0.04 | 83959 | ENSG00000088836 |
| MDM4 | 2.59 | 0.00 | 4194 | ENSG00000198625 |
| TMSB10 | 2.59 | 0.00 | 9168 | ENSG00000034510 |
| SMARCC2 | 2.59 | 0.00 | 6601 | ENSG00000139613 |
| STX18 | 2.59 | 0.02 | 53407 | ENSG00000168818 |
| GIGYF1 | 2.59 | 0.01 | 64599 | ENSG00000146830 |
| TIMM17B | 2.58 | 0.02 | 10245 | ENSG00000126768 |
| TOB1 | 2.58 | 0.00 | 10140 | ENSG00000141232 |
| MTERFD1 | 2.58 | 0.01 | 51001 | ENSG00000156469 |
| DGUOK | 2.58 | 0.00 | 1716 | ENSG00000114956 |
| GMIP | 2.58 | 0.00 | 51291 | ENSG00000089639 |
| ALKBH3 | 2.58 | 0.00 | 221120 | ENSG00000166199 |
| PER2 | 2.57 | 0.03 | 8864 | ENSG00000132326 |
| ZC3HC1 | 2.56 | 0.01 | 51530 | ENSG00000091732 |

FIG. 19L

| | | | | |
|---|---|---|---|---|
| ACSF2 | 2.55 | 0.01 | 80221 | ENSG00000167107 |
| TBC1D13 | 2.55 | 0.00 | 54662 | ENSG00000107021 |
| FOXP1 | 2.55 | 0.01 | 27086 | ENSG00000114861 |
| WDR55 | 2.55 | 0.00 | 54853 | ENSG00000120314 |
| SHMT1 | 2.54 | 0.00 | 6470 | ENSG00000176974 |
| ATP1B3 | 2.54 | 0.00 | 483 | ENSG00000069849 |
| MRPS15 | 2.53 | 0.00 | 64960 | ENSG00000116898 |
| THEM6 | 2.53 | 0.00 | 51337 | ENSG00000130193 |
| CDK4 | 2.53 | 0.00 | 1019 | ENSG00000135446 |
| IRAK4 | 2.53 | 0.02 | 51135 | ENSG00000198001 |
| | 2.53 | 0.02 | | ENSG00000261774 |
| NFYC | 2.53 | 0.01 | 4802 | ENSG00000066136 |
| FBXO32 | 2.53 | 0.00 | 114907 | ENSG00000156804 |
| LINC00338 | 2.52 | 0.04 | 654434 | ENSG00000234912 |
| PPP1R37 | 2.52 | 0.00 | 284352 | ENSG00000104866 |
| FAM35CP | 2.52 | 0.00 | | ENSG00000259096 |
| GNAS | 2.52 | 0.00 | 2778 | ENSG00000087460 |
| ZHX2 | 2.51 | 0.03 | 22882 | ENSG00000178764 |
| PHF19 | 2.50 | 0.00 | 26147 | ENSG00000119403 |
| DCAF15 | 2.50 | 0.02 | 90379 | ENSG00000132017 |
| SPNS2 | 2.49 | 0.00 | 124976 | ENSG00000183018 |
| FBXL6 | 2.49 | 0.04 | 26233 | ENSG00000182325 |
| OGFRL1 | 2.49 | 0.05 | 79627 | ENSG00000119900 |
| NABP2 | 2.48 | 0.01 | 79035 | ENSG00000139579 |
| FBXO18 | 2.48 | 0.00 | 84893 | ENSG00000134452 |
| ZNF282 | 2.48 | 0.01 | 8427 | ENSG00000170265 |
| NAGPA | 2.48 | 0.00 | 51172 | ENSG00000103174 |
| GAPDHP65 | 2.48 | 0.00 | | ENSG00000235587 |
| PAK4 | 2.47 | 0.01 | 10298 | ENSG00000130669 |
| MXI1 | 2.47 | 0.01 | 4601 | ENSG00000119950 |
| TGFBR2 | 2.47 | 0.00 | 7048 | ENSG00000163513 |
| RQCD1 | 2.47 | 0.00 | 9125 | ENSG00000144580 |
| ZNF2 | 2.46 | 0.03 | 7549 | ENSG00000163067 |
| PTTG1 | 2.46 | 0.00 | 9232 | ENSG00000164611 |
| SF3B5 | 2.45 | 0.01 | 83443 | ENSG00000169976 |
| SPC25 | 2.45 | 0.03 | 57405 | ENSG00000152253 |
| ATG9A | 2.45 | 0.00 | 79065 | ENSG00000198925 |
| CCNJL | 2.43 | 0.01 | 79616 | ENSG00000135083 |
| REEP3 | 2.43 | 0.00 | 221035 | ENSG00000165476 |
| PREB | 2.43 | 0.00 | 10113 | ENSG00000138073 |
| DHCR7 | 2.43 | 0.00 | 1717 | ENSG00000172893 |
| AK3 | 2.43 | 0.02 | 50808 | ENSG00000147853 |
| MED19 | 2.43 | 0.04 | 219541 | ENSG00000156603 |
| AFG3L1P | 2.43 | 0.01 | 172 | ENSG00000223959 |
| ZNF281 | 2.43 | 0.00 | 23528 | ENSG00000162702 |
| AHCY | 2.43 | 0.00 | 191 | ENSG00000101444 |
| BRK1 | 2.42 | 0.00 | 55845 | ENSG00000254999 |

FIG. 19M

| | | | | |
|---|---|---|---|---|
| MYB | 2.42 | 0.01 | 4602 | ENSG00000118513 |
| TMEM205 | 2.42 | 0.00 | 374882 | ENSG00000105518 |
| N4BP1 | 2.42 | 0.00 | 9683 | ENSG00000102921 |
| DUSP2 | 2.42 | 0.01 | 1844 | ENSG00000158050 |
| MRPL28 | 2.42 | 0.00 | 10573 | ENSG00000086504 |
| LDOC1L | 2.42 | 0.00 | 84247 | ENSG00000188636 |
| TOM1 | 2.42 | 0.04 | 10043 | ENSG00000100284 |
| CMIP | 2.42 | 0.01 | 80790 | ENSG00000153815 |
| C12orf29 | 2.41 | 0.00 | 91298 | ENSG00000133641 |
| EAF1 | 2.41 | 0.00 | 85403 | ENSG00000144597 |
| EFHD2 | 2.41 | 0.01 | 79180 | ENSG00000142634 |
| SNORA23 | 2.41 | 0.01 | 677808 | ENSG00000201998 |
| TMED8 | 2.40 | 0.00 | 283578 | ENSG00000100580 |
| NTPCR | 2.40 | 0.00 | 84284 | ENSG00000135778 |
| POP7 | 2.40 | 0.00 | 10248 | ENSG00000172336 |
| CMC2 | 2.40 | 0.02 | 56942 | ENSG00000103121 |
| | 2.39 | 0.00 | | ENSG00000242527 |
| TRIM62 | 2.38 | 0.05 | 55223 | ENSG00000116525 |
| GHDC | 2.38 | 0.04 | 84514 | ENSG00000167925 |
| CCNDBP1 | 2.38 | 0.02 | 23582 | ENSG00000166946 |
| CDC20P1 | 2.38 | 0.00 | | ENSG00000231007 |
| TMEM101 | 2.37 | 0.00 | 84336 | ENSG00000091947 |
| GGA1 | 2.37 | 0.01 | 26088 | ENSG00000100083 |
| | 2.37 | 0.04 | | ENSG00000213867 |
| | 2.36 | 0.05 | | ENSG00000236654 |
| CSRP1 | 2.36 | 0.02 | 1465 | ENSG00000159176 |
| AMZ2 | 2.35 | 0.01 | 51321 | ENSG00000196704 |
| TP53 | 2.35 | 0.00 | 7157 | ENSG00000141510 |
| SIRT1 | 2.35 | 0.00 | 23411 | ENSG00000096717 |
| CCNI | 2.35 | 0.00 | 10983 | ENSG00000118816 |
| BTBD2 | 2.35 | 0.00 | 55643 | ENSG00000133243 |
| SERPINB7 | 2.35 | 0.00 | 8710 | ENSG00000166396 |
| DENND6A | 2.35 | 0.00 | 201627 | ENSG00000174839 |
| CDCA8 | 2.35 | 0.01 | 55143 | ENSG00000134690 |
| ELL2 | 2.34 | 0.00 | 22936 | ENSG00000118985 |
| KRT80 | 2.34 | 0.00 | 144501 | ENSG00000167767 |
| RNF44 | 2.34 | 0.00 | 22838 | ENSG00000146083 |
| INHBB | 2.34 | 0.00 | 3625 | ENSG00000163083 |
| PTP4A2 | 2.34 | 0.00 | 8073 | ENSG00000184007 |
| SNTA1 | 2.33 | 0.01 | 6640 | ENSG00000101400 |
| MAP2K7 | 2.33 | 0.01 | 5609 | ENSG00000076984 |
| S100A16 | 2.32 | 0.00 | 140576 | ENSG00000188643 |
| ZDHHC9 | 2.32 | 0.00 | 51114 | ENSG00000188706 |
| SEMA4D | 2.32 | 0.01 | 10507 | ENSG00000187764 |
| GTF2E2 | 2.32 | 0.01 | 2961 | ENSG00000197265 |
| TMBIM1 | 2.32 | 0.00 | 64114 | ENSG00000135926 |
| SNX4 | 2.31 | 0.01 | 8723 | ENSG00000114520 |

FIG. 19N

| | | | | |
|---|---|---|---|---|
| KLHDC3 | 2.31 | 0.00 | 116138 | ENSG00000124702 |
| RAB20 | 2.31 | 0.00 | 55647 | ENSG00000139832 |
| ADO | 2.31 | 0.00 | 84890 | ENSG00000181915 |
| TMEM141 | 2.30 | 0.00 | 85014 | ENSG00000244187 |
| SLC44A2 | 2.30 | 0.00 | 57153 | ENSG00000129353 |
| LPCAT1 | 2.30 | 0.00 | 79888 | ENSG00000153395 |
| PDE7A | 2.30 | 0.00 | 5150 | ENSG00000205268 |
| SAP130 | 2.30 | 0.01 | 79595 | ENSG00000136715 |
| IMPDH1 | 2.30 | 0.01 | 3614 | ENSG00000106348 |
| RNF34 | 2.30 | 0.01 | 80196 | ENSG00000170633 |
| GAPDHP60 | 2.30 | 0.03 | | ENSG00000248180 |
| MOV10 | 2.30 | 0.00 | 4343 | ENSG00000155363 |
| CLK3 | 2.29 | 0.02 | 1198 | ENSG00000179335 |
| MRPL44 | 2.29 | 0.04 | 65080 | ENSG00000135900 |
| IMP3 | 2.29 | 0.01 | 55272 | ENSG00000177971 |
| UNG | 2.28 | 0.00 | 7374 | ENSG00000076248 |
| ZNF76 | 2.28 | 0.00 | 7629 | ENSG00000065029 |
| DUSP4 | 2.28 | 0.01 | 1846 | ENSG00000120875 |
| PAFAH1B3 | 2.28 | 0.00 | 5050 | ENSG00000079462 |
| FAM32A | 2.27 | 0.00 | 26017 | ENSG00000105058 |
| GAS2L1 | 2.27 | 0.05 | 10634 | ENSG00000185340 |
| C7orf73 | 2.27 | 0.04 | 647087 | ENSG00000243317 |
| IGFBP4 | 2.26 | 0.00 | 3487 | ENSG00000141753 |
| CYB5B | 2.26 | 0.00 | 80777 | ENSG00000103018 |
| FAM64A | 2.26 | 0.05 | 54478 | ENSG00000129195 |
| TMEM243 | 2.26 | 0.01 | 79161 | ENSG00000135185 |
| C2orf49 | 2.26 | 0.01 | 79074 | ENSG00000135974 |
| NLRX1 | 2.26 | 0.02 | 79671 | ENSG00000160703 |
| HIST1H3D | 2.26 | 0.00 | 8350 | ENSG00000197409 |
| ZSCAN9 | 2.26 | 0.03 | 7746 | ENSG00000137185 |
| HGS | 2.26 | 0.00 | 9146 | ENSG00000185359 |
| CNIH | 2.25 | 0.01 | 10175 | ENSG00000100528 |
| ATP5H | 2.25 | 0.00 | 10476 | ENSG00000167863 |
| IFNLR1 | 2.24 | 0.00 | 163702 | ENSG00000185436 |
| TES | 2.24 | 0.00 | 26136 | ENSG00000135269 |
| ATG4D | 2.24 | 0.00 | 84971 | ENSG00000130734 |
| CRIPT | 2.23 | 0.00 | 9419 | ENSG00000119878 |
| SNX17 | 2.23 | 0.00 | 9784 | ENSG00000115234 |
| SLC6A9 | 2.22 | 0.01 | 6536 | ENSG00000196517 |
| MIER2 | 2.22 | 0.03 | 54531 | ENSG00000105556 |
| TOM1L2 | 2.22 | 0.02 | 146691 | ENSG00000175662 |
| LRRC41 | 2.22 | 0.00 | 10489 | ENSG00000132128 |
| COQ9 | 2.22 | 0.00 | 57017 | ENSG00000088682 |
| | 2.21 | 0.01 | | ENSG00000213661 |
| NACC1 | 2.21 | 0.00 | 112939 | ENSG00000160877 |
| RPLP0 | 2.21 | 0.00 | 6175 | ENSG00000089157 |
| SOX4 | 2.21 | 0.00 | 6659 | ENSG00000124766 |

FIG. 19O

| | | | | |
|---|---|---|---|---|
| IFRD2 | 2.21 | 0.00 | 7866 | ENSG00000214706 |
| AIP | 2.21 | 0.00 | 9049 | ENSG00000110711 |
| PPIAP31 | 2.20 | 0.05 | | ENSG00000217094 |
| FBXO25 | 2.20 | 0.02 | 26260 | ENSG00000147364 |
| HMG20B | 2.20 | 0.01 | 10362 | ENSG00000064961 |
| SESN2 | 2.19 | 0.04 | 83667 | ENSG00000130766 |
| IST1 | 2.19 | 0.00 | 9798 | ENSG00000182149 |
| PDLIM1 | 2.19 | 0.04 | 9124 | ENSG00000107438 |
| FBXO10 | 2.19 | 0.03 | 26267 | ENSG00000147912 |
| ELOVL1 | 2.18 | 0.01 | 64834 | ENSG00000066322 |
| SDCBP | 2.18 | 0.04 | 6386 | ENSG00000137575 |
| RPS18P9 | 2.17 | 0.04 | | ENSG00000220848 |
| KLF10 | 2.17 | 0.00 | 7071 | ENSG00000155090 |
| RNMTL1 | 2.17 | 0.01 | 55178 | ENSG00000171861 |
| SCARNA6 | 2.17 | 0.00 | 677772 | ENSG00000251791 |
| CBX8 | 2.16 | 0.02 | 57332 | ENSG00000141570 |
| VASN | 2.16 | 0.02 | 114990 | ENSG00000168140 |
| BHLHE40 | 2.16 | 0.00 | 8553 | ENSG00000134107 |
| DNAJC24 | 2.16 | 0.01 | 120526 | ENSG00000170946 |
| ORMDL3 | 2.15 | 0.02 | 94103 | ENSG00000172057 |
| WDR85 | 2.15 | 0.02 | 92715 | ENSG00000148399 |
| FAM102A | 2.15 | 0.04 | 399665 | ENSG00000167106 |
| PPP1CA | 2.14 | 0.00 | 5499 | ENSG00000172531 |
| SDAD1 | 2.14 | 0.04 | 55153 | ENSG00000198301 |
| MCTS1 | 2.14 | 0.04 | 28985 | ENSG00000232119 |
| PPP3R1 | 2.13 | 0.00 | 5534 | ENSG00000221823 |
| ELOF1 | 2.13 | 0.03 | 84337 | ENSG00000130165 |
| TOMM40 | 2.13 | 0.02 | 10452 | ENSG00000130204 |
| RRS1 | 2.13 | 0.04 | 23212 | ENSG00000179041 |
| IGFBP3 | 2.13 | 0.00 | 3486 | ENSG00000146674 |
| STOML2 | 2.13 | 0.00 | 30968 | ENSG00000165283 |
| NOL10 | 2.13 | 0.00 | 79954 | ENSG00000115761 |
| SUOX | 2.12 | 0.05 | 6821 | ENSG00000139531 |
| FGFBP1 | 2.12 | 0.00 | 9982 | ENSG00000137440 |
| SEPN1 | 2.12 | 0.01 | 57190 | ENSG00000162430 |
| MAP3K13 | 2.12 | 0.03 | 9175 | ENSG00000073803 |
| SMG9 | 2.11 | 0.00 | 56006 | ENSG00000105771 |
| CDC37 | 2.10 | 0.00 | 11140 | ENSG00000105401 |
| GLCE | 2.10 | 0.01 | 26035 | ENSG00000138604 |
| RPL37AP1 | 2.10 | 0.00 | | ENSG00000226243 |
| NCEH1 | 2.10 | 0.01 | 57552 | ENSG00000144959 |
| CDC23 | 2.10 | 0.00 | 8697 | ENSG00000094880 |
| ATP6V0A1 | 2.09 | 0.04 | 535 | ENSG00000033627 |
| CEP55 | 2.09 | 0.00 | 55165 | ENSG00000138180 |
| RPL14 | 2.09 | 0.00 | 9045 | ENSG00000188846 |
| CDC42P6 | 2.09 | 0.05 | | ENSG00000237350 |
| TPI1P1 | 2.08 | 0.00 | | ENSG00000226415 |

FIG. 19P

| | | | | |
|---|---|---|---|---|
| PPP6C | 2.08 | 0.00 | 5537 | ENSG00000119414 |
| EIF2B2 | 2.08 | 0.04 | 8892 | ENSG00000119718 |
| C17orf76-AS1 | 2.07 | 0.00 | 26800 | ENSG00000175061 |
| RGP1 | 2.07 | 0.00 | 9827 | ENSG00000107185 |
| ANP32A | 2.07 | 0.01 | 8125 | ENSG00000140350 |
| ZNF576 | 2.06 | 0.04 | 79177 | ENSG00000124444 |
| MARCH2 | 2.06 | 0.05 | 51257 | ENSG00000099785 |
| RBBP4P1 | 2.06 | 0.00 | | ENSG00000249485 |
| AKT1S1 | 2.05 | 0.04 | 84335 | ENSG00000204673 |
| POMGNT1 | 2.05 | 0.00 | 55624 | ENSG00000085998 |
| RFXANK | 2.05 | 0.01 | 8625 | ENSG00000064490 |
| CCDC71L | 2.04 | 0.00 | 168455 | ENSG00000253276 |
| ZSWIM4 | 2.04 | 0.00 | 65249 | ENSG00000132003 |
| LRRC40 | 2.04 | 0.01 | 55631 | ENSG00000066557 |
| SPINT1 | 2.04 | 0.00 | 6692 | ENSG00000166145 |
| CREB3 | 2.04 | 0.01 | 10488 | ENSG00000107175 |
| DTYMK | 2.04 | 0.01 | 1841 | ENSG00000168393 |
| SNRPD2 | 2.04 | 0.00 | 6633 | ENSG00000125743 |
| SHARPIN | 2.04 | 0.05 | 81858 | ENSG00000179526 |
| LMF2 | 2.04 | 0.03 | 91289 | ENSG00000100258 |
| ZNF682 | 2.04 | 0.02 | 91120 | ENSG00000197124 |
| CFL1 | 2.03 | 0.00 | 1072 | ENSG00000172757 |
| RPUSD3 | 2.03 | 0.02 | 285367 | ENSG00000156990 |
| ARF5 | 2.03 | 0.03 | 381 | ENSG00000004059 |
| C2orf68 | 2.03 | 0.00 | 388969 | ENSG00000168887 |
| MBD3 | 2.03 | 0.01 | 53615 | ENSG00000071655 |
| HDAC1 | 2.03 | 0.00 | 3065 | ENSG00000116478 |
| CLPTM1 | 2.03 | 0.01 | 1209 | ENSG00000104853 |
| | 2.02 | 0.01 | | ENSG00000220472 |
| ELL2P1 | 2.02 | 0.02 | | ENSG00000227295 |
| TMED4 | 2.02 | 0.00 | 222068 | ENSG00000158604 |
| CHP1 | 2.02 | 0.00 | 11261 | ENSG00000187446 |
| QPRT | 2.02 | 0.01 | 23475 | ENSG00000103485 |
| RARG | 2.01 | 0.00 | 5916 | ENSG00000172819 |
| RBBP4P2 | 2.01 | 0.02 | | ENSG00000242457 |
| HDDC2 | 2.00 | 0.03 | 51020 | ENSG00000111906 |

FIG. 20A

| Gene Name | Pulldown-seq Fold enrichment | Pulldown-seq p-value | EntrezGene ID | Ensembl Gene ID |
|---|---|---|---|---|
|  | Inf | 0.00 | 100506083 | ENSG00000261777 |
| OTX1 | Inf | 0.04 | 5013 | ENSG00000115507 |
| SLMO1 | Inf | 0.05 | 10650 | ENSG00000141391 |
| PLK3 | Inf | 0.00 | 1263 | ENSG00000173846 |
| ASTL | Inf | 0.04 | 431705 | ENSG00000188886 |
| OR7E14P | Inf | 0.01 | 10819 | ENSG00000184669 |
| PIGUP1 | Inf | 0.00 |  | ENSG00000224437 |
| S100A11P2 | Inf | 0.04 |  | ENSG00000236592 |
| ALG3P1 | Inf | 0.02 |  | ENSG00000251568 |
|  | Inf | 0.05 |  | ENSG00000259079 |
| ADA | 198.91 | 0.00 | 100 | ENSG00000196839 |
| TRAPPC1 | 85.95 | 0.00 | 58485 | ENSG00000170043 |
|  | 74.83 | 0.01 |  | ENSG00000237999 |
|  | 63.38 | 0.00 |  | ENSG00000260282 |
|  | 53.12 | 0.01 |  | ENSG00000253251 |
| PIGU | 37.51 | 0.00 | 128869 | ENSG00000101464 |
| ALG3 | 36.78 | 0.00 | 10195 | ENSG00000214160 |
| TMEM143 | 33.87 | 0.00 | 55260 | ENSG00000161558 |
| SLC29A1 | 32.21 | 0.00 | 2030 | ENSG00000112759 |
| TMEM38A | 31.06 | 0.00 | 79041 | ENSG00000072954 |
| PCYOX1L | 28.94 | 0.00 | 78991 | ENSG00000145882 |
|  | 26.20 | 0.00 |  | ENSG00000213959 |
| HMGA1P2 | 25.72 | 0.03 |  | ENSG00000248641 |
| FUCA1 | 25.35 | 0.00 | 2517 | ENSG00000179163 |
| H19 | 24.99 | 0.00 | 283120 | ENSG00000130600 |
| CALM3 | 24.74 | 0.00 | 801 | ENSG00000160014 |
| DUSP7 | 23.92 | 0.00 | 1849 | ENSG00000164086 |
| PRSS22 | 22.20 | 0.00 | 64063 | ENSG00000005001 |
| HOXA1 | 21.97 | 0.00 | 3198 | ENSG00000105991 |
| APBB3 | 20.91 | 0.01 | 10307 | ENSG00000113108 |
| S100A11P1 | 19.30 | 0.00 |  | ENSG00000237632 |
| TMEM8A | 19.29 | 0.01 | 58986 | ENSG00000129925 |
| COX14 | 18.70 | 0.00 | 84987 | ENSG00000178449 |
|  | 18.02 | 0.01 |  | ENSG00000213742 |
| ECE2 | 17.61 | 0.00 | 9718 | ENSG00000145194 |
| CTSA | 17.42 | 0.00 | 5476 | ENSG00000064601 |
| GPR39 | 16.83 | 0.01 | 2863 | ENSG00000183840 |
| FKBP1A | 16.78 | 0.00 | 2280 | ENSG00000088832 |
| NUP62CL | 16.60 | 0.00 | 54830 | ENSG00000198088 |
| GYG1 | 16.50 | 0.00 | 2992 | ENSG00000163754 |
| ERP29 | 16.36 | 0.00 | 10961 | ENSG00000089248 |
| RPS6KB2 | 16.32 | 0.00 | 6199 | ENSG00000175634 |
| C1orf85 | 16.15 | 0.00 | 112770 | ENSG00000198715 |
| CERCAM | 15.98 | 0.00 | 51148 | ENSG00000167123 |
| TNFSF9 | 15.93 | 0.00 | 8744 | ENSG00000125657 |
| IL22RA1 | 15.86 | 0.03 | 58985 | ENSG00000142677 |

FIG. 20B

| | | | | |
|---|---|---|---|---|
| TMCO6 | 15.72 | 0.01 | 55374 | ENSG00000113119 |
| ARID3B | 15.14 | 0.01 | 10620 | ENSG00000179361 |
| S100A11 | 15.02 | 0.00 | 6282 | ENSG00000163191 |
| TMEM101 | 15.02 | 0.00 | 84336 | ENSG00000091947 |
| SWSAP1 | 15.02 | 0.00 | 126074 | ENSG00000173928 |
| FADS3 | 14.94 | 0.00 | 3995 | ENSG00000221968 |
| EDN1 | 14.66 | 0.00 | 1906 | ENSG00000078401 |
| B3GNT7 | 13.91 | 0.01 | 93010 | ENSG00000156966 |
| COIL | 13.87 | 0.00 | 8161 | ENSG00000121058 |
| PCTP | 13.54 | 0.00 | 58488 | ENSG00000141179 |
| ZNF341 | 13.45 | 0.00 | 84905 | ENSG00000131061 |
| CDC34 | 13.35 | 0.00 | 997 | ENSG00000099804 |
| C19orf55 | 13.32 | 0.00 | 148137 | ENSG00000167595 |
| GYG2 | 12.91 | 0.00 | 8908 | ENSG00000056998 |
| SLC5A6 | 12.90 | 0.00 | 8884 | ENSG00000138074 |
| | 12.81 | 0.00 | | ENSG00000259100 |
| ZCCHC3 | 12.79 | 0.04 | 85364 | ENSG00000177764 |
| GYLTL1B | 12.46 | 0.00 | 120071 | ENSG00000165905 |
| KIAA0895L | 12.46 | 0.00 | 653319 | ENSG00000196123 |
| TTLL11 | 12.32 | 0.00 | 158135 | ENSG00000175764 |
| SLC35D2 | 12.25 | 0.00 | 11046 | ENSG00000130958 |
| MYCN | 12.19 | 0.00 | 4613 | ENSG00000134323 |
| TST | 12.12 | 0.00 | 7263 | ENSG00000128311 |
| ZDHHC12 | 12.01 | 0.00 | 84885 | ENSG00000160446 |
| C11orf84 | 11.91 | 0.00 | 144097 | ENSG00000168005 |
| ABT1 | 11.86 | 0.00 | 29777 | ENSG00000146109 |
| CYP2R1 | 11.85 | 0.00 | 120227 | ENSG00000186104 |
| HDHD1 | 11.77 | 0.00 | 8226 | ENSG00000130021 |
| | 11.77 | 0.00 | | ENSG00000228974 |
| YIPF1 | 11.71 | 0.00 | 54432 | ENSG00000058799 |
| ERP29P1 | 11.58 | 0.00 | | ENSG00000233347 |
| SMCO4 | 11.57 | 0.00 | 56935 | ENSG00000166002 |
| ZNF689 | 11.50 | 0.00 | 115509 | ENSG00000156853 |
| ADRB1 | 11.50 | 0.02 | 153 | ENSG00000043591 |
| KPNA7 | 11.15 | 0.01 | 402569 | ENSG00000185467 |
| EIF1AD | 11.11 | 0.00 | 84285 | ENSG00000175376 |
| SNX16 | 10.80 | 0.00 | 64089 | ENSG00000104497 |
| | 10.80 | 0.03 | | ENSG00000205596 |
| SLC52A3 | 10.80 | 0.00 | 113278 | ENSG00000101276 |
| SMIM3 | 10.78 | 0.00 | 85027 | ENSG00000256235 |
| SMARCB1 | 10.55 | 0.00 | 6598 | ENSG00000099956 |
| TMEM147 | 10.47 | 0.00 | 10430 | ENSG00000105677 |
| ECHDC3 | 10.42 | 0.00 | 79746 | ENSG00000134463 |
| ABCC10 | 10.40 | 0.00 | 89845 | ENSG00000124574 |
| C8orf58 | 10.33 | 0.00 | 541565 | ENSG00000241852 |
| OXA1L | 10.29 | 0.00 | 5018 | ENSG00000155463 |
| FBXL12 | 10.25 | 0.00 | 54850 | ENSG00000127452 |

FIG. 20C

| | | | | |
|---|---|---|---|---|
| ULK3 | 10.21 | 0.00 | 25989 | ENSG00000140474 |
| TP53INP2 | 10.17 | 0.01 | 58476 | ENSG00000078804 |
| DPAGT1 | 10.13 | 0.00 | 1798 | ENSG00000172269 |
| | 10.11 | 0.00 | | ENSG00000251235 |
| ZCCHC9 | 10.08 | 0.00 | 84240 | ENSG00000131732 |
| PDSS1 | 10.07 | 0.00 | 23590 | ENSG00000148459 |
| CYB5R1 | 9.99 | 0.00 | 51706 | ENSG00000159348 |
| OXGR1 | 9.95 | 0.01 | 27199 | ENSG00000165621 |
| PDK2 | 9.84 | 0.02 | 5164 | ENSG00000005882 |
| CDC25C | 9.84 | 0.00 | 995 | ENSG00000158402 |
| TIMM17B | 9.78 | 0.00 | 10245 | ENSG00000126768 |
| C1orf159 | 9.67 | 0.00 | 54991 | ENSG00000131591 |
| GINS2 | 9.35 | 0.00 | 51659 | ENSG00000131153 |
| ZFP36 | 9.30 | 0.00 | 7538 | ENSG00000128016 |
| DNAJB9 | 9.26 | 0.00 | 4189 | ENSG00000128590 |
| FTLP3 | 9.20 | 0.01 | | ENSG00000226608 |
| N4BP2L1 | 9.16 | 0.02 | 90634 | ENSG00000139597 |
| CBLC | 9.14 | 0.00 | 23624 | ENSG00000142273 |
| FAM222B | 9.12 | 0.00 | 55731 | ENSG00000173065 |
| E2F5 | 9.04 | 0.00 | 1875 | ENSG00000133740 |
| CPA4 | 8.83 | 0.00 | 51200 | ENSG00000128510 |
| SNRPC | 8.68 | 0.01 | 6631 | ENSG00000124562 |
| LYPD3 | 8.62 | 0.01 | 27076 | ENSG00000124466 |
| ANKRD46 | 8.61 | 0.00 | 157567 | ENSG00000186106 |
| FKBP1C | 8.58 | 0.00 | | ENSG00000198225 |
| HOXC11 | 8.49 | 0.02 | 3227 | ENSG00000123388 |
| ATP6V0D1 | 8.49 | 0.00 | 9114 | ENSG00000159720 |
| LIPT2 | 8.49 | 0.04 | 387787 | ENSG00000175536 |
| ANKRD39 | 8.48 | 0.05 | 51239 | ENSG00000213337 |
| RBMS1P1 | 8.46 | 0.00 | | ENSG00000225422 |
| CASP4 | 8.40 | 0.00 | 837 | ENSG00000196954 |
| GMPPA | 8.36 | 0.00 | 29926 | ENSG00000144591 |
| RAD9A | 8.30 | 0.00 | 5883 | ENSG00000172613 |
| CISH | 8.18 | 0.03 | 1154 | ENSG00000114737 |
| GPR157 | 8.15 | 0.01 | 80045 | ENSG00000180758 |
| DBF4 | 8.09 | 0.00 | 10926 | ENSG00000006634 |
| RBMS1 | 8.08 | 0.00 | 5937 | ENSG00000153250 |
| PIGC | 8.05 | 0.00 | 5279 | ENSG00000135845 |
| SKP2 | 7.99 | 0.00 | 6502 | ENSG00000145604 |
| TMEM120A | 7.97 | 0.01 | 83862 | ENSG00000189077 |
| NR6A1 | 7.94 | 0.00 | 2649 | ENSG00000148200 |
| ADRB2 | 7.93 | 0.00 | 154 | ENSG00000169252 |
| NR4A1 | 7.91 | 0.04 | 3164 | ENSG00000123358 |
| PIGP | 7.88 | 0.00 | 51227 | ENSG00000185808 |
| TARBP2 | 7.83 | 0.00 | 6895 | ENSG00000139546 |
| ITM2C | 7.82 | 0.00 | 81618 | ENSG00000135916 |
| KLK6 | 7.75 | 0.00 | 5653 | ENSG00000167755 |

FIG. 20D

| | | | | |
|---|---|---|---|---|
| H2AFX | 7.65 | 0.00 | 3014 | ENSG00000188486 |
| THG1L | 7.65 | 0.01 | 54974 | ENSG00000113272 |
| CDKN1B | 7.64 | 0.00 | 1027 | ENSG00000111276 |
| RNF170 | 7.58 | 0.00 | 81790 | ENSG00000120925 |
| PPP1CA | 7.57 | 0.00 | 5499 | ENSG00000172531 |
| TRIB1 | 7.52 | 0.00 | 10221 | ENSG00000173334 |
| PBX3 | 7.51 | 0.00 | 5090 | ENSG00000167081 |
| TTC9C | 7.50 | 0.01 | 283237 | ENSG00000162222 |
| SIGMAR1 | 7.48 | 0.03 | 10280 | ENSG00000147955 |
| ARID3A | 7.46 | 0.01 | 1820 | ENSG00000116017 |
| FBXL6 | 7.45 | 0.04 | 26233 | ENSG00000182325 |
| PCBP4 | 7.44 | 0.00 | 57060 | ENSG00000090097 |
| LMBR1L | 7.42 | 0.00 | 55716 | ENSG00000139636 |
| MAL2 | 7.41 | 0.00 | | ENSG00000147676 |
| SLC7A6 | 7.33 | 0.00 | 9057 | ENSG00000103064 |
| RPUSD3 | 7.23 | 0.00 | 285367 | ENSG00000156990 |
| DOLK | 7.22 | 0.00 | 22845 | ENSG00000175283 |
| MRPS9 | 7.21 | 0.00 | 64965 | ENSG00000135972 |
| MFSD10 | 7.20 | 0.01 | 10227 | ENSG00000109736 |
| | 7.20 | 0.01 | | ENSG00000232327 |
| PGAP2 | 7.20 | 0.00 | 27315 | ENSG00000148985 |
| PQLC2 | 7.19 | 0.04 | 54896 | ENSG00000040487 |
| TIRAP | 7.17 | 0.00 | 114609 | ENSG00000150455 |
| OGG1 | 7.16 | 0.00 | 4968 | ENSG00000114026 |
| AURKB | 7.15 | 0.00 | 9212 | ENSG00000178999 |
| XRCC1 | 7.13 | 0.02 | 7515 | ENSG00000073050 |
| EIF4EBP2 | 7.12 | 0.00 | 1979 | ENSG00000148730 |
| RABL2B | 7.11 | 0.02 | 11158 | ENSG00000079974 |
| NAT14 | 7.10 | 0.00 | 57106 | ENSG00000090971 |
| ALG8 | 7.09 | 0.00 | 79053 | ENSG00000159063 |
| SLC27A3 | 7.08 | 0.03 | 11000 | ENSG00000143554 |
| CCNE2 | 7.05 | 0.00 | 9134 | ENSG00000175305 |
| MYC | 7.04 | 0.01 | 4609 | ENSG00000136997 |
| CYB5R3 | 6.99 | 0.00 | 1727 | ENSG00000100243 |
| CHN2 | 6.97 | 0.01 | 1124 | ENSG00000106069 |
| CCNJ | 6.95 | 0.00 | 54619 | ENSG00000107443 |
| STX3 | 6.90 | 0.00 | 6809 | ENSG00000166900 |
| | 6.87 | 0.00 | | ENSG00000256756 |
| CEBPD | 6.84 | 0.00 | 1052 | ENSG00000221869 |
| | 6.83 | 0.04 | | ENSG00000228510 |
| ATP6V1F | 6.83 | 0.01 | 9296 | ENSG00000128524 |
| NME4 | 6.75 | 0.00 | 4833 | ENSG00000103202 |
| FAM103A2P | 6.70 | 0.04 | | ENSG00000235272 |
| MIER2 | 6.70 | 0.00 | 54531 | ENSG00000105556 |
| CRY2 | 6.68 | 0.00 | 1408 | ENSG00000121671 |
| ZCCHC10 | 6.67 | 0.00 | 54819 | ENSG00000155329 |
| TNFSF10 | 6.66 | 0.00 | 8743 | ENSG00000121858 |

FIG. 20E

| Gene | Value | p | ID | Ensembl |
|---|---|---|---|---|
| SYVN1 | 6.60 | 0.01 | 84447 | ENSG00000162298 |
| WIPI1 | 6.59 | 0.00 | 55062 | ENSG00000070540 |
| TTLL4 | 6.56 | 0.00 | 9654 | ENSG00000135912 |
| BRI3 | 6.56 | 0.00 | 25798 | ENSG00000164713 |
| PFKFB4 | 6.56 | 0.00 | 5210 | ENSG00000114268 |
| PBX2P1 | 6.55 | 0.01 | | ENSG00000244171 |
| FMO4 | 6.54 | 0.01 | 2329 | ENSG00000076258 |
| PIAS4 | 6.54 | 0.00 | 51588 | ENSG00000105229 |
| TGFBR3 | 6.54 | 0.00 | 7049 | ENSG00000069702 |
| MAPK7 | 6.53 | 0.04 | 5598 | ENSG00000166484 |
| CLDN12 | 6.50 | 0.00 | 9069 | ENSG00000157224 |
| TPP1 | 6.48 | 0.04 | 1200 | ENSG00000166340 |
| LRRC42 | 6.46 | 0.00 | 115353 | ENSG00000116212 |
| FLAD1 | 6.46 | 0.00 | 80308 | ENSG00000160688 |
| SPATA7 | 6.39 | 0.05 | 55812 | ENSG00000042317 |
| | 6.39 | 0.00 | | ENSG00000248699 |
| FTL | 6.33 | 0.00 | 2512 | ENSG00000087086 |
| GPR137B | 6.30 | 0.00 | 7107 | ENSG00000077585 |
| MPC1 | 6.30 | 0.00 | 51660 | ENSG00000060762 |
| SPRYD4 | 6.20 | 0.00 | 283377 | ENSG00000176422 |
| ATP5G2 | 6.19 | 0.00 | 517 | ENSG00000135390 |
| TEX261 | 6.15 | 0.00 | 113419 | ENSG00000144043 |
| UTP11L | 6.13 | 0.00 | 51118 | ENSG00000183520 |
| TUBG1 | 6.10 | 0.00 | 7283 | ENSG00000131462 |
| TBC1D13 | 6.10 | 0.00 | 54662 | ENSG00000107021 |
| PATL1 | 6.08 | 0.00 | 219988 | ENSG00000166889 |
| TUSC2 | 6.08 | 0.01 | 11334 | ENSG00000114383 |
| LRCH4 | 6.05 | 0.01 | 4034 | ENSG00000077454 |
| DUSP6 | 6.02 | 0.02 | 1848 | ENSG00000139318 |
| SPINT1 | 5.98 | 0.00 | 6692 | ENSG00000166145 |
| MED19 | 5.97 | 0.02 | 219541 | ENSG00000156603 |
| TMEM53 | 5.95 | 0.01 | 79639 | ENSG00000126106 |
| GSAP | 5.94 | 0.01 | 54103 | ENSG00000186088 |
| SERTAD1 | 5.92 | 0.00 | 29950 | ENSG00000197019 |
| PEX11B | 5.91 | 0.00 | 8799 | ENSG00000131779 |
| RPN2 | 5.90 | 0.00 | 6185 | ENSG00000118705 |
| BIN3 | 5.88 | 0.02 | 55909 | ENSG00000147439 |
| VRK3 | 5.86 | 0.00 | 51231 | ENSG00000105053 |
| NIPSNAP1 | 5.86 | 0.00 | 8508 | ENSG00000184117 |
| S100A8 | 5.86 | 0.00 | 6279 | ENSG00000143546 |
| ACTG1 | 5.82 | 0.01 | 71 | ENSG00000184009 |
| GPRC5A | 5.81 | 0.00 | 9052 | ENSG00000013588 |
| DCAF15 | 5.78 | 0.01 | 90379 | ENSG00000132017 |
| TBKBP1 | 5.76 | 0.02 | 9755 | ENSG00000198933 |
| | 5.76 | 0.03 | | ENSG00000234072 |
| GJB3 | 5.75 | 0.01 | 2707 | ENSG00000188910 |
| PLA2G15 | 5.75 | 0.01 | 23659 | ENSG00000103066 |

FIG. 20F

| | | | | |
|---|---|---|---|---|
| HIC2 | 5.74 | 0.03 | 23119 | ENSG00000169635 |
| SLC16A3 | 5.73 | 0.01 | 9123 | ENSG00000141526 |
| INPP5A | 5.71 | 0.00 | 3632 | ENSG00000068383 |
| UBXN8 | 5.69 | 0.00 | | ENSG00000104691 |
| ARHGEF39 | 5.68 | 0.00 | 84904 | ENSG00000137135 |
| SLC25A13 | 5.68 | 0.00 | 10165 | ENSG00000004864 |
| TAF5L | 5.66 | 0.00 | 27097 | ENSG00000135801 |
| ACTBP11 | 5.61 | 0.01 | | ENSG00000188460 |
| COX10 | 5.59 | 0.00 | 1352 | ENSG00000006695 |
| ARL4D | 5.59 | 0.00 | 379 | ENSG00000175906 |
| TSPAN2 | 5.57 | 0.02 | 10100 | ENSG00000134198 |
| | 5.51 | 0.00 | | ENSG00000263311 |
| PLD3 | 5.48 | 0.01 | 23646 | ENSG00000105223 |
| SRD5A3 | 5.46 | 0.01 | 79644 | ENSG00000128039 |
| RNFT1 | 5.46 | 0.01 | 51136 | ENSG00000189050 |
| SCAMP5 | 5.44 | 0.00 | 192683 | ENSG00000198794 |
| SESN2 | 5.41 | 0.04 | 83667 | ENSG00000130766 |
| PYGO2 | 5.40 | 0.01 | 90780 | ENSG00000163348 |
| | 5.39 | 0.03 | | ENSG00000225333 |
| RBMS2P1 | 5.36 | 0.02 | | ENSG00000213250 |
| DBF4P1 | 5.36 | 0.00 | | ENSG00000235489 |
| GLB1 | 5.34 | 0.01 | 2720 | ENSG00000170266 |
| MKNK2 | 5.34 | 0.01 | 2872 | ENSG00000099875 |
| NDST2 | 5.31 | 0.01 | 8509 | ENSG00000166507 |
| KDM6A | 5.31 | 0.00 | 7403 | ENSG00000147050 |
| FAM57A | 5.31 | 0.04 | 79850 | ENSG00000167695 |
| ACTB | 5.30 | 0.00 | 60 | ENSG00000075624 |
| DUSP1 | 5.30 | 0.01 | 1843 | ENSG00000120129 |
| RAB11A | 5.30 | 0.00 | 8766 | ENSG00000103769 |
| ATP6V1G1 | 5.23 | 0.00 | 9550 | ENSG00000136888 |
| C18orf21 | 5.22 | 0.01 | 83608 | ENSG00000141428 |
| GOLGA7 | 5.22 | 0.00 | 51125 | ENSG00000147533 |
| CCDC71L | 5.20 | 0.00 | 168455 | ENSG00000253276 |
| ABHD17C | 5.16 | 0.02 | 58489 | ENSG00000136379 |
| ARRDC3 | 5.15 | 0.00 | 57561 | ENSG00000113369 |
| NMNAT2 | 5.13 | 0.00 | 23057 | ENSG00000157064 |
| CCNA2 | 5.07 | 0.00 | 890 | ENSG00000145386 |
| ACTBP2 | 5.06 | 0.03 | | ENSG00000213763 |
| PARS2 | 5.06 | 0.02 | 25973 | ENSG00000162396 |
| ART4 | 5.05 | 0.01 | 420 | ENSG00000111339 |
| THEM4 | 5.02 | 0.01 | 117145 | ENSG00000159445 |
| CDCA8 | 5.01 | 0.00 | 55143 | ENSG00000134690 |
| NOP10 | 5.00 | 0.00 | 55505 | ENSG00000182117 |
| MRPS2 | 4.98 | 0.02 | 51116 | ENSG00000122140 |
| ZDHHC9 | 4.98 | 0.00 | 51114 | ENSG00000188706 |
| NME6 | 4.94 | 0.00 | 10201 | ENSG00000172113 |
| TTC17 | 4.94 | 0.00 | 55761 | ENSG00000052841 |

FIG. 20G

| | | | | |
|---|---|---|---|---|
| MAPK6PS4 | 4.94 | 0.02 | | ENSG00000215179 |
| C14orf2 | 4.94 | 0.00 | 9556 | ENSG00000156411 |
| SOCS1 | 4.93 | 0.01 | 8651 | ENSG00000185338 |
| SLC44A2 | 4.90 | 0.01 | 57153 | ENSG00000129353 |
| MARS2 | 4.87 | 0.02 | 92935 | ENSG00000247626 |
| DUSP2 | 4.83 | 0.03 | 1844 | ENSG00000158050 |
| C17orf53 | 4.82 | 0.04 | 78995 | ENSG00000125319 |
| LRRC28 | 4.82 | 0.00 | 123355 | ENSG00000168904 |
| C5orf51 | 4.80 | 0.00 | 285636 | ENSG00000205765 |
| ANKRD49 | 4.79 | 0.00 | 54851 | ENSG00000168876 |
| FOXI1 | 4.79 | 0.00 | 2299 | ENSG00000168269 |
| AKR1E2 | 4.77 | 0.03 | 83592 | ENSG00000165568 |
| CCDC25 | 4.74 | 0.00 | 55246 | ENSG00000147419 |
| GALE | 4.72 | 0.01 | 2582 | ENSG00000117308 |
| FAM43A | 4.69 | 0.00 | 131583 | ENSG00000185112 |
| CCNF | 4.69 | 0.01 | 899 | ENSG00000162063 |
| PDLIM7 | 4.68 | 0.02 | 9260 | ENSG00000196923 |
| WNT9A | 4.67 | 0.00 | 7483 | ENSG00000143816 |
| ADCK1 | 4.65 | 0.03 | 57143 | ENSG00000063761 |
| KCTD21 | 4.63 | 0.02 | 283219 | ENSG00000188997 |
| E2F4 | 4.63 | 0.02 | 1874 | ENSG00000205250 |
| MFSD5 | 4.58 | 0.00 | 84975 | ENSG00000182544 |
| RHOB | 4.55 | 0.01 | 388 | ENSG00000143878 |
| NAP1L1P3 | 4.54 | 0.02 | | ENSG00000213371 |
| COQ10B | 4.53 | 0.00 | 80219 | ENSG00000115520 |
| IL15RA | 4.53 | 0.01 | 3601 | ENSG00000134470 |
| ZNF256 | 4.52 | 0.01 | 10172 | ENSG00000152454 |
| C19orf53 | 4.50 | 0.05 | 28974 | ENSG00000104979 |
| DPH3 | 4.49 | 0.01 | 285381 | ENSG00000154813 |
| RNF216P1 | 4.49 | 0.03 | 441191 | ENSG00000196204 |
| NDUFV3 | 4.48 | 0.00 | 4731 | ENSG00000160194 |
| MARS | 4.48 | 0.02 | 4141 | ENSG00000166986 |
| MARCH3 | 4.48 | 0.05 | 115123 | ENSG00000173926 |
| RP9P | 4.47 | 0.01 | 441212 | ENSG00000205763 |
| ATPAF1 | 4.45 | 0.00 | 64756 | ENSG00000123472 |
| RNF31 | 4.45 | 0.00 | 55072 | ENSG00000092098 |
| SLC16A6 | 4.44 | 0.01 | 9120 | ENSG00000108932 |
| EIF3J | 4.44 | 0.00 | 8669 | ENSG00000104131 |
| EGR1 | 4.42 | 0.00 | 1958 | ENSG00000120738 |
| PRSS8 | 4.42 | 0.02 | 5652 | ENSG00000052344 |
| PPP4C | 4.42 | 0.01 | 5531 | ENSG00000149923 |
| GOLT1B | 4.41 | 0.00 | 51026 | ENSG00000111711 |
| TMEM79 | 4.41 | 0.02 | 84283 | ENSG00000163472 |
| | 4.41 | 0.00 | 100996307 | ENSG00000213904 |
| PTPRU | 4.41 | 0.04 | 10076 | ENSG00000060656 |
| TAZ | 4.35 | 0.03 | 6901 | ENSG00000102125 |
| C9orf40 | 4.35 | 0.00 | 55071 | ENSG00000135045 |

FIG. 20H

| | | | | |
|---|---|---|---|---|
| PIGM | 4.33 | 0.00 | 93183 | ENSG00000143315 |
| EIF4EBP1 | 4.33 | 0.01 | 1978 | ENSG00000187840 |
| C8orf76 | 4.33 | 0.04 | 84933 | ENSG00000189376 |
| DUSP10 | 4.32 | 0.00 | 11221 | ENSG00000143507 |
| ZNF200 | 4.28 | 0.00 | 7752 | ENSG00000010539 |
| DUSP18 | 4.28 | 0.03 | 150290 | ENSG00000167065 |
| LIMD2 | 4.27 | 0.02 | 80774 | ENSG00000136490 |
| POLR2D | 4.27 | 0.00 | 5433 | ENSG00000144231 |
| PARD6B | 4.27 | 0.00 | 84612 | ENSG00000124171 |
| TMEM234 | 4.27 | 0.01 | 56063 | ENSG00000160055 |
| ATP5G2P4 | 4.26 | 0.01 | | ENSG00000228847 |
| ZNF625 | 4.25 | 0.03 | 90589 | ENSG00000257591 |
| ZNF823 | 4.24 | 0.00 | 55552 | ENSG00000197933 |
| | 4.22 | 0.00 | | ENSG00000242615 |
| GTF2B | 4.21 | 0.00 | 2959 | ENSG00000137947 |
| CLP1 | 4.20 | 0.00 | 10978 | ENSG00000172409 |
| ZNF579 | 4.20 | 0.01 | 163033 | ENSG00000218891 |
| AGPAT9 | 4.19 | 0.00 | 84803 | ENSG00000138678 |
| SGK3 | 4.17 | 0.00 | 23678 | ENSG00000104205 |
| PSENEN | 4.16 | 0.03 | 55851 | ENSG00000205155 |
| HMGA1 | 4.15 | 0.01 | 3159 | ENSG00000137309 |
| SLC48A1 | 4.15 | 0.04 | 55652 | ENSG00000211584 |
| SPHK2 | 4.14 | 0.04 | 56848 | ENSG00000063176 |
| SMUG1 | 4.11 | 0.00 | 23583 | ENSG00000123415 |
| C6orf120 | 4.10 | 0.00 | 387263 | ENSG00000185127 |
| C14orf28 | 4.07 | 0.01 | 122525 | ENSG00000179476 |
| PGRMC1 | 4.03 | 0.00 | 10857 | ENSG00000101856 |
| LY6K | 4.02 | 0.05 | 54742 | ENSG00000160886 |
| RAB28 | 4.00 | 0.01 | 9364 | ENSG00000157869 |
| TMEM243 | 3.99 | 0.01 | 79161 | ENSG00000135185 |
| PCGF3 | 3.98 | 0.00 | 10336 | ENSG00000185619 |
| RAB40C | 3.98 | 0.03 | 57799 | ENSG00000197562 |
| TMED5 | 3.94 | 0.00 | 50999 | ENSG00000117500 |
| | 3.94 | 0.01 | | ENSG00000227267 |
| ZFAND5 | 3.94 | 0.00 | 7763 | ENSG00000107372 |
| JUNB | 3.93 | 0.01 | 3726 | ENSG00000171223 |
| UBAP2L | 3.92 | 0.00 | 9898 | ENSG00000143569 |
| NT5C3B | 3.89 | 0.00 | 115024 | ENSG00000141698 |
| PAQR7 | 3.89 | 0.00 | 164091 | ENSG00000182749 |
| MAPK6PS3 | 3.89 | 0.03 | | ENSG00000237263 |
| NHLRC3 | 3.89 | 0.00 | 387921 | ENSG00000188811 |
| GIPC1 | 3.88 | 0.01 | 10755 | ENSG00000123159 |
| CERS2 | 3.87 | 0.02 | 29956 | ENSG00000143418 |
| MAPK6 | 3.85 | 0.01 | 5597 | ENSG00000069956 |
| PRDM2 | 3.84 | 0.00 | 7799 | ENSG00000116731 |
| PNKD | 3.84 | 0.02 | 25953 | ENSG00000127838 |
| DNAJC27 | 3.83 | 0.00 | 51277 | ENSG00000115137 |

FIG. 20I

| | | | | |
|---|---|---|---|---|
| LIPH | 3.82 | 0.03 | 200879 | ENSG00000163898 |
| RHOG | 3.79 | 0.04 | 391 | ENSG00000177105 |
| YOD1 | 3.78 | 0.00 | 55432 | ENSG00000180667 |
| LBH | 3.78 | 0.01 | 81606 | ENSG00000213626 |
| LPCAT3 | 3.77 | 0.00 | 10162 | ENSG00000111684 |
| TEAD4 | 3.76 | 0.02 | 7004 | ENSG00000197905 |
| S100PBP | 3.75 | 0.00 | 64766 | ENSG00000116497 |
| SEMA4C | 3.74 | 0.03 | 54910 | ENSG00000168758 |
| S100A7 | 3.74 | 0.02 | 6278 | ENSG00000143556 |
| ZNF267 | 3.72 | 0.00 | 10308 | ENSG00000185947 |
| TMEM138 | 3.71 | 0.03 | 51524 | ENSG00000149483 |
| SUV420H2 | 3.71 | 0.00 | 84787 | ENSG00000133247 |
| SFXN2 | 3.70 | 0.02 | 118980 | ENSG00000156398 |
| POLE2 | 3.70 | 0.00 | 5427 | ENSG00000100479 |
| GNG5 | 3.67 | 0.01 | 2787 | ENSG00000174021 |
| ATP6V0D2 | 3.66 | 0.02 | 245972 | ENSG00000147614 |
| STK40 | 3.65 | 0.02 | 83931 | ENSG00000196182 |
| ASF1B | 3.65 | 0.00 | 55723 | ENSG00000105011 |
| PARP16 | 3.64 | 0.03 | 54956 | ENSG00000138617 |
| P2RX5 | 3.62 | 0.03 | 5026 | ENSG00000083454 |
| RNF5P1 | 3.62 | 0.01 | | ENSG00000253570 |
| SMAD7 | 3.62 | 0.01 | 4092 | ENSG00000101665 |
| PLAGL2 | 3.61 | 0.02 | 5326 | ENSG00000126003 |
| TK1 | 3.61 | 0.02 | 7083 | ENSG00000167900 |
| EFHD2 | 3.60 | 0.04 | 79180 | ENSG00000142634 |
| PHF19 | 3.59 | 0.01 | 26147 | ENSG00000119403 |
| CRTAP | 3.57 | 0.00 | 10491 | ENSG00000170275 |
| MED28 | 3.56 | 0.01 | 80306 | ENSG00000118579 |
| HDAC3 | 3.56 | 0.02 | 8841 | ENSG00000171720 |
| EPC1 | 3.56 | 0.00 | 80314 | ENSG00000120616 |
| GRK6P1 | 3.56 | 0.02 | | ENSG00000215571 |
| ETNK2 | 3.55 | 0.03 | 55224 | ENSG00000143845 |
| TRIP13 | 3.55 | 0.01 | 9319 | ENSG00000071539 |
| C3orf52 | 3.52 | 0.01 | 79669 | ENSG00000114529 |
| ELF3 | 3.51 | 0.02 | 1999 | ENSG00000163435 |
| HMMR | 3.50 | 0.00 | 3161 | ENSG00000072571 |
| PAQR3 | 3.49 | 0.00 | 152559 | ENSG00000163291 |
| GLB1L | 3.48 | 0.04 | 79411 | ENSG00000163521 |
| C15orf39 | 3.44 | 0.03 | 56905 | ENSG00000167173 |
| ERRFI1 | 3.43 | 0.00 | 54206 | ENSG00000116285 |
| NFKBIB | 3.43 | 0.05 | 4793 | ENSG00000104825 |
| AP3M1 | 3.42 | 0.00 | 26985 | ENSG00000185009 |
| LYPLA2 | 3.40 | 0.01 | 11313 | ENSG00000011009 |
| NAP1L4P3 | 3.38 | 0.04 | | ENSG00000234145 |
| MANSC1 | 3.38 | 0.01 | 54682 | ENSG00000111261 |
| E2F8 | 3.38 | 0.00 | 79733 | ENSG00000129173 |
| DHRS1 | 3.37 | 0.03 | 115817 | ENSG00000157379 |

FIG. 20J

| | | | | |
|---|---|---|---|---|
| ZNF526 | 3.37 | 0.03 | 116115 | ENSG00000167625 |
| XYLT2 | 3.37 | 0.04 | 64132 | ENSG00000015532 |
| PDE12 | 3.34 | 0.00 | 201626 | ENSG00000174840 |
| GGA3 | 3.34 | 0.02 | 23163 | ENSG00000125447 |
| GLTP | 3.33 | 0.01 | 51228 | ENSG00000139433 |
| TMEM54 | 3.33 | 0.02 | 113452 | ENSG00000121900 |
| RTCA | 3.33 | 0.00 | 8634 | ENSG00000137996 |
| WDR77 | 3.32 | 0.02 | 79084 | ENSG00000116455 |
| LYPLA1 | 3.32 | 0.00 | 10434 | ENSG00000120992 |
| CEBPG | 3.30 | 0.00 | 1054 | ENSG00000153879 |
| SERPINB8 | 3.30 | 0.03 | 5271 | ENSG00000166401 |
| GLMN | 3.29 | 0.01 | 11146 | ENSG00000174842 |
| ASTE1 | 3.28 | 0.02 | 28990 | ENSG00000034533 |
| SDE2 | 3.28 | 0.00 | 163859 | ENSG00000143751 |
| TCERG1 | 3.26 | 0.00 | 10915 | ENSG00000113649 |
| PRPF31 | 3.26 | 0.05 | 26121 | ENSG00000105618 |
| TMED4 | 3.25 | 0.03 | 222068 | ENSG00000158604 |
| CHRAC1 | 3.25 | 0.01 | 54108 | ENSG00000104472 |
| SECISBP2 | 3.24 | 0.01 | 79048 | ENSG00000187742 |
| ADIPOR1 | 3.24 | 0.01 | 51094 | ENSG00000159346 |
| MRPL15 | 3.24 | 0.00 | 29088 | ENSG00000137547 |
| MTF2 | 3.23 | 0.00 | 22823 | ENSG00000143033 |
| SPDEF | 3.22 | 0.01 | 25803 | ENSG00000124664 |
| TFAP2A | 3.22 | 0.00 | 7020 | ENSG00000137203 |
| MAGEA12 | 3.21 | 0.03 | 4111 | ENSG00000213401 |
| C3orf38 | 3.21 | 0.02 | 285237 | ENSG00000179021 |
| CNOT11 | 3.20 | 0.00 | 55571 | ENSG00000158435 |
| VAV3 | 3.20 | 0.00 | 10451 | ENSG00000134215 |
| LINC00116 | 3.20 | 0.05 | 205251 | ENSG00000175701 |
| CDC45 | 3.19 | 0.02 | 8318 | ENSG00000093009 |
| TMPRSS2 | 3.19 | 0.01 | 7113 | ENSG00000184012 |
| NAGA | 3.18 | 0.04 | 4668 | ENSG00000198951 |
| SLC10A7 | 3.16 | 0.02 | 84068 | ENSG00000120519 |
| SLC38A9 | 3.15 | 0.02 | 153129 | ENSG00000177058 |
| PMAIP1 | 3.13 | 0.01 | 5366 | ENSG00000141682 |
| TMEM41A | 3.13 | 0.00 | 90407 | ENSG00000163900 |
| TTC39A | 3.12 | 0.05 | 22996 | ENSG00000085831 |
| VEZT | 3.11 | 0.00 | 55591 | ENSG00000028203 |
| SLC37A4 | 3.11 | 0.03 | 2542 | ENSG00000137700 |
| BTF3L4P1 | 3.11 | 0.04 | | ENSG00000232260 |
| KDELR1 | 3.11 | 0.05 | 10945 | ENSG00000105438 |
| KIAA0141 | 3.10 | 0.03 | 9812 | ENSG00000081791 |
| DIAPH2 | 3.10 | 0.00 | 1730 | ENSG00000147202 |
| RMI2 | 3.09 | 0.01 | 116028 | ENSG00000175643 |
| C7orf43 | 3.08 | 0.04 | 55262 | ENSG00000146826 |
| BACH1 | 3.07 | 0.00 | 571 | ENSG00000156273 |
| SCYL1 | 3.07 | 0.03 | 57410 | ENSG00000142186 |

FIG. 20K

| | | | | |
|---|---|---|---|---|
| PIGA | 3.07 | 0.00 | 5277 | ENSG00000165195 |
| ERGIC2 | 3.06 | 0.00 | 51290 | ENSG00000087502 |
| WARS2 | 3.06 | 0.01 | 10352 | ENSG00000116874 |
| | 3.05 | 0.02 | | ENSG00000198744 |
| MAPKAPK5 | 3.03 | 0.00 | 8550 | ENSG00000089022 |
| TMEM237 | 3.03 | 0.00 | 65062 | ENSG00000155755 |
| LRP8 | 3.02 | 0.00 | 7804 | ENSG00000157193 |
| SLC35E3 | 3.01 | 0.05 | 55508 | ENSG00000175782 |
| SLC19A2 | 3.01 | 0.01 | 10560 | ENSG00000117479 |
| CDKAL1 | 3.00 | 0.01 | 54901 | ENSG00000145996 |
| COX18 | 2.98 | 0.01 | 285521 | ENSG00000163626 |
| AP1S1 | 2.98 | 0.04 | 1174 | ENSG00000106367 |
| PHACTR4 | 2.98 | 0.02 | 65979 | ENSG00000204138 |
| TRIM41 | 2.98 | 0.02 | 90933 | ENSG00000146063 |
| GPX8 | 2.95 | 0.00 | 493869 | ENSG00000164294 |
| NAP1L1 | 2.95 | 0.00 | 4673 | ENSG00000187109 |
| SLC35C2 | 2.95 | 0.05 | 51006 | ENSG00000080189 |
| TSPYL5 | 2.94 | 0.01 | 85453 | ENSG00000180543 |
| BIVM | 2.92 | 0.00 | 54841 | ENSG00000134897 |
| NLK | 2.88 | 0.05 | 51701 | ENSG00000087095 |
| PIGT | 2.86 | 0.01 | 51604 | ENSG00000124155 |
| ANP32E | 2.85 | 0.01 | 81611 | ENSG00000143401 |
| PAPD4 | 2.85 | 0.01 | 167153 | ENSG00000164329 |
| LACE1 | 2.85 | 0.02 | 246269 | ENSG00000135537 |
| LRIG3 | 2.85 | 0.00 | 121227 | ENSG00000139263 |
| FAM96A | 2.84 | 0.01 | 84191 | ENSG00000166797 |
| SERTAD3 | 2.83 | 0.05 | 29946 | ENSG00000167565 |
| RHOBTB3 | 2.82 | 0.00 | 22836 | ENSG00000164292 |
| SNX4 | 2.82 | 0.01 | 8723 | ENSG00000114520 |
| PLOD2 | 2.81 | 0.00 | 5352 | ENSG00000152952 |
| LYPLA1P3 | 2.81 | 0.03 | | ENSG00000218350 |
| TUBGCP3 | 2.81 | 0.03 | 10426 | ENSG00000126216 |
| BMP5 | 2.79 | 0.02 | 653 | ENSG00000112175 |
| FAM220A | 2.79 | 0.00 | 84792 | ENSG00000178397 |
| HES1 | 2.78 | 0.01 | 3280 | ENSG00000114315 |
| HSF2 | 2.78 | 0.00 | 3298 | ENSG00000025156 |
| TMTC4 | 2.78 | 0.03 | 84899 | ENSG00000125247 |
| DUSP4 | 2.78 | 0.01 | 1846 | ENSG00000120875 |
| LDB1 | 2.77 | 0.03 | 8861 | ENSG00000198728 |
| BORA | 2.77 | 0.02 | 79866 | ENSG00000136122 |
| DDHD1 | 2.76 | 0.01 | 80821 | ENSG00000100523 |
| PITPNM3 | 2.76 | 0.00 | 83394 | ENSG00000091622 |
| KLF8 | 2.75 | 0.03 | 11279 | ENSG00000102349 |
| SLC35F6 | 2.75 | 0.00 | 54978 | ENSG00000213699 |
| RANBP17 | 2.74 | 0.01 | 64901 | ENSG00000204764 |
| EYA3 | 2.74 | 0.02 | 2140 | ENSG00000158161 |
| TMEM167A | 2.73 | 0.03 | 153339 | ENSG00000174695 |

FIG. 20L

| | | | | |
|---|---|---|---|---|
| ZNF391 | 2.72 | 0.03 | 346157 | ENSG00000124613 |
| MED8 | 2.72 | 0.03 | 112950 | ENSG00000159479 |
| BTF3L4 | 2.71 | 0.01 | 91408 | ENSG00000134717 |
| GARS | 2.71 | 0.01 | 2617 | ENSG00000106105 |
| HM13 | 2.69 | 0.04 | 81502 | ENSG00000101294 |
| STX17 | 2.68 | 0.02 | 55014 | ENSG00000136874 |
| ARHGAP28 | 2.68 | 0.01 | 79822 | ENSG00000088756 |
| ABHD14B | 2.67 | 0.05 | 84836 | ENSG00000114779 |
| AMD1 | 2.66 | 0.00 | 262 | ENSG00000123505 |
| DHCR24 | 2.66 | 0.03 | 1718 | ENSG00000116133 |
| | 2.66 | 0.04 | | ENSG00000260000 |
| ARHGEF38 | 2.65 | 0.04 | 54848 | ENSG00000236699 |
| MOB4 | 2.64 | 0.00 | 25843 | ENSG00000115540 |
| CXXC5 | 2.63 | 0.05 | 51523 | ENSG00000171604 |
| GRK6 | 2.63 | 0.03 | 2870 | ENSG00000198055 |
| CDC25A | 2.62 | 0.03 | 993 | ENSG00000164045 |
| E2F6 | 2.62 | 0.02 | 1876 | ENSG00000169016 |
| KRT5 | 2.62 | 0.03 | 3852 | ENSG00000186081 |
| MCU | 2.62 | 0.01 | 90550 | ENSG00000156026 |
| CTPS2 | 2.59 | 0.02 | 56474 | ENSG00000047230 |
| ZNF738 | 2.59 | 0.04 | | ENSG00000172687 |
| CENPC1 | 2.59 | 0.04 | 1060 | ENSG00000145241 |
| MMD | 2.58 | 0.03 | 23531 | ENSG00000108960 |
| UBE2L6 | 2.57 | 0.01 | 9246 | ENSG00000156587 |
| RGS3 | 2.57 | 0.01 | 5998 | ENSG00000138835 |
| SNHG16 | 2.56 | 0.04 | 677848 | ENSG00000163597 |
| APH1A | 2.56 | 0.02 | 51107 | ENSG00000117362 |
| GPR115 | 2.55 | 0.03 | 221393 | ENSG00000153294 |
| RBM38 | 2.55 | 0.04 | 55544 | ENSG00000132819 |
| DNAJC1 | 2.54 | 0.04 | 64215 | ENSG00000136770 |
| RAB8B | 2.54 | 0.03 | 51762 | ENSG00000166128 |
| PNPO | 2.54 | 0.02 | 55163 | ENSG00000108439 |
| FCHO2 | 2.53 | 0.05 | 115548 | ENSG00000157107 |
| UBE2G2 | 2.52 | 0.03 | 7327 | ENSG00000184787 |
| ATG9A | 2.52 | 0.02 | 79065 | ENSG00000198925 |
| SERINC3 | 2.51 | 0.00 | 10955 | ENSG00000132824 |
| RAB40B | 2.49 | 0.04 | 10966 | ENSG00000141542 |
| CSNK1E | 2.49 | 0.03 | 1454 | ENSG00000213923 |
| SUB1 | 2.48 | 0.00 | 10923 | ENSG00000113387 |
| | 2.48 | 0.02 | | ENSG00000259144 |
| BIRC3 | 2.47 | 0.02 | 330 | ENSG00000023445 |
| PLP2 | 2.47 | 0.04 | 5355 | ENSG00000102007 |
| SLC35D1 | 2.47 | 0.01 | 23169 | ENSG00000116704 |
| RAD18 | 2.46 | 0.01 | 56852 | ENSG00000070950 |
| TBC1D20 | 2.45 | 0.04 | 128637 | ENSG00000125875 |
| FAR1 | 2.44 | 0.00 | 84188 | ENSG00000197601 |
| HN1 | 2.43 | 0.03 | 51155 | ENSG00000189159 |

FIG. 20M

| | | | | |
|---|---|---|---|---|
| TMEM41B | 2.42 | 0.01 | 440026 | ENSG00000166471 |
| KLHL42 | 2.42 | 0.01 | 57542 | ENSG00000087448 |
| SMARCAD1 | 2.41 | 0.00 | 56916 | ENSG00000163104 |
| DONSON | 2.41 | 0.01 | 29980 | ENSG00000159147 |
| NSMCE2 | 2.41 | 0.05 | 286053 | ENSG00000156831 |
| H2AFV | 2.41 | 0.00 | 94239 | ENSG00000105968 |
| VTA1 | 2.40 | 0.00 | 51534 | ENSG00000009844 |
| CTD-2369P2.2 | 2.37 | 0.03 | | ENSG00000175898 |
| C11orf57 | 2.37 | 0.02 | 55216 | ENSG00000150776 |
| GPR110 | 2.37 | 0.02 | 266977 | ENSG00000153292 |
| TGOLN2 | 2.35 | 0.00 | 10618 | ENSG00000152291 |
| LMNB1 | 2.35 | 0.01 | 4001 | ENSG00000113368 |
| IST1 | 2.34 | 0.01 | 9798 | ENSG00000182149 |
| ALG6 | 2.33 | 0.01 | 29929 | ENSG00000088035 |
| | 2.33 | 0.03 | | ENSG00000231386 |
| DNA2 | 2.32 | 0.00 | 1763 | ENSG00000138346 |
| VAMP3 | 2.32 | 0.02 | 9341 | ENSG00000049245 |
| CPNE2 | 2.31 | 0.01 | 221184 | ENSG00000140848 |
| ZNF443 | 2.31 | 0.05 | 10224 | ENSG00000180855 |
| RFFL | 2.30 | 0.02 | 117584 | ENSG00000092871 |
| C9orf41 | 2.30 | 0.05 | 138199 | ENSG00000156017 |
| NFS1 | 2.30 | 0.03 | 9054 | ENSG00000244005 |
| TOMM40 | 2.29 | 0.03 | 10452 | ENSG00000130204 |
| MED6 | 2.28 | 0.03 | 10001 | ENSG00000133997 |
| LRIG2 | 2.28 | 0.03 | 9860 | ENSG00000198799 |
| NOC3L | 2.27 | 0.00 | 64318 | ENSG00000173145 |
| RIOK2 | 2.27 | 0.05 | 55781 | ENSG00000058729 |
| ZNF697 | 2.27 | 0.02 | 90874 | ENSG00000143067 |
| MIDN | 2.26 | 0.02 | 90007 | ENSG00000167470 |
| HIST1H2AK | 2.25 | 0.04 | 8329 | ENSG00000184348 |
| CCNG1 | 2.25 | 0.01 | 900 | ENSG00000113328 |
| SLC6A9 | 2.24 | 0.03 | 6536 | ENSG00000196517 |
| ZNF141 | 2.24 | 0.02 | 7700 | ENSG00000131127 |
| PROSER1 | 2.23 | 0.04 | 80209 | ENSG00000120685 |
| MMGT1 | 2.22 | 0.00 | 93380 | ENSG00000169446 |
| FOXP1 | 2.21 | 0.04 | 27086 | ENSG00000114861 |
| KDELR2 | 2.21 | 0.03 | 11014 | ENSG00000136240 |
| ETFDH | 2.20 | 0.01 | 2110 | ENSG00000171503 |
| DPF2 | 2.20 | 0.04 | 5977 | ENSG00000133884 |
| MEF2C | 2.20 | 0.03 | 4208 | ENSG00000081189 |
| ATG12 | 2.19 | 0.02 | 9140 | ENSG00000145782 |
| | 2.18 | 0.04 | | ENSG00000249286 |
| KHSRP | 2.18 | 0.03 | 8570 | ENSG00000088247 |
| SSX2IP | 2.17 | 0.00 | 117178 | ENSG00000117155 |
| HBP1 | 2.16 | 0.01 | 26959 | ENSG00000105856 |
| B4GALT5 | 2.16 | 0.01 | 9334 | ENSG00000158470 |
| CHCHD1 | 2.16 | 0.01 | 118487 | ENSG00000172586 |

FIG. 20N

| | | | | |
|---|---|---|---|---|
| ZNF567 | 2.15 | 0.01 | 163081 | ENSG00000189042 |
| DZIP1 | 2.14 | 0.02 | 22873 | ENSG00000134874 |
| WDR37 | 2.14 | 0.04 | 22884 | ENSG00000047056 |
| PPP1R15B | 2.14 | 0.02 | 84919 | ENSG00000158615 |
| ATG16L1 | 2.13 | 0.03 | 55054 | ENSG00000085978 |
| CMAS | 2.11 | 0.00 | 55907 | ENSG00000111726 |
| MOB1A | 2.10 | 0.00 | 55233 | ENSG00000114978 |
| WDR41 | 2.10 | 0.01 | 55255 | ENSG00000164253 |
| C5orf30 | 2.09 | 0.02 | 90355 | ENSG00000181751 |
| CCNY | 2.08 | 0.02 | 219771 | ENSG00000108100 |
| GPCPD1 | 2.08 | 0.02 | 56261 | ENSG00000125772 |
| B4GALT4 | 2.08 | 0.03 | 8702 | ENSG00000121578 |
| DNAJB14 | 2.07 | 0.04 | 79982 | ENSG00000164031 |
| USPL1 | 2.07 | 0.02 | 10208 | ENSG00000132952 |
| SLC41A3 | 2.06 | 0.04 | 54946 | ENSG00000114544 |
| SOX13 | 2.06 | 0.04 | 9580 | ENSG00000143842 |
| SLC2A12 | 2.05 | 0.01 | 154091 | ENSG00000146411 |
| IKBKE | 2.04 | 0.03 | 9641 | ENSG00000143466 |
| LEPROTL1 | 2.02 | 0.02 | 23484 | ENSG00000104660 |
| CDH19 | 2.02 | 0.03 | 28513 | ENSG00000071991 |
| LYPD6 | 2.02 | 0.02 | 130574 | ENSG00000187123 |
| MRS2 | 2.02 | 0.01 | 57380 | ENSG00000124532 |
| HMGCS1 | 2.01 | 0.02 | 3157 | ENSG00000112972 |
| XPO6 | 2.00 | 0.02 | 23214 | ENSG00000169180 |

MIRNA TARGETS

RELATED APPLICATIONS

This application is the U.S. national stage pursuant to 35 U.S.C. § 371, of U.S. international application Ser. No. PCT/US2014/012046, filed Jan. 17, 2014, designating the United States and published in English on Jul. 24, 2014 as publication WO 2014/113668 A1, which claims priority to U.S. Provisional Application No. 61/754,392, filed Jan. 18, 2013. The entire contents of the aforementioned patent applications are incorporated herein by this reference.

STATEMENT OF RIGHTS TO INVENTIONS MADE UNDER FEDERALLY SPONSORED RESEARCH

This work was supported by the following grant from the Department of Defense (DOD) Breast Cancer Research Program (BCRP), Award No. W81XWH-11-1-0027. The Government has certain rights in the invention.

INCORPORATION BY REFERENCE

The Sequence Listing submitted in an ASCII text file, in accordance with 37 C.F.R. § 1.821(c) and (e), is incorporated by herein by reference. The text file name is "48218-528N01US_ST25.txt", the date of creation of the text file is Jun. 5, 2017, and the size of the ASCII text file in bytes is 1,128.

BACKGROUND OF THE INVENTION microRNAs (miRNAs) regulate key steps of cell differentiation and development by suppressing gene expression in a sequence-specific manner. In mammals, the active strand miRNA sequence (typically ~22 base pairs) is partially complementary to binding sites in the 3'UTR of genes, often with full complementarity to 7 or 8 nucleotides in the "seed region" (residues 2-9) of the miRNA. miRNAs can also bind to 5'UTRs and Coding regions (CDS) of mRNAs, as well as non-coding RNAs (ncRNAs). The partial/full complementarity to the seed region has been shown to be important, but not essential. miRNAs regulate the stability and expression of target mRNAs in a sequence-dependent manner to control most biological processes (Ambros, 2004; Bartel, 2009; He and Hannon, 2004). More than a thousand miRNAs are expressed in human cells, each potentially able to target hundreds of mRNAs. Most mRNAs, perhaps as many as 90%, are regulated by miRNAs (Lewis et al., 2005; Miranda et al., 2006). miRNAs can also regulate the stability/function of noncoding RNAs. Identification of miRNA target genes and the specific sequences they bind (miRNA recognition elements, MREs) is important for understanding miRNA function. Gene suppression in mammals is thought to occur primarily by inhibiting translation. However, miRNAs in mammals also cause mRNA decay.

Current approaches to identify miRNA targets are insufficient. The major tools that have been used are (1) bioinformatic algorithms that predict potential target genes that contain conserved complementary sequences in their 3'UTR to a seed region at the 5'-end of the miRNA active strand, and (2) analysis of mRNAs that are down-regulated when a miRNA is over-expressed.

The bioinformatic approach is hampered by the fact that the existing algorithms have a high margin of error (the majority of predicted genes are not real targets and some of the key targets, such as RAS for let-7, are not predicted). For many miRNAs, current algorithms predict hundreds or even thousands of potential targets, making it difficult to identify the most important targets.

Gene expression array analysis does not readily distinguish direct mRNA targets from mRNAs down-regulated through secondary effects and misses most target genes that are regulated by blocking translation rather than by mRNA degradation. Moreover, even when mRNA degradation occurs, changes in mRNA levels may be small (often less than 2-fold) and may be difficult to distinguish from background fluctuations, especially in genomewide surveys.

Even combining these 2 approaches still is not helpful in many situations. mRNA targets of miRNAs have been identified by their enrichment in co-immunoprecipitates with tagged Argonaute proteins in *Drosophila* and human cell lines overexpressing the miRNA of interest. However these studies have not been shown to identify new miRNA targets. Argonaute over-expression globally increases miRNA levels, perhaps obscuring the effect of an individual over-expressed miRNA. Accordingly, there is a need for new methods of isolating miRNA targets.

SUMMARY OF THE INVENTION

As described below, the present invention features methods for characterizing miRNA interactions and for detecting and isolating miRNA targets. The present invention provides a method for identifying miRNA targets involving isolating miRNA bound to RNAs and sequencing the RNAs to identify miRNA targets and consensus miRNA binding sites (miRNA response elements, or MREs). As applicants have found, this approach is useful and effective for identifying miRNA-regulated genes, for example miRNA targets of miR-522, which is implicated in triple-negative breast cancers. Triple-negative breast cancer (TNBC) refers to any breast cancer that does not express the genes for estrogen receptor (ER), progesterone receptor (PR) and Her2/neu. Triple-negative breast cancers (TNBCs) are defined by their lack of estrogen (ER), progesterone (PR), and Her2 receptors, and are an especially aggressive group of tumors that typically afflict younger women and have the worst prognosis of any breast tumor subtype.

In one aspect, the present invention provides a method of identifying a target of an miRNA (e.g., miR-522, miR-34a or let-7a), the method comprising isolating from a cell an miRNA-RNA complex; and identifying an RNA sequence as a target of the miRNA.

In one embodiment, the method further comprises contacting the isolated miRNA-RNA complex with RNase under conditions sufficient to degrade the RNA associated with the miRNA-RNA complex into RNA fragments. In a further embodiment, the method comprises determining the nucleic acid sequence of the RNA fragments.

In another aspect, the invention provides a method of identifying a target of an miRNA (e.g., miR-522, miR-34a or let-7a) involving isolating an miRNA-RNA complex from a cell; contacting the isolated miRNA-RNA complex with RNase under conditions sufficient to degrade the RNA associated with the miRNA-RNA complex into RNA fragments; determining the nucleic acid sequence of one or more of the RNA fragments; identifying an RNA sequence having the RNA fragment sequence as a target of the miRNA. In preferred embodiments, the miRNA is miR-522. In other preferred embodiments, the miRNA is miR-34a. In other preferred embodiments, the miRNA is let-7a.

In another aspect, the invention provides a method of identifying a microRNA response element involving isolating an miRNA-RNA complex from a cell; contacting the isolated miRNA-RNA complex with RNase under conditions sufficient to degrade the RNA associated with the miRNA-RNA complex into RNA fragments; determining the nucleic acid sequence of one or more of the RNA fragments to thereby identify an microRNA response element. In a related aspect, the invention provides a target RNA identified according to a method of any aspect described herein.

In another related aspect, the invention provides a miRNA response element identified according to a method of any aspect described herein.

In an additional related aspect, the invention provides a kit comprising components for performing a method of any aspect described herein. In various embodiments, the kit includes an RNase; one or more of nucleic acid standards, a biotinylated miRNA or miRNA mimic, streptavidin beads, reagents for labeling miRNAs, reagents for quantifying degree of target RNA enrichment, nucleic acid polymerases, nucleotides, nucleotide analogs, buffers, antibodies, labels, and combinations thereof. In certain embodiments, the kit further comprises one or more components that regulate the concentration or the downstream effects of the one or more interacting RNAs.

In various embodiments of any of the aspects delineated herein, the miRNA-RNA complex is isolated using a miRNA linked to biotin and a capture reagent comprising streptavidin. In various embodiments of any of the aspects delineated herein, the miRNA-RNA complex is isolated in the presence of a molecular crowding agent. In particular embodiments, the molecular crowding agent is one or more of Ficoll PM400, Ficoll PM70, dextran sulfate, Ficoll (Fc) 70 kDa (Fc70), Fc400 kDa (Fc400), trehalose, proline, polyethylene glycol (PEG) 4 kDa, and Dextran 670 kDa. In various embodiments of any of the aspects delineated herein, the miRNA-RNA complex is isolated in the presence of EDTA (10, 25, 50, 100, 200, 250, 500 mM).

In various embodiments of any of the aspects delineated herein, the RNase is an RNase capable of degrading single-stranded RNA. In particular embodiments, the RNase may be one or more of RNase T1, RNase A, RNase If, or MNase. In various embodiments of any of the aspects delineated herein, the miRNA-RNA complex is contacted with the RNase for 5, 10, 15, 20, 25, 30, 45, or 60 minutes. In various embodiments of any of the aspects delineated herein, the RNA fragments generated range in length from 5-500, 5-250, 5-100, 10-100, 15-60, or 15-50 nucleotides.

In various embodiments of any of the aspects delineated herein, the nucleic acid sequence of the RNA fragment is determined (e.g., by generating cDNA of the RNA fragments) by ion semiconductor sequencing, pyrosequencing, sequencing by synthesis, sequencing by ligation, or chain termination sequencing.

In various embodiments of any of the aspects delineated herein, the method comprises determining that one or more RNAs isolated in complex with the miRNA is enriched compared to one or more of cellular expression levels or control miR levels.

In various embodiments of any of the aspects delineated herein, the method further comprises analyzing one or more interacting RNAs isolated in complex with the miRNA by a technique selected from the group consisting of: reverse transcription (RT), polymerase chain reaction (PCR), sequence analysis, RNA and protein expression level analysis, network analysis, and combinations thereof.

In various embodiments of any of the aspects delineated here, the method further comprises target functional analysis.

The invention provides methods for isolating miRNA targets. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

By "biologic sample" is meant any tissue, cell, fluid, or other material derived from an organism.

As used herein, the term "biomarker" generally refers to a molecule that is differentially present in a sample taken from a subject of one phenotypic status (e.g., having a disease) as compared with another phenotypic status (e.g., not having the disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and of drug toxicity.

The term "combination therapy", as used herein, refers to those situations in which two or more different pharmaceutical agents are administered in overlapping regimens so that the subject is simultaneously exposed to both agents.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

As used herein, "expression" of a nucleic acid sequence refers to one or more of the following events: (1) production of an RNA template from a DNA sequence (e.g., by transcription); (2) processing of an RNA transcript (e.g., by splicing, editing, and/or 3' end formation); (3) translation of an RNA into a polypeptide or protein; (4) post-translational modification of a polypeptide or protein.

As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode RNA molecules (e.g., functional RNA molecules, such as rRNAs and/or tRNAs). For the purpose of clarity it is noted that, as used in the present application, the term "gene" generally refers to a portion of a nucleic acid that encodes an rRNA or a sensitive fungal gene, as will be clear from context to those of ordinary skill in the art.

As used herein, the term "gene product" or "expression product" generally refers to an RNA transcribed from the gene (pre- and/or post-processing) or a polypeptide (pre- and/or post-modification) encoded by an RNA transcribed from the gene.

As used herein, the term "hybridize" refers to the interaction between two complementary nucleic acid sequences. The phrase "hybridizes under high stringency conditions" describes an interaction that is sufficiently stable that it is maintained under art-recognized high stringency conditions. Guidance for performing hybridization reactions can be found, for example, in Current Protocols in Molecular Biology, John Wiley & Sons, N.Y., 6.3.1-6.3.6, 1989 (and in more recent updated editions), and in Sambrook et al., Molecular Cloning: A Laboratory Manual, 3rd ed., Cold Spring Harbor Laboratory Press, Cold Spring Harbor, 2001. Aqueous and nonaqueous methods are described in these references, and either can be used. Typically, for nucleic acid sequences over approximately 50-100 nucleotides in length, various levels of stringency are defined, such as low stringency (e.g., 6× sodium chloride/sodium citrate (SSC) at about 45° C., followed by two washes in 0.2×SSC, 0.1% SDS at least at 50° C. (the temperature of the washes can be increased to 55° C. for medium-low stringency conditions)); 2) medium stringency hybridization conditions utilize 6×SSC at about 45° C., followed by one or more washes in 0.2×SSC, 0.1% SDS at 60° C.; 3) high stringency hybridization conditions utilize 6×SSC at about 45° C., followed by one or more washes in 0.2×SSC, 0.1% SDS at 65° C.; and 4) very high stringency hybridization conditions are 0.5M sodium phosphate, 0.1% SDS at 65° C., followed by one or more washes at 0.2×SSC, 1% SDS at 65° C.) Hybridization under high stringency conditions occurs between sequences with a very high degree of complementarity. One of ordinary skill in the art will recognize that the parameters for different degrees of stringency will generally differ based various factors such as the length of the hybridizing sequences, whether they comprise RNA or DNA, etc. For example, appropriate temperatures for high, medium, or low stringency hybridization will generally be lower for shorter sequences such as oligonucleotides than for longer sequences.

As used herein, the term "identity" refers to the overall relatedness between polymeric molecules, e.g. between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95% or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using a NWSgapdna.CMP matrix.

As used herein, the term "IMPACT-seq (Identification of MREs by Pull-down and Alignment of Captive Transcripts—sequencing)" is meant to refer to a method used to identify miRNA target RNAs and MREs. In preferred embodiments, IMPACT-seq combines Pulldown-seq with RNase digestion.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel.

The term "microarray" or "array" is meant to include a collection or panel of nucleic acids or polypeptides arranged on a solid support (for example, a chip, plate, or bead).

As used herein, the term "microRNA" or "miRNA" refers to an RNAi agent that is approximately 21-23 nucleotides (nt) in length. miRNAs can range between 18-26 nucleotides in length. Typically, miRNAs are single-stranded. However, in various embodiments, miRNAs may be at least partially double-stranded. In certain embodiments, miRNAs may comprise an RNA duplex (referred to herein as a "duplex region") and may optionally further comprises one or two single-stranded overhangs. In various embodiments, an RNAi agents comprises a duplex region ranging from 15 to 29 bp in length and optionally further comprising one or two single-stranded overhangs. A miRNA may be formed from two RNA molecules that hybridize together, or may alternatively be generated from a single RNA molecule that includes a self-hybridizing portion. In general, free 5' ends of miRNA molecules have phosphate groups, and free 3' ends have hydroxyl groups. The duplex portion of an miRNA usually, but does not necessarily, comprise one or more bulges consisting of one or more unpaired nucleotides. One strand of an miRNA includes a portion that hybridizes with a target RNA. In certain embodiments of the invention, one strand of the miRNA is not precisely complementary with a region of the target RNA, meaning that the miRNA hybridizes to the target RNA with one or more mismatches. In other embodiments of the invention, one strand of the miRNA is precisely complementary with a region of the target RNA, meaning that the miRNA hybridizes to the target RNA with no mismatches. Typically, miRNAs are thought to mediate inhibition of gene expression by inhibiting translation of target transcripts. However, in various embodiments, miRNAs may mediate inhibition of gene expression by causing degradation of target transcripts.

A "microRNA agent" as that term is used herein, refers to an entity whose nucleotide sequence is substantially identical to that of a natural miRNA. As will be appreciated by those of ordinary skill in the art, naturally-occurring miRNAs are comprised of RNA. As will be further appreciated by those of ordinary skill in the art, RNA is a particularly labile chemical. Furthermore, a variety of strategies are known for preparing molecules that are structural mimics of RNA (and therefore have a "sequence" in the same sense as RNA) but that may, for example, have greater stability and/or somewhat altered hybridization characteristics. For example, in various embodiments, such structural mimics include one or more backbone modifications (e.g., substitution of phosphorothioate backbone structures for phosphodiester structures found in RNA) and/or one or more base modifications (e.g., 2'-OMe modifications). In various embodiments, such structural mimics are encompassed within "microRNA agent" as that term is used herein.

As used herein, the term, "miRNA response element (MRE)" refers to binding sites in RNA that microRNAs bind (e.g., in the 3' UTR of mRNAs). However, an miRNA may exhibit only partial complementarity to an mRNA target. MREs typically have a conserved stretch of ~7 nucleotides that are able to base pair with the 5' region of corresponding miRNAs. Matching sequences in miRNAs may be conserved and are termed "seed" regions, while the remainder of the MRE sequence is diverse.

As used herein, the term, "macromolecular crowding agent" refers to an agent that alters the properties of molecules in a solution by reducing the solvent available for other molecules (solvent exclusion), which has the result of increasing their effective concentrations. Crowding occurs when high concentrations of macromolecules are present (e.g., 300-400 mg/mL macromolecules), such as proteins in the cytosol of a cell. Useful macromolecular crowding agents are used at high concentration and are inert. Exemplary crowding agents include, without limitation, Ficoll PM400, Ficoll PM70, dextran sulfate, Ficoll (Fc) 70 kDa (Fc70), Fc400 kDa (Fc400), trehalose, proline, polyethylene glycol (PEG) 4 kDa, and Dextran 670 kDa.

As used herein, the term "miRNA target regulating factor" in its broadest sense, refers to any agent that, when administered to a cell, alters level and/or activity of an RNA that is also the target of an miRNA. In various embodiments, miRNA target regulating factors alters the level/activity to be higher in presence of agent than in absence. In various embodiments, the level or activity is at least about 1.1, about 1.2, about 1.3, about 1.4, about 1.5, about 1.6, about 1.7, about 1.8, about 1.9, about 2, about 2.5, about 3, about 3.5, about 4, about 4.5, about 5, about 6, about 7, about 8, about 9, about 10, about 11, about 12, about 13, about 14, about 15, about 16, about 17, about 18, about 19, about 20, to about 200 fold or even higher in the cell as to regulate the effect of this target as compared to not administering the siRNA. In various embodiments, miRNA target regulating factors alters the level/activity to be lower in presence of agent than in absence. In various embodiments, the level or activity is at least about 1.1, about 1.2, about 1.3, about 1.4, about 1.5, about 1.6, about 1.7, about 1.8, about 1.9, about 2, about 2.5, about 3, about 3.5, about 4, about 4.5, about 5, about 6, about 7, about 8, about 9, about 10, about 11, about 12, about 13, about 14, about 15, about 16, about 17, about 18, about 19, about 20, to about 200 fold or even lower in the cell as to regulate the effect of this target as compared to not administering the siRNA. In various embodiments, exemplary miRNA target regulating factors can include siRNA, shRNA, and/or miRNA. In various embodiments the siRNA, shRNA and/or miRNA targets RNA. Generally, miRNA target regulating factors include a portion that is substantially complementary to a target RNA. In various embodiments, miRNA target regulating factors are at least partly double-stranded. In various embodiments, miRNA target regulating factors are single-stranded. In various embodiments, miRNA target regulating factors may be composed entirely of natural RNA nucleotides (i.e., adenine, guanine, cytosine, and uracil). In various embodiments, miRNA target regulating factors may include one or more non-natural RNA nucleotides (e.g., nucleotide analogs, DNA nucleotides, etc.). Inclusion of non-natural RNA nucleic acid residues may be used to make the miRNA target regulating factors more resistant to cellular degradation than RNA. In various embodiments, the term "miRNA target regulating factor" may refer to any RNA, RNA derivative, and/or nucleic acid encoding an RNA that induces an RNAi effect (e.g., degradation of target RNA and/or inhibition of translation). In various embodiments, the miRNA target regulating factors may comprise a blunt-ended (i.e., without overhangs) dsRNA that can act as a Dicer substrate. For example, such an miRNA target regulating factor may comprise a blunt-ended dsRNA which is >25 base pairs length, which may optionally be chemically modified to abrogate an immune response.

As used herein, "non-coding RNAs (ncRNAs)" refers to non-protein coding transcripts longer than 200 nucleotides. The length limit distinguishes long ncRNAs from small regulatory RNAs such as microRNAs (miRNAs), short interfering RNAs (siRNAs), Piwi-interacting RNAs (piRNAs), and small nucleolar RNAs (snoRNAs). Non-coding RNAs include, for example, pseudogenes, antisense RNAs, promoter-associated long RNAs, transfer RNA (tRNA) and ribosomal RNA (rRNA), long intronic RNA (lncRNAs) and long intergenic non-coding RNAs (lincRNAs). Lnc RNA and lincRNA refers to long non-coding RNAs. LincRNAs are transcribed from non-coding DNA sequences between protein-coding genes.

As used herein, the term "nucleic acid," in its broadest sense, refers to any compound and/or substance that can be incorporated into an oligonucleotide chain. In various embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns.

As used herein, the term "pulldown-seq" is meant to refer to a pull-down method used to identify miRNA target RNAs by sequencing. A pull-down assay such a pulldown-seq tests direct, physical interaction between an miRNA of interest and its target(s). In preferred embodiments, pulldown-seq comprises streptavidin pull-down and sequencing of RNAs bound to a transfected biotinylated miRNA mimic.

By "reference" is meant a standard of comparison. For example, to validate RNA targets, one may compare the amount of enrichment pulled down by a miRNA compared to a control miRNA.

As used herein, the term "RNA interference" or "RNAi" refers to sequence-specific inhibition of gene expression and/or reduction in target RNA levels mediated by an at least partly double-stranded RNA, which RNA comprises a portion that is substantially complementary to a target RNA. Typically, at least part of the substantially complementary portion is within the double stranded region of the RNA. In various embodiments, RNAi can occur via selective intracellular degradation of RNA. In various embodiments, RNAi can occur by translational repression.

As used herein, the term "RNAi agent" refers to an RNA, optionally including one or more nucleotide analogs or modifications, having a structure characteristic of molecules that can mediate inhibition of gene expression through an RNAi mechanism. In various embodiments, RNAi agents mediate inhibition of gene expression by causing degradation of target transcripts. In various embodiments, RNAi agents mediate inhibition of gene expression by inhibiting translation of target transcripts. Generally, an RNAi agent includes a portion that is substantially complementary to a target RNA. In various embodiments, RNAi agents are at least partly double-stranded. In various embodiments, RNAi agents are single-stranded. In various embodiments, exemplary RNAi agents can include siRNA, shRNA, and/or miRNA. In various embodiments, RNAi agents may be composed entirely of natural RNA nucleotides (i.e., adenine, guanine, cytosine, and uracil). In various embodiments, RNAi agents may include one or more non-natural RNA nucleotides (e.g., nucleotide analogs, DNA nucleotides, etc.). Inclusion of non-natural RNA nucleic acid residues may be used to make the RNAi agent more resistant to cellular degradation than RNA. In various embodiments, the term "RNAi agent" may refer to any RNA, RNA derivative, and/or nucleic acid encoding an RNA that induces an RNAi effect (e.g., degradation of target RNA and/or inhibition of translation). In various embodiments, an RNAi agent may comprise a blunt-ended (i.e., without overhangs) dsRNA that can act as a Dicer substrate. For example, such an RNAi agent may comprise a blunt-ended dsRNA which is .gtoreq.25 base pairs length, which may optionally be chemically modified to abrogate an immune response.

As used herein, the term "RNAi-inducing entity" encompasses any entity that delivers, regulates, and/or modifies the activity of an RNAi agent. In various embodiments, RNAi-inducing entities may include vectors (other than naturally occurring molecules not modified by the hand of man) whose presence within a cell results in RNAi and leads to reduced expression of a transcript to which the RNAi-inducing entity is targeted. In various embodiments, RNAi-inducing entities are RNAi-inducing vectors. In various embodiments, RNAi-inducing entities are compositions comprising RNAi agents and one or more pharmaceutically acceptable excipients and/or carriers.

As used herein, the term "RNAi-inducing vector" refers to a vector whose presence within a cell results in production of one or more RNAs that self-hybridize or hybridize to each other to form an RNAi agent (e.g. siRNA, shRNA, and/or miRNA). In various embodiments of the invention this term encompasses plasmids, e.g., DNA vectors (whose sequence may comprise sequence elements derived from a virus), or viruses (other than naturally occurring viruses or plasmids that have not been modified by the hand of man), whose presence within a cell results in production of one or more RNAs that self-hybridize or hybridize to each other to form an RNAi agent. In general, the vector comprises a nucleic acid operably linked to expression signal(s) so that one or more RNAs that hybridize or self-hybridize to form an RNAi agent are transcribed when the vector is present within a cell.

Thus the vector provides a template for intracellular synthesis of the RNA or RNAs or precursors thereof. For purposes of inducing RNAi, presence of a viral genome in a cell (e.g., following fusion of the viral envelope with the cell membrane) is considered sufficient to constitute presence of the virus within the cell. In addition, for purposes of inducing RNAi, a vector is considered to be present within a cell if it is introduced into the cell, enters the cell, or is inherited from a parental cell, regardless of whether it is subsequently modified or processed within the cell. An RNAi-inducing vector is considered to be targeted to a transcript if presence of the vector within a cell results in production of one or more RNAs that hybridize to each other or self-hybridize to form an RNAi agent that is targeted to the transcript, i.e., if presence of the vector within a cell results in production of one or more RNAi agents targeted to the transcript.

As used herein, the term "short, interfering RNA" or "siRNA" refers to an RNAi agent comprising an RNA duplex (referred to herein as a "duplex region") that is approximately 19 basepairs (bp) in length and optionally further comprises one or two single-stranded overhangs. In various embodiments, an RNAi agents comprises a duplex region ranging from 15 to 29 bp in length and optionally further comprising one or two single-stranded overhangs. An siRNA may be formed from two RNA molecules that hybridize together, or may alternatively be generated from a single RNA molecule that includes a self-hybridizing portion. In general, free 5' ends of siRNA molecules have phosphate groups, and free 3' ends have hydroxyl groups. The duplex portion of an siRNA may, but typically does not, comprise one or more bulges consisting of one or more unpaired nucleotides. One strand of an siRNA includes a portion that hybridizes with a target RNA. In certain embodiments of the invention, one strand of the siRNA is precisely complementary with a region of the target RNA, meaning that the siRNA hybridizes to the target RNA without a single mismatch. In other embodiments of the invention one or more mismatches between the siRNA and the targeted portion of the target RNA may exist. In various embodiments of the invention in which perfect complementarity is not achieved, any mismatches are generally located at or near the siRNA termini. In various embodiments, siRNAs mediate inhibition of gene expression by causing degradation of target transcripts.

As used herein, the term "short hairpin RNA" or "shRNA" refers to an RNAi agent comprising an RNA having at least two complementary portions hybridized or capable of hybridizing to form a double-stranded (duplex)

structure sufficiently long to mediate RNAi (typically at least approximately 19 bp in length), and at least one single-stranded portion, typically ranging between approximately 1 and 10 nucleotides (nt) in length that forms a loop. In various embodiments, an shRNA comprises a duplex portion ranging from 15 to 29 bp in length and at least one single-stranded portion, typically ranging between approximately 1 and 10 nt in length that forms a loop. The duplex portion may, but typically does not, comprise one or more bulges consisting of one or more unpaired nucleotides. In various embodiments, siRNAs mediate inhibition of gene expression by causing degradation of target transcripts. shRNAs are thought to be processed into siRNAs by the conserved cellular RNAi machinery. Thus shRNAs may be precursors of siRNAs. Regardless, siRNAs in general are capable of inhibiting expression of a target RNA, similar to siRNAs.

As used herein, the term, a "small molecule" is understood in the art to be an organic molecule that is less than about 5 kilodaltons (Kd) in size. In various embodiments, the small molecule is less than about 3 Kd, 2 Kd, or 1 Kd. In various embodiments, the small molecule is less than about 800 daltons (D), 600 D, 500 D, 400 D, 300 D, 200 D, or 100 D. In various embodiments, small molecules are non-polymeric. In various embodiments, small molecules are not proteins, peptides, or amino acids. In various embodiments, small molecules are not nucleic acids or nucleotides. In various embodiments, small molecules are not saccharides or polysaccharides.

The term "subject" or "patient" refers to an animal, which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "specifically binds" is meant an affinity agent (e.g., an miRNA) that recognizes and binds a compound or agent of interest (e.g., a RNA), but which does not substantially recognize and bind other molecules in a sample, for example, a biological sample.

As used herein, the terms "prevent," "preventing," "prevention," "prophylactic treatment," and the like, refer to reducing the probability of developing a disease or condition in a subject, who does not have, but is at risk of or susceptible to developing a disease or condition, e.g., neoplasia.

As used herein, the terms "treat," treating," "treatment," and the like refer to reducing or ameliorating a disease or condition, e.g., neoplasia, and/or symptoms associated therewith. It will be appreciated that, although not precluded, treating a disease or condition does not require that the disease, condition, or symptoms associated therewith be completely eliminated.

As used herein, the term "target functional analysis" is meant to refer to a method of analysis based on the combinatorial functional and pathway analysis of identified miRNA target genes and their potential regulatory transcription factors, as well as miRNA-downregulated genes.

As used herein, "vector" refers to a nucleic acid molecule capable of mediating entry of (e.g., transferring, transporting, etc.) a second nucleic acid molecule into a cell. The transferred nucleic acid is generally linked to (e.g., inserted into) the vector nucleic acid molecule. A vector may include sequences that direct autonomous replication, or may include sequences sufficient to allow integration into cellular DNA.

As used herein, the terms "comprises," "comprising," "containing," "having" and the like can have the meaning ascribed to them in U.S. Patent law and can mean "includes," "including," and the like. The term "including" is used herein to mean, and is used interchangeably with, the phrase "including but not limited to." The terms "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. Unless specifically stated or obvious from context, as used herein, the term "or" is understood to be inclusive. Any compounds, compositions, or methods provided herein can be combined with one or more of any of the other compositions and methods provided herein.

BRIEF DESCRIPTION OF THE DRAWINGS

FIGS. 3A-B depict technical validation of miR-522 Pulldown-seq and over-expression microarray datasets by RT-PCR.

FIGS. 6A-C show bioinformatics analysis of miR-522 target genes. (A) TRANSFAC analysis of promoter regions of miR-522 target genes identified enrichment of binding sites for 4 transcription factors. (B) Top enriched functions of directly associated miRNA-522 targets by Ingenuity Pathway Analysis (IPA). IPA Score=−log 10(p-value). Epithelial-mesenchymal transition (EMT)-related functions are indicated in grey. (C) Bubble plot of the IPA molecular function p-values of directly associated miR-522 targets plotted against interactome genes that were down-regulated by miR-522 over-expression (p-value <0.0001, FC >1.5). The size of each bubble is proportional to the number of miR-522 target genes assigned to that molecular function. Bubbles are selectively annotated based on low p-values and large size and noted by overall function.

FIGS. 9A-C show whether miR-522 affects stem cell or epithelial marker expression. (A) Expression of epithelial genes encoding E-cadherin (CDH1) or the cytokeratins (KRT14, KRT18, KRT19) did not change, but stem cell marker genes CD44 and CD133 increased upon miR-522 overexpression. (B) and (C) show data related to whether miR-522 induced changes in the stem cell-like population, as defined by the CD44+/CCD24low/− phenotype.

FIG. 12 is a chart showing summary Statistics for Pulldown-seq+IMPACT-seq miRNA Target Discovery Strategy. A summary is shown of the various experiments used to validate miRNA targets as identified by this strategy, showing a post-transcriptional positive validation rate of more than 70%.

FIG. 14 shows bioinformatics analysis of miR-34a target genes. (A) TRANSFAC analysis of promoter regions of miR-34a target genes identified enrichment of binding sites for 5 transcription factors. (B) Top enriched functions of directly associated miR-34a targets by Ingenuity Pathway Analysis (IPA). IPA Score=−log 10(p-value). Developmentally related functions are indicated in grey.

FIG. 18A-FIG. 18L is a Table that shows common molecular functions overrepresented in both the Pulldown-seq interactome and set of 205 directly connected genes whose mRNAs were significantly down-regulated by microarray analysis after miR-522 over-expression (p-value <0.0001 and fold change >1.5).

FIG. 19A-FIG. 19P is a Table that details the RNA targets for miR-34a identified by Pulldown-seq.

FIG. 20A-FIG. 20N is a Table that details the RNA targets for let-7a identified by Pulldown-seq.

DETAILED DESCRIPTION OF THE INVENTION

Figure 1A:
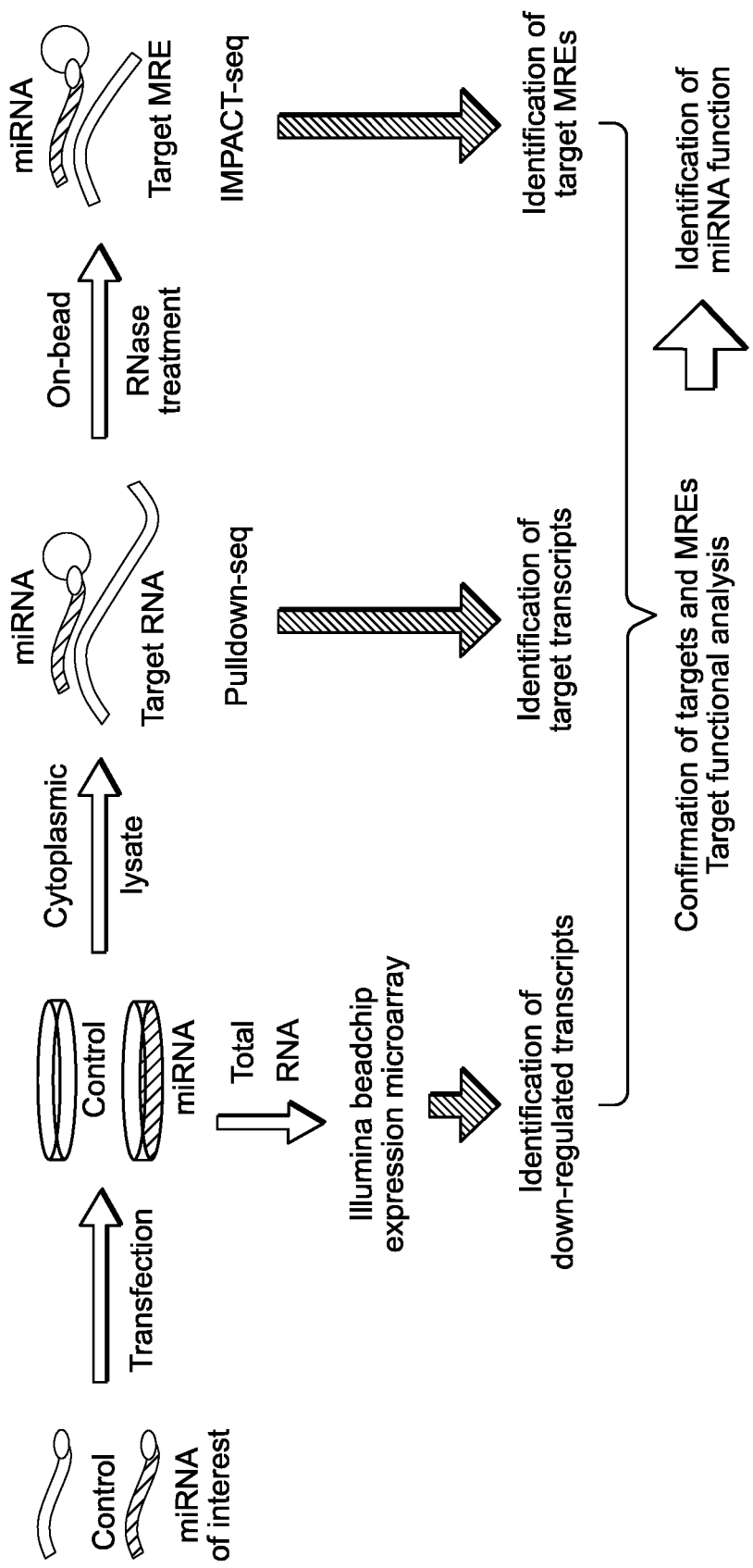
FIG. 1A is a schematic depicting the three-pronged strategy (Pulldown-seq, IMPACT-seq and Target Functional Analysis) for defining and validating miRNA target RNAs and MREs.

The invention features systems and methods for identifying, isolating, and/or characterizing microRNAs and their targets. The present invention provides, among other things, a discovery that a combination of biochemical interaction assays involving the use of a tagged microRNA (herein referred to as "pull-down assays") and sequence analysis of RNAs isolated as bound to the tagged microRNA (e.g., sequencing and sequence alignment) allowed for the ready identification of biologically relevant targets of microRNAs. Although some examples of miRNA gene regulation pathways have emerged by thoughtful mining of miRNA target prediction algorithms and differential mRNA expression profiling, the unpublished examples of failures using this approach are probably much more common. In some cases predicted target RNA/MREs are not biologically functional/relevant (e.g., if the miRNA and the candidate miRNA target are differentially expressed temporally). Other methods have been developed, for example CLIP-seq or PAR-CLIP, which pull-down Ago2 to identify all miRNAs and their targets. The disadvantage with these methods is that they sequence the miRNAs separately from the mRNAs, and subsequently identify specific miRNA targets based on target prediction algorithms.

As described herein, the methods of the invention identified RNAs and MREs, including those that were novel and not predicted by algorithms, as well as those predicted by target algorithms. The approach taken in the present invention is a biochemical one that takes a specific miRNA of interest and shows direct interaction with its target RNAs in a specific cell of interest. The present invention demonstrates that biologically interacting targets of miRNAs may differ from those predicted by available algorithms and other techniques. The present invention also provides kits for the detection of miRNAs and identification of drug targets, as well as drug screening and therapeutic applications.

As detailed herein, miRNAs post-transcriptionally regulate the stability and expression of their RNA targets in a sequence-dependent manner to regulate many diverse and fundamental biological processes. The identification of miRNA targets and the regions they bind to (miRNA response elements, or MREs) is important for understanding miRNA function, and has traditionally relied on target prediction algorithms. Presented here is a novel biochemical and bioinformatics strategy to identify miRNA targets, and more importantly, MREs, as well as predict miRNA biological function. These methods are: Pulldown-seq, involving streptavidin pull-down and sequencing of RNAs bound to a transfected biotinylated miRNA mimic, IMPACT-seq (Identification of MREs by Pull-down and Alignment of Captive Transcripts—sequencing) which combines Pulldown-seq with RNase digestion, and Target functional analysis, based on the combinatorial functional and pathway analysis of identified miRNA target genes and their potential regulatory transcription factors, as well as miRNA-down-regulated genes. As proof of principle, known and predicted target mRNAs for let-7a and miR-34a were identified and validated.

Through its exemplary application to miR-522, the present invention, among other things, demonstrates that miR-522, a previously uncharacterized primate-specific miRNA implicated in triple-negative breast cancers (TNBCs), regulates a network of genes that control cell proliferation, detachment, migration, and epithelial-mesenchymal transition. miR-522 overexpression reduced mRNA and protein levels, and luciferase activity of >70% of a random list of candidate target genes and MREs. Target functional analysis predicted that miR-522 regulates cell proliferation, detachment, migration, and epithelial-mesenchymal transition. Experimentally, miR-522 induces G1 cell-cycle arrest, causes cells to detach without anoikis, become invasive, and express mesenchymal genes. Thus, it was demonstrated that this strategy provides a specific, sensitive and high-throughput method to identify biologically relevant candidate miRNA-regulated RNAs and their MREs, without relying on target prediction algorithms.

Accordingly, the invention provides for systems and methods that are useful in methods for identifying, isolating, and/or characterizing microRNAs and their targets. The invention further provides also provides kits for the detection of miRNAs and identification of drug targets, as well as drug screening and therapeutic applications.

MicroRNAs

A microRNA (miRNA) is a small RNA molecule (~22 nucleotides) that functions in the post-transcriptional regulation of gene expression. Encoded by eukaryotic nuclear DNA, miRNAs function via base-pairing with complementary sequences within mRNA molecules, usually resulting in gene silencing via translational repression or target degradation. The human genome may encode over 1000 miRNAs, which may target more than 60% of mammalian genes and are abundant in many human cell types.

miRNAs are well conserved in eukaryotic organisms and are thought to be a vital and evolutionarily ancient component of genetic regulation. While core components of the microRNA pathway are conserved between plants and animals, miRNA repertoires in the two kingdoms appear to have evolved independently with different modes of function. Plant miRNAs usually have perfect or near-perfect pairing with their messenger RNA targets and induce gene repression through degradation of their target transcripts. Animal miRNAs typically exhibit only partial complementarity to their mRNA targets. A 'seed region' of about 6-8 nucleotides in length at the 5' end of an animal miRNA is thought to be an important determinant of target specificity. Combinatorial regulation is a feature of miRNA regulation. A given miRNA may have multiple different mRNA targets, and a given target might similarly be targeted by multiple miRNAs.

The mature miRNA (~22 nucleotides) is part of an active RNA-induced silencing complex (RISC) containing Dicer and many associated proteins. RISC is also known as a microRNA ribonucleoprotein complex (miRNP); RISC with incorporated miRNA is sometimes referred to as "miRISC." Dicer processing of the pre-miRNA is thought to be coupled with unwinding of the duplex. Generally, only one strand is incorporated into the miRISC, selected on the basis of its thermodynamic instability and weaker base-pairing relative to the other strand. The position of the stem-loop may also influence strand choice. The other strand, called the passenger strand due to its lower levels in the steady state, is denoted with an asterisk (*) and is normally degraded. In some cases, both strands of the duplex are viable and become functional miRNA that target different mRNA populations.

Members of the Argonaute (Ago) protein family are central to RISC function. Argonautes are needed for miRNA-induced silencing and contain two conserved RNA binding domains: a PAZ domain that can bind the single stranded 3' end of the mature miRNA and a PIWI domain that structurally resembles ribonuclease-H and functions to interact with the 5' end of the guide strand. They bind the mature miRNA and orient it for interaction with a target mRNA. Some argonautes, for example human Ago2, cleave target transcripts directly; argonautes may also recruit additional proteins to achieve translational repression. The human genome encodes eight argonaute proteins divided by sequence similarities into two families: AGO (with four members present in all mammalian cells and called E1F2C/hAgo in humans), and PIWI (found in the germ line and hematopoietic stem cells). Additional RISC components include TRBP [human immunodeficiency virus (HIV) trans-activating response RNA (TAR) binding protein], PACT (protein activator of the interferon induced protein kinase (PACT), the SMN complex, fragile X mental retardation protein (FMRP), Tudor staphylococcal nuclease-domain-containing protein (Tudor-SN), the putative DNA helicase MOV10, and the RNA recognition motif containing protein TNRC6B The present invention provides systems that allow identification of targets of microRNAs. As will be appreciated by those of ordinary skill, the inventive methods can be applied to identify targets of any of a variety of microRNAs. Representative such miRNAs include, for example, let-7 (e.g., let-7a, let-7b, let-7c, let-7d, let-7e, let-7f, let-7g, let-7i), miR-89, miR-522, miR-519a, miR-22, miR-125a, miR-24 (e.g., miR-24-1, miR-24-2), miR-23 (e.g., miR-23a, miR-23B), miR-27 (e.g., miR-27a, miR-27b), miR-17, miR-18, miR-19, miR-20, miR-34 (e.g., miR-34a, miR-34b, miR-34c), miR-92, miR-125, miR-146a, miR-155, miR-181a, 200a, miR-48, and miR-84. In preferred embodiments, the miRNA is miR-522. In other preferred embodiments, the miRNA is miR-34a. In other preferred embodiments, the miRNA is let-7a.

In various embodiments, the miRNA whose targets are identified in accordance with the present invention is one whose expression level increases or decreases during a particular developmental stage of interest or in response to a particular trigger or event of interest. For example, in various embodiments, the miRNA is one whose expression level changes during terminal differentiation. To give but one specific example, in various embodiments, the miRNA is up-regulated during terminal differentiation of hematopoietic cells.

In various embodiments, an miRNA whose expression changes during a particular developmental stage of interest, or in response to a particular trigger or event of interest, increases or decreases at least about 2, 3, 4, 5, 6, 7, 8, 9, 10, 20, 30, 40, 50, 60, 70, 80, 90, 100 fold or more.

In various embodiments, the miRNA whose targets are identified in accordance with the present invention is one that regulates cell cycle progression. In various embodiments, the miRNA suppresses the expression of cell cycle regulator genes. In various embodiments, the miRNA is characterized in that its overexpression increases the number of cells in the G1 phase; in various embodiments, the miRNA is characterized in that its inhibition causes differentiating cells to keep proliferating.

In various embodiments, the miRNA targets genes that initiate pathways such as synthesis of DNA building blocks; DNA replication; DNA damage recognition; expression, transcriptional regulation, and/or post-translational modification of cyclins, cyclin-dependent kinases, and/or other cell cycle regulators. In various embodiments, the miRNA targets MYC, E2F, and/or their targets.

In various embodiments, the miRNA targets genes that are implicated in progression through the cell cycle, for example, through G1, the G1/S checkpoint, S, and/or G2/M.

In various embodiments, the miRNA is selected from the group consisting of miR-522 and/or other miRNAs in the same cluster. In various embodiments, the miRNA is miR-22 or miR-125a. For example, in various embodiments, the miRNA is selected from the group consisting of miR-522, miR-24 (e.g., miR-24-1; miR-24-2), miR-23 (e.g., miR-23a, miR-23B), and miR-27 (e.g., miR-27a, miR-27b), etc. In various embodiments, the miRNA is a member of the let-7 family of miRNAs. In various embodiments, the miRNA is selected from the group consisting of miR-48, miR-84, and miR-241. In various embodiments, the miRNA is selected from the group consisting of miR-17, miR-18, miR-19, miR-20, miR-34a, miR-92, miR-125, miR-146a, miR-155, miR-181a, 200a. In various embodiments, the miRNA is one that is found on chromosome 9, or on chromosome 19. In various embodiments, the miRNA is one that is found in an intergenic region of a chromosome (e.g., chromosome 19). In various embodiments, the miRNA is a viral miRNA. In various embodiments, the miRNA is a member of the Herpes virus family. In various embodiments, the miRNA is miR-K12-11.

Pull-Down Technologies

The present invention combines use of interaction assays, or pull-down assays, with the analyses (e.g. bioinformatic analyses), to identify targets of microRNAs.

According to the present invention, a pull-down assay tests direct, physical interaction between an miRNA of interest and its target(s). In various embodiments, pull-down technologies for use in accordance with the present invention isolate RNAs (e.g. mRNAs, non-coding RNAs (ncRNAs), Long intergenic non-coding RNAs (lincRNAs), and the like) that are specifically bound to an miRNA and/or miRNA complex of interest.

For example, in various embodiments, interacting RNAs are isolated by increasing levels of the miRNA of interest in a cell, and then identifying RNAs (or other factors) associated with the overexpressed miRNA. An increase in miRNA level can be achieved by any of a variety of available means including, for example, transfection, injection, induction, etc. Those of ordinary skill in the art will appreciate that pull-down assays may be performed utilizing a natural miRNA molecule, but will further appreciate that a variety of strategies are known for preparing molecules that are structural mimics of RNA (and therefore have a "sequence" in the same sense as RNA) but that may, for example, have greater stability and/or somewhat altered hybridization characteristics.

For example, in various embodiments, such structural mimics include one or more backbone modifications (e.g., substitution of phosphorothioate backbone structures for phosphodiester structures found in RNA) and/or one or more base modifications (e.g., 2'-OMe modifications). In various embodiments, such structural mimics are locked nucleic acids (LNAs; see, for example, U.S. Pat. No. 6,977,295). Use of such miRNA mimics is encompassed by the present invention; those of ordinary skill will readily appreciate when discussions of miRNAs herein can relate to such mimics. In various embodiments, such miRNAs mimics have increased stability as compared with the natural miRNA. In various embodiments, miRNA mimics bind with greater affinity and/or specificity to the same target(s) bound by the natural miRNA. In various embodiments, such greater affinity and/or specificity is at least about 1.5, 2, 2.5, 3, 3.5, 4, 4.5, 5, 5.5, 6, 6.5, 7, 7.5, 8, 8.5, 9, 9.5, 10 or more (e.g. 15, 20, 25, 30, 35, 40, 45, 50, 75, 100, 200, 300, 400, 500, 1000 or more) fold higher than that observed with the natural miRNA.

In various embodiments, an increased level of miRNA is about at least 1, 2, 3, 4, 5, 6, 7, 8, 9, 10, or more (e.g. 20, 30, 40, 50, 60, 70, 80, 90, 100 or more) fold compared with levels of endogenous miRNA. Those of ordinary skill in the art will readily appreciate that different target RNAs (and/or different amounts of a given target RNA) may be found in (and therefore identified and/or isolated from as described herein) different cell types.

In various embodiments, interacting RNAs are isolated by increasing levels of the miRNA of interest in a cell that itself underexpresses the miRNA of interest (e.g. has a low endogenous expression level as compared with other cells).

In various embodiments, miRNA-target complexes are isolated. In various embodiments, such isolation includes isolation of a cellular fraction. In various embodiments, the cellular fraction is or comprises a polysome fraction. In various embodiments, the present invention encompasses the recognition that isolation of a cellular fraction (e.g. a polysome fraction) can improve accuracy of target identification. In various embodiments, the present invention provides the recognition that the miRNA profile maybe greater than 80% in the dense polysome fractions. In various embodiments, the miRNA profile in polysome fractions may be indistinguishable from the profile of endogenous miRNA in the same cells.

According to other embodiments, the isolating step is performed in the presence of a macromolecular crowding agent. As described herein, a macromolecular crowding agent is an agent that alters the properties of molecules in a solution by reducing the solvent available for other molecules (solvent exclusion), which has the result of increasing their effective concentrations. Exemplary crowding agents include, without limitation, Ficoll PM400, Ficoll PM70, dextran sulfate, Ficoll (Fc) 70 kDa (Fc70), Fc400 kDa (Fc400), trehalose, proline, polyethylene glycol (PEG) 4 kDa, and Dextran 670 kDa.

In various embodiments, the overexpressed miRNA is labeled (e.g. directly or indirectly). In various embodiments, an miRNA sense strand is labeled; in various embodiments, and miRNA anti-sense strand is labeled; in various embodiments, both sense and antisense strands are labeled. In various embodiments, a label is covalently associated with the miRNA. In various embodiments, a label is covalently or non-covalently associated with the 5' end of an miRNA strand. In various embodiments a label is covalently or non-covalently associated with the 3' end of an miRNA strand.

It may be desirable to utilize a label that does not interfere with activity of the miRNA. For example, in various embodiments, labeled miRNA is still incorporated into RISC. Ability to be incorporated into RISC can be assayed by any of a variety of means including, for example, by (1) microscopy to show colocalization of the labeled miRNA with processing bodies (P bodies), and (2) immunoblot analysis of Ago1 and Ago2 enrichment in pull-down fractions. In various embodiments, labeled miRNA retains silencing activity, for example when tested on a model silencing construct. As will be clear to those of ordinary skill in the art, any of a variety of labels may be utilized in accordance with the present invention. In various embodiments, the label is one that facilitates isolation of the miRNA, for example when complexed with one or more target RNAs. According to the present invention, as illustrated in the Examples, biotin represents an appropriate and useful label, as biotin has high affinity for streptavidin, which can be used to capture biotin tagged molecules. In various embodiments of the present invention, pull-down assays enrich target RNAs by a factor of 2, 3, 4, 5, 6, 7, 8, 9, 10, 20, 30, 40, 50, 60, 70, 80, 90, 100, 120, 140, 160, 180, 200, 250, 300, 350, 400, 450, 500, 550, 600, 650, 700, 750, 800, 850, 900, 950, 1000, or more as compared with their cellular expression level. Among other things, the present invention encompasses the recognition that normalization of pulled-down target RNA levels to cellular levels of the same RNA can materially facilitate determination of true targets. Those of ordinary skill in the art will be aware of a variety of strategies for performing such normalization including, for example, comparison with any of a variety of controls.

In various embodiments, specificity of pull-down assays is assessed. In various embodiments, miRNA-target RNA complex formation within an intact cell is assessed. In various embodiments, exogenous miRNAs in excess of that which is overexpressed in the cell are added to the pull-down assay (e.g., after cell lysis). In various embodiments, quantitative analysis (e.g. quantitative RT-PCR) is used to determine the amount of target RNA bound by the miRNA.

In various embodiments, pull-down assays may be normalized. Non-normalized pull-down may identify overlapping sets of highly abundant transcripts, such as ribosomal protein mRNAs, that can be pulled down using any of a variety of different miRNAs (often including non-specific control miRNAs). For analyzing the results of pull-down assay, normalization may be performed within the software (e.g., DESeq, as used herein to identify Pulldown-seq targets).

In various embodiments of the present invention, target RNAs are identified in pull-down assays as those that are enriched. In particular embodiments, cut-off values are p-value <0.05 and Fold enrichment >2, as in the examples which used DESeq for analysis. In other embodiments, cut off values are an FDR <0.1.

In various embodiments, pull-down assays utilized in accordance with the present invention simultaneously or sequentially assess interaction with at least one factor other than the relevant miRNA. According to the present invention, such approaches can increase specificity of assay results as compared with miRNA-only pull-down assays. For example, in various embodiments, the second factor comprises a cellular component (other than a target RNA) with which the miRNA interacts. In various embodiments, the second factor comprises a cellular component with which all miRNAs interact. For example, in various embodiments, the second factor comprises one or more components of RISC. To give but a few specific examples, those of ordinary skill in the art will appreciate that the RISC complex can be pulled down using an antibody such as Ago antibody. In various embodiments, a second factor is pulled down using a pull-down reagent that differs from the pull-down reagent used to pull down the miRNA. For example, in various embodiments, an antibody is used for one and a different category of binding agent (e.g., biotin/streptavidin) is used for the other. In various embodiments, multiple factors are pulled down.

Analysis of Targets

Targets (e.g., target RNAs) identified and/or isolated as described herein may be characterized by any of a variety of means. In various embodiments, for example, RNAs are subjected to reverse transcription (RT) and/or polymerase chain reaction (PCR). In various embodiments, RT and/or PCR are performed under conditions that permit quantification of the target RNA (quantitative reverse-transcription-polymerase-chain-reaction, qRT-PCR).

Target RNAs identified and/or isolated as described herein may be characterized through sequence analysis (e.g. deep sequencing). In various embodiments, presence or absence of a canonical miRNA binding site in the 5'UTR of a putative target RNA is determined. Among other things, the present invention demonstrates that not all miRNA targets in fact have canonical miRNA binding sites in their 5'UTRs. For example, as specifically exemplified herein, only 54 of the genes pulled-down from MDA-MD-468 breast cancer cell line using miR-522 are predicted miR-522 target genes by TargetScan 6.2. For miR-34 and let-7a pulldowns, only 54 and 59 genes, respectively, are predicted by TargetScan 6.2. As was observed, most of the pulled-down targets do not have evolutionarily conserved recognition sites. Other similar algorithms based on evolutionary conservation and seed region pairing give similar results, although the predicted gene sets are not identical. A high degree of experimental validation of a subset of pulled-down target genes suggests that most of the set are true targets. The implication is that a relaxation of the identical seed pairing requirement (for instance taking into account G:U wobbles or extensive pairing elsewhere in the sequence) and/or the requirement of evolutionary conservation for each particular site built into these algorithms might be desirable. Analysis of the set of pull-down genes for miR-522 and other miR-NAs might provide a useful data set for training and developing alternate prediction algorithms Target RNAs identified and/or isolated as described herein may be characterized through analysis of the extent to which their expression level is affected by expression of the miRNA with which they interact. The present invention encompasses the finding that target RNAs often are affected by levels of their cognate miRNAs. That is, according to the present invention, the expression level of many target RNAs is significantly affected in response to increases in expression levels of the miRNA of interest. However, it is clear that utilizing RNA expression level solely to identify miRNA targets is inadequate. The present invention specifically demonstrates that broad gene expression analysis technologies (e.g., arrays) may be particularly poorly suited for the identification of miRNA target RNAs.

Accordingly, the invention provides a method of predicting the biological function of a microRNA involving a combination of bioinformatics analysis of known and predicted common transcription factors regulating the expression of its identified target genes; bioinformatics analysis of known and predicted function and pathways of its identified targets; bioinformatics analysis of known and predicted function and pathways of its downregulated genes.

In various embodiments, targets of miRNAs identified and/or isolated as described herein are cloned (e.g. introduced into a vector) as is known in the art.

To give a specific example, in the analysis of miR-522 targets described in the Examples, ~60% of targets that were identified for miR-522, miR-34a and let-7a are also down-regulated, as detected by microarray transcript expression analysis. Without wishing to be bound by any particular theory, it is noted that regulated mRNAs may decline indirectly because of reduced transcription and/or directly by miRNA-mediated accelerated mRNA decay. It seems likely that global analysis of differential protein expression, may be preferable in the analysis of miRNA targets.

The foregoing notwithstanding, in various embodiments, one or more target RNAs show expression levels that respond to changes in level of miRNA of interest. In various embodiments, target RNA levels are increased or decreased by at least 2 fold or more (e.g., 3, 4, 5, 6, 7, 8, 9, or even 10 fold or more) in response to corresponding changes in miRNA levels.

In various embodiments of the present invention, target RNAs identified using pull-down technologies are subjected to network analyses to identify biological processes that are represented (or over-represented) among pulled-down RNAs. These include functional and pathway analysis of identified miRNA target genes and their potential regulatory transcription factors, as well as miRNA-downregulated genes. For example, as exemplified herein, genes involved in cell proliferation, detachment, migration, and epithelial-mesenchymal transition are over-represented among RNAs enriched in pull-down analyses with miR-522.

Sequencing

DNA sequencing may be used to evaluate cDNA isolated in the present invention. One DNA sequencing method is the Sanger method, which is also referred to as dideoxy sequencing or chain termination. The Sanger method is based on the use of dideoxynucleotides (ddNTP's) in addition to the normal nucleotides (NTP's) found in DNA. Dideoxynucleotides are essentially the same as nucleotides except they contain a hydrogen group on the 3' carbon instead of a hydroxyl group (OH). These modified nucleotides, when integrated into a sequence, prevent the addition of further nucleotides. This occurs because a phosphodiester bond cannot form between the dideoxynucleotide and the next incoming nucleotide, and thus the DNA chain is terminated. Using this method, optionally coupled with amplification of the nucleic acid target, one can now rapidly sequence large numbers of target molecules, usually employing automated sequencing apparati. Such techniques are well known to those of skill in the art.

High demand for low-cost sequencing has driven the development of high-throughput sequencing (or next-generation sequencing) technologies that parallelize the sequencing process, producing thousands or millions of sequences at once. High-throughput sequencing technologies are intended to lower the cost of DNA sequencing beyond what is possible with standard dye-terminator methods. In ultra-high-throughput sequencing as many as 500, 000 sequencing-by-synthesis operations may be run in parallel. Examples of such sequencing methods include ion semiconductor sequencing, pyrosequencing, sequencing by synthesis, sequencing by ligation, DNA nanoball sequencing, Heliscope single molecule sequencing, Single molecule real time (SMRT) sequencing, and Polony sequencing, Massively Parallel Signature Sequencing (MPSS).

Ion semiconductor sequencing (ION TORRENT Systems Inc.; NEB; Life Technologies) is a system based on using standard sequencing chemistry, but with a novel, semiconductor based detection system. This method of sequencing is based on the detection of hydrogen ions that are released during the polymerization of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

Sequencing by ligation (SOLID; Illumina; Applied Biosystems, Life Technologies) is a sequencing method where a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing single copies of the same DNA molecule, are deposited on a glass slide. [47] The result is sequences of quantities and lengths comparable to Illumina sequencing. [20]

Pyrosequencing is another method of DNA sequencing that may be used to evaluate a polymorphism of the present invention, for example as described in U.S. Pat. Publ. No. 2006008824; herein incorporated by reference). Pyrosequencing, which is also referred to as sequencing by synthesis, involves taking a single strand of the DNA to be sequenced, synthesizing its complementary strand enzymatically one base pair at a time, and detecting by chemiluminescence the base that is added. In one embodiment, the template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. The templates for pyrosequencing can be made both by solid phase template preparation (streptavidin-coated magnetic beads) and enzymatic template preparation (apyrase+exonuclease).

In a specific embodiment, ssDNA template is hybridized to a sequencing primer and incubated with the enzymes DNA polymerase, ATP sulfurylase, luciferase and apyrase, and with the substrates adenosine 5' phosphosulfate (APS) and luciferin. The addition of one of the four deoxynucleotide triphosphates (dNTPs) (in place of dATP, dATPaS is added, which is not a substrate for a luciferase) initiates the second step. DNA polymerase incorporates the correct, complementary dNTPs onto the template, and the incorporation of the nucleotide releases pyrophosphate (PPi) stoichiometrically. ATP sulfurylase quantitatively converts PPi to ATP in the presence of adenosine 5' phosphosulfate. The ATP generated acts to catalyze the luciferase-mediated conversion of luciferin to oxyluciferin and generates visible light in amounts that are proportional to the amount of ATP. The light produced in the luciferase-catalyzed reaction is detected by a camera and analyzed in a program. Unincorporated nucleotides and ATP are degraded by the apyrase, and the reaction can restart with another nucleotide. Pyrosequencing, optionally coupled with amplification of the nucleic acid target, can sequence large numbers of target molecules, usually employing automated sequencing apparati, including long sequences (e.g., 400 million bp/10 hr in a single run).

Kits and/or Compositions

The present invention also provides kits or compositions including components useful in the identification of miRNA target RNAs and/or drug targets as described herein. Such kits may be of particular use in both academic and commercial research applications.

For example, in various embodiments, inventive such kits include one or more control miRNAs and/or reagents for labeling miRNAs and/or for quantification of degree of target RNA enrichment relative to cellular expression levels. In various embodiments, such kits include one or more reagents useful in performing reverse transcription, polymerase chain reaction, nucleic acid sequencing, analysis of RNA expression levels, etc. In various embodiments, such kits include one or more antibodies. In various embodiments, such kits include one or more nucleic acid standards (e.g., size standards, known miRNAs, etc.). In various embodiments, such kits include nucleotide analogs useful in preparation of miRNA mimics.

In other exemplary embodiments, kits include a macromolecular crowding agent. Preferably, the macromolecular crowding agent is one or more of Ficoll PM400, Ficoll PM70, dextran sulfate, Ficoll (Fc) 70 kDa (Fc70), Fc400 kDa (Fc400), trehalose, proline, polyethylene glycol (PEG) 4 kDa, and Dextran 670 kDa.

To give but a few examples, in various embodiments, inventive kits include, for example, biotin and/or streptavidin reagents suitable for labeling miRNAs. In various embodiments, such reagents achieve covalent attachment of the label (e.g., biotin or streptavidin) to an miRNA. In various embodiments, such reagents achieve non-covalent attachment of the label to an miRNA. For example, a labeling reagent may associate a label with an miRNA via hybridization. To give but one example, in various embodiments, inventive kits comprise a means for attaching a standard sequence element to an miRNA (e.g., via expression of the miRNA in a vector containing the sequence element, direct linkage of a nucleic acid fragment containing the sequence element, etc.), and further comprise a label attached to the complement of the sequence element.

In various embodiments, inventive kits comprise one or more of a reverse transcriptase enzyme, deoxyribonucleotides, DNA polymerase (e.g., thermostable DNA polymerase), chain-terminating nucleotides, detectable (e.g., fluorescent, radioactive) nucleotides, one or more buffers, distilled water, etc.

In various embodiments, the present invention provides kits or compositions containing one or more agents that regulates mRNA levels; in some such embodiments, the present invention provides kits or compositions containing one or more agents that regulate levels of one or more miRNA targets. In various embodiments, such a provided kit or compositions will include one or more siRNA, for example targeting a specific miRNA target. The present invention therefore provides systems (including methods and compositions) for regulating an miRNA target RNA through administration of a miRNA target regulating factor. In various embodiments, miRNA target regulating factors alters the level/activity to be higher in presence of agent than in absence. In various embodiments, the level or activity is at least about 1.1, about 1.2, about 1.3, about 1.4, about 1.5, about 1.6, about 1.7, about 1.8, about 1.9, about 2, about 2.5, about 3, about 3.5, about 4, about 4.5, about 5, about 6, about 7, about 8, about 9, about 10, about 11, about 12, about 13, about 14, about 15, about 16, about 17, about 18, about 19, about 20, to about 200 fold or even higher in the cell as to regulate the effect of this target as compared to not administering the siRNA. In various embodiments, miRNA target regulating factors alters the level/activity to be lower in presence of agent than in absence. In various embodiments, the level or activity is at least about 1.1, about 1.2, about 1.3, about 1.4, about 1.5, about 1.6, about 1.7, about 1.8, about 1.9, about 2, about 2.5, about 3, about 3.5, about 4, about 4.5, about 5, about 6, about 7, about 8, about 9, about 10, about 11, about 12, about 13, about 14, about 15, about 16, about 17, about 18, about 19, about 20, to about 200 fold or even lower in the cell as to regulate the effect of this target as compared to not administering the siRNA. In various embodiments, exemplary miRNA target regulating factors can include siRNA, shRNA, and/or miRNA. In various embodiments the siRNA, shRNA and/or miRNA targets RNA. In various embodiments, the mixture comprises a RNA mimic, which is a sequence that is analogous to another RNA sequence. In various embodiments the mixture comprises a small molecule agent or moiety that regulates the levels of the target miRNA. In various embodiments, these components will be administered together. In various embodiments, these components will be administered separately.

In certain embodiments, inventive such kits contain all of the components necessary to perform a relevant assay (e.g., detection assay, regulation assay, and the like), including all controls, directions for performing assays, and any necessary software for analysis and presentation of results.

In various embodiments, components of inventive kits are provided in individual containers and multiple such containers are provided together in a common housing.

EXAMPLES

Sequencing and Systems Analysis of Captive Target Transcripts Identifies Primate-Specific miR-522 as an Inducer of Mesenchymal Transition.

A three-pronged strategy was developed for defining and validating miRNA target RNAs and MREs involving miRNA pulldown of RNAs, RNase treatment, sequencing the RNA transcripts, identification of the obtained sequences and prediction of its biological function. A schematic of this strategy is shown in FIG. 1A. The three methods are: Pulldown-seq, involving streptavidin pull-down and sequencing of RNAs bound to a transfected biotinylated miRNA mimic, IMPACT-seq (Identification of MREs by Pull-down and Alignment of Captive Transcripts—sequencing) which combines Pulldown-seq with RNase digestion, and Target functional analysis, based on the combinatorial functional and pathway analysis of identified miRNA target genes and their potential regulatory transcription factors, as well as miRNA-downregulated genes.

Figure 1B:
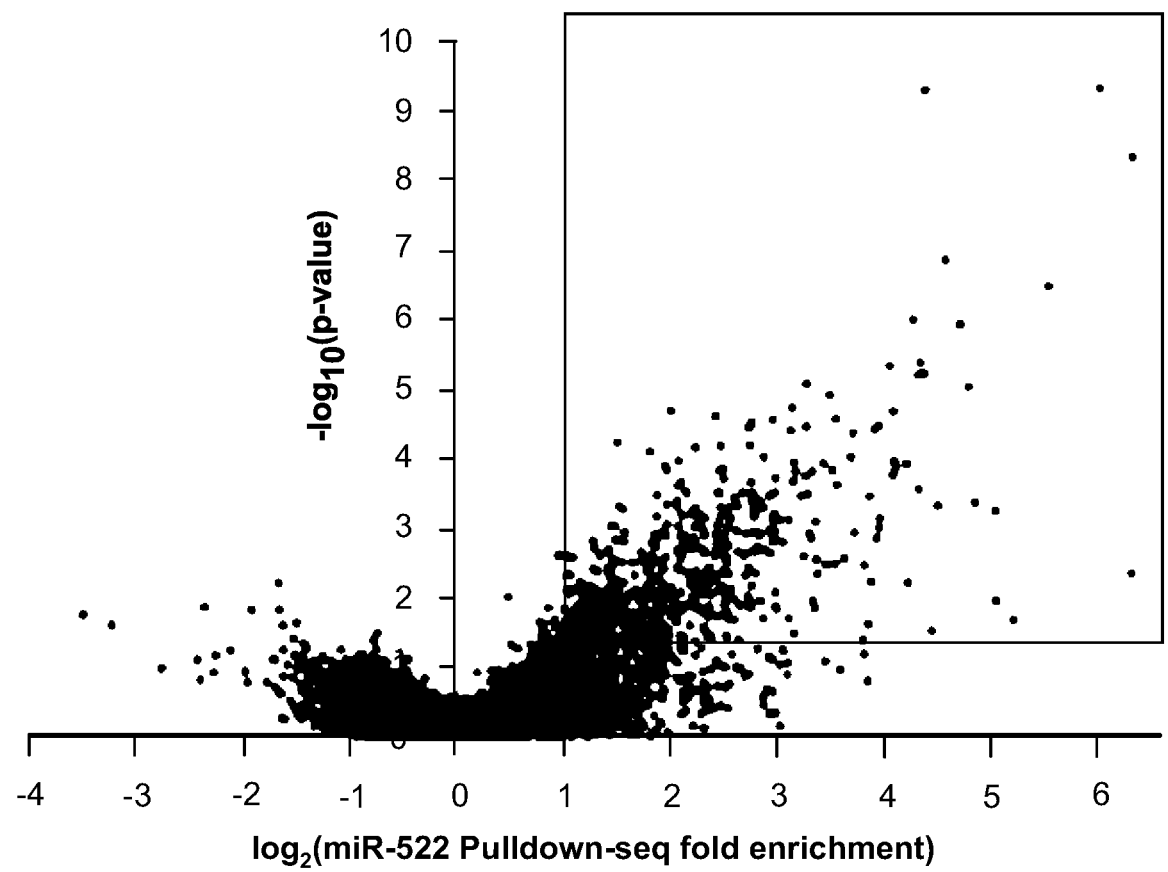
FIG. 1B shows a table depicting the number of miRNA targets as identified by Pulldown-seq (DESeq cut-off >2-fold enrichment, p-value<0.05) and a volcano plot of gene enrichment in miR-522 versus control Pulldown-seq dataset. A boxed region denotes genes that had a fold enrichment (FE) >2, and p-value <0.05.
Figure 1C:
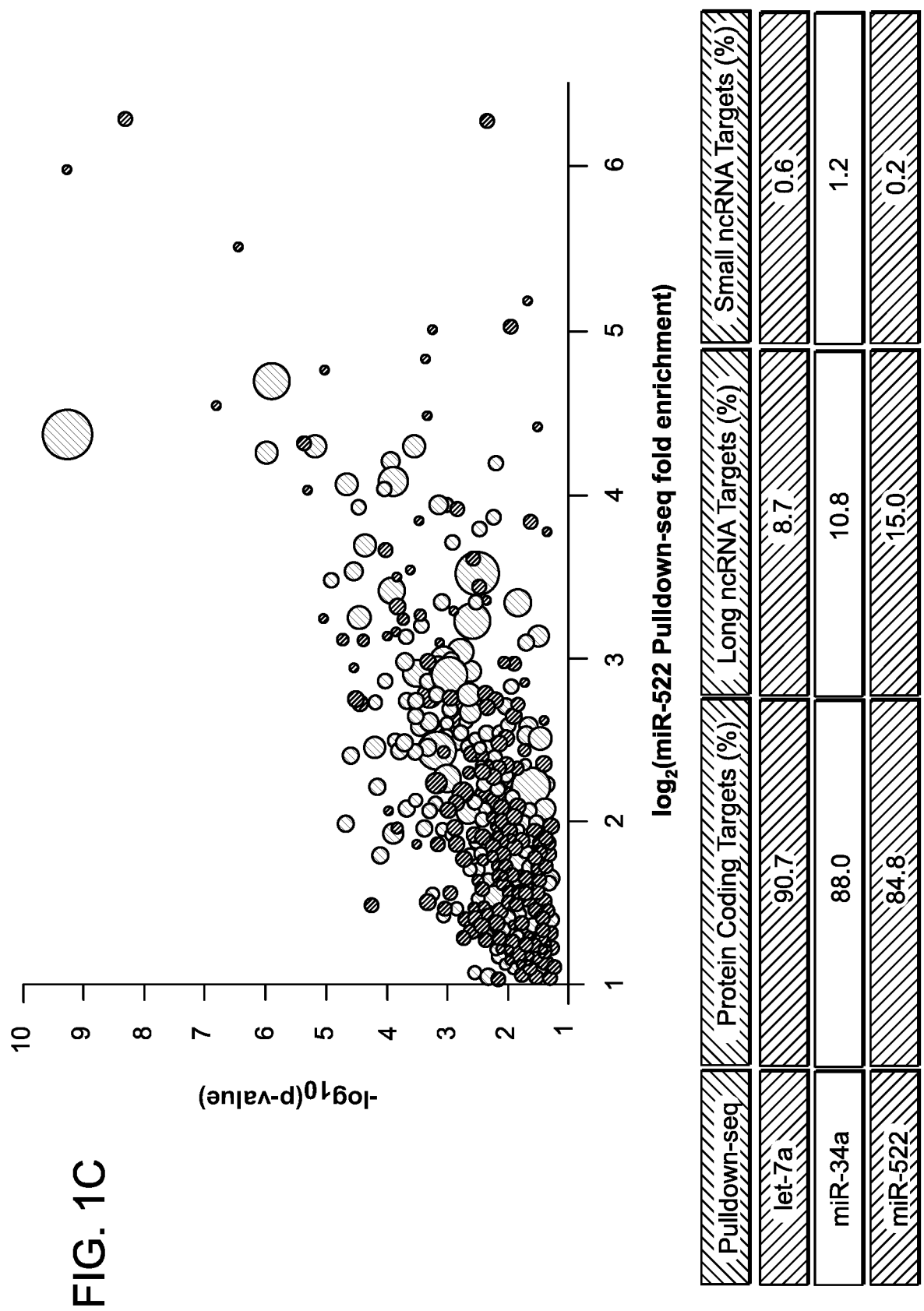
FIG. 1C shows a table depicting the protein coding targets (%), long ncRNA targets (%) and small ncRNA targets (%) for miR-34a, let-7a and miR-522, and a bubble plot of miR-522 target genes in the box in (B). Bubble regions indicate genes that were significantly downregulated upon miR-522 overexpression (FDR <0.1).
Figure 1D:
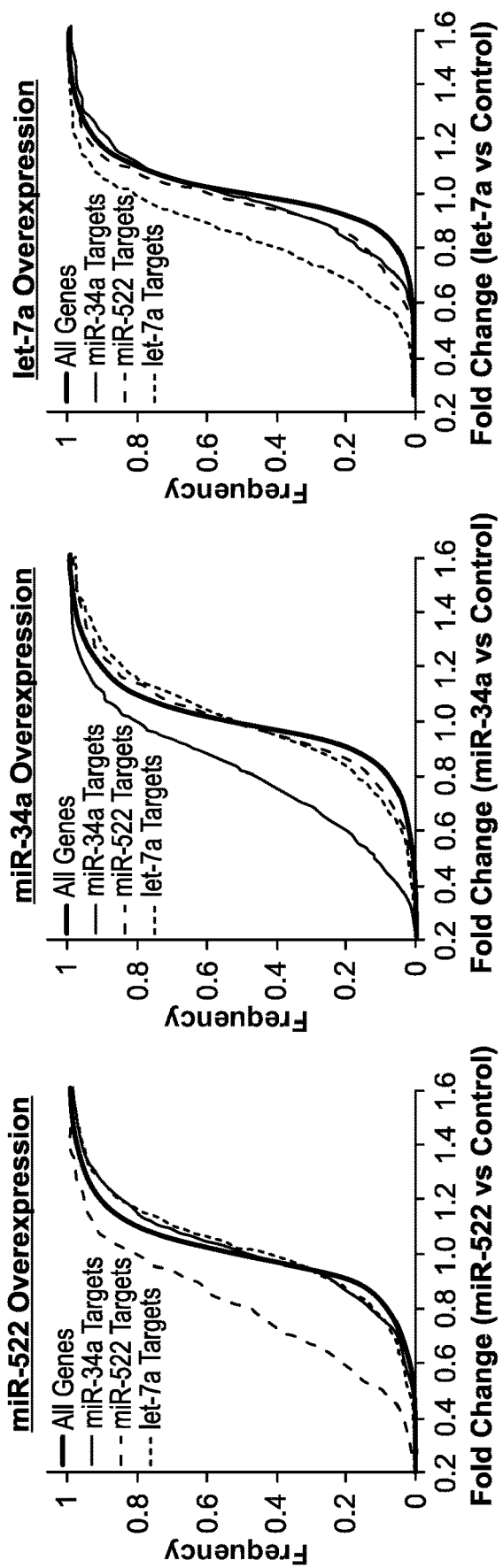
FIG. 1D depicts the validation of Pulldown-seq specificity. Cumulative plot of transcript expression fold change after 48 hrs of miR-522, miR-34a, or let-7a overexpression (left to right), comparing all three target lists in each plot. Only the target gene list of the specific miRNA that is overexpressed in each graph is significantly different from the All Genes group (p-value <0.001), as analyzed by the Kolmogorov-Smirnov test.
Figure 1E:
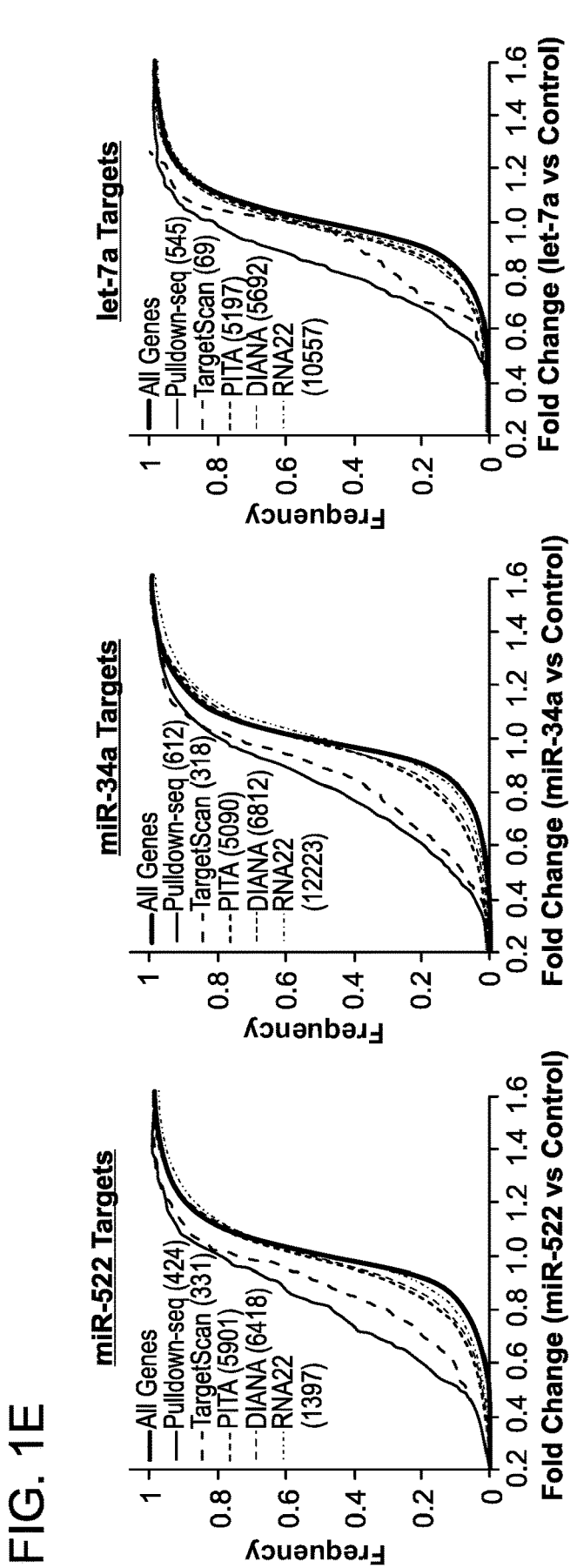
FIG. 1E depicts the validation of Pulldown-seq performance. Cumulative plot of transcript expression fold change after 48 hrs of miR-522, miR-34a, or let-7a overexpression (left to right), comparing the Pulldown-seq target list for each miRNA to target genes predicted by various commonly-used algorithms. Only the target gene lists identified by Pulldown-seq and those predicted by TargetScan are significantly different from the All Genes group (p-value <0.001), as analyzed by the Kolmogorov-Smirnov test (except for the let-7a TargetScan list). Pulldown-seq gene lists are larger, but yet better predictors of miRNA targets.
Figure 2B:
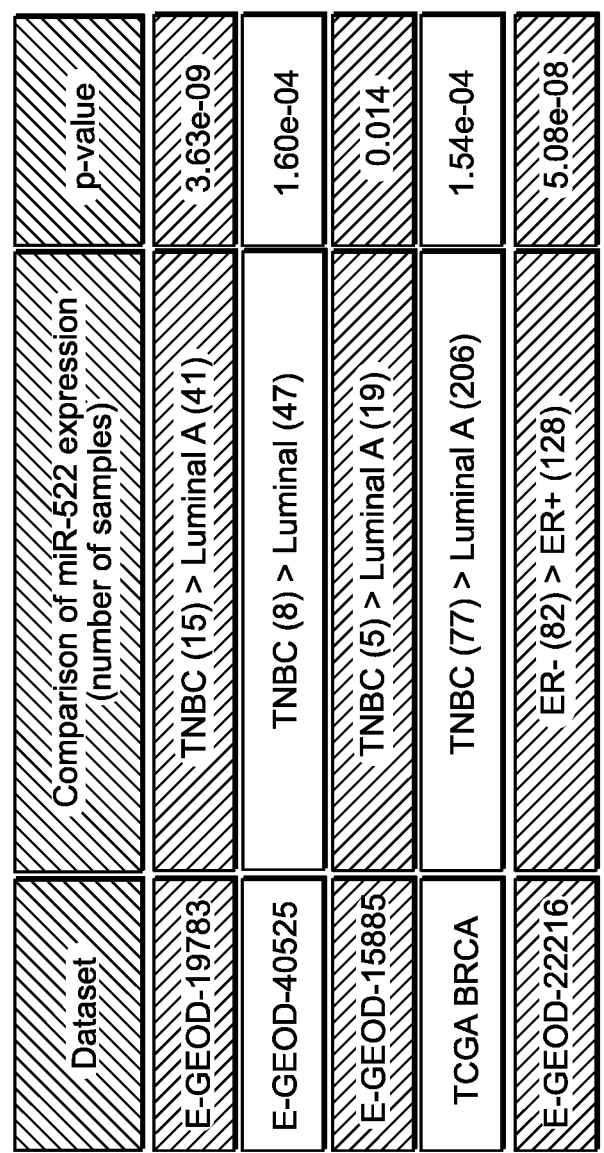
FIGS. 2A-B show that miR-522 is over-expressed in TNBCs and other aggressive cancers, and in TNBC cell lines compared to luminal breast cancer cell lines.
Figure 2A:
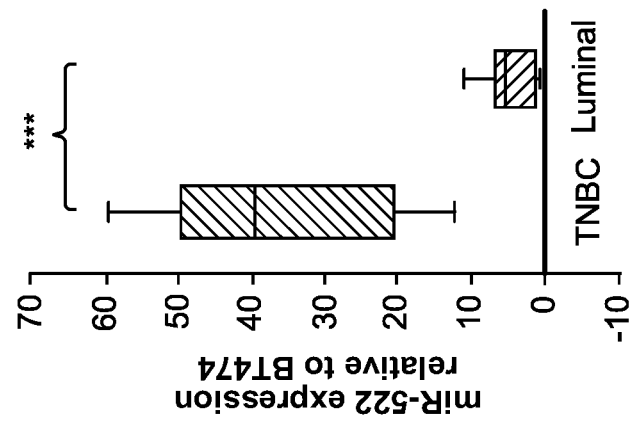
Figure 7:
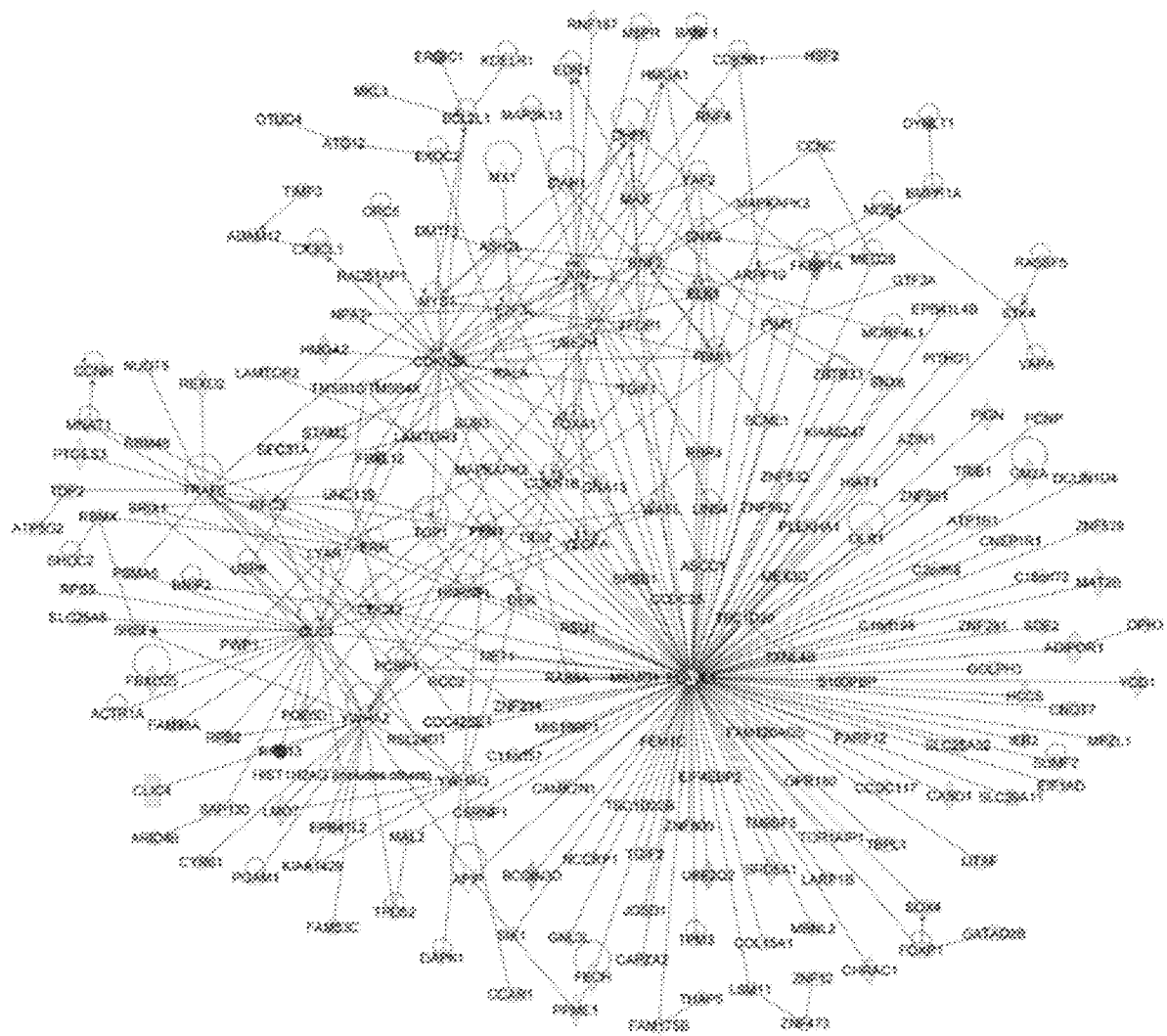
FIG. 7 depicts miR-522 targets in interacting protein networks, showing relative level of enrichment in Pulldown-seq (shading).

In a first set of experiments miRNA targets identified by Pulldown-seq for miRNAs miR-522, miR-34a and let-7a were 547, 740 and 634 respectively (DESeq cut-off >2-fold enrichment, p-value<0.05) (FIG. 1B, see Tables in FIG. 18, FIG. 21 and FIG. 22 respectively). Pulldown-seq results were validated by examining the enrichment, specificity, and performance. Cumulative plot of transcript expression fold change after 48 hrs of miR-522, miR-34a, or let-7a overexpression (left to right), comparing all three target lists in each plot. Only the target gene list of the specific miRNA that is overexpressed in each graph was significantly different from the All Genes group (p-value <0.001), as analyzed by the Kolmogorov-Smirnov test. This confirmed Pulldown-seq specificity for the miR-522, miR-34a, and let-7a targets. As validation of Pulldown-seq performance, cumulative plots of transcript expression fold change after 48 hrs of miR-522, miR-34a, or let-7a overexpression were generated (FIG. 1E). The plots compared the Pulldown-seq target list for each miRNA to target genes predicted by various commonly-used algorithms. The target gene lists identified by Pulldown-seq and those predicted by TargetScan were significantly different from the All Genes group (p-value <0.001), as analyzed by the Kolmogorov-Smirnov test (except for the let-7a TargetScan list). While the pulldown-seq gene lists were larger, they were better predictors of miRNA targets. A network analysis showed several of the identified and validated miR-522 targets as being part of the same interactive networks (FIG. 7).

miR-522 is a member of the chromosome 19 miRNA cluster (C19MC), a 100 kb primate-restricted region that encodes for ~54 tandem miRNAs—the largest cluster of miRNAs in the human genome. The maternal allele is imprinted, and expression of the cluster from the paternal chromosome is mostly restricted to the placenta and embryo and embryonic and tissue stem cells (Noguer-Dance et al., 2010). C19MC is highly expressed in human embryonic stem cells and poorly differentiated, aggressive tumors (Li et al., 2009; Rippe et al., 2010). The cluster is the site of translocations in thyroid adenomas and is genetically amplified in aggressive primitive neuroectodermal brain tumors. Moreover multiple members of the family, some of which share a common seed, have been shown to regulate key pathways in stem cell biology that are dysregulated in cancers, including the Wnt pathway and the tumor suppressor gene and cell cycle inhibitor CDKN1A (p21Cip1/Waf1) (Wu et al., 2010). miR-522 is highly expressed in triple negative breast cancers (TNBC), compared to more well differentiated luminal cancers and normal breast tissue (Biagioni et al., 2012; Enerly et al., 2011; TCGA, 2012). Most TNBC tumors arise from bipotent epithelial progenitor cells and have a high frequency of tumor-initiating cells, also known as cancer stem cells. Thus C19MC has the hallmarks of an oncogenic miRNA cluster. However, nothing is known about the targets or function of miR-522. Described herein is a novel method demonstrating that miR-522 enhances the ability of TNBC cells to survive detachment, invade through a membrane and express mesenchymal genes, properties associated with metastasis. At the same time it causes cells to arrest at G1/S, reducing cell proliferation.

miR-522 is Over-Expressed in TNBCs and Other Aggressive Cancers and its Amplification is Associated with Poor Prognosis In the gene expression databases for breast cancer, miR-522 was significantly over-expressed in poorly differentiated ER- or TNBC, relative to more differentiated ER+ and luminal breast cancers or normal breast tissue (FIG. 1A). Similarly miR-522 was significantly up-regulated in testicular cancers compared to normal tissues (Navon et al., 2009). The difference in miR-522 expression between luminal breast cancer and more poorly differentiated TNBCs was confirmed by comparing expression levels in 10 representative cell lines (FIG. 1B). These data suggest that miR-522 might be an oncomiR.

Figure 4A:
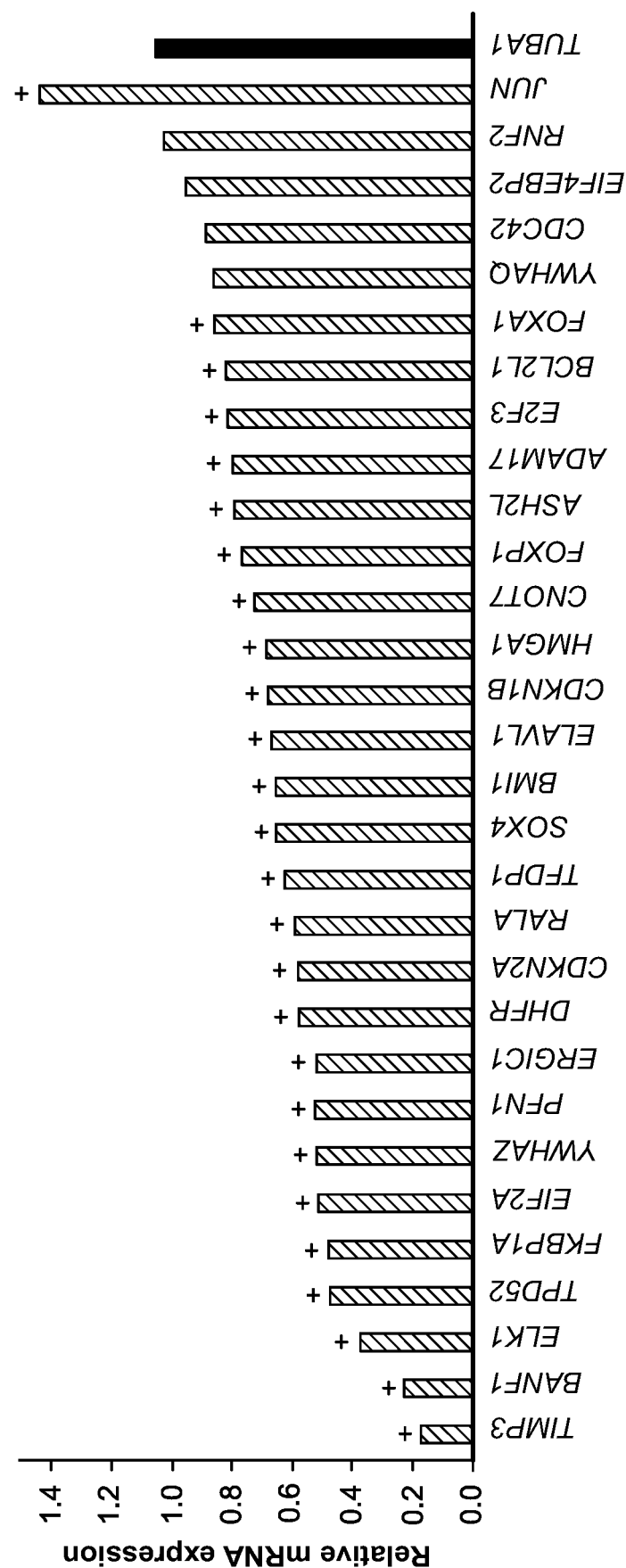
FIGS. 4A-C show most miR-522 Pulldown-seq targets have reduced mRNA and protein after miR-522 overexpression. A random set of 30 miR-522 Pulldown-seq targets was analyzed for changes in mRNA and protein expression after miR-522 over-expression. (A) Microarray analysis of cubic spline-normalized mRNA expression after miR-522 over-expression, compared to control miRNA expression. Representative immunoblots (B) and mean±S.D. signal intensity relative to β-actin of 3 independent experiments (C), comparing signal intensity of cells transfected with miR-522 and control miRNA. (*, p<0.05; +, FDR <0.1).
Figure 4B:
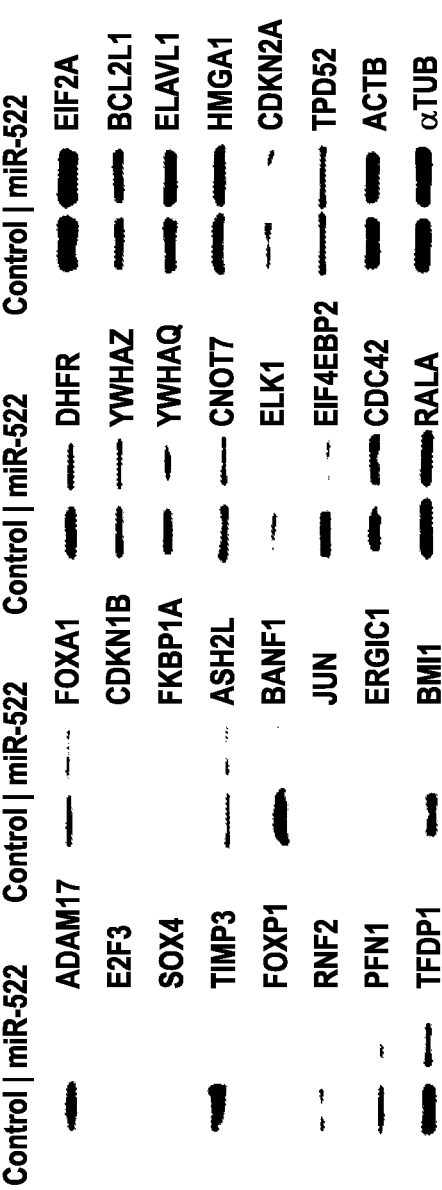
Figure 4C:
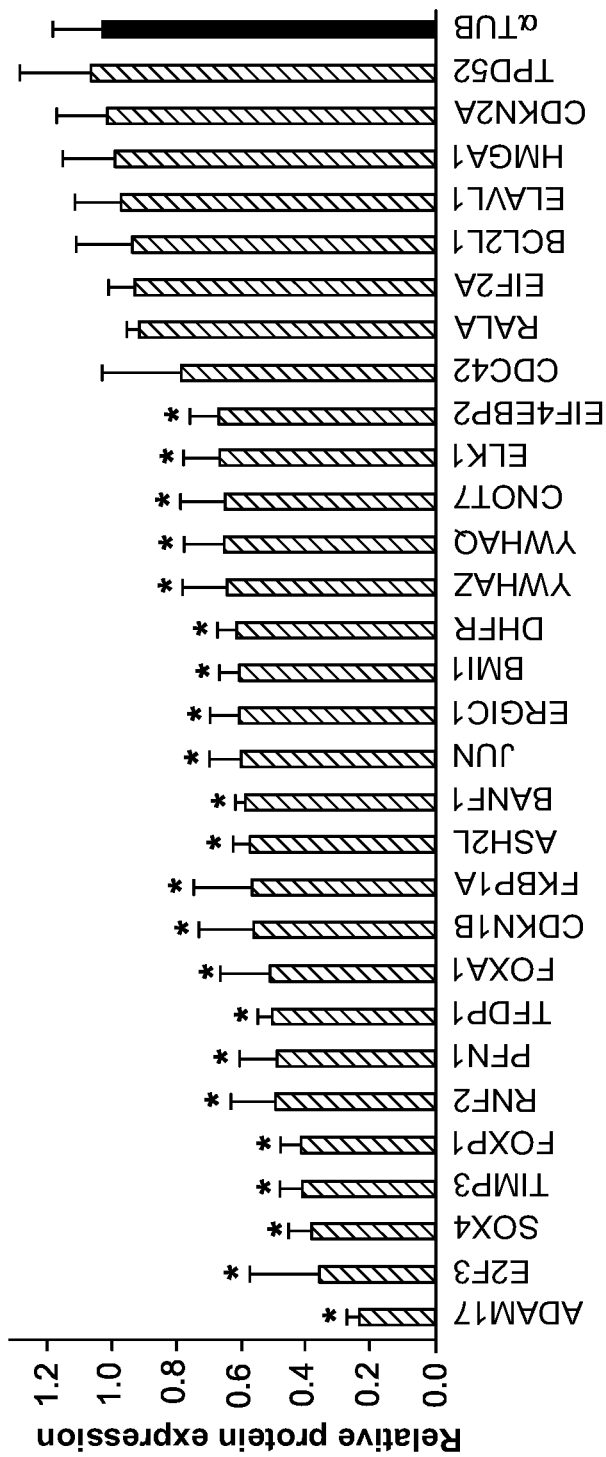
Figure 17G:
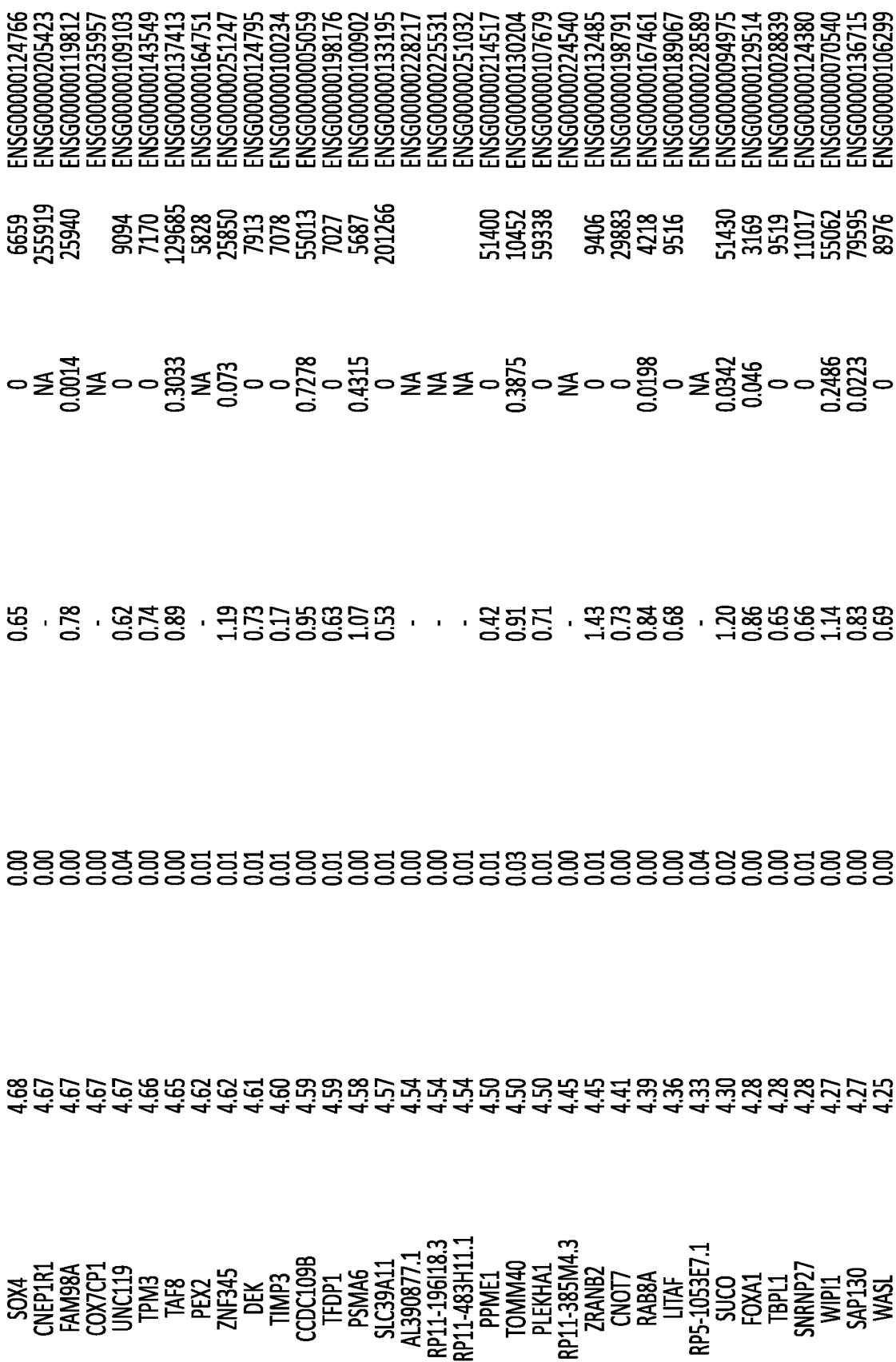
FIG. 17A-FIG. 17Q is a Table that details the RNA targets for miR-522 identified by Pulldown-seq and their expression levels upon miR-522 overexpression.

Most miR-522-Associated Genes had Reduced mRNA and Protein after miR-522 Over-Expression To further evaluate the specificity of the pulldown, a random list of 30 genes, which represented the full range of FE and p-values of identified miR-522 targets, was chosen to assess the effect of miR-522 over-expression on mRNA and protein levels by microarray and immunoblot densitometry, respectively (FIG. 4A-C and the Table shown in FIG. 17). 83% of these genes (25 of 30) showed significant reductions in mRNA and 73% had significantly reduced protein (22 of 30). These data taken together show that Pulldown-seq is specific for identifying miRNA targets.

Identification of miR-522 Target MREs by IMPACT-Seq

MRE prediction algorithms work best for evolutionarily conserved miRNAs and target sequences. To identify MREs of primate-specific miRNAs, like miR-522, alternate approaches are especially needed. Therefore, a method was developed to identify MREs using the pulldown, termed IMPACT-seq. IMPACT-seq requires no cross-linking and only a mild single RNase treatment of bead-captured miRISCs. As in Pulldown-seq, cel-miR-67 miRNA was used as a control to reduce background from RNAs that bound nonspecifically to the beads or miRISC. 3.6 and 1.6 million bases were sequenced for control miRNA and miR-522, respectively, that mapped uniquely to the transcriptome. Importantly, more than 70% of all reads had a guanine residue at the 3' end, an indication that most of these reads were generated by RNase T1 cleavage. To determine miR-522 MREs, CLIPper (github.com/YeoLab/clipper/) was used, a tool developed to define peaks in CLIP experiments, to identify read clusters or "peaks" that correspond to potential MREs in each sample. miR-522 peaks were compared to control miRNA peaks and the significance of each potential MRE was computed based on a Poisson distribution. The number of normalized reads was also computed for each sample (see Table shown in FIG. 18). With p-value<0.05 and FE>2 cut-offs, 4848 peaks in 2966 transcripts that had at least 5 reads in the miR-522 sample were identified as possible MREs. Of these MREs, 743 were in 306 of the 547 Pulldown-seq transcripts. Thus potential MREs were identified in 56% of the Pulldown-seq miR-522 targets. These included all of the mRNAs in the random gene list that had decreased both protein and mRNA levels. The lack of MREs for the remaining 44% of Pulldown-seq mRNAs indicates that the sensitivity of IMPACT-seq could be improved.

Figure 5A:
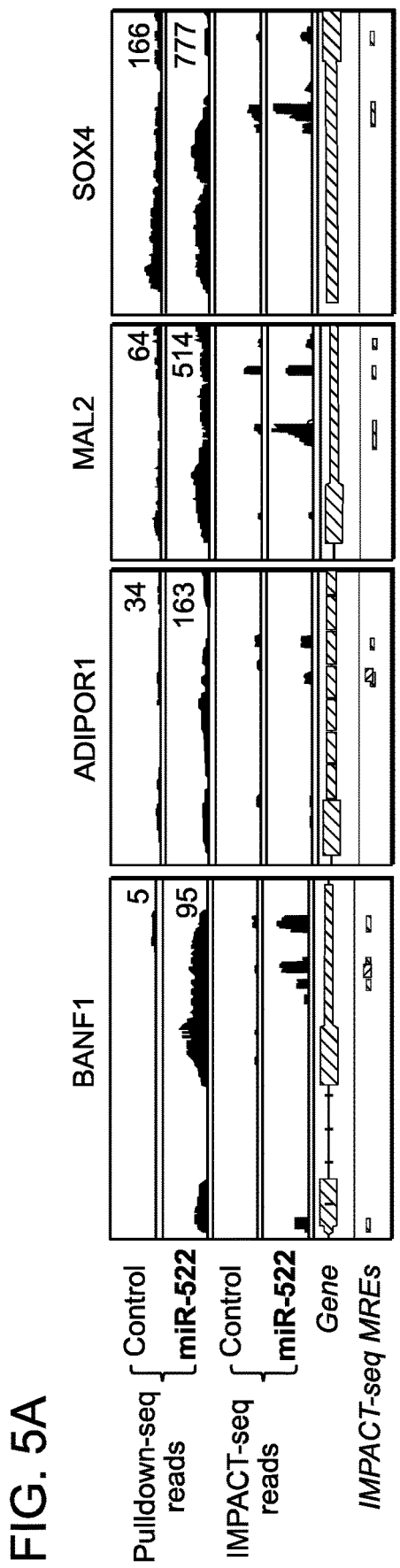
FIGS. 5A-E show identification of miR-522 miRNA response elements by IMPACT-seq. (A) Sequencing reads of 4 identified miR-522 targets and MREs. Numbers in Pulldown-seq plots indicate mean FPKM (Scale: Pulldown-seq 0-100 reads, IMPACT-seq 0-50 reads). IMPACT-seq identified MREs are indicated below; 2 of these also predicted by Miranda are shown. (B) Length distribution of identified miR-522 MREs. Most MREs were between 20 and 40 bp. (C) Distribution of miR-522 MREs amongst RNA classes. the majority of predicted mREs were in the 3'UTR of mRNAs. (D) GLAM2 gapped motif analysis of 1887 MREs between 25-35 bp shows enrichment of a 3' supplementary motif in 1639 MREs, and a non-canonical seed in 1753 MREs (left box, seed sequence underlined). Scrambled sequences of the same MREs resulted in a non-matching motif with a much lower score (right box). (E) Dual luciferase assay of 30 randomly selected MREs. RC indicates the miR-522 reverse complement sequence used as positive control (6th, 18th, 19th, and 23th bars), C indicates negative control sequences not bound by miR-522 and PC2 denotes the empty vector (5 bars from the right). 25 of 30 MREs were functional by luciferase assay. Error bars depict the S.D. of 3 biological replicates. (*, p<0.05 compared to all 5 controls).
Figure 5B:
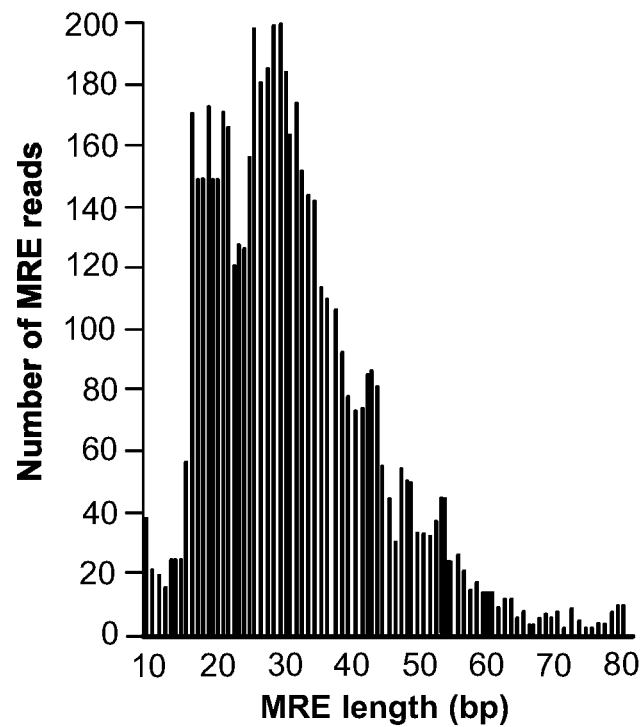
Figure 5C:
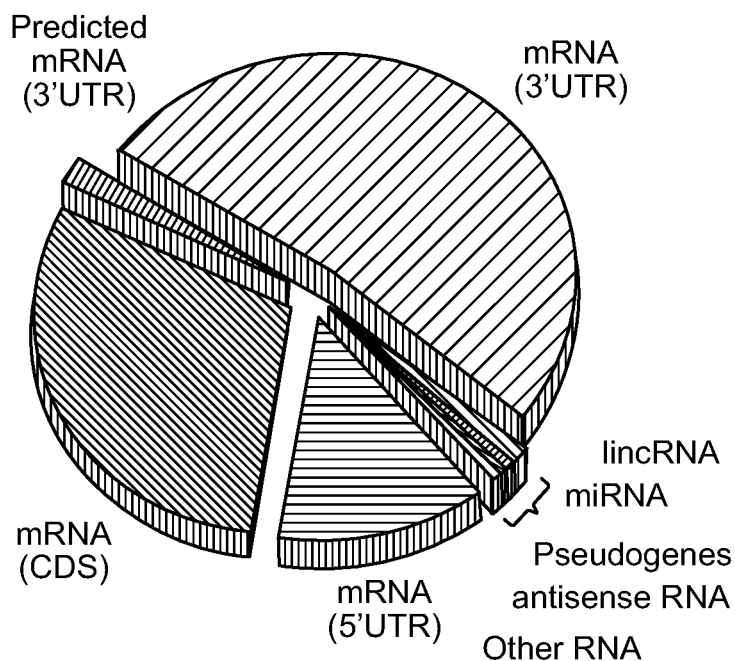

IMPACT-seq generated sharp, distinct peaks, making it relatively easy for MRE identification either with CLIPper or manually using a genome browser (FIG. 5A). A large proportion of the RNase-protected sequences (64%) were between 20-40 bp, enabling the identification of complementary sequences without much difficulty (FIG. 5B). 96% of miR-522 candidate MREs were located in protein-coding transcripts, with 53% in the 3' UTR, 30% in the CDS, and 13% in the 5'UTR (FIG. 5C and the Table shown in FIG. 18). The remaining 4% were aligned to lincRNAs, miRNAs, pseudogenes and antisense RNAs. Of the 3'UTR MREs, 111 had sequences that contained MREs that were predicted by PITA, miRanda and/or TargetScan. However, only 13 were predicted by TargetScan6.2, the algorithm that best identified genes down-regulated by miR-522 over-expression (FIG. 1D).

Figure 5D:
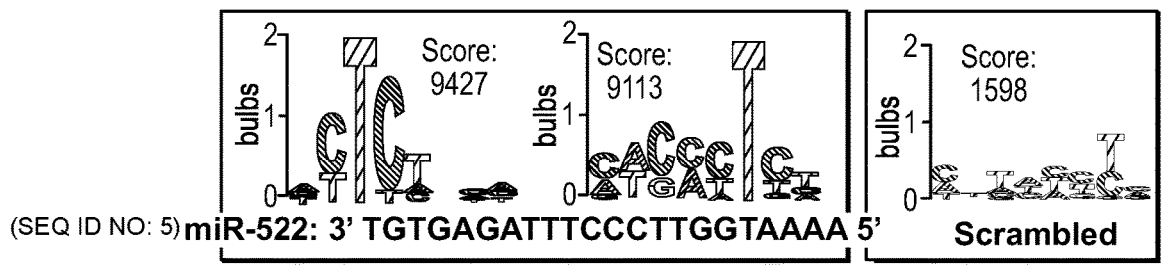

To analyze the regions of miR-522 complementarity in the RNase protected sequences, the GLAM2 tool within the MEME suite of motif-based sequence analysis tools (which allows for gaps or bulges) was used to discover motif(s) (Frith et al., 2008). Reasoning that MREs between 25 and 35 bases in length would contain only single miR-522 binding sites, analysis was limited to these 1887 sequences. 1639 sequences contained the enriched motif [acu][cu]ucu[acug][ac][acu], partially complementary to residues 13-20 of miR-522 (with a score of 9426.39), and 1753 contained the enriched motif [ac][au][cg][ac][cu]u[cu][cu], partially complementary to residues 2-9 in the seed region of miR-522 (with a score of 9113.21). Scrambling the sequences of the RNase-protected sequences as a control resulted in an unrecognizable motif that had a low score of 1597.71 (FIG. 5D). Since most sequences contained motifs partially complementary to both the 5' and 3' ends of miR-522, miR-522 is an example of a recently described class of miRNAs whose MREs, which include let-7e, are complementary to both ends of an miRNA (Helwak et al., 2013).

Figure 5E:
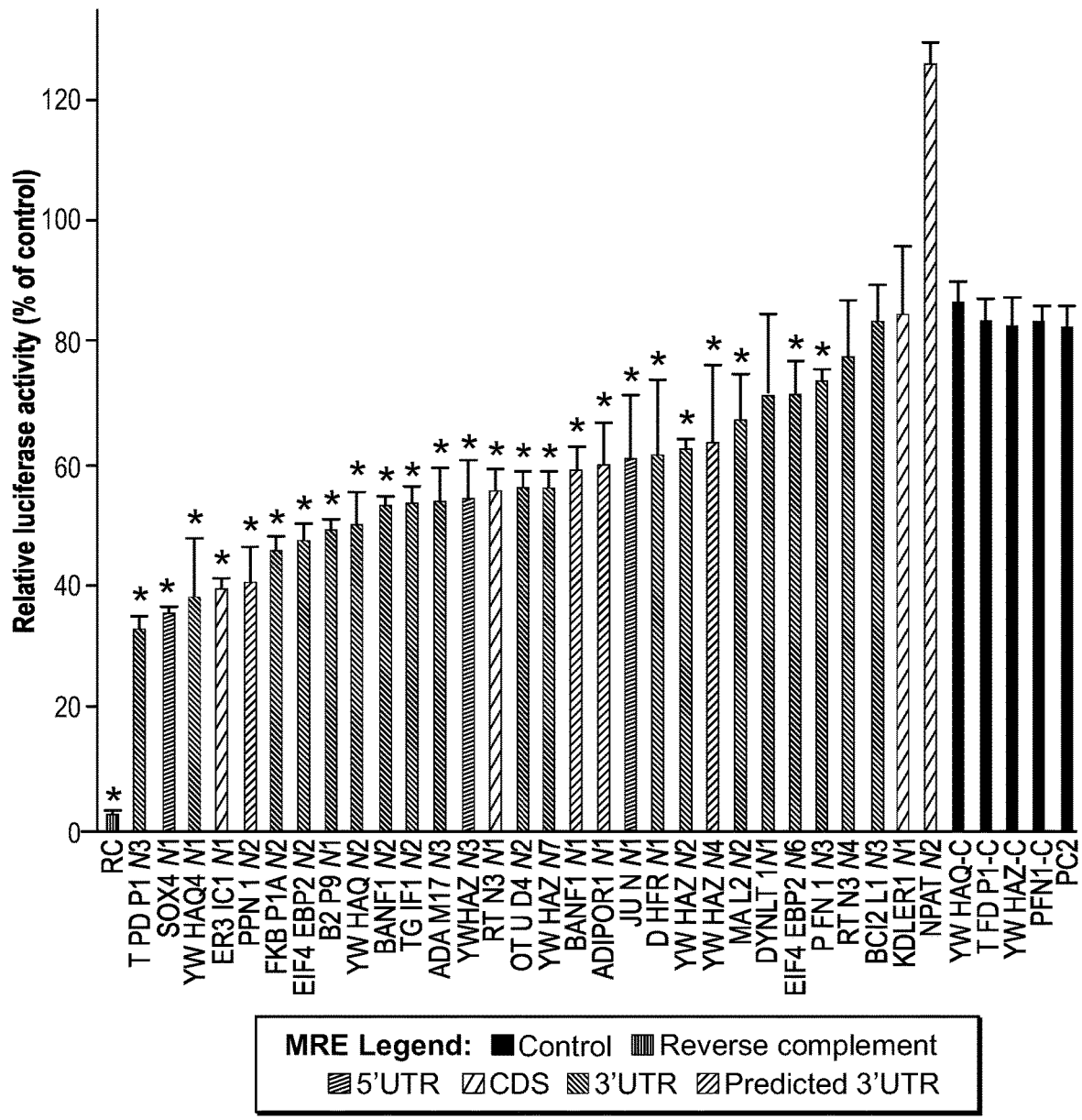

To determine how specific IMPACT-seq is for identifying MREs, a random set of 30 peak sequences were cloned, representative of the range of read number and FE scores, and performed luciferase reporter assays (Table shown in FIG. 19). In line with the MEME analysis, most of these sequences showed imperfect complementarity to both the 5' and 3' ends of miR-522. Only 4 were predicted targets and only 5 (17%) had a perfect 6 nt seed match. Four sequences of similar length that were not identified as MREs, but were encoded in the genes that contained identified MREs, were used as controls. 25 of the candidate MREs (83%) reduced luciferase activity (FIG. 5E), suggesting that IMPACT-seq is very specific.

Bioinformatic Analysis for miR-522 Targets

To uncover the function of miR-522, several bioinformatics tools were combined to analyze the Pulldown-seq dataset. First, TRANSFAC was used, a well-curated knowledge-base of eukaryotic transcription factors (Matys et al., 2006), to search for over-represented transcription factors predicted to bind to the promoter regions upstream of the identified miR-522 target genes. Binding sites for 4 transcription factors were significantly enriched in the promoters of the set of 547 Pulldown-seq genes—ELK1 (113 genes, $p<2\times10^{-5}$), E2F (281 genes, $p<1\times10^{-4}$), TEAD2 (184 genes, $p<9\times10^{-4}$), and PAX3 (101 genes, $p<4\times10^{-3}$) (FIG. 6A). ELK1 and E2F3, a member of the E2F family, were also identified as miR-522 target genes, enriched 17- and 2.8-fold in the pulldown, respectively, and significantly down-regulated at both the protein and mRNA levels by miR-522 over-expression (Table shown in FIG. 17 and FIG. 5). Both ELK1 and PAX3 regulate the epithelial-mesenchymal transition (EMT). ELK1 regulated genes were shown by TRANSFAC analysis to be down-regulated during TGF-β-induced EMT (Venkov et al., 2011), and PAX3 enhances mesenchymal epithelial transition (MET) (Wiggan et al., 2002). In addition TEAD2 transcriptionally activates PAX3 (Milewski et al., 2004). This analysis suggests that miR-522 might foster EMT. E2F transcription factors promote G1/S progression in the cell cycle (Fan and Bertino, 1997), suggesting that miR-522 might inhibit cell cycle progression at this phase of the cell cycle.

To accomplish their biological functions, miRNAs target multiple genes that encode for interacting proteins that participate in common pathways (Gurtan and Sharp, 2013; Lal et al., 2009; Lal et al., 2011). Therefore IPA was used next, a knowledge-base containing curated biological interactions and functional annotations (INGENUITY Systems, on the world wide web at ingenuity.com), to identify and connect all directly-related miR-522 target genes (FIG. 7).

Figure 6C:
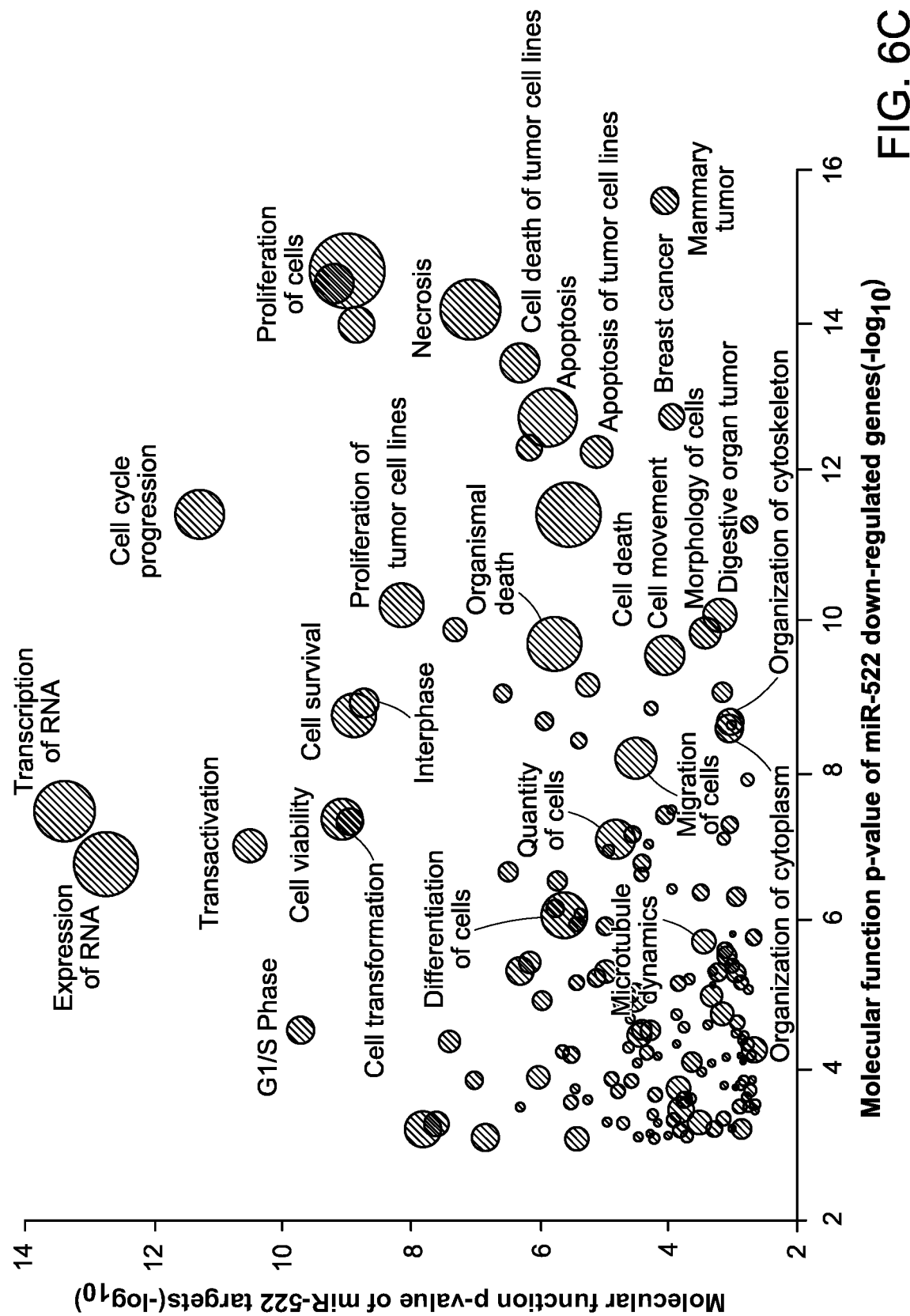

This interactome of 221 genes was then functionally analyzed by IPA to identify the top associated network functions (FIG. 6B). These included cellular movement and morphology (which are functional components of EMT), embryonic development (of which EMT is an essential component), as well as cell cycle, corroborating the TRANSFAC analysis. To include possible indirect functional effects of miR-522, next identified were common molecular functions overrepresented in both the Pulldown-seq interactome and set of 205 directly connected genes whose mRNAs were significantly down-regulated by microarray analysis after miR-522 over-expression (p-value <0.0001 and fold change >1.5) (see Table shown in FIG. 20). The p-values for each common over-represented molecular function were then displayed in a bubble plot, where the number of miR-522 target genes identified by Pulldown-seq for each function is proportional to the bubble size (FIG. 6C). The most significantly enriched functions, for which more than 10 target genes were annotated, fell into 4 large functional categories: proliferation, apoptosis, cell cycle, and cell morphology and transformation. The latter two categories also stood out in both the TRANSFAC and IPA analyses. Based on these analyses taken together, it is hypothesized that miR-522 may function to regulate G1/S cell cycle progression, cell transformation and survival, cell motility and the EMT.

miR-522 Over-Expression Induces Mesenchymal Properties

Figure 8C:
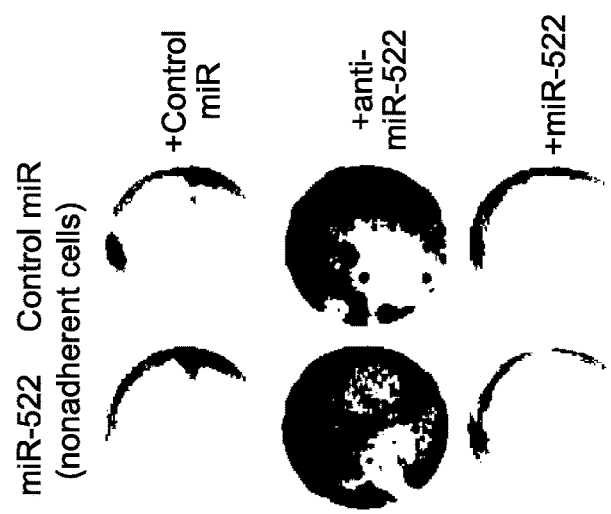
FIGS. 8A-J show over-expression of miR-522 induces hallmarks of epithelial-mesenchymal transition. (A) qRT-PCR analysis of miRNA levels in untransfected MDA-MB-468 cells showed a higher level of miR-522 in nonadherent cells. (B) Trypan blue exclusion cell counts of adherent and nonadherent cells 3 days after transfection with miR-522 or control miRNA showed a higher number of miR-522-transfected live cells in suspension. (C) Nonadherent cells transfected with control or miR-522 were re-transfected with anti-miR-522, control antisense miRNA or miR-522. Only anti-miR-522 transfection resulted in adherent colonies (stained with crystal violet, representative photos of 3 independent experiments shown). qRT-PCR analysis of EMT markers in adherent and nonadherent cells 3 (D) and 5 (E) days after transfection with miR-522- or control miRNA, normalized to GAPDH expression. Note the difference in the scale of expression levels. (F) TRANSWELL invasion assay demonstrates that miR-522 over-expression increases crystal violet-stained invading cells (representative photos). (G) Quantification of TRANSWELL invasion assay by Calcein AM staining. (H) An increased number of live cells in suspension from the bottom chamber of the invasion assay was also detected by CELLTITER-GLO luminescence assay. Assay was performed 2 days after miR-522 transfection. Error bars depict the S.D. of 3 independent experiments. (I, J) Cell cycle analysis of cells transfected with miR-522 compared to control, showing an increase in cells in the G1 phase. (I) shows a representative plot) and (J), mean±S.D. of 3 independent experiments. (*, p<0.05; **, p <0.01).
Figure 8B:
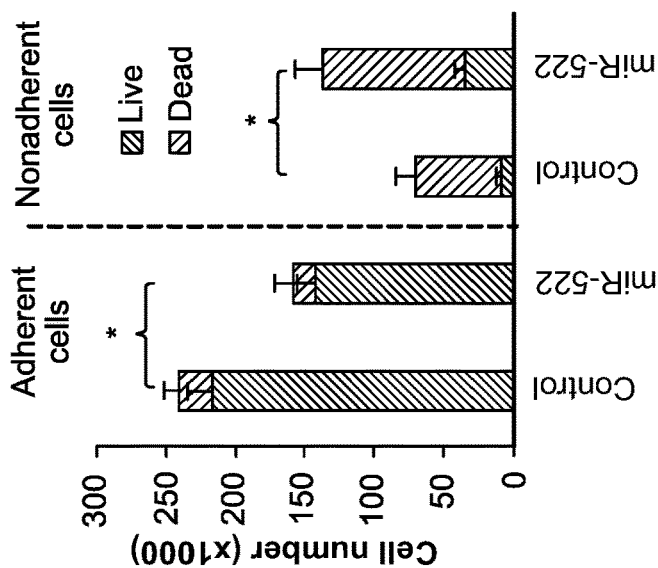
Figure 8A:
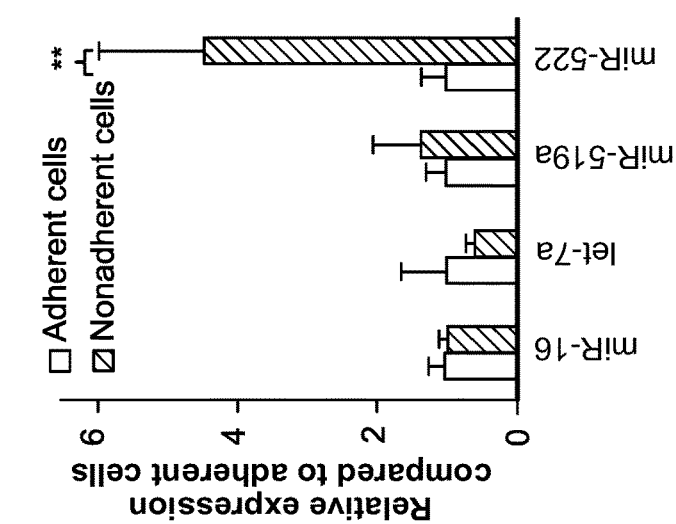

The biological functions of miR-522 in MDA-MB-468 TNBC cells were next investigated. Loss of cellular adhesion is an easily detectable phenotype that involves changes in cell morphology, movement and cytoskeletal organization and is an important step in EMT (Yang and Weinberg, 2008). In tissue culture most MDA-MB-468 cells adhere to the tissue culture dish, but some detach and remain viable. It was first assessed by TAQMAN PCR whether miR-522 levels might be different in adherent vs nonadherent cells. miR-522 expression in nonadherent cells was significantly greater than in adherent cells, but levels of another C19MC miRNA, miR-519a, and 2 control miRNAs, miR-16 and let-7a, were similar (FIG. 8A). Over-expression of miR-522 decreased the number of live cells attached to the tissue culture dish and increased the number of live cells in suspension (FIG. 8B). To assess whether miR-522 expression was responsible for loss of adhesivity, the suspension cells that were transfected 48 hr previously with either control miRNA or miR-522 were collected, and an equal number of each were re-transfected with control miRNA, miR-522 or anti-miR-522. Only cells transfected with anti-miR-522 were able to re-adhere to tissue culture dishes and form colonies (FIG. 8C). Thus miR-522 promotes the detachment and viability of detached cells.

Figure 8D:
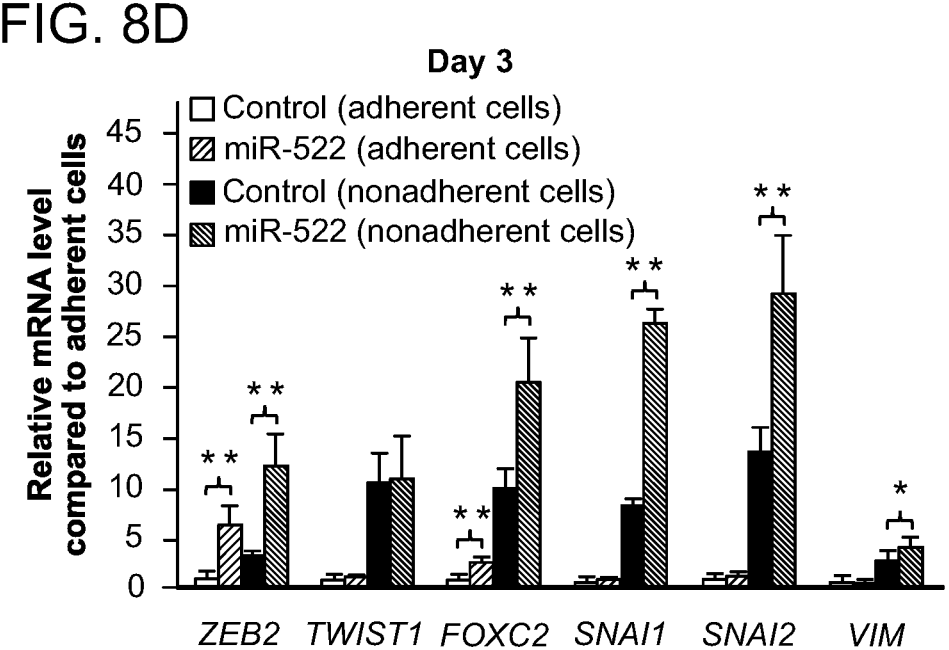
Figure 8E:
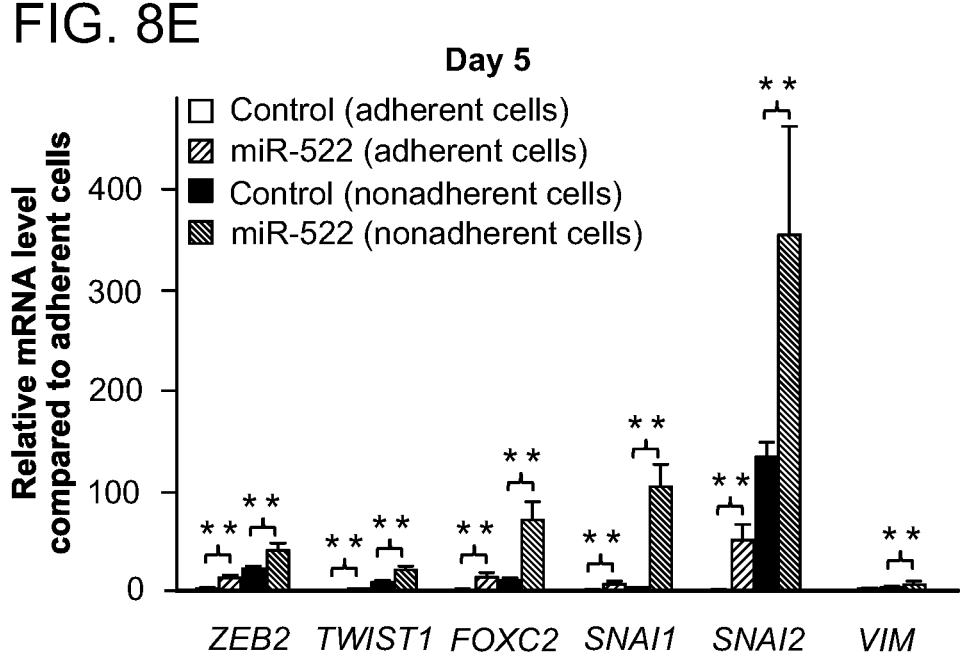
Figure 8F:
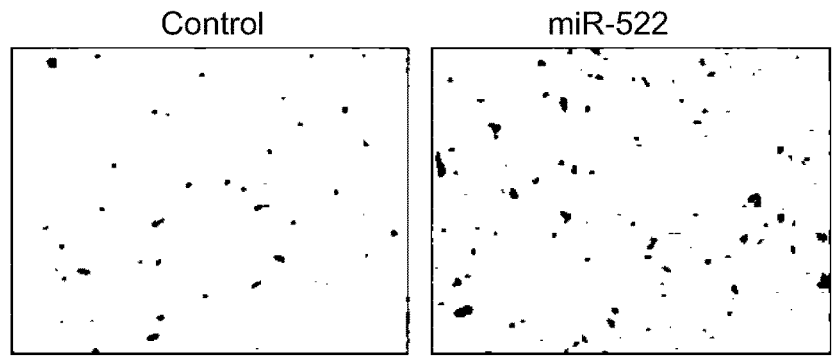
Figure 8G:
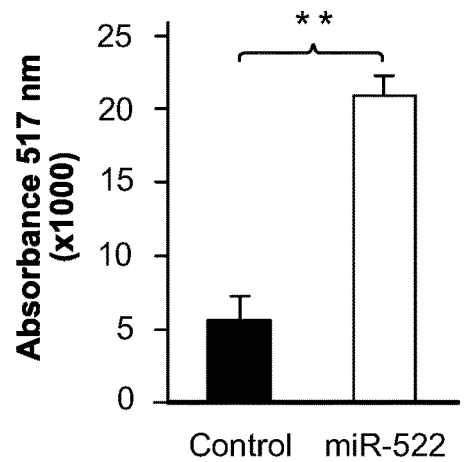
Figure 8H:
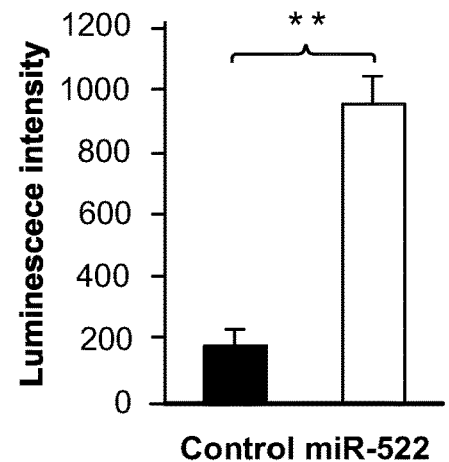

It was next investigated whether miR-522 promotes EMT, which has been linked to metastasis. Changes in the mRNA levels of important mesenchymal genes, ZEB2, TWIST1, FOXC2, SNAIL SNAI2 and VIM, were assessed by qRT-PCR in both adherent and nonadherent cells 3 and 5 d after miR-522 or control miRNA transfection (FIGS. 8D and 8E). Notably, expression of all six genes in both adherent cells and cells in suspension, strongly and significantly increased by day 5, except for VIM in adherent cells. The increase in mesenchymal gene expression, especially for FOXC2, SNAI1 and SNAI2, was markedly higher on day 5 compared to day 3. However, when epithelial genes encoding E-cadherin (CDH1) or the cytokeratins (KRT14, KRT18, KRT19) were assessed in parallel, there was no change in epithelial gene mRNA for both time points (FIG. 9A). These results are consistent with the notion that poorly differentiated cancer cells exhibit plasticity in their epithelial and mesenchymal properties and can simultaneously show features of both states (Granit et al., 2012). A small but significant increase in the stem/early progenitor cell marker genes CD44 and CD133 (FIG. 9A) was detected. Upregulation of CD133 has been shown to induce EMT (Chen et al., 2011). Probing further, it was next asked if miR-522 induced changes in the stem cell-like population, as defined by the CD44+/CCD24low/− phenotype (FIGS. 9B and 9C). Although most of the control cells were CD44+ already, miR-522 over-expression reduced CD24 levels. Invasivity is linked to the mesenchymal state. In invasion assays, miR-522 overexpression significantly increased by 4-5-fold, compared to control miRNA, the numbers of cells that migrated through a membrane and either adhered to the membrane or remained viable in suspension in the lower chamber (FIGS. 8F, 8G and 8H). These data collectively suggest that miR-522 over-expression promotes important hallmarks of EMT.

miR-522 Over-Expression Induces Arrest at G1/S

Figure 8I:
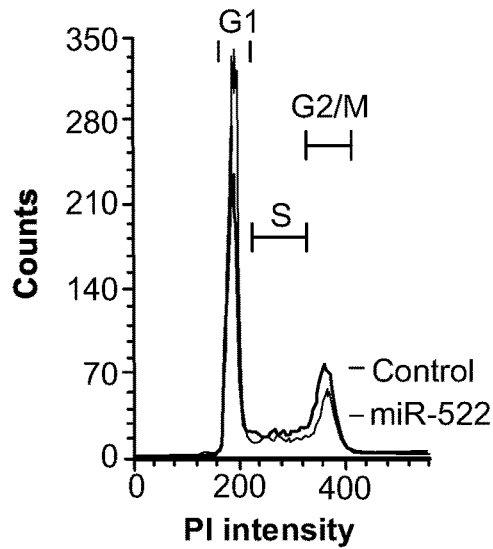
Figure 8J:
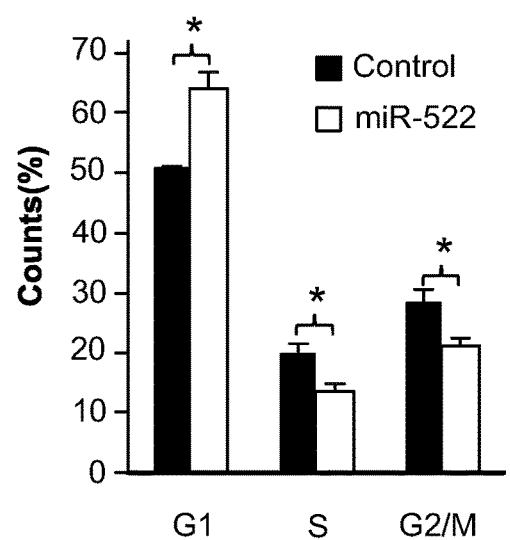

To examine whether miR-522 regulates cell cycle progression, adherent miR-522 and control miRNA-transfected cells were analyzed by propidium iodide staining and flow cytometry. miR-522 overexpression significantly increased the number of cells in the G1 phase and correspondingly decreased cells in S and G2/M, compared to control miRNA (FIGS. 8I and 8J). Thus, as suggested by the bioinformatics analysis, miR-522 induces G1 cell cycle arrest.

Target Gene Knockdown Partially Recapitulates miR-522 Over-Expression Phenotype

Figure 10A:
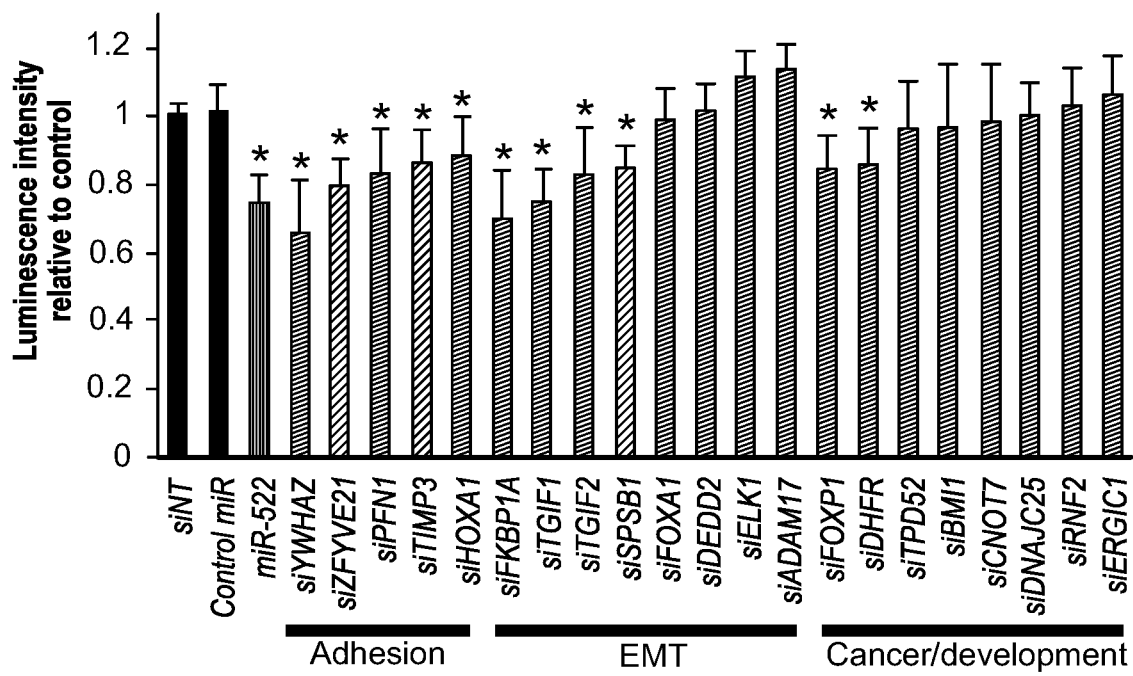
FIGS. 10A-C show knockdown of target genes partially recapitulates characteristics of mir-522 over-expression. (A, B) CELLTITER-GLO assay was used to quantify live adherent (A) and nonadherent cells (B) 3 days after siRNA transfection, normalized to non-targeting siRNA control (siNT) transfection. Bars (right) indicate genes that induced both a decrease in live adherent cells and an increase in live nonadherent cells. (C) qRT-PCR analysis of relative EMT marker gene mRNA in adherent cells 5 days after siRNA transfection. Relative mRNA level normalized to GAPDH was compared to cells transfected with siNT. Genes in the boxed regions significantly enhanced the expression of all 3 mesenchymal transcription factors. Error bars depict the S.D. of 3 independent experiments. (*, p<0.05).
Figure 10B:
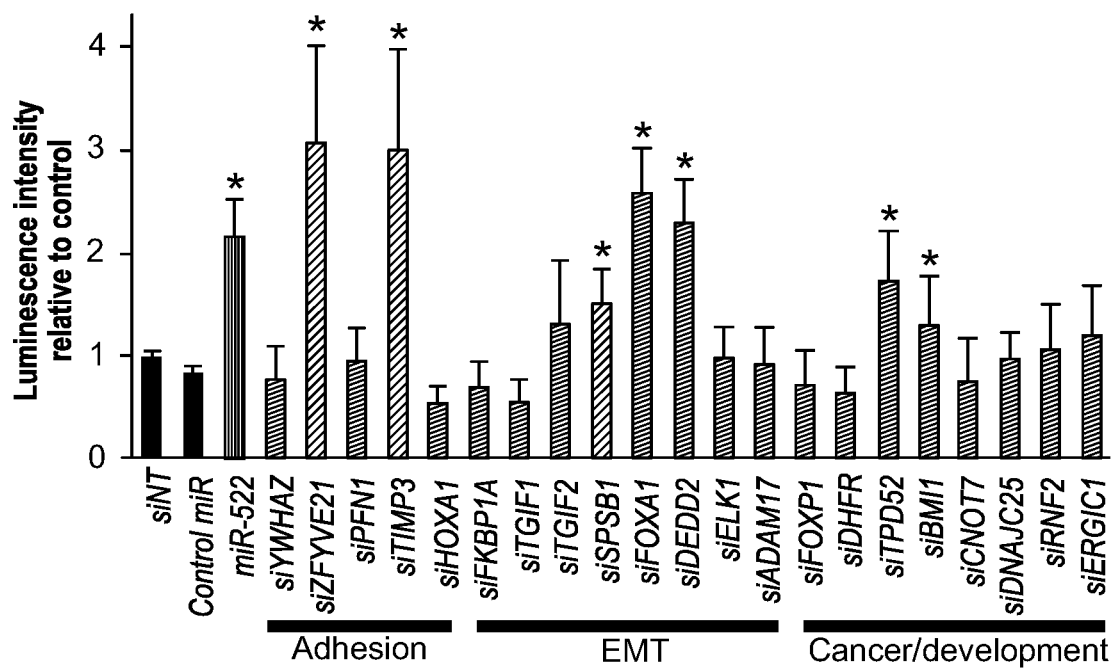

To test the importance of miR-522 regulation of individual target genes, 21 genes in the Pulldown-seq dataset that are known to function in adhesion, EMT, cellular transformation or stem cell biology were chosen for experimental verification. These genes were grouped into three categories: (1) Adhesion: matrix metalloproteinase inhibitor TIMP3 (Visse and Nagase, 2003), focal adhesion regulator ZFYVE21 (Nagano et al., 2010), cell-matrix interaction regulator YWHAZ (Goc et al., 2012), developmental transcription factor and cell adhesion regulator HOXA1 (Lambert et al., 2012), and epithelial cell-cell adhesion regulator PFN1 (Zou et al., 2007); (2) EMT—genes whose knockdown induces EMT (ADAM17 (Liu et al., 2009), FOXA1 (Song et al., 2010), DEDD2 (Lv et al., 2012), and SPSB1 (Liu, 2012)), repressors of TGF-β signaling (FKBP1A (Wang et al., 1994), TGIF1 and TGIF2 (Powers et al., 2010)), and ELK1 (Venkov et al., 2011); (3) Cancer/development: tumor suppressors FOXP1 and DNAJC25 (Banham et al., 2001; Liu et al., 2012), breast cancer-amplified tumor gene TPD52 (Shehata et al., 2008), cycling membrane protein ERGIC1 (Breuza et al., 2004), polycomb group genes and developmental regulators BMI1 and RNF2 (Bracken et al., 2006), Ccr4-NOT deadenylase subunit CNOT7 (Aslam et al., 2009), and antifolate drug target DHFR (Askari and Krajinovic, 2010). It was first investigated whether knockdown of each of these genes recapitulated the effect of miR-522 of increasing detachment without anoikis. Using CELLTITER-GLO as a measure of cell viability, knockdown of 10 of the 21 genes, including all five adhesion-related genes and half of the EMT-related genes, significantly decreased the number of attached viable cells 3 days later (FIG. 10A). However, when the cells in suspension were analyzed, knockdown of only 3 of these (ZFYVE21, TIMP3, SPSB1) resulted in a corresponding increase in the number of live cells in suspension (FIG. 10B). Knockdown of 3 additional genes (FOXA1, DEDD2 and TPD52) also increased the numbers of viable cells in suspension.

Figures 10C, 11:
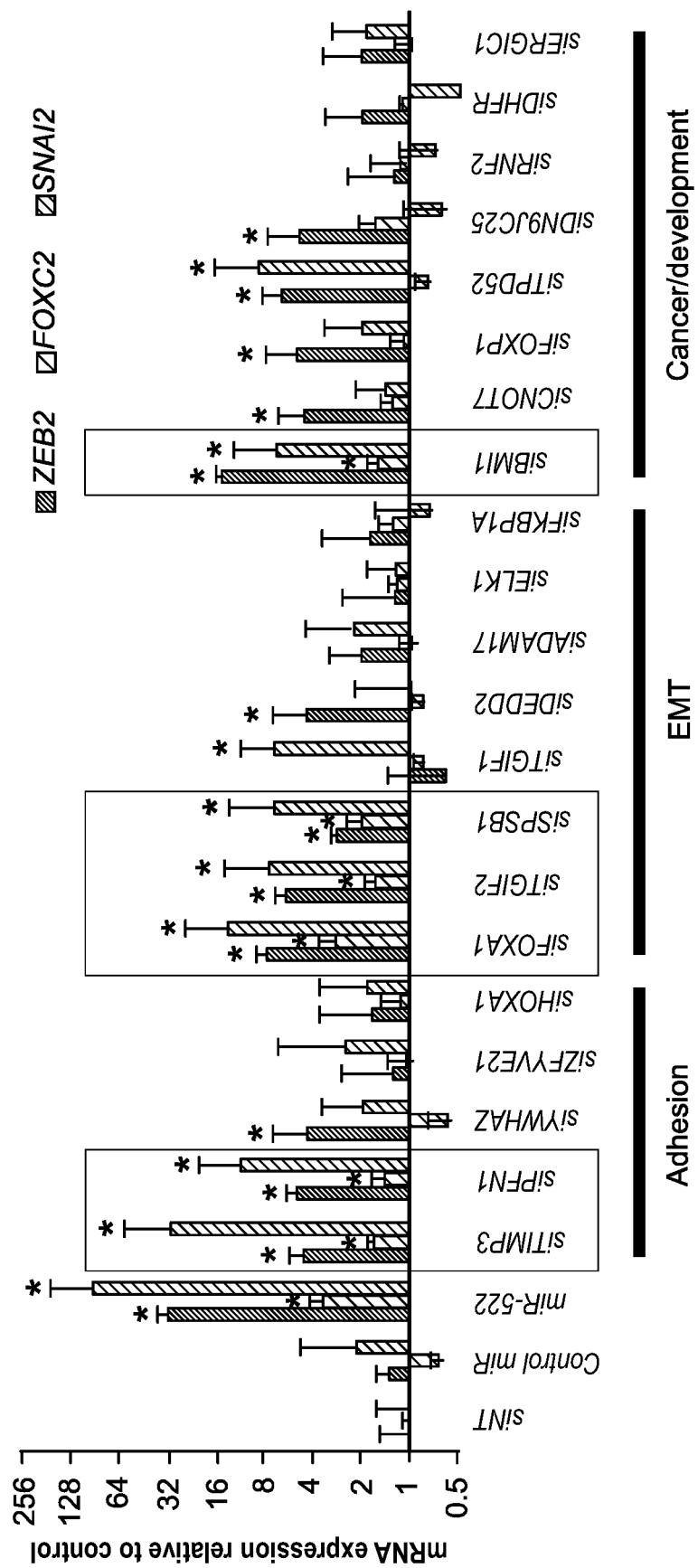
FIG. 11 shows a summary of experimental results to validate the specificity of pulldown-seq and IMPACT-seq for identifying miR-522 target mRNAs and MREs.

Next, qRT-PCR was used to examine whether knockdown of any of the same 21 genes enhanced the expression of the mesenchymal transcription factor genes ZEB2, FOXC2 and SNAI2 that were upregulated by miR-522 (FIG. 10C). Knocking down TIMP3, PFN1, FOXA1, TGIF2, SPSB1 or BMI1 individually upregulated all 3 transcription factor mRNAs 5 days later, although less robustly than miR-522 over-expression. These data suggest that miR-522 regulates invasivity and mesenchymal gene expression by suppressing the expression of multiple genes identified by IMPACT-seq.

Target MRE Identification and Bioinformatic Analysis for Let-7a and miR-34a

Figure 13:
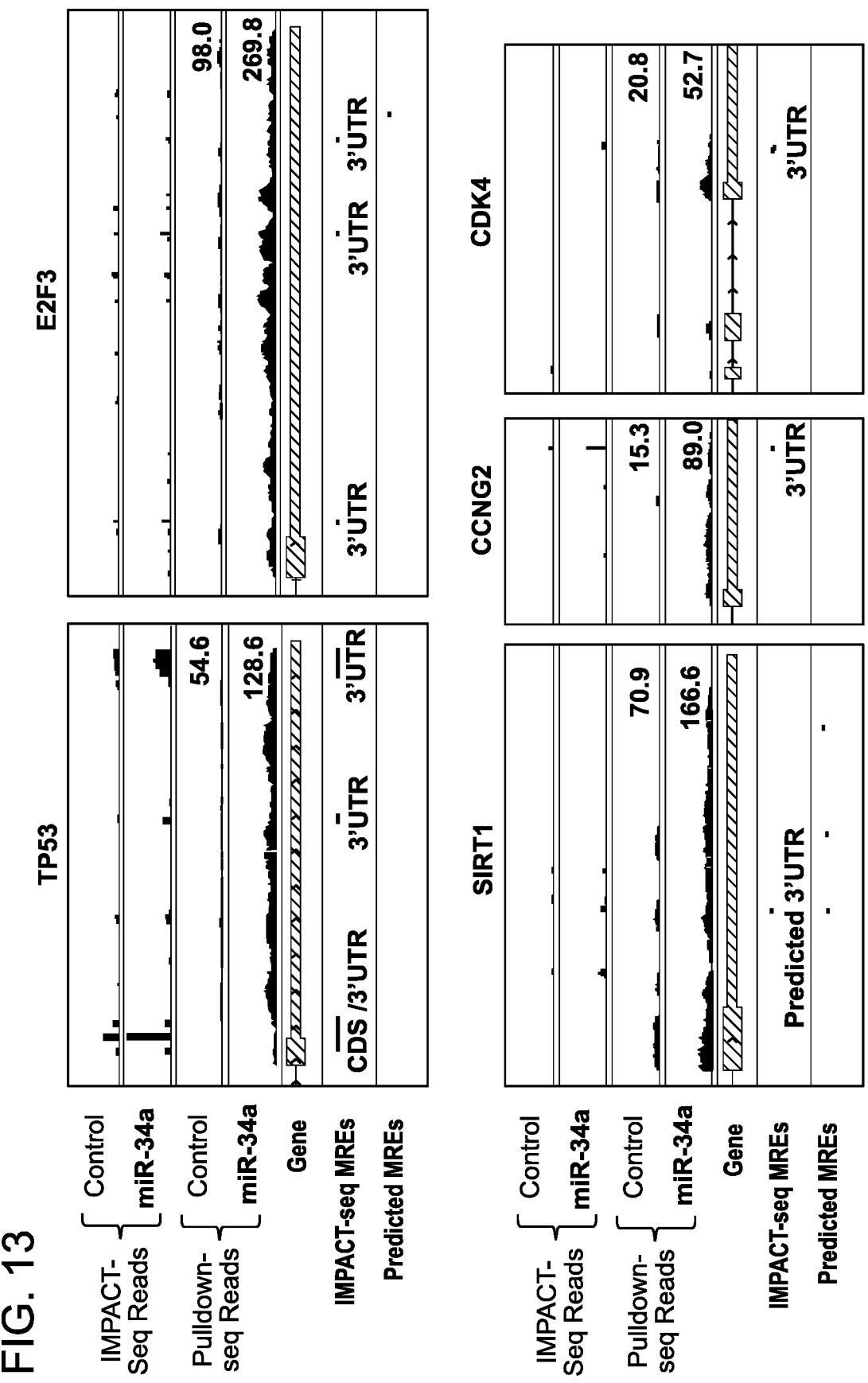
FIG. 13 shows sequencing reads of representative identified miR-34a targets and MREs. Numbers in Pulldown-seq plots indicate mean FPKM (Scale: Pulldown-seq 0-100 reads, IMPACT-seq 0-50 reads). IMPACT-seq identified MREs are indicated below; with 1 of these also predicted by Miranda.
Figure 15:
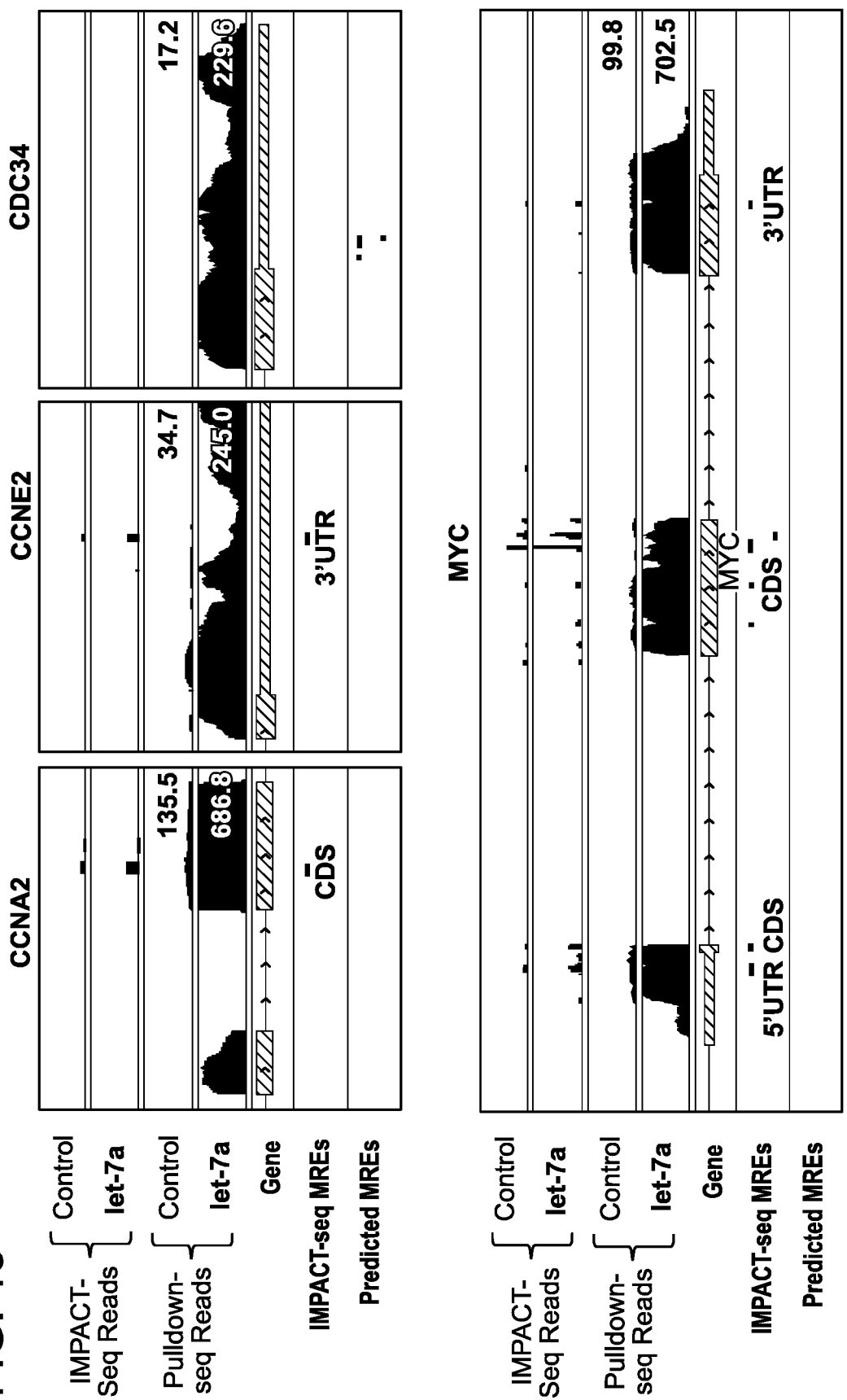
FIG. 15 shows sequencing reads of representative identified let-7a targets and MREs. Numbers in Pulldown-seq plots indicate mean FPKM (Scale: Pulldown-seq 0-100 reads, IMPACT-seq 0-50 reads). IMPACT-seq identified MREs are indicated below.
Figure 16:
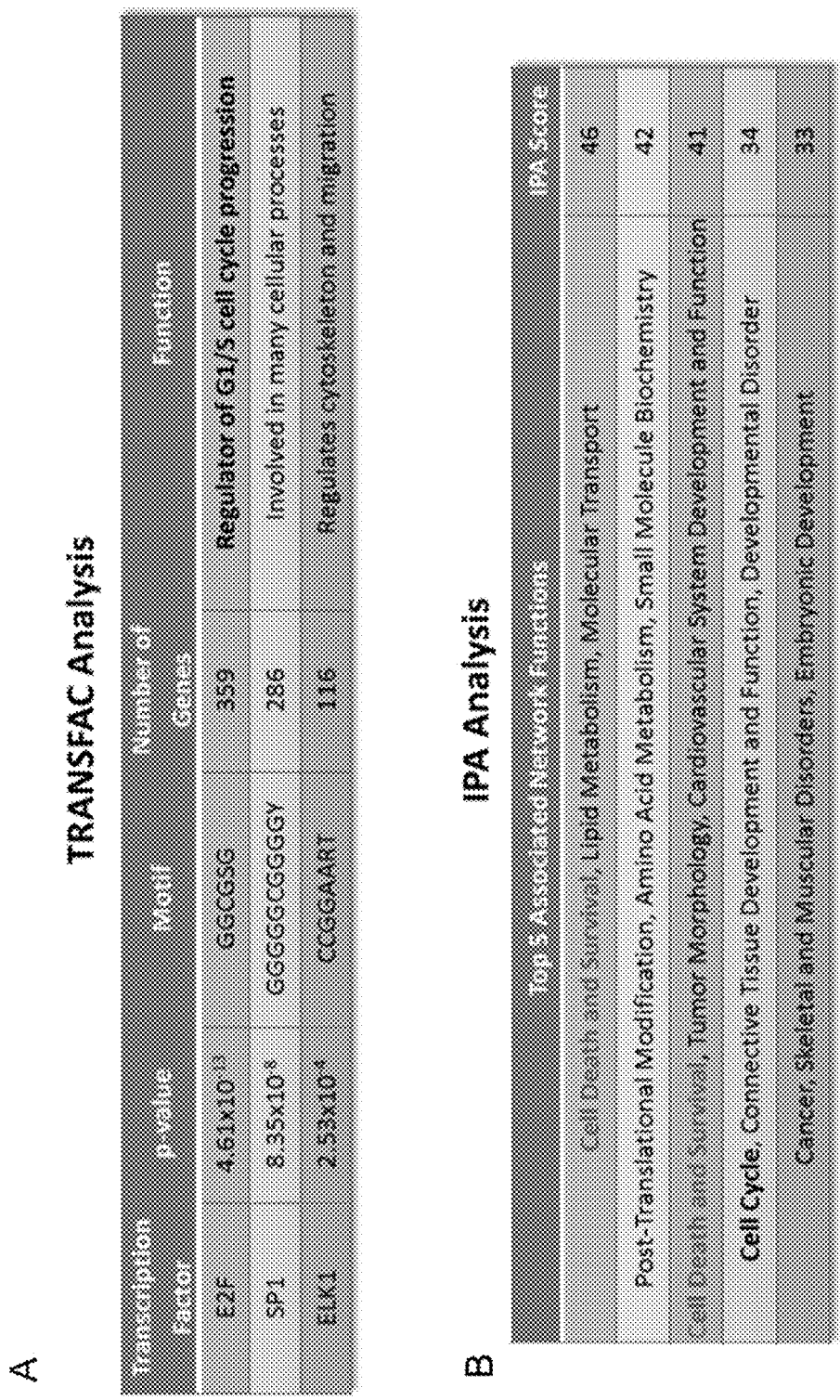
FIG. 16 shows bioinformatics analysis of let-7a target genes. (A) TRANSFAC analysis of promoter regions of let-7a target genes identified enrichment of binding sites for 3 transcription factors. (B) Top enriched functions of directly associated let-7a targets by Ingenuity Pathway Analysis (IPA). IPA Score=−log 10(p-value). Survival-related functions are indicated in grey.

Utilizing the same methods and cut-offs as for miR-522, MREs were identified for both miR-34a and let-7a. For miR-34a, 3892 peaks in 2656 transcripts were identified as possible MREs (FIG. 13 and Table shown in FIG. 23). For let-7a, 1119 peaks in 940 transcripts were identified as possible MREs (FIG. 15 and see Table shown in FIG. 24). With the same bioinformatic analysis methods as used for miR-522, biological function was predicted for both miR-34a and let-7a (FIG. 14 and FIG. 16, respectively).

The studies described herein set forth a systems-based strategy for miRNA functional characterization, and demonstrate its ability to identify miR-522, miR-34a and let-7a target transcripts, MREs and function, directly and readily, with a high degree of specificity. Most of the identified MREs did not follow canonical target recognition rules, but most of the target genes had reduced mRNA and protein levels when miR-522 was over-expressed and most of the identified MREs tested were active by luciferase assay (FIG. 11). The method can be performed with as few as a million cells and is relatively simple to execute. Other advantages include freedom from assumptions about target recognition rules, reduced sequence-based biases from cross-linking, direct genome-wide identification of regulated mRNAs and MREs, and the ability to identify novel transcripts and non-coding RNAs as miRNA targets.

As described herein, in exemplary embodiments a novel bioinformatics analytical approach was used, that combined TRANSFAC promoter analysis with interactome and gene ontology functional analysis of both pulled down and downregulated genes to expedite identifying the biological function of miR-522. This streamlined approach will be useful for uncovering the hidden meaning of large genome-wide datasets. As described herein, it resulted in robust predictions of miR-522 function that directed experimental efforts into fruitful investigations and avoided unproductive searching.

miR-522 recognized its mRNA targets largely via a non-canonical seed coupled with a 3' supplementary motif. Increasingly other studies have been finding that individual miRNAs differ in their mode of recognizing their target MREs, and that across the genome non-canonical miRNA binding motifs may be more prevalent than canonical seed-based base-pairing (Loeb et al., 2012; Xia et al., 2012). In fact, seed-only interactions were found to occur in fewer than 1 in 5 endogeneous miRNA-MRE pairs identified by CLASH (Helwak et al., 2013). Here, a set of miR-522 MREs were functionally verified, that were located in the CDS, 3'- and 5-UTRs of target mRNAs, corroborating previous studies that suggested that miRNAs can recognize regions outside of the 3'-UTR (Grey et al., 2010; Lal et al., 2011; Tay et al., 2008). The 3'-UTR was over-represented and was where most MREs were located. However, given that 3'UTRs make up 43% of RefSeq sequences, this finding that 56% of the identified miR-522 MREs were in the 3'-UTR suggests only a modest overrepresentation of functional miR-522 MREs in the 3'UTR. This is similar to the PAR-CLIP dataset, which also reported a moderate overrepresentation of global miRNA target sequences in the 3'UTR (Hafner et al., 2010).

The cut-offs chosen to define targets are somewhat arbitrary. Increasing the stringency reduces false positives, but also reduces the sensitivity for identifying bona fide targets. For example, changing the fold enrichment cutoff in the pulldown from 2 to 4, significantly improved the cumulative gene expression plot, but at the cost of dramatically reducing the number of candidate targets by about a third. However, the targets most downregulated by miR-522, may be more enriched in the pull-down (FIG. 1D). With the current cut-offs, more potential miR-522 targets were identified with IMPACT-seq than with Pulldown-seq. This apparent discrepancy can be explained by the fact that IMPACT-seq looks at a much smaller sequence window. If a transcript contains MREs for both control miR and miR-522 in different locations, Pulldown-seq will not be able to identify this transcript as a target unless it is pulled down with different efficiencies (1704 transcripts have at least one MRE in both control and miR-522, data not shown). However, MREs were identified for more than half of the miR-522 target transcripts, an impressive statistic considering that the datasets were generated from distinct experiments using two different sequencing platforms. To improve the overlap of regulated mRNAs and MRE-containing transcripts, the stringency of Pulldown-seq cut-offs could be relaxed and/or the sequencing coverage of IMPACT-seq could be improved. With this current method and cutoffs, these two methods of identifying miRNA targets can be viewed as complimentary.

miR-522 caused G1 cell cycle arrest and loss of adhesion without anoikis and induced mesenchymal genes and properties in the TNBC cell line MDA-MB-468. Acquisition of mesenchymal properties is thought to promote cancer progression and metastasis, especially in breast cancer (Yang and Weinberg, 2008). Although miR-522 induced mesenchymal genes and mesenchymal properties, it did not downregulate epithelial gene expression in this breast cancer cell line. Breast cancer circulating tumor cells (CTCs), which are thought to be the intermediary between primary tumor and secondary metastatic cells, highly express mesenchymal markers even though most primary solid tumors and their metastases are epithelial (Aktas et al., 2009; Kallergi et al., 2011). It is increasingly being recognized that breast cancer CTCs, like the miR-522-over-expressing MDA-MB-468 cells in this study, coexpress epithelial and mesenchymal genes. Rather than undergoing an EMT, it might be more accurate to characterize metastasizing cancer cells as occupying a metastable state between these two fixed lineages. Expression of miR-522 may turn on this metastatic program by increasing motility and survival and numbers of CTCs. In line with the hypothesis that miR-522 instigates metastasis, miR-522 was expressed at a higher level in CTCs from patients with primary TNBC tumors that are prone to metastasize compared to patients with better prognosis primary estrogen receptor-positive tumors or healthy blood donors (Sieuwerts et al., 2011). There is currently no targeted therapy for TNBC, the breast cancer with the worst prognosis. In the future, miR-522 antagonists could be evaluated for treating TNBC patients, especially for those whose tumors contain C19MC amplification.

The above Examples were performed using, but not limited to, the following methods and materials.

Cell Culture and Transfection

TNBC cell lines HCC1187, HCC1937, Hs578T, MDA-MB-231 and MDA-MB-468, and luminal breast cancer cell lines BT474, HCC202, SKBR3, T47D and ZR-75-1 were obtained from ATCC, and cultured as recommended. Unless otherwise stated, DharmaFECT 1 reagent (Dharmacon) was used for transfection; 50 nM of control miRNA (cel-miR-67) or miR-522 mimic (ThermoScientific) was used to transfect 100,000 MDA-MB-468 cells/well in suspension in 12-well dishes as per manufacturer's protocol, and medium was changed after 24 hr.

RNA Isolation and Quantitative RT-PCR

Total RNA was extracted from cells using Trizol reagent (Invitrogen) as per the manufacturer's instructions and column purified with the RNEASY kit (QIAGEN). The High Capacity cDNA Archive kit (Applied Biosystems) was used to generate cDNA; miRNA reverse transcription was performed with the microRNA reverse transcription kit (Applied Biosystems) according to manufacturer's instructions. qRT-PCR was performed using the CFX96 Real-Time PCR Detection System (Bio-Rad), with TAQMAN chemistry (Applied Biosystems) for miRNA quantification and iQ SYBR green chemistry (Bio-Rad) for mRNA quantification. Primers for SYBR green assays were designed using the Universal Probe Library Assay Design Center (Roche).

Protein Extraction and Western Blot

Transfected MDA-MB-468 cells were washed with cold PBS after 48 hr, and lysed directly in the wells by incubating with RIPA buffer (with proteasome inhibitors) on ice for 20 min. Lysates were cleared by centrifugation at 4° C., and protein concentrations determined using BCA reagent (Pierce). Proteins were analyzed by SDS-PAGE, transferred to nitrocellulose membranes and probed with the following antibodies: Cell Signaling—ADAM17, ASH2L, BCL2L1, BMI1, CDC42, ELK1, FOXP1, PFN1, RALA, RNF2, TIMP3 and YWHAZ; Santa Cruz—CDKN1B, CDKN2A, DHFR, E2F3, EIF2A, EIF4EBP2, ELAVL1 and JUN; Abcam—HMGA1, TFDP1, CNOT7, FOXA1, TPD52 and YWHAQ; ProteinTech—ERGIC1 and FKBP1A; Sigma—aTUB and ACTB (used as controls); Diagenode—SOX4; and Millipore—BANF1. Western blots were quantified by densitometry utilizing ImageJ (rsbweb.nih.gov/ij/index-.html), and internally normalized to β-actin levels.

Microarray

Total RNA was extracted from cells after 48 hr of transfection in biological triplicates using TRIZOL reagent (Invitrogen) as per the manufacturer's instructions and column purified with the RNEASY kit (QIAGEN). cDNA and cRNA were generated and hybridized to HT-12 v4 beadchips (Illumina) according to manufacturer's protocols. Cubic spline-normalized (without background normalization; Schmid et al., 2010) data was subsequently analyzed by the NIA Array Analysis tool to identify transcripts that were down-regulated upon miR-522 over-expression.

Pulldown-Seq Experimental Protocol

MDA-MB-468 pulldown experiments were with control miRNA (cel-miR-522) and miR-522 mimic (both Thermo-Scientific) conducted as described previously with the modification of including "molecular crowders" in the lysis buffer to improve efficiency (Lal et al., 2011; Lareu et al., 2007). Briefly, cell pellets were collected 24 hr post-transfection, washed twice with cold PBS and incubated with lysis buffer [20 mM Tris (pH 7), 25 mM EDTA (pH 8), 100 mM KCl, 5 mM MgCl2 (all Ambion), 2.5 mg/ml Ficoll PM400, 7.5 mg/ml Ficoll PM70 (GE Healthcare), 0.25 mg/ml dextran sulfate 670 k, 0.3% NP-40 (Fluka), 50 U each of RNase OUT and SUPERase In (Invitrogen) and complete protease inhibitor cocktail (Roche Applied Science)] on ice for 20 min. The cytoplasmic lysate was then isolated by centrifugation at 5,000 g for 5 min. This was added to 1 mg/ml yeast tRNA and 1 mg/ml BSA (Ambion)-blocked streptavidin-coated magnetic beads (Invitrogen), and incubated in a rotator for 4 hr at 4° C. The beads were then washed five times with 1 ml lysis buffer, and bead-bound RNA extracted using TRIZOL LS (Invitrogen). Ribosomal RNA was then depleted using the RIBO-ZERO rRNA removal kit (Epicentre). Sequencing libraries were generated using the NEB-NEXT Multiplex Small RNA Library Prep Set with modified adaptors and primers compatible for ION TORRENT Sequencing Platform (NEB), and sequenced on the ION TORRENT platform using the 314 Chip (Invitrogen) according to manufacturer's protocols.

IMPACT-seq Experimental Protocol

The IMPACT-seq protocol is an extension of the pulldown protocol, with an additional RNase T1 (25 U/µl) on-bead digestion step for 10 min at 37° C. after overnight incubation and before bead washing. Bead-bound RNA, extracted using TRIZOL LS, was treated with T4 Polynucleotide Kinase (NEB) to obtain 5'-phosphate ends for subsequent ligation steps. RNA was then passed through Nuc-Away columns (Ambion) to remove RNAs <20 bp in length. Sequencing libraries were generated using the NEBNext Small RNA Sample Prep Set for Illumina chemistry (NEB), and cDNA fragments corresponding to an insert size of between 20-60 bp were gel-extracted and sequenced on the HiSeq platform (Illumina) according to manufacturer's protocols.

RNA-Seq Quality Control and Alignment

Pre-alignment and post-alignment libraries were screened for quality, specificity of mapping and contaminant sequences using a combination of FASTQC (bioinformatics.babraham.ac.uk/projects/fastqc/), RSeQC (Wang et al., 2012), and RNA-SeQC (DeLuca et al., 2012). Prior to alignment, low quality bases, homopolymer sequences and sequences matching the first 13 bp, and the reverse complement of the adapter sequences for IonTorrent or Illumina were trimmed using cutadapt version 1.2.1 (Martin, 2011). After trimming, reads that were smaller than 30 bp for Pulldown-seq and 20 bp for IMPACT-seq were discarded. For the Pulldown-seq dataset, reads were mapped to the GRCh37 assembly of the human genome augmented with the Ensembl 68 genome annotation using Novoalign (www.novocraft.com) with the following parameters: -H -k -n 250 -F STDFQ -r all 10 -e 10 -g 15 -x 4. Reads mapping non-uniquely to the genome were discarded from further analysis. For the IMPACT-seq dataset, reads were mapped to the GRCh37 assembly of the human genome augmented with the Ensembl 72 genome annotation (Flicek et al., 2013), using Tophat version 2.0.8b (Trapnell et al., 2009), allowing only uniquely mapped reads with at most two mismatches. Quality control, trimming and alignment were performed using the bipy and bcbio-nextgen automated sequencing analysis pipelines.

Pulldown-Seq Target Identification

Post-alignment gene-level counts were generated using htseq-count 0.5.4p3 with the counts aggregated by gene_id of the Ensembl 68 annotation. Differentially expressed transcripts were called with DESeq version 1.5.23 (Anders and Huber, 2010), calculating per-condition dispersions. The top hits with fold enrichments greater than two and a p-value of less than 0.05 were flagged as candidates for downstream biological verification.

IMPACT seq HIRE Identification

Peaks were called on both control miRNA and miR-522 IMPACT-seq samples using CLIPper (github.com/YeoLab/clipper/) with the following parameters: --poisson-cutoff=0.05 --superlocal --max_gap=0 --processors=8 -b $file -s hg19 -o $file. MREs were then identified by filtering the peaks with the following criteria: a) the peak must have 5 reads or more in the miR-522 sample, b) the peak must have at least twice as many normalized reads mapped in the miR-522 sample compared to control, and c) the Poisson probability of the miR-522 sample having more reads in a peak than the control sample must be more than 95%.

miRNA Target Predictions

Predicted MREs for miR-522 were identified and downloaded from the following websites using their respective default settings: TargetScan (.targetscan.org), miRanda (microrna.org), PITA (genie.weizmann.ac.il/pubs/mir07/mir07_prediction.html), DIANA (diana.cslab.ece.ntua.gr) and RNA22 (cm.jefferson.edu/rna22v1.0-*Homo_sapiens*).

Target Functional Analysis

This consists of three parts.

First, possible common transcription factor binding sites are identified in all the miR-522 target genes identified by Pulldown-seq with TRANSFAC (gene-regulation.com) analysis.

Second, IPA (.ingenuity.com) is used to connect all miR-522 target genes that are directly related, as defined by the curated IPA database. This list of genes was then subject to a Core analysis, resulting in a list of IPA scores for the top associated network functions, as well as a list of significantly enriched molecular functions.

Third, a similar IPA core analysis is performed on directly-related genes that were significantly downregulated upon miR-522 over-expression, and compare the significantly enriched molecular functions with those from the second step to identify common phenotypic themes.

MRE Luciferase Assay and Motif Analysis

MRE luciferase assays were performed as described previously (Lal et al., 2011). Briefly, MRE sequences were cloned into psiCHECK-2 (PC2) by annealing complementary oligomers matching each sequence. MDA-MD-468 cells (100,000 cells/well) were seeded on 24-well plates 24 hr before transfection. PC2 or PC2+MRE vector (50 ng) was co-transfected with 50 nM of either control miRNA or miR-522 mimic (both ThermoScientific) using Lipofectamine 2000 according to the manufacturer's instructions. Firefly and *Renilla* luciferase activities were measured 48 hr after transfection with the dual-luciferase reporter system (Promega) using a luminometer (BioTek). *Renilla* reads were normalized to Firefly reads to control for transfection efficiency. The reverse complement of miR-522 was used as a positive control, and the empty vector PC2 was used as a negative control. As additional negative controls, a set of four random sequences in genes identified as miR-522 targets, but not contained in identified MRE locations were also cloned into PC2: PFN1 (TCCGTCTGGGCCGCCGTCCCCGGGAAAA: SEQ ID NO: 1), TFDP1 (TCAACTTTTTAACAATAACACCAT-CAACCTTATTG: SEQ ID NO: 2), YWHAQ (AAAACTAAATCCATACAGGGTGTCATCCTTCTTTC: SEQ ID NO: 3) and YWHAZ (AAGC-CACAATGTTCTTGGCCCATCATG: SEQ ID NO: 4). Motif analysis was performed using the GLAM2 tool (meme.nbcr.net/meme/cgi-bin/glam2.cgi), with all MREs between 25-35 bp as input sequences and the following settings: /opt/meme_4.9.0/bin/glam2 -Q -O. -z 2 -a 2 -b 50 -w 8 -r 10 -n 2000 -D 0.1 -E 2 -I 0.02 -J 1 (Frith et al., 2008).

Cell Counts, Quantification and Cell Cycle Analysis

Trypan blue exclusion dye (Invitrogen) was used to distinguish live and dead cells in automated cell counts using the TC10 (BioRad). Quantification of the number of viable cells was also assessed using CELLTITER-GLO (Promega) by directly adding the reagent to adherent cells on the plate, or to collected cells in suspension, according to the manufacturer's protocol. Luminescence was measured with a luminometer (BioTek). Cell cycle analysis was performed as previously described (Lal et al., 2011), by flow cytometry analysis (FACS Calibur, BD Biosciences) of cells stained with 4 mg/ml propidium iodide (Sigma-Aldrich).

Reattachment Assay

MDA-MB-468 cells were first transfected with either control miRNA (cel-miR-67) or miR-522 mimic (both ThermoScientific), and plated onto 2 12-well plates each. After 3 days, 50,000 live nonadherent cells from each sample were transfected again with 50 nM of either control miRNA (cel-miR-67), miR-522 mimic, or anti-miR-522 hairpin inhibitor (all ThermoScientific), and plated onto 12-well plates. For visualization, adherent cell colonies were stained with 0.1% crystal violet after 10 days.

TRANSWELL Invasion Assays

MDA-MB-468 cells (200,000/well), transfected with either control miRNA (cel-miR-67) or miR-522 mimic (both ThermoScientific) in suspension, were placed in ultra-low attachment 6-well plates (Corning). 48 hr later, 100,000 live cells for each sample were resuspended in serum-free media and plated onto BD BioCoat MATRIGEL Invasion Chambers (BD Biosciences), with serum-containing medium in the lower chamber. The invasion chambers were processed 24 h later, as per the manufacturer's protocol; cells that invaded and adhered to the bottom of the invasion chamber were visualized by staining with 0.1% crystal violet. To quantify the number of adherent cells on each insert, the BD Falcon FluoroBlok Insert System (BD Biosciences) was used, stained with Calcein AM and signal intensity was measured at 517 nm (BioTek), according to the manufacturer's protocol. To quantify the number of cells that invaded, but did not adhere to the inserts (i.e. that migrated across the membrane into the lower well), CellTiter-Glo was used.

Immunostaining and Flow Cytometry

At day 5 after transfection of either control miRNA (cel-miR-67) or miR-522 mimic (both ThermoScientific), MDA-MB-468 cells were collected and resuspended in FACS buffer (0.5% BSA, 1 mM EDTA, 25 mM HEPES in DPBS). Samples were incubated with CD24-PE and CD44-FITC antibodies (BD Pharmingen) at 1:50 dilution for 30 min on ice. Immunostained cells were then analyzed with the FACS Canto (BD Biosciences) using FLOWJO software.

siRNAs

The siRNAs used in this study were from Sigma: non-targeting control siNT (Universal Negative Control #1, SIC001), ADAM17 (SASI_Hs01_00027257), BMI1 (SASI_Hs01_00175764), CUL1 (SASI_Hs02_00335921), DEDD2 (SASI_Hs01_00168512), DNAJC25 (SASI_Hs01_00234349), ELK1 (SASI_Hs02_00326324), ERGIC1 (SASI_Hs01_00145079), FKBP1A (SASI_Hs02_00303248), HOXA1 (SASI_Hs02_00339739), PFN1 (SASI_Hs01_00225745), RNF2 (SASI_Hs01_00213463), SPSB1 (SASI_Hs01_00098647), TGIF1 (SASI_Hs01_00196951), TGIF2 (SASI_Hs01_00107440), TIMP3 (SASI_Hs01_00106686), TPD52 (SASI_Hs01_00170503), YWHAZ (SASI_Hs01_00210834), ZFYVE21

(SASI_Hs01_00241376), and ThermoScientific: DHFR (M-008799-02), FOXA1 (M-010319-01) and FOXP1 (M-004256-01).

Accession Numbers

Pulldown and IMPACT RNA-seq, and over-expression microarray datasets are available in the ArrayExpress database (ebi.ac.uk/arrayexpress) under accession numbers E-MTAB-2112, E-MTAB-2119 and E-MTAB-2110 respectively.

Statistical Analysis

In vitro data were analyzed using unpaired Student's t test; cumulative distribution plots were analyzed using the Kolmogorov-Smirnov test (K-S test). Values of $p<0.05$ were considered statistically significant. *, $p<0.05$; , $p<0.01$; *, $p<0.001$. The mean±SD of three or more independent experiments is reported.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to U.S. patent application Ser. No. 13/063,156, which is the U.S. national phase application, pursuant to 35 U.S.C. § 371, of International Patent Application No.: PCT/US2009/057498, filed Sep. 18, 2009, which claims the benefit of U.S. Provisional Application Ser. Nos. 61/098,696 and 61/098,707, the disclosures of which are hereby incorporated herein in their entireties by reference.

All patents and publications mentioned in this specification are herein incorporated by reference to the same extent as if each independent patent and publication was specifically and individually indicated to be incorporated by reference.

REFERENCES

Aktas, B., Tewes, M., Fehm, T., Hauch, S., Kimmig, R., and Kasimir-Bauer, S. (2009). Stem cell and epithelial-mesenchymal transition markers are frequently overexpressed in circulating tumor cells of metastatic breast cancer patients. Breast Cancer Res 11, R46.

Ambros, V. (2004). The functions of animal microRNAs. Nature 431, 350-355.

Anders, S., and Huber, W. (2010). Differential expression analysis for sequence count data. Genome Biol 11, R106.

Askari, B. S., and Krajinovic, M. (2010). Dihydrofolate reductase gene variations in susceptibility to disease and treatment outcomes. Curr Genomics 11, 578-583.

Aslam, A., Mittal, S., Koch, F., Andrau, J. C., and Winkler, G. S. (2009). The Ccr4-NOT deadenylase subunits CNOT7 and CNOT8 have overlapping roles and modulate cell proliferation. Mol Biol Cell 20, 3840-3850.

Banham, A. H., Beasley, N., Campo, E., Fernandez, P. L., Fidler, C., Gaffer, K., Jones, M., Mason, D. Y., Prime, J. E., Trougouboff, P., et al. (2001). The FOXP1 winged helix transcription factor is a novel candidate tumor suppressor gene on chromosome 3p. Cancer Res 61, 8820-8829.

Bartel, D. P. (2009). MicroRNAs: target recognition and regulatory functions. Cell 136, 215-233.

Biagioni, F., Bossel Ben-Moshe, N., Fontemaggi, G., Canu, V., Mori, F., Antoniani, B., Di Benedetto, A., Santoro, R., Germoni, S., De Angelis, F., et al. (2012). miR-10b*, a master inhibitor of the cell cycle, is down-regulated in human breast tumours. EMBO Mol Med 4, 1214-1229.

Bonnomet, A., Syne, L., Brysse, A., Feyereisen, E., Thompson, E. W., Noel, A., Foidart, J. M., Birembaut, P., Polette, M., and Gilles, C. (2011). A dynamic in vivo model of epithelial-to-mesenchymal transitions in circulating tumor cells and metastases of breast cancer. Oncogene 31, 3741-3753.

Bracken, A. P., Dietrich, N., Pasini, D., Hansen, K. H., and Helin, K. (2006). Genome-wide mapping of Polycomb target genes unravels their roles in cell fate transitions. Genes Dev 20, 1123-1136.

Breuza, L., Halbeisen, R., Jeno, P., Otte, S., Barlowe, C., Hong, W., and Hauri, H. P. (2004). Proteomics of endoplasmic reticulum-Golgi intermediate compartment (ERGIC) membranes from brefeldin A-treated HepG2 cells identifies ERGIC-32, a new cycling protein that interacts with human Erv46. J Biol Chem 279, 47242-47253.

Chen, Y. S., Wu, M. J., Huang, C. Y., Lin, S. C., Chuang, T. H., Yu, C. C., and Lo, J. F. (2011). CD133/Src axis mediates tumor initiating property and epithelial-mesenchymal transition of head and neck cancer. PLoS One 6, e28053.

Chi, S. W., Hannon, G. J., and Darnell, R. B. (2012). An alternative mode of microRNA target recognition. Nat Struct Mol Biol 19, 321-327.

Chi, S. W., Zang, J. B., Mele, A., and Darnell, R. B. (2009). Argonaute HITS-CLIP decodes microRNA-mRNA interaction maps. Nature 460, 479-486.

Cloonan, N., Wani, S., Xu, Q., Gu, J., Lea, K., Heater, S., Barbacioru, C., Steptoe, A. L., Martin, H. C., Nourbakhsh, E., et al. (2011). MicroRNAs and their isomiRs function cooperatively to target common biological pathways. Genome Biol 12, R126.

DeLuca, D. S., Levin, J. Z., Sivachenko, A., Fennell, T., Nazaire, M. D., Williams, C., Reich, M., Winckler, W., and Getz, G. (2012). RNA-SeQC: RNA-seq metrics for quality control and process optimization. Bioinformatics 28, 1530-1532.

Enerly, E., Steinfeld, I., Kleivi, K., Leivonen, S. K., Aure, M. R., Russnes, H. G., Ronneberg, J. A., Johnsen, H., Navon, R., Rodland, E., et al. (2011). miRNA-mRNA integrated analysis reveals roles for miRNAs in primary breast tumors. PLoS One 6, e16915.

Fan, J., and Bertino, J. R. (1997). Functional roles of E2F in cell cycle regulation. Oncogene 14, 1191-1200.

Flicek, P., Ahmed, I., Amode, M. R., Barrell, D., Beal, K., Brent, S., Carvalho-Silva, D., Clapham, P., Coates, G., Fairley, S., et al. (2013). Ensembl 2013. Nucleic Acids Res 41, D48-55.

Frith, M. C., Saunders, N. F., Kobe, B., and Bailey, T. L. (2008). Discovering sequence motifs with arbitrary insertions and deletions. PLoS Comput Biol 4, e1000071.

Goc, A., Abdalla, M., Al-Azayzih, A., and Somanath, P. R. (2012). Rac1 activation driven by 14-3-3zeta dimerization promotes prostate cancer cell-matrix interactions, motility and transendothelial migration. PLoS One 7, e40594.

Granit, R. Z., Gabai, Y., Hadar, T., Karamansha, Y., Liberman, L., Waldhom, I., Gat-Viks, I., Regev, A., Maly, B., Darash-Yahana, M., et al. (2012). EZH2 promotes a bi-lineage identity in basal-like breast cancer cells. Oncogene 32, 3886-3895.

Grey, F., Tirabassi, R., Meyers, H., Wu, G., McWeeney, S., Hook, L., and Nelson, J. A. (2010). A viral microRNA down-regulates multiple cell cycle genes through mRNA 5'UTRs. PLoS Pathog 6, e1000967.

Guo, H., Ingolia, N. T., Weissman, J. S., and Bartel, D. P. (2010). Mammalian microRNAs predominantly act to decrease target mRNA levels. Nature 466, 835-840.

Gurtan, A. M., and Sharp, P. A. (2013). The role of miRNAs in regulating gene expression networks. J Mol Biol 425, 3582-3600.

Hafner, M., Landthaler, M., Burger, L., Khorshid, M., Hausser, J., Berninger, P., Rothballer, A., Ascano, M., Jr., Jungkamp, A. C., Munschauer, M., et al. (2010). Transcriptome-wide identification of RNA-binding protein and microRNA target sites by PAR-CLIP. Cell 141, 129-141.

He, L., and Hannon, G. J. (2004). MicroRNAs: small RNAs with a big role in gene regulation. Nat Rev Genet 5, 522-531.

Helwak, A., Kudla, G., Dudnakova, T., and Tollervey, D. (2013). Mapping the Human miRNA Interactome by CLASH Reveals Frequent Noncanonical Binding. Cell 153, 654-665.

Kallergi, G., Papadaki, M. A., Politaki, E., Mavroudis, D., Georgoulias, V., and Agelaki, S. (2011). Epithelial to mesenchymal transition markers expressed in circulating tumour cells of early and metastatic breast cancer patients. Breast Cancer Res 13, R59.

Kang, H., Davis-Dusenbery, B. N., Nguyen, P. H., Lal, A., Lieberman, J., Van Aelst, L., Lagna, G., and Hata, A. (2012). Bone morphogenetic protein 4 promotes vascular smooth muscle contractility by activating microRNA-21 (miR-21), which down-regulates expression of family of dedicator of cytokinesis (DOCK) proteins. J Biol Chem 287, 3976-3986.

Keene, J. D., Komisarow, J. M., and Friedersdorf, M. B. (2006). RIP-Chip: the isolation and identification of mRNAs, microRNAs and protein components of ribonucleoprotein complexes from cell extracts. Nat Protoc 1, 302-307.

Khorshid, M., Hausser, J., Zavolan, M., and van Nimwegen, E. (2013). A biophysical miRNA-mRNA interaction model infers canonical and noncanonical targets. Nat Methods 10, 253-255.

Kishore, S., Jaskiewicz, L., Burger, L., Hausser, J., Khorshid, M., and Zavolan, M. (2011). A quantitative analysis of CLIP methods for identifying binding sites of RNA-binding proteins. Nat Methods 8, 559-564.

Kong, W., Yang, H., He, L., Zhao, J. J., Coppola, D., Dalton, W. S., and Cheng, J. Q. (2008). MicroRNA-155 is regulated by the transforming growth factor beta/Smad pathway and contributes to epithelial cell plasticity by targeting RhoA. Mol Cell Biol 28, 6773-6784.

Lal, A., Navarro, F., Maher, C. A., Maliszewski, L. E., Yan, N., O'Day, E., Chowdhury, D., Dykxhoorn, D. M., Tsai, P., Hofmann, O., et al. (2009). miR-24 Inhibits cell proliferation by targeting E2F2, MYC, and other cell-cycle genes via binding to "seedless" 3'UTR microRNA recognition elements. Mol Cell 35, 610-625.

Lal, A., Thomas, M. P., Altschuler, G., Navarro, F., O'Day, E., Li, X. L., Concepcion, C., Han, Y. C., Thiery, J., Rajani, D. K., et al. (2011). Capture of microRNA-bound mRNAs identifies the tumor suppressor miR-34a as a regulator of growth factor signaling. PLoS Genet 7, e1002363.

Lambert, B., Vandeputte, J., Remade, S., Bergiers, I., Simonis, N., Twizere, J. C., Vidal, M., and Rersohazy, R. (2012). Protein interactions of the transcription factor Hoxa1. BMC Dev Biol 12, 29.

Lamouille, S., Subramanyam, D., Blelloch, R., and Derynck, R. (2013). Regulation of epithelial-mesenchymal and mesenchymal-epithelial transitions by microRNAs. Curr Opin Cell Biol 25, 200-207.

Lareu, R. R., Harve, K. S., and Raghunath, M. (2007). Emulating a crowded intracellular environment in vitro dramatically improves RT-PCR performance. Biochem Biophys Res Commun 363, 171-177.

Le, M. T., Shyh-Chang, N., Khaw, S. L., Chin, L., Teh, C., Tay, J., O'Day, E., Korzh, V., Yang, H., Lal, A., et al. (2011). Conserved regulation of p53 network dosage by microRNA-125b occurs through evolving miRNA-target gene pairs. PLoS Genet 7, e1002242.

Lewis, B. P., Burge, C. B., and Bartel, D. P. (2005). Conserved seed pairing, often flanked by adenosines, indicates that thousands of human genes are microRNA targets. Cell 120, 15-20.

Li, M., Lee, K. F., Lu, Y., Clarke, I., Shih, D., Eberhart, C., Collins, V. P., Van Meter, T., Picard, D., Zhou, L., et al. (2009). Frequent amplification of a chr19q13.41 microRNA polycistron in aggressive primitive neuroectodermal brain tumors. Cancer Cell 16, 533-546.

Liu, C., Xu, P., Lamouille, S., Xu, J., and Derynck, R. (2009). TACE-mediated ectodomain shedding of the type I TGF-beta receptor downregulates TGF-beta signaling. Mol Cell 35, 26-36.

Liu, S. (2012). Regulation of receptors in TGF-β signaling and its impact in diseases. In Department of Surgery (RMH), Faculty of Medicine, Dentistry and Health Sciences (Melboune, The University of Melbourne).

Liu, T., Jiang, W., Han, D., and Yu, L. (2012). DNAJC25 is downregulated in hepatocellular carcinoma and is a novel tumor suppressor gene. Oncol Lett 4, 1274-1280.

Loeb, G. B., Khan, A. A., Canner, D., Hiatt, J. B., Shendure, J., Darnell, R. B., Leslie, C. S., and Rudensky, A. Y. (2012). Transcriptome-wide miR-155 binding map reveals widespread noncanonical microRNA targeting. Mol Cell 48, 760-770.

Lv, Q., Wang, W., Xue, J., Hua, F., Mu, R., Lin, H., Yan, J., Lv, X., Chen, X., and Hu, Z. W. (2012). DEDD interacts with PI3KC3 to activate autophagy and attenuate epithelial-mesenchymal transition in human breast cancer. Cancer Res 72, 3238-3250.

Ma, L., Young, J., Prabhala, H., Pan, E., Mestdagh, P., Muth, D., Teruya-Feldstein, J., Reinhardt, F., Onder, T. T., Valastyan, S., et al. (2010). miR-9, a MYC/MYCN-activated microRNA, regulates E-cadherin and cancer metastasis. Nat Cell Biol 12, 247-256.

Martin, M. (2011). Cutadapt removes adapter sequences from high-throughput sequencing reads. EMBnetjournal 17, 3.

Matys, V., Kel-Margoulis, O. V., Fricke, E., Liebich, I., Land, S., Barre-Dirrie, A., Reuter, I., Chekmenev, D., Krull, M., Hornischer, K., et al. (2006). TRANSFAC and its module TRANSCompel: transcriptional gene regulation in eukaryotes. Nucleic Acids Res 34, D108-110.

Milewski, R. C., Chi, N. C., Li, J., Brown, C., Lu, M. M., and Epstein, J. A. (2004). Identification of minimal enhancer elements sufficient for Pax3 expression in neural crest and implication of Tead2 as a regulator of Pax3. Development 131, 829-837.

Miranda, K. C., Huynh, T., Tay, Y., Mg, Y. S., Tam, W. L., Thomson, A. M., Lim, B., and Rigoutsos, I. (2006). A pattern-based method for the identification of MicroRNA binding sites and their corresponding heteroduplexes. Cell 126, 1203-1217.

Nagano, M., Hoshino, D., Sakamoto, T., Kawasaki, N., Koshikawa, N., and Seiki, M. (2010). ZF21 protein regulates cell adhesion and motility. J Biol Chem 285, 21013-21022.

Navon, R., Wang, H., Steinfeld, I., Tsalenko, A., Ben-Dor, A., and Yakhini, Z. (2009). Novel rank-based statistical methods reveal microRNAs with differential expression in multiple cancer types. PLoS One 4, e8003.

Noguer-Dance, M., Abu-Amero, S., Al-Khtib, M., Lefevre, A., Coullin, P., Moore, G. E., and Cavaille, J. (2010). The primate-specific microRNA gene cluster (C19MC) is imprinted in the placenta. Hum Mol Genet 19, 3566-3582.

Orom, U. A., Nielsen, F. C., and Lund, A. H. (2008). MicroRNA-10a binds the 5'UTR of ribosomal protein mRNAs and enhances their translation. Mol Cell 30, 460-471.

Papadimitriou, E., Vasilaki, E., Vorvis, C., Iliopoulos, D., Moustakas, A., Kardassis, D., and Stournaras, C. (2012). Differential regulation of the two RhoA-specific GEF isoforms Net1/Net1A by TGF-beta and miR-24: role in epithelial-to-mesenchymal transition. Oncogene 31, 2862-2875.

Poliseno, L., Salmena, L., Zhang, J., Carver, B., Haveman, W. J., and Pandolfi, P. P. (2010). A coding-independent function of gene and pseudogene mRNAs regulates tumour biology. Nature 465, 1033-1038.

Rippe, V., Dittbemer, L., Lorenz, V. N., Drieschner, N., Nimzyk, R., Sendt, W., Junker, K., Beige, G., and Bullerdiek, J. (2010). The two stem cell microRNA gene clusters C19MC and miR-371-3 are activated by specific chromosomal rearrangements in a subgroup of thyroid adenomas. PLoS One 5, e9485.

Shehata, M., Bieche, I., Boutros, R., Weidenhofer, J., Fanayan, S., Spalding, L., Zeps, N., Byth, K., Bright, R. K., Lidereau, R., et al. (2008). Nonredundant functions for tumor protein D52-like proteins support specific targeting of TPD52. Clin Cancer Res 14, 5050-5060.

Sieuwerts, A. M., Mostert, B., Bolt-de Vries, J., Peeters, D., de Jongh, F. E., Stouthard, J. M., Dirix, L. Y., van Dam, P. A., Van Galen, A., de Weerd, V., et al. (2011). mRNA and microRNA expression profiles in circulating tumor cells and primary tumors of metastatic breast cancer patients. Clin Cancer Res 17, 3600-3618.

Song, S. J., Poliseno, L., Song, M. S., Ala, U., Webster, K., Ng, C., Beringer, G., Brikbak, N.J., Yuan, X., Cantley, L. C., et al. (2013). MicroRNA-antagonism regulates breast cancer stemness and metastasis via TET-family-dependent chromatin remodeling. Cell 154, 311-324.

Song, Y., Washington, M. K, and Crawford, H. C. (2010). Loss of FOXA1/2 is essential for the epithelial-to-mesenchymal transition in pancreatic cancer. Cancer Res 70, 2115-2125.

Su, H., Trombly, M. I., Chen, J., and Wang, X. (2009). Essential and overlapping functions for mammalian Argonautes in microRNA silencing. Genes Dev 23, 304-317.

Tay, Y., Zhang, J., Thomson, A. M., Lim, B., and Rigoutsos, I. (2008). MicroRNAs to Nanog, Oct4 and Sox2 coding regions modulate embryonic stem cell differentiation. Nature 455, 1124-1128.

TCGA (2012). Comprehensive molecular portraits of human breast tumours. Nature 490, 61-70.

Thomas, M., Lieberman, J., and Lal, A. (2010). Desperately seeking microRNA targets. Nat Struct Mol Biol 17, 1169-1174.

Trapnell, C., Pachter, L., and Salzberg, S. L. (2009). TopHat: discovering splice junctions with RNA-Seq. Bioinformatics 25, 1105-1111.

Vella, M. C., Choi, E. Y., Lin, S. Y., Reinert, K., and Slack, F. J. (2004). The C. elegans microRNA let-7 binds to imperfect let-7 complementary sites from the lin-41 3'UTR. Genes Dev 18, 132-137.

Venkov, C., Plieth, D., Ni, T., Karmaker, A., Bian, A., George, A. L., Jr., and Neilson, E. G. (2011). Transcriptional networks in epithelial-mesenchymal transition. PLoS One 6, e25354.

Vetter, G., Saumet, A., Moes, M., Vallar, L., Le Bechec, A., Laurini, C., Sabbah, M., Arar, K., Theillet, C., Lecellier, C. H., et al. (2010). miR-661 expression in SNAI1-induced epithelial to mesenchymal transition contributes to breast cancer cell invasion by targeting Nectin-1 and StarD10 messengers. Oncogene 29, 4436-4448.

Visse, R., and Nagase, H. (2003). Matrix metalloproteinases and tissue inhibitors of metalloproteinases: structure, function, and biochemistry. Circ Res 92, 827-839.

Wang, L., Wang, S., and Li, W. (2012). RSeQC: quality control of RNA-seq experiments. Bioinformatics 28, 2184-2185.

Wiggan, O., Fadel, M. P., and Hamel, P. A. (2002). Pax3 induces cell aggregation and regulates phenotypic mesenchymal-epithelial interconversion. J Cell Sci 115, 517-529.

Wu, S., Huang, S., Ding, J., Zhao, Y., Liang, L., Liu, T., Zhan, R., and He, X. (2010). Multiple microRNAs modulate p21Cip1/Waf1 expression by directly targeting its 3' untranslated region. Oncogene 29, 2302-2308.

Xia, Z., Clark, P., Huynh, T., Loher, P., Zhao, Y., Chen, H. W., Ren, P., Rigoutsos, I., and Zhou, R. (2012). Molecular dynamics simulations of Ago silencing complexes reveal a large repertoire of admissible 'seed-less' targets. Sci Rep 2, 569.

Yang, J., and Weinberg, R. A. (2008). Epithelial-mesenchymal transition: at the crossroads of development and tumor metastasis. Dev Cell 14, 818-829.

Zisoulis, D. G., Lovci, M. T., Wilbert, M. L., Hutt, K R., Liang, T. Y., Pasquinelli, A. E., and Yeo, G. W. (2010). Comprehensive discovery of endogenous Argonaute binding sites in Caenorhabditis elegans. Nat Struct Mol Biol 17, 173-179.

Zou, L., Jaramillo, M., Whaley, D., Wells, A., Panchapakesa, V., Das, T., and Roy, P. (2007). Profilin-1 is a negative regulator of mammary carcinoma aggressiveness. Br J Cancer 97, 1361-1371.

What is claimed is:

1. A method of identifying miRNA response elements (MREs), the method comprising:
   conducting an affinity assay and a sequencing assay comprising the following steps:
   (a) transfecting a cell with a biotinylated miRNA, wherein the biotinylated miRNA binds to an RNA target sequence and forms a biotinylated miRNA-RNA complex inside the cell;
   (b) lysing the cell in lysis buffer containing a macromolecular crowding agent;
   (c) isolating the biotinylated miRNA-RNA complex by binding the biotinylated miRNA in the complex to streptavidin-coated beads in the presence of the macromolecular crowding agent;
   (d) generating a biotinylated miRNA-RNA fragment by contacting the biotinylated miRNA-RNA complex attached to streptavidin-coated beads with an RNase under conditions sufficient to degrade single stranded RNA associated with the miRNA-RNA complex into RNA fragments and a bead-bound biotinylated miRNA-RNA fragment complex;
   (e) separating the bead-bound biotinylated miRNA-RNA fragment complex from single stranded RNA fragments;
   (f) extracting the RNA fragment from the bead; and (g) sequencing each nucleic acid sequence of the extracted RNA fragments wherein each extracted RNA fragment represents an miRNA response element; thereby (h) identifying the miRNA response element nucleic acid sequence.

2. The method of claim 1, wherein the macromolecular crowding agent is one or more of Ficoll PM400, Ficoll PM70, dextran sulfate, Ficoll (Fc) 70 kDa (Fc70), Fc400 kDa (Fc400), trehalose, proline, polyethylene glycol (PEG) 4 kDa, and Dextran 670 kDa.

3. The method of claim 1, wherein the isolating step is performed in the presence of EDTA.

4. The method of claim 1, wherein the RNase is one or more of RNase T1, RNase A, RNase If, MNase, or an RNase capable of degrading single-stranded RNA.

5. The method of claim 1, wherein the miRNA-RNA complex is contacted with the RNase for 5, 10, 15, 20, 25, 30, 45, or 60 minutes.

6. The method of claim 1, wherein the RNA fragment sequence ranges in length of 5-500, 5-250, 10-100, or 15-60 nucleotides.

7. The method of claim 1, wherein the nucleic acid sequence of the extracted RNA fragment is determined by ion semiconductor sequencing, pyrosequencing, sequencing by synthesis, sequencing by ligation, or chain termination sequencing.

8. The method of claim 1, wherein the miRNA is selected from the group consisting of: miR-522, miR24, miR34a and let-7a.

* * * * *

SEQUENCE LISTING

<160> NUMBER OF SEQ ID NOS: 5

<210> SEQ ID NO 1
<211> LENGTH: 28
<212> TYPE: DNA
<213> ORGANISM: Artificial Sequence
<220> FEATURE:
<223> OTHER INFORMATION: PC2: PFN1

<400> SEQUENCE: 1
tccgtctggg ccgccgtccc cgggaaaa                                28

<210> SEQ ID NO 2
<211> LENGTH: 35
<212> TYPE: DNA
<213> ORGANISM: Artificial Sequence
<220> FEATURE:
<223> OTHER INFORMATION: TFDP1

<400> SEQUENCE: 2 tcaactttt aacaataaca ccatcaacct tattg                         35

<210> SEQ ID NO 3
<211> LENGTH: 35
<212> TYPE: DNA
<213> ORGANISM: Artificial Sequence
<220> FEATURE:
<223> OTHER INFORMATION: YWHAQ

<400> SEQUENCE: 3 tcaactttt aacaataaca ccatcaacct tattg                         35

<210> SEQ ID NO 4
<211> LENGTH: 27
<212> TYPE: DNA
<213> ORGANISM: Artificial Sequence
<220> FEATURE:
<223> OTHER INFORMATION: YWHAZ

<400> SEQUENCE: 4
aagccacaat gttcttggcc catcatg                                 27

<210> SEQ ID NO 5
<211> LENGTH: 22
<212> TYPE: DNA
<213> ORGANISM: Artificial Sequence
<220> FEATURE:
<223> OTHER INFORMATION: miR-522 complementary target

<400> SEQUENCE: 5
tgtgagattt cccttggtaa aa                                      22